US012667614B2

(12) United States Patent
Tan et al.

(10) Patent No.:  US 12,667,614 B2
(45) Date of Patent:     Jun. 30, 2026

(54) BACTERIAL MICROCOMPARTMENT VIRUS-LIKE PARTICLES

(71) Applicant: National University of Singapore, Singapore (SG)

(72) Inventors: Yong Quan Tan, Singapore (SG); Bo Xue, Singapore (SG); Maybelle Darlene Kho Go, Singapore (SG); Wen Shan Yew, Singapore (SG)

(73) Assignee: National University of Singapore, Singapore (SG)

( * ) Notice: Subject to any disclaimer, the term of this patent is extended or adjusted under 35 U.S.C. 154(b) by 601 days.

(21) Appl. No.: 18/033,282

(22) PCT Filed: Oct. 21, 2021

(86) PCT No.: PCT/SG2021/050639
§ 371 (c)(1),
(2) Date: Apr. 21, 2023

(87) PCT Pub. No.: WO2022/086450
PCT Pub. Date: Apr. 28, 2022

(65) Prior Publication Data
US 2023/0302124 A1     Sep. 28, 2023

(30) Foreign Application Priority Data
Oct. 23, 2020    (SG) .......................... 10202010547W

(51) Int. Cl.
| | |
|---|---|
| *A61K 39/385* | (2006.01) |
| *C07K 14/32* | (2006.01) |
| *C12N 15/70* | (2006.01) |
| *C12N 15/81* | (2006.01) |
| *A61K 39/00* | (2006.01) |

(52) U.S. Cl.
CPC ............ *A61K 39/385* (2013.01); *C07K 14/32* (2013.01); *C12N 15/70* (2013.01); *C12N 15/81* (2013.01); *A61K 2039/5256* (2013.01); *A61K 2039/5258* (2013.01)

(58) Field of Classification Search
CPC .... A61K 2039/5256; A61K 2039/5258; C12N 15/70; Y02A 50/30
See application file for complete search history.

(56) References Cited

U.S. PATENT DOCUMENTS

| | | | | |
|---|---|---|---|---|
| 10,913,777 | B2 * | 2/2021 | Hagen ...................... | C12P 21/02 |
| 11,130,788 | B2 * | 9/2021 | Hagen ................ | B01D 15/3804 |
| 11,198,880 | B2 * | 12/2021 | Kerfeld .................. | C12N 15/70 |
| 12,071,455 | B2 * | 8/2024 | Hagen .................. | B01D 15/363 |

FOREIGN PATENT DOCUMENTS

| | | |
|---|---|---|
| CN | 110438095 A | 11/2019 |
| WO | 2011/094765 A2 | 8/2011 |
| WO | 2013/045562 A1 | 4/2013 |
| WO | 2022074380 A1 | 4/2022 |

OTHER PUBLICATIONS

Yu, Z. et al; "Utilizing Dynamic Light Scattering as a Process Analytical Technology for Protein Folding and Aggregation Monitoring in Vaccine Manufacturing"; Journal of Pharmaceutical Sciences, vol. 102, No. 12, Dec. 2013, pp. 4284-4290 (8 pages).
Zhang, K.; "Gctf: Real-time CTF determination and correction"; Journal of Structural Biology, vol. 193, No. 1, Jan. 2016, pp. 1-2 (12 pages).
Zhang, Y. et al; "Proximity does not contribute to activity enhancement in the glucose oxidase-horseradish peroxidase cascade"; Nature Communication, vol. 7, No. 13982, Dec. 22, 2016 (9 pages).
Liu Y. et al; "Deciphering molecular details in the assembly of alpha-type carboxysome"; Scientific Report, vol. 8, No. 15062, Oct. 10, 2018 (10 pages).
Kinney J. N.. et al; "Elucidating Essential Role of Conserved Carboxysomal Protein CcmN Reveals Common Feature of Bacterial Microcompartment Assembly"; The Journal of Biological Chemistry, vol. 287, No. 21, May 18, 2012, pp. 17729-17736 (8 pages).
Extended European Search Report issued in counterpart European Patent Application No. 21883435.6, mailed on May 2, 2025 (14 pages).
International Preliminary Report on Patentability issued in Application No. PCT/SG2021/050639, mailed on Apr. 13, 2023 (10 pages).
Adams, Paul D. et al.; "PHENIX: a comprehensive Python-based system for macromolecular structure solution"; Acta Crystallographica Section D Biological Crystallography, research papers, Dec. 2009, pp. 213-221 (9 pages).
(Continued)

*Primary Examiner* — Bao Q Li
(74) *Attorney, Agent, or Firm* — Osha Bergman Watanabe & Burton LLP

(57) ABSTRACT

The present invention relates to a method for producing a bacterial microcompartment virus-like particle (VLP) carrying a cargo molecule, the method comprising introducing and expressing in a host cell or organism one or more polynucleotides comprising (a) a first sequence encoding bacterial microcompartment shell protomers and a second sequence encoding a cargo molecule fused to an encapsulation peptide comprising the sequence SKITGSSGNDTQGSLITYSGGARG, and forming a microcompartment that encapsulates the cargo molecule, or (b) a first sequence encoding bacterial microcompartment shell protomers and a second sequence encoding at least one of said protomers fused with a cargo molecule or a biochemical tag, and forming a microcompartment that expresses the cargo molecule or biochemical tag on an exterior surface. In one embodiment, the bacterial microcompartment protomers are CsoS1A and CsoS4A from *Halothiobacillus neapolitanus*, or HO-H, HO-P and HO-T1 from *Haliangium ochraceum*.

17 Claims, 19 Drawing Sheets

Specification includes a Sequence Listing.

(56) References Cited

OTHER PUBLICATIONS

Anderson, J. Christopher; "Registry of Standard Biological Parts"; Catalog Collections (2 pages).

Baneyx, F.; "Recombinant protein expression in *Escherichia coli*"; Expression vectors and delivery systems, pp. 411-421 (2 pages).

Bonacci, W. et al.; "Modularity of a carbon-fixing protein organelle"; PNAS, vol. 109, No. 2, Jan. 10, 2012, pp. 478-483 (6 pages).

Cai, F. et al.; "Production and Characterization of Synthetic Carboxysome Shells with Incorporated Luminal Proteins"; Plant Physiology, vol. 170, Mar. 2016, pp. 1868-1877 (10 pages).

Cai, F. et al.; "Advances in Understanding Carboxysome Assembly in Prochlorococcus and Synechococcus Implicate CsoS2 as a Critical Component"; Life, vol. 5, 2015, pp. 1141-1171 (31 pages).

Das, S. et al.; "Enzyme Stabilization by Virus-Like Particles"; Biochemistry, vol. 59, 2020, pp. 2870-2881 (12 pages).

Demchuk, A. M. et al.; "The biomedical and bioengineering potential of protein nanocompartments"; Biotechnology Advances, vol. 41, Apr. 12, 2020 (21 pages).

Dunn, K. W. et al.; "A practical guide to evaluating colocalization in biological microscopy"; Am J Physiol Cell Physiol, vol. 300, Jan. 5, 2011, pp. C723-C742 (20 pages).

Emsley, P. et al.; "Coot: model-building tools for molecular graphics"; Acta Crystallographica Section D Biological Crystallography, Aug. 4, 2004, pp. 2126-2132 (7 pages).

Fletcher, J. M. et al.; "Self-Assembling Cages from Coiled-Coil Peptide Modules"; Science, vol. 340, May 3, 2013, pp. 595-599 (5 pages).

Gietz, R. D. et al.; "High-efficiency yeast transformation using the LiAc/SS carrier DNA/PEG methos"; Nature Protocols, vol. 2, No. 1, Jan. 31, 2007, pp. 31-34 (6 pages).

Golan, R. et al.; "Inhibition of *Escherichia coli* b-galactosidase by 2-nitro-1-(4,5-dimethoxy-2-nitrophenyl) ethyl, a photoreversible thiol label"; Biochimica et Biophysica Acta, vol. 1293, 1996, pp. 238-242 (5 pages).

Goldstein, L.; "Microenvironmental Effects on Enzyme Catalysis. A Kinetic Study of Polyanionic and Polycationic Derivative of Chymotrypsin"; Biochemistry, vol. 11, No. 22, 1972, pp. 4072-4084 (5 pages).

Goldstein, L. et al; "A Water-insoluble Polyanionic Derivative of Trypsin. II. Effect of the Polyelectrolyte Carrier on the Kinetic Behavior of the Bound Trypsin"; Biochemistry, vol. 3, No. 12, Dec. 1964, pp. 1913-1919 (7 pages).

Guo, Y.et al; "YeastFab: the design and construction of standard biological parts for metabolic engineering in *Saccharomyces cerevisiae*"; Nucleic Acids Research, vol. 43, No. 13, May 8, 2015 (14 pages).

Hagen, A.et al; "Programmed loading and rapid purification of engineered bacterial microcompartment shells"; Nature Communications, vol. 9, No. 2881, 2018 (10 pages).

Juers, D. H. et al; "Structural Basis for the Altered Activity of Gly794 Variants of *Escherichia coli* b-Galactosidase"; Biochemistry, vol. 42, No. 46, Aug. 21, 2003, pp. 13505-13511(10 pages).

Kalnins, G. et al; "Encapsulation mechanisms and structural studies of GRM2 bacterial microcompartment particles"; Nature Communications, vol. 11, No. 388, Jan. 20, 2020 (13 pages).

Keeble, A. H. et al; "Insider information on successful covalent protein coupling with help from SpyBank"; ScienceDirect, vol. 617, Jan. 25, 2019 (18 pages).

Klein, M. G. et al; "Identification and Structural Analysis of a Novel Carboxysome Shell Protein with Implications for Metabolite Transport"; Journal of Molecular Biology, vol. 392, No. 2, Sep. 2009, pp. 319-333 (50 pages).

Kuchler, A. et al.; "Enzymatic Reactions in Confined Environments"; Nature Nanotechnology, vol. 11, May 2016, pp. 490-420 (42 pages).

Lam, S. S. et al; "Directed evolution of APEX2 for electron microscopy and proximity labeling"; Nature Methods, vol. 12, No. 1, Jan. 2015, pp. 51-54 (10 pages).

Lassila, J. K. et al; "Assembly of Robust Bacterial Microcompartment Shells Using Building Blocks from an Organelle of Unknown Function"; J. Mol. Biol., vol. 426, No. 11, May 29, 2014, pp. 2217-2228 (12 pages).

Kerfeld, C. A. et al; "Bacterial microcompartments"; Nature Reviews, Microbiology, vol. 16, May 2018, pp. 277-290 (14 pages).

Lawrence, A. D. et al; "Solution Structure of a Bacterial Microcompartment Targeting Peptide and Its Application in the Construction of an Ethanol Bioreactor"; ACS Synthetic Biology, vol. 3, No. 7, Jan. 30, 2014, pp. 454-465 (12 pages).

Liebschner, D. et al; "Macromolecular structure determination using X-rays, neutrons and electrons: recent developments in Phenix"; Acta Cryst., vol. 75, No. 10, Oct. 2019, pp. 861-877 (17 pages).

Neher, S. B. et al.; "Distinct peptide signals in the UmuD and UmuD subunits of UmuD/D Mediate tethering and substrate processing by the ClpXP protease"; PNAS, vol. 100, No. 23, Nov. 11, 2003, pp. 13219-13224 (6 pages).

Pettersen, E. F. et al; "UCSF Chimera-A Visualization System for Exploratory Research and Analysis"; Journal of Computational Chemistry, vol. 25, No. 13, Jul. 1, 2004, pp. 1605-1612 (8 pages).

Nichols, T. M. et al; "Cargo encapsulation in bacterial microcompartments: Methods and analysis"; Methods in Enzymology, vol. 617, 2019, pp. 155-186 (32 pages).

Winn, M. D. et al; "Overview of the CCP4 suite and current developments"; Acta Crystallographica Section D Biological Crystallography, vol. 67, Nov. 7, 2010, pp. 235-242 (8 pages).

Patterson, D. et al; "Nanoreactors by Programmed Enzyme Encapsulation Inside the Capsid of the Bacteriophage P22"; ACS NANO, vol. 6, No. 6, May 24, 2012, pp. 5000-5009 (10 pages).

Patterson, D. P. et al; "Virus-like particle nanoreactors: Programmed encapsulation of the thermostable CelB glycosidase inside the P22 capsid"; The Royal Society of Chemistry, Soft Matter, vol. 8, 2012, pp. 10158-10166 (10 pages).

Sanchez-Sanchez, L. et al; "Design of a VLP-nanovehicle for CYP450 enzymatic activity delivery"; Journal of Nanobiotechnology, vol. 13, No. 66, Oct. 9, 2015 (10 pages).

Schwarz, B. et al; "Biomedical and Catalytic Opportunities of Virus-Like Particles in Nanotechnology"; Advances in Virus Research, vol. 97, 2017 (60 pages).

Sewalt, V. et al; "The Generally Recognized as Safe (GRAS) Process for Industrial Microbial Enzymes"; Industrial Biotechnology, vol. 12, No. 5, Oct. 2016, pp. 295-302 (8 pages).

Shifrin, S. et al; "Effect of Alcohols on the Enzymatic Activity and Subunit Association of -bGalactosidase"; Archives of Biochemistry and Biophysics, vol. 130, 1969, pp. 530-535 (6 pages).

Sievers, F. et al; "Clustal Omega, Accurate Alignment of Very Large Numbers of Sequences"; Methods Mol Biol., vol. 1079, 2014, pp. 102-116 (12 pages).

Silva, C. et al; "Practical insights on enzyme stabilization"; Critical Reviews in Biotechnology, vol. 38, No. 3, 2018, pp. 335-350 (17 pages).

Sudbery, P. E. et al; "The expression of recombinant proteins in yeasts"; Current Opinion in Biotechnology, vol. 7, No. 5, Oct. 1996, pp. 517-524 (8 pages).

Sutter, M. et al; "Assembly principles and structure of a 6.5-MDa bacterial microcompartment shell"; Science, vol. 356, No. 6344, Jun. 23, 2017, pp. 1293-1297 (5 pages).

Sutter, M. et al; "Structure of a Synthetic beta-Carboxysome Shell"; Plant Physiology, vol. 181, No. 3, Nov. 2019, pp. 1050-1058 (9 pages).

Tan, Y. Q. et al; "Structure of a Minimal a-Carboxysome-Derived Shell and Its Utility in Enzyme Stabilization"; Biomacromolecules, vol. 22, No. 10, Aug. 12, 2021, pp. 4095-4109 (15 pages).

Tan, Y. Q. et al; "Genetically Encodable Scaffolds for Optimizing Enzyme Function"; Molecules, vol. 26, No. 5, 1389, Mar. 4, 2021 (33 pages).

Tanaka, S. et al; "Atomic-Level Models of the Bacterial Carboxysome Shell"; Science, vol. 319, No. 5866, Feb. 22, 2008, pp. 1083-1086 (4 pages).

Thomas, F. et al; "A Set of de Novo Designed Parallel Heterodimeric Coiled Coils with Quantified Dissociation Constants in the Micromolar to Sub-nanomolar Regime"; JACS, vol. 135, No. 13, Mar. 11, 2013, pp. 5161-5166 (6 pages).

(56) References Cited

OTHER PUBLICATIONS

Tsai, Y. et al; "Structural Analysis of CsoS1A and the Protein Shell of the Halothiobacillus neapolitanus Carboxysome"; PloS Biology, vol. 5, No. 6, e144, Jun. 2007, pp. 1345-1354 (10 pages).

Turmo, A. et al; "Carboxysomes: metabolic modules for CO2 fixation"; FEMS Microbiology Letters, vol. 364, No. 18, Sep. 2017, fnx176, (7 pages).

Waterhouse, A. M. et al; "Jalview Version 2-a multiple sequence alignment editor and analysis workbench"; Bioinformatics, vol. 25, No. 9, May 2009, pp. 1189-1191(3 pages).

Zivanov, J. et al; "New tools for automated high-resolution cryo-EM structure determination in RELION-3"; eLIFE, vol. 7, e42166, Nov. 9, 2018 (22 pages).

Oltrogge L.M. et al., "Multivalent interactions between CsoS2 and Rubisco mediate a-carboxysome formation" Nat Struct Mo/ Biol, Mar. 2, 2020, vol. 27, No. 3, pp. 281-287 (35 pages).

Aussignargues C. et al., "Bacterial microcompartment assembly: The key role of encapsulation peptides" Communicative & Integrative Biology, May 1, 2015, vol. 8, No. 3, pp. e1039755: 1-10 (10 pages).

Tan Y.Q. et al., Structure of a Minimal a-Carboxysome-Derived Shell and Its Utility in Enzyme Stabilization. Biomacromolecules, Aug. 12, 2021, vol. 22, No. 10, pp. 4095-4109 (15 pages).

International Search Report issued in International application No. PCT/SG2021/050639 dated Jan. 10, 2022 (8 pages).

Written Opinion issued in International application No. PCT/SG2021/050639 dated Jan. 10, 2022 (8 pages).

* cited by examiner

Figure 1

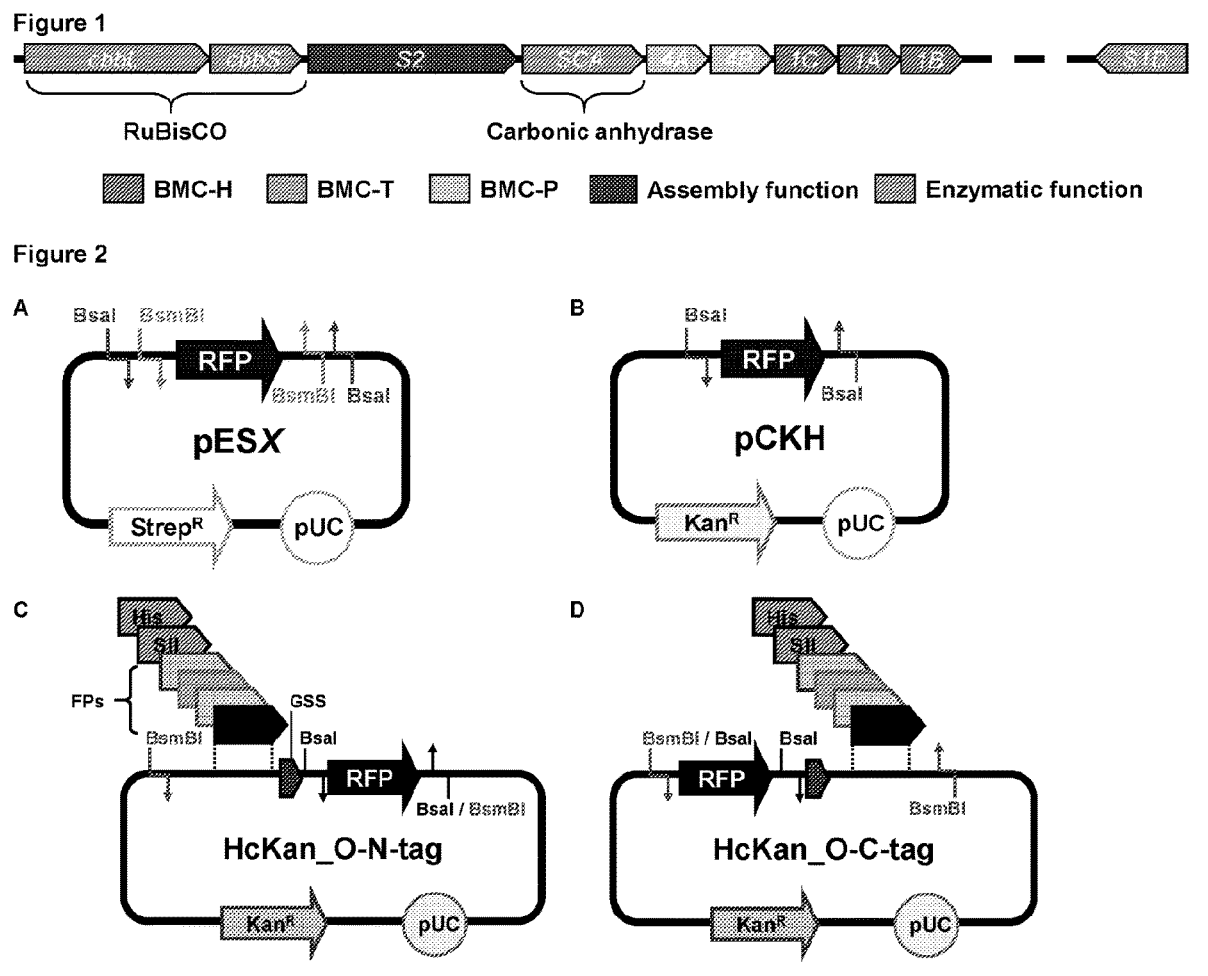

RuBisCO    Carbonic anhydrase

BMC-H    BMC-T    BMC-P    Assembly function    Enzymatic function

Bsal    BsmBl
RFP
BsmBl    Bsal pESX

StrepR    pUC

B

Bsal
RFP
Bsal pCKH

KanR    pUC

C

His
Sll
FPs
GSS
BsmBl    Bsal
RFP
Bsal / BsmBl

HcKan_O-N-tag

KanR    pUC

D

His
Sll
BsmBl / Bsal    Bsal
RFP
BsmBl

HcKan_O-C-tag

KanR    pUC

Construct   Schematic representation

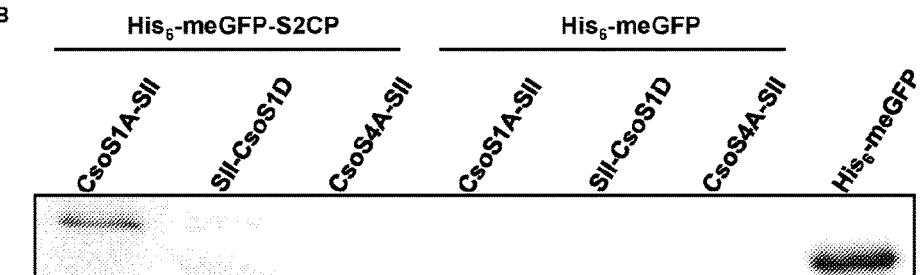

```
                                        1210        1220        1230
H. neapolitanus               KP E KP - GS  I TGSSGNDTQGSL I TYSGGA G    SEQ ID NO: 94
Acidithiobacillus ferrivorans RP E LP - I S  VTGSSGNDARGSF I TYSGGA G    SEQ ID NO: 95
Burkholderiales bacterium     RP E VR - PS  VTGSSGNTERGATVTLSGGA G       SEQ ID NO: 96
Gallionellaceae bacterium     RP E LP - VS  VTGSSGNDAKGSA I TYSGGA G     SEQ ID NO: 97
Hydrogenophilales bacterium   HP AL A - PG  VTGSSGNS TAGS AVTLSGGA G     SEQ ID NO: 98
Thiobacillus thioparus        AP AP T - AS  I TGSSGNS S AGAA I TVSGGA G  SEQ ID NO: 99
Comamonadaceae bacterium      RAE VP - PS P VTGSSGNTGRGAMVT I SGGA G     SEQ ID NO: 100
Acidithiobacillus ferridurans RP AL P - TS  VTGSSGNDAKGSP I TYSGGA G     SEQ ID NO: 101
Betaproteobacteria bacterium  HP AL A - PG  VTGSSGNS TAGS AVTLSGGA G     SEQ ID NO: 102
Ferrovum sp. Z-31             HLQVP - PS  VTGSSGNAATGST I TYSGGA G       SEQ ID NO: 103
```

Figure 5:
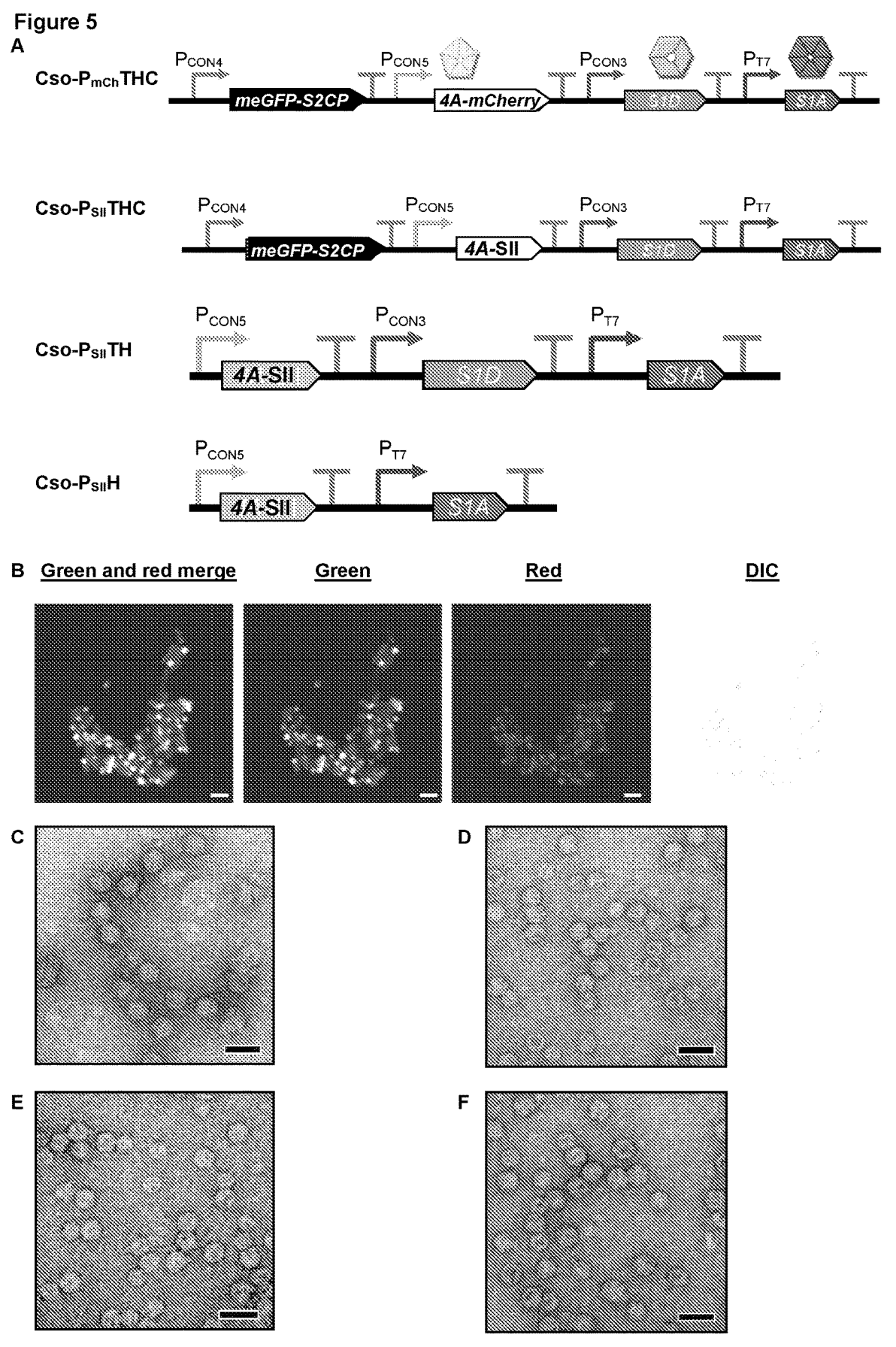

Cso-P_{mCh}THC

P_{CON4}    P_{CON5}    P_{CON3}    P_{T7} meGFP-S2CP    4A-mCherry    S1B    S1A

Cso-P_{SII}THC

P_{CON4}    P_{CON5}    P_{CON3}    P_{T7} meGFP-S2CP    4A-SII    S1B    S1A

Cso-P_{SII}TH

P_{CON5}    P_{CON3}    P_{T7}

4A-SII    S1B    S1A

Cso-P_{SII}H

P_{CON5}    P_{T7}

4A-SII    S1A

B    Green and red merge    Green    Red    DIC

Fluorescence                          DIC

Figure 10
A
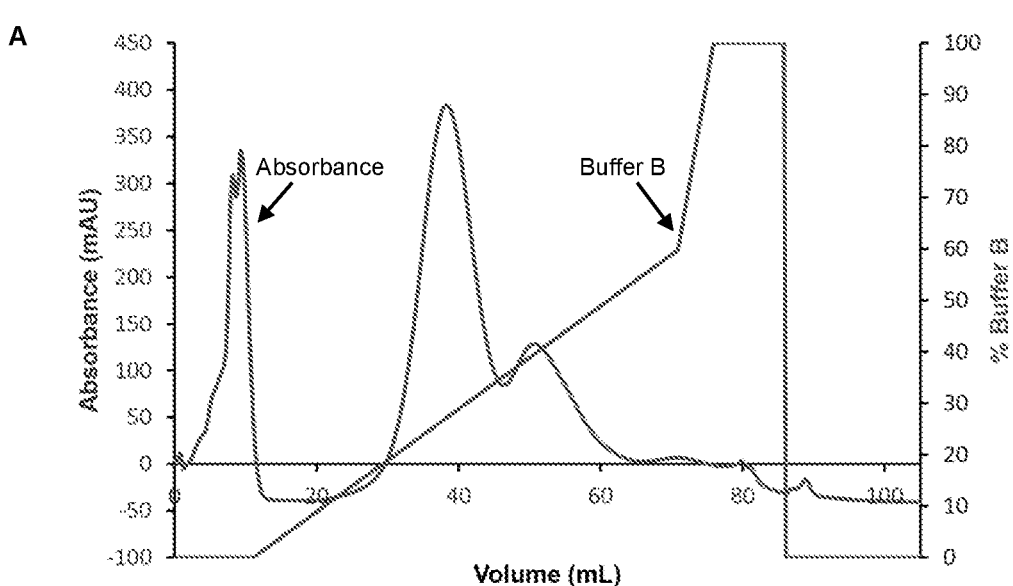
B
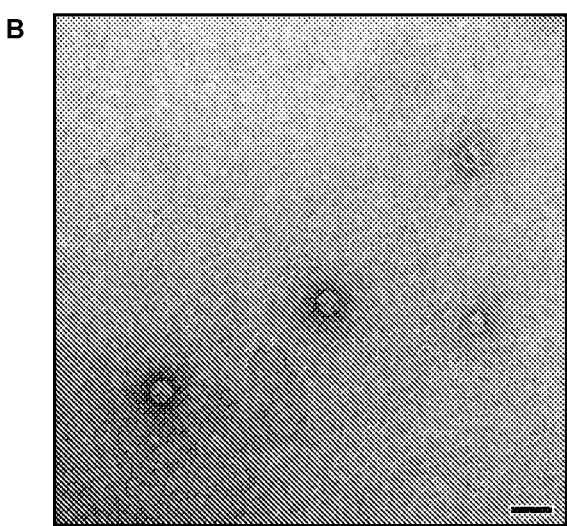

Figure 11
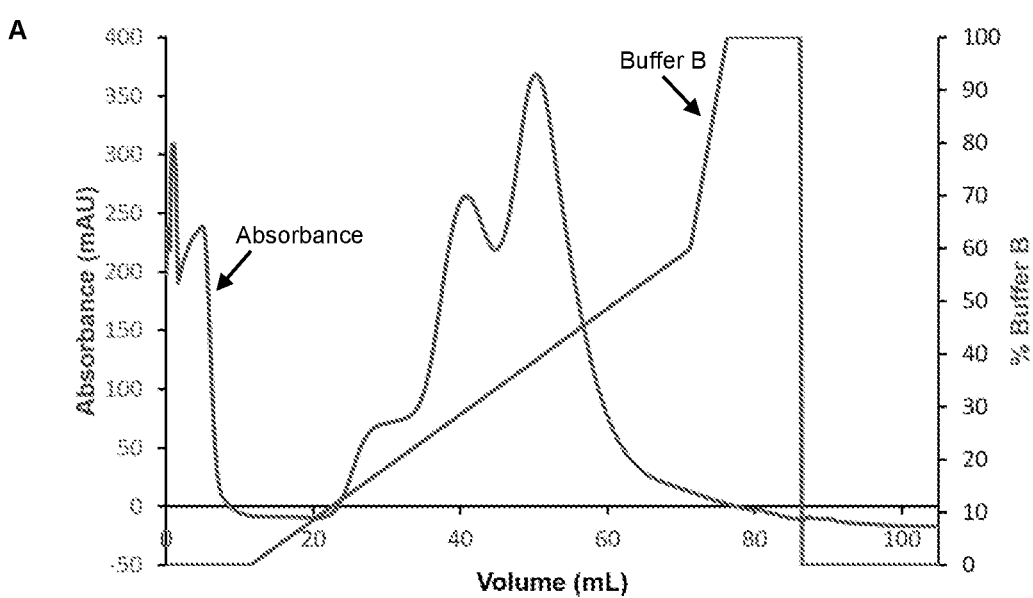
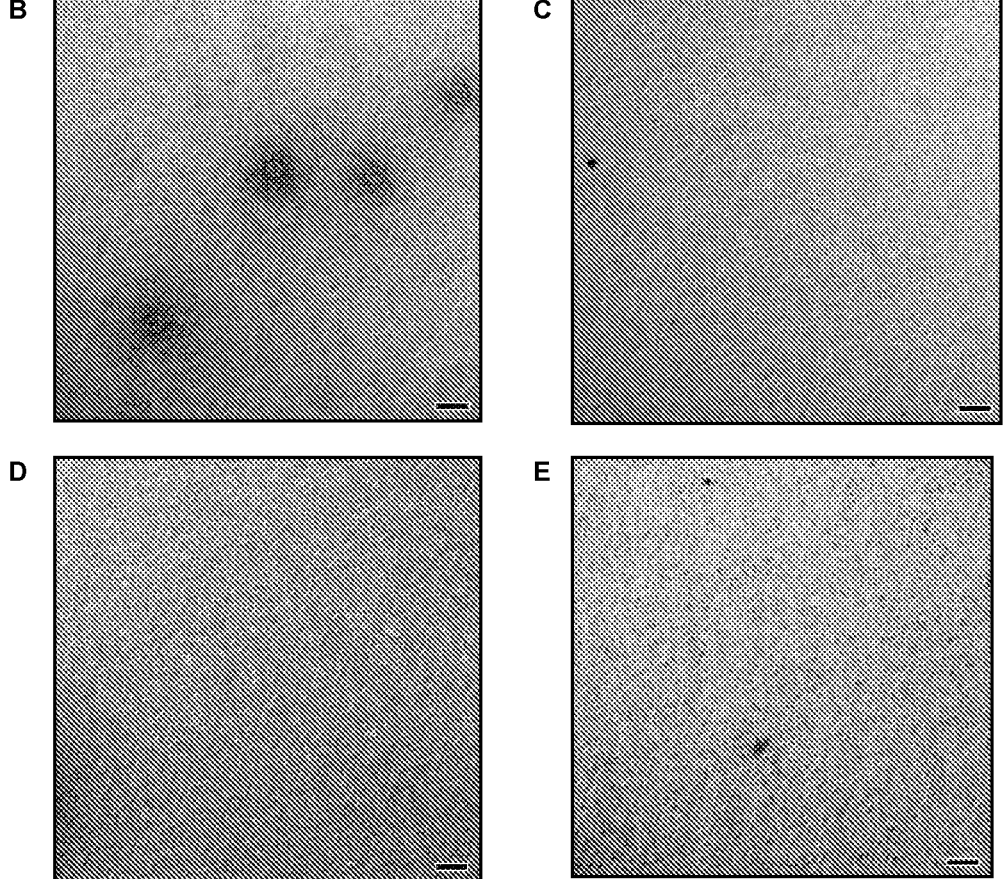

Figure 12
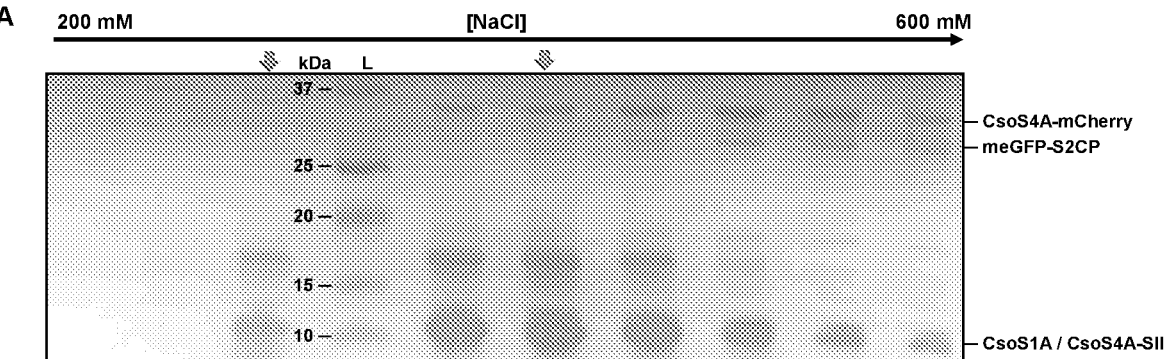
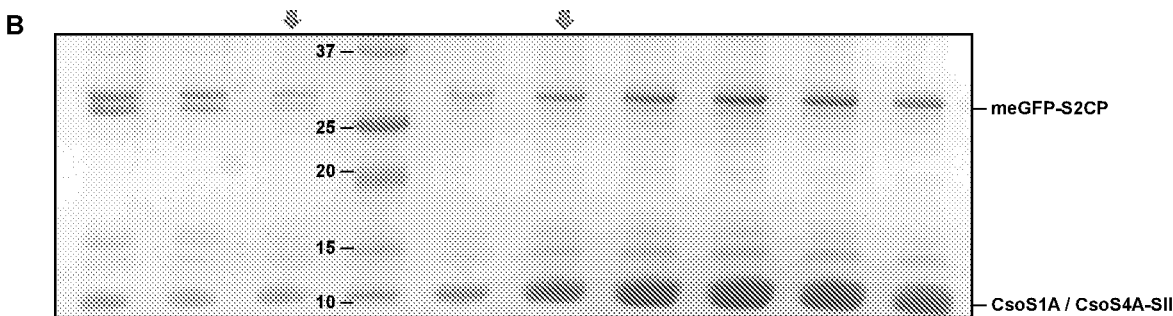
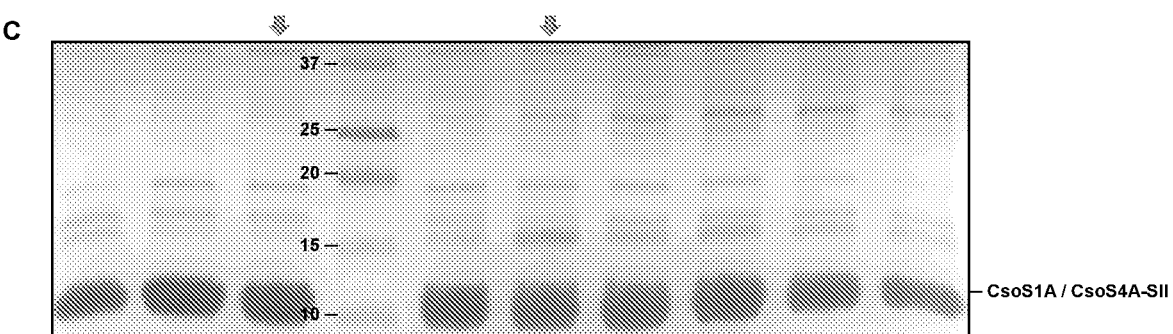
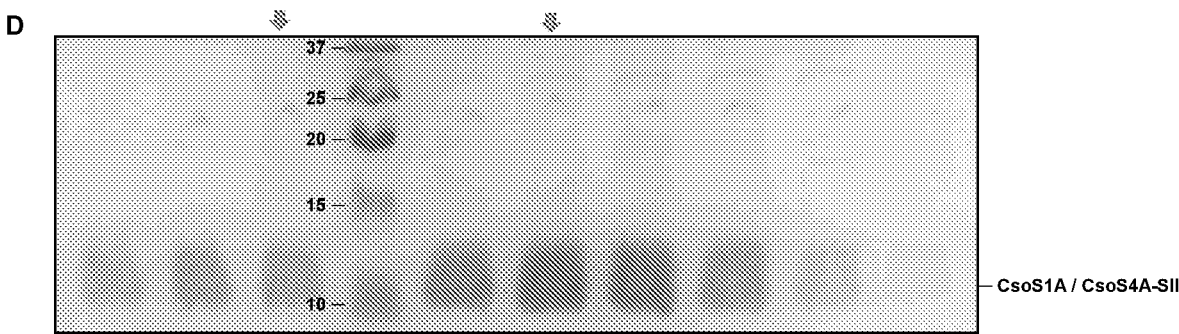

Figure 13
A
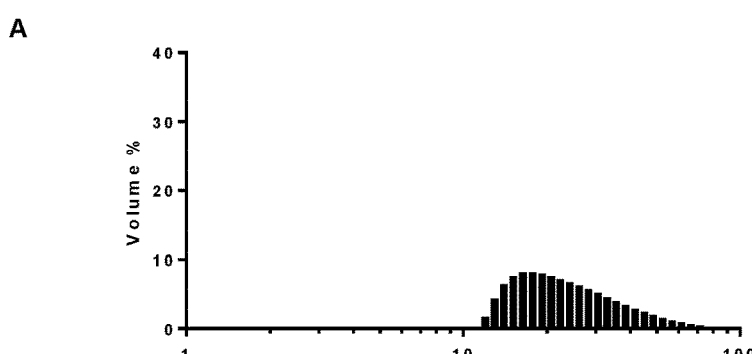
B
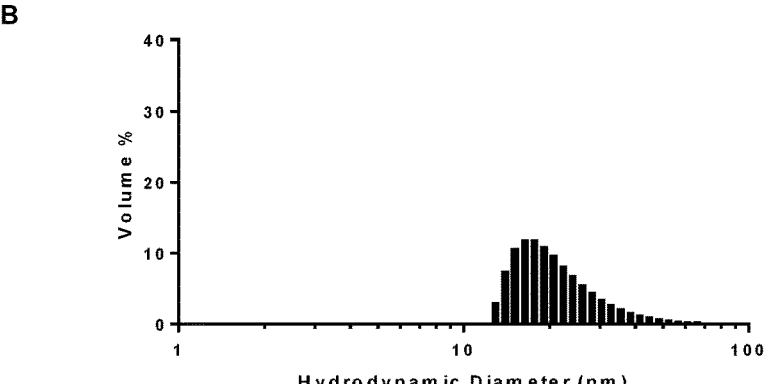
C
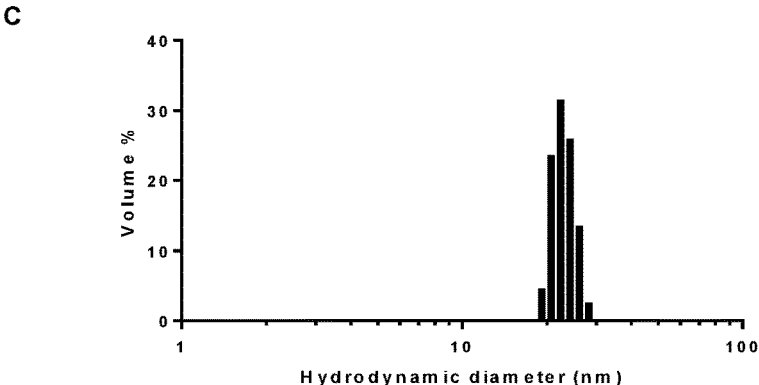
D
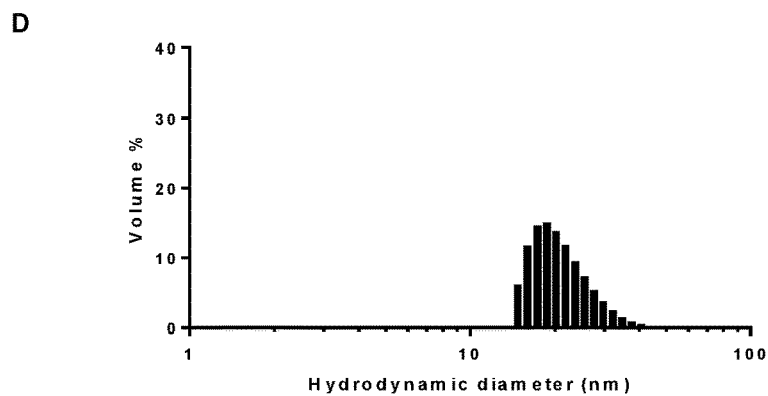

Figure 14

| VLP type: | Cso-BMC | HO-BMC |
|---|---|---|
| Surface representations of atomic-scale structures<br><br>Protomer color:<br>Hexamer, dark grey<br>Pentamer, white<br>Trimer (only HO-BMC), grey | | |
| TEM micrograph<br><br>Scale bar (bottom right) represents 50 nm | | |
| Structure obtained: | Our group, unpublished data | Kerfeld and co-workers |
| Diameter: | 220 Å | 380 Å |
| Estimated molecular mass: | 1.7 MDa | 6.5 MDa |
| Expression system: | *Escherichia coli* | *Saccharomyces cerevisiae* |
| Proteins expressed / GenBank accession number: | CsoS1A / WP_012823794.1<br>CsoS4A / WP_012823797.1 | HO-BMC-H / WP_012830883.1<br>HO-BMC-P / WP_012830882.1<br>HO-BMC-T1 / WP_012830880.1 |
| Protein composition: | CsoS1A – 120 copies<br>CsoS4A – 60 copies | HO-BMC-H – 360 copies<br>HO-BMC-P – 60 copies<br>HO-BMC-T1 – 60 copies |
| SDS-PAGE analysis | | |
| Titer (per gram wet cell pellet): | 2.0 mg | 0.1 mg |
| Typical absolute yield per run: | 20.0 mg | 1.0 mg |
| Polydispersity percentage: | 24.7 % | 22.3 % |
| $T_{agg, 266 nm}$ | 78 °C | 47 °C |

| Lane | Cso-P$_{SII}$H + UmuD$^{1-}$ $^{40}$-GFP-S2CP variant | GFP-S2CP variant band peak area | Shell protein (CsoS1A / CsoS4A-SII) band peak area |
|---|---|---|---|
| 1 | S2CP(30) | 14655700 | 88304035 |
| 2 | S2CP | 4088330 | 88535150 |

Figure 19
A
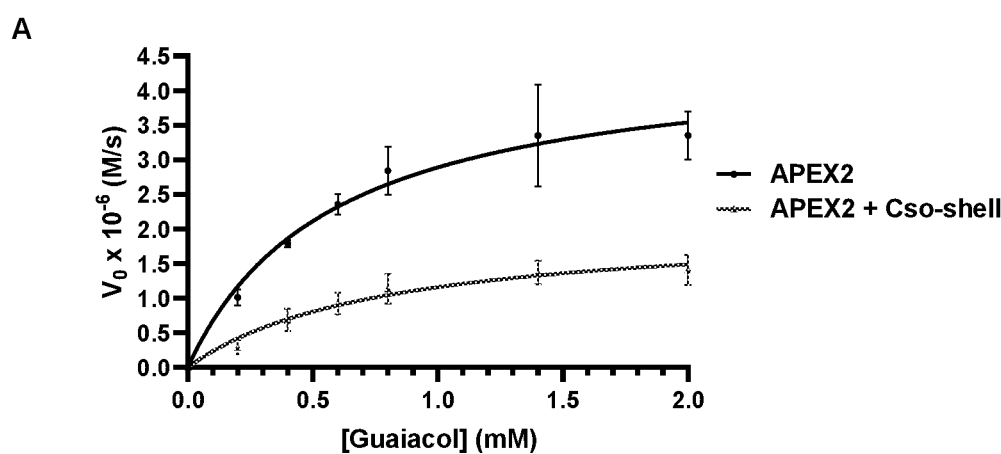
B
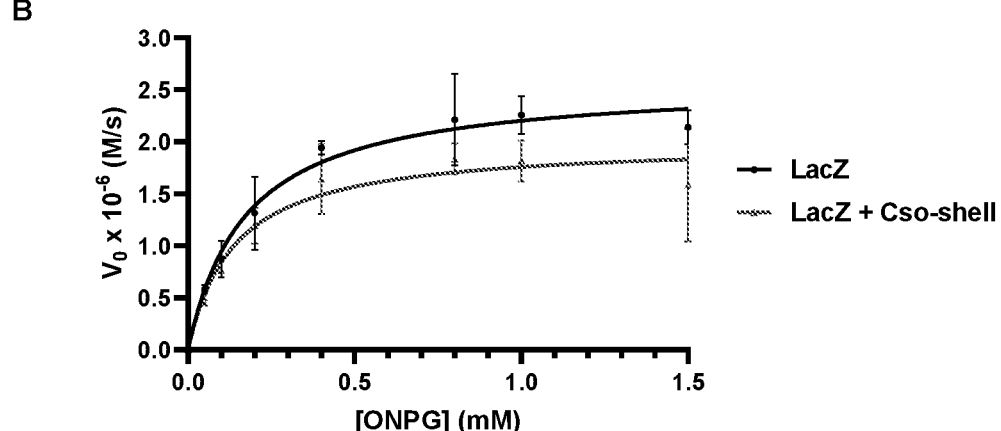

Figure 20
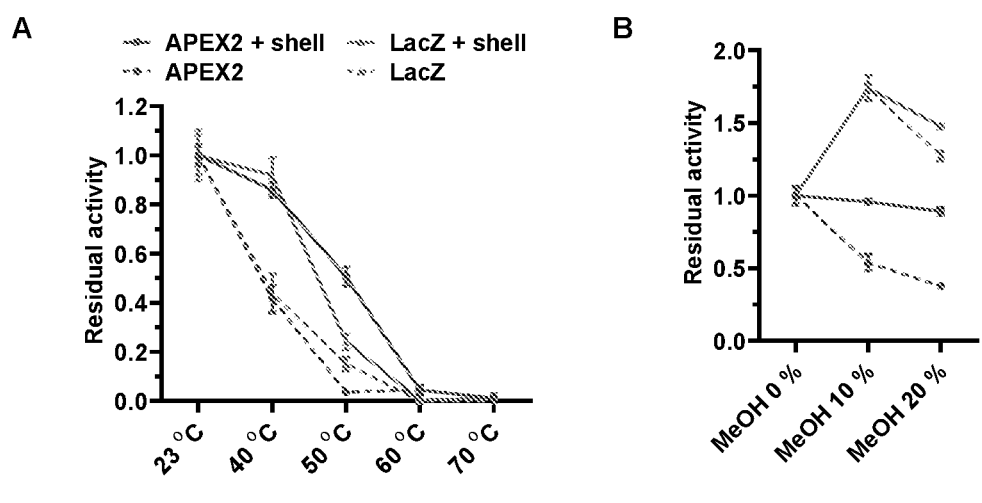
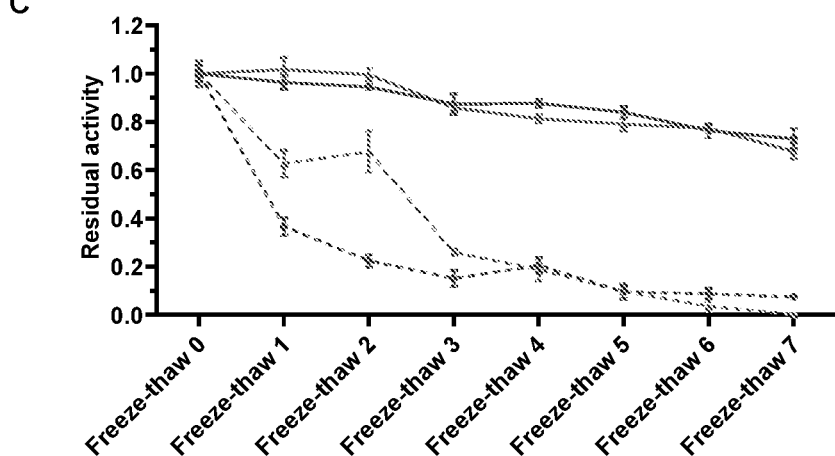
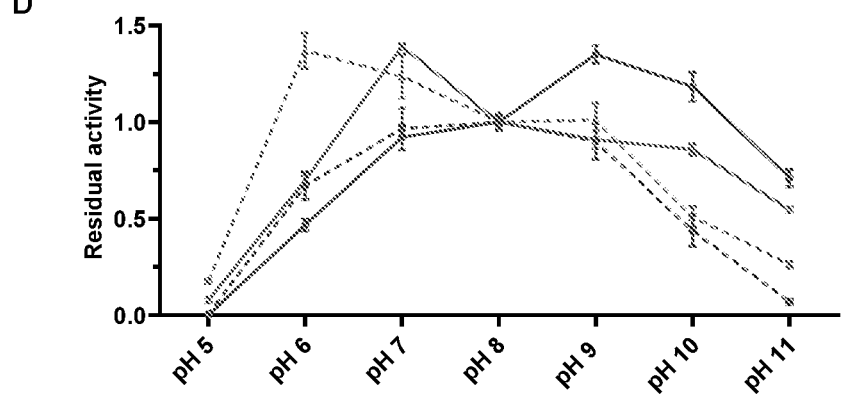

Figure 21
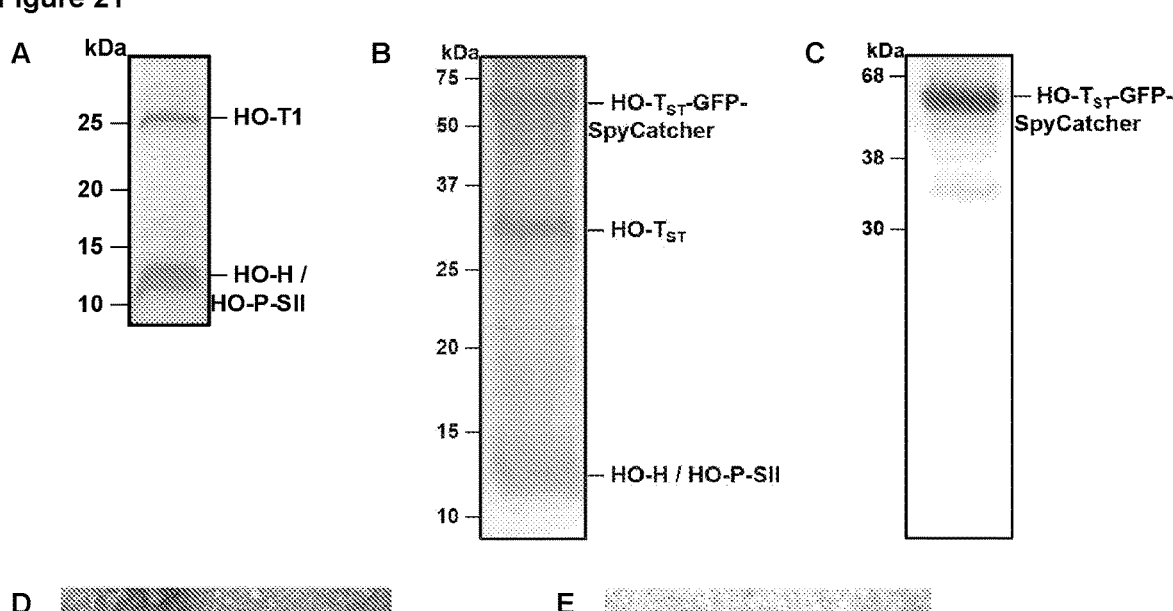
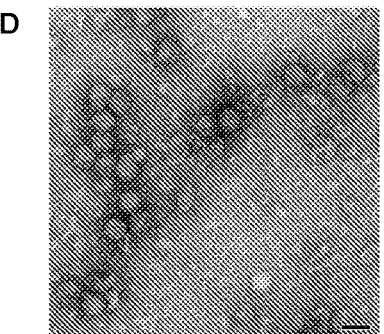
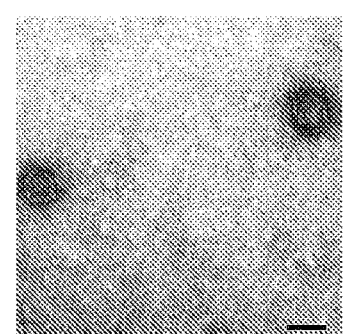

SEQUENCE LISTING

```
<160> NUMBER OF SEQ ID NOS: 121

<210> SEQ ID NO 1
<211> LENGTH: 24
<212> TYPE: PRT
<213> ORGANISM: Artificial Sequence
<220> FEATURE:
<223> OTHER INFORMATION: S2CP amino acid sequence

<400> SEQUENCE: 1

Ser Lys Ile Thr Gly Ser Ser Gly Asn Asp Thr Gln Gly Ser Leu Ile
1               5                   10                  15

Thr Tyr Ser Gly Gly Ala Arg Gly
            20

<210> SEQ ID NO 2
<211> LENGTH: 98
<212> TYPE: PRT
<213> ORGANISM: Artificial Sequence
<220> FEATURE:
<223> OTHER INFORMATION: CsoS1A amino acid sequence

<400> SEQUENCE: 2

Met Ala Asp Val Thr Gly Ile Ala Leu Gly Met Ile Glu Thr Arg Gly
1               5                   10                  15

Leu Val Pro Ala Ile Glu Ala Ala Asp Ala Met Thr Lys Ala Ala Glu
            20                  25                  30

Val Arg Leu Val Gly Arg Gln Phe Val Gly Gly Gly Tyr Val Thr Val
        35                  40                  45

Leu Val Arg Gly Glu Thr Gly Ala Val Asn Ala Ala Val Arg Ala Gly
    50                  55                  60

Ala Asp Ala Cys Glu Arg Val Gly Asp Gly Leu Val Ala Ala His Ile
65                  70                  75                  80

Ile Ala Arg Val His Ser Glu Val Glu Asn Ile Leu Pro Lys Ala Pro
                85                  90                  95

Gln Ala

<210> SEQ ID NO 3
<211> LENGTH: 83
<212> TYPE: PRT
<213> ORGANISM: Artificial Sequence
<220> FEATURE:
<223> OTHER INFORMATION: CsoS4A amino acid sequence

<400> SEQUENCE: 3

Met Lys Ile Met Gln Val Glu Lys Thr Leu Val Ser Thr Asn Arg Ile
1               5                   10                  15

Ala Asp Met Gly His Lys Pro Leu Leu Val Val Trp Glu Lys Pro Gly
            20                  25                  30

Ala Pro Arg Gln Val Ala Val Asp Ala Ile Gly Cys Ile Pro Gly Asp
```

-continued

```
            35                  40                  45

Trp Val Leu Cys Val Gly Ser Ser Ala Ala Arg Glu Ala Ala Gly Ser
    50                  55                  60

Lys Ser Tyr Pro Ser Asp Leu Thr Ile Ile Gly Ile Ile Asp Gln Trp
65                  70                  75                  80

Asn Gly Glu

<210> SEQ ID NO 4
<211> LENGTH: 99
<212> TYPE: PRT
<213> ORGANISM: Artificial Sequence
<220> FEATURE:
<223> OTHER INFORMATION: HO-H amino acid sequence

<400> SEQUENCE: 4

Met Ala Asp Ala Leu Gly Met Ile Glu Val Arg Gly Phe Val Gly Met
1               5                   10                  15

Val Glu Ala Ala Asp Ala Met Val Lys Ala Ala Lys Val Glu Leu Ile
            20                  25                  30

Gly Tyr Glu Lys Thr Gly Gly Gly Tyr Val Thr Ala Val Val Arg Gly
        35                  40                  45

Asp Val Ala Ala Val Lys Ala Ala Thr Glu Ala Gly Gln Arg Ala Ala
    50                  55                  60

Glu Arg Val Gly Glu Val Val Ala Val His Val Ile Pro Arg Pro His
65                  70                  75                  80

Val Asn Val Asp Ala Ala Leu Pro Leu Gly Arg Thr Pro Gly Met Asp
                85                  90                  95

Lys Ser Ala

<210> SEQ ID NO 5
<211> LENGTH: 96
<212> TYPE: PRT
<213> ORGANISM: Artificial Sequence
<220> FEATURE:
<223> OTHER INFORMATION: HO-P amino acid sequence

<400> SEQUENCE: 5

Met Val Leu Gly Lys Val Val Gly Thr Val Val Ala Ser Arg Lys Glu
1               5                   10                  15

Pro Arg Ile Glu Gly Leu Ser Leu Leu Leu Val Arg Ala Cys Asp Pro
            20                  25                  30

Asp Gly Thr Pro Thr Gly Gly Ala Val Val Cys Ala Asp Ala Val Gly
        35                  40                  45

Ala Gly Val Gly Glu Val Val Leu Tyr Ala Ser Gly Ser Ser Ala Arg
    50                  55                  60

Gln Thr Glu Val Thr Asn Asn Arg Pro Val Asp Ala Thr Ile Met Ala
65                  70                  75                  80

Ile Val Asp Leu Val Glu Met Gly Gly Asp Val Arg Phe Arg Lys Asp
                85                  90                  95

<210> SEQ ID NO 6
<211> LENGTH: 205
<212> TYPE: PRT
<213> ORGANISM: Artificial Sequence
<220> FEATURE:
<223> OTHER INFORMATION: HO-T1 amino acid sequence

<400> SEQUENCE: 6

Met Asp His Ala Pro Glu Arg Phe Asp Ala Thr Pro Pro Ala Gly Glu
```

```
1                5                   10                  15

Pro Asp Arg Pro Ala Leu Gly Val Leu Glu Leu Thr Ser Ile Ala Arg
            20              25              30

Gly Ile Thr Val Ala Asp Ala Ala Leu Lys Arg Ala Pro Ser Leu Leu
            35              40              45

Leu Met Ser Arg Pro Val Ser Ser Gly Lys His Leu Leu Met Met Arg
        50              55              60

Gly Gln Val Ala Glu Val Glu Glu Ser Met Ile Ala Ala Arg Glu Ile
65              70              75              80

Ala Gly Ala Gly Ser Gly Ala Leu Leu Asp Glu Leu Glu Leu Pro Tyr
                85              90              95

Ala His Glu Gln Leu Trp Arg Phe Leu Asp Ala Pro Val Val Ala Asp
            100             105             110

Ala Trp Glu Glu Asp Thr Glu Ser Val Ile Ile Val Glu Thr Ala Thr
            115             120             125

Val Cys Ala Ala Ile Asp Ser Ala Asp Ala Ala Leu Lys Thr Ala Pro
        130             135             140

Val Val Leu Arg Asp Met Arg Leu Ala Ile Gly Ile Ala Gly Lys Ala
145             150             155             160

Phe Phe Thr Leu Thr Gly Glu Leu Ala Asp Val Glu Ala Ala Ala Glu
                165             170             175

Val Val Arg Glu Arg Cys Gly Ala Arg Leu Leu Glu Leu Ala Cys Ile
            180             185             190

Ala Arg Pro Val Asp Glu Leu Arg Gly Arg Leu Phe Phe
        195             200             205

<210> SEQ ID NO 7
<211> LENGTH: 72
<212> TYPE: DNA
<213> ORGANISM: Artificial Sequence
<220> FEATURE:
<223> OTHER INFORMATION: S2CP nucleotide sequence

<400> SEQUENCE: 7
tctaagatta ctggttcttc tggtaacgat acccaaggtt ctttgattac ttactctggt        60
ggtgctagag gt                                                             72

<210> SEQ ID NO 8
<211> LENGTH: 294
<212> TYPE: DNA
<213> ORGANISM: Artificial Sequence
<220> FEATURE:
<223> OTHER INFORMATION: CsoS1A nucleotide sequence

<400> SEQUENCE: 8
atggctgatg ttactggtat tgctttgggt atgattgaaa ctagaggttt ggttccagct        60
atcgaagctg ctgacgctat gaccaaggcc gctgaagtca gattggtcgg tagacaattt       120
gttggaggtg gttacgtcac tgttttggtt cgtggtgaaa ccggtgccgt taacgctgct       180
gttagagctg gtgctgatgc ttgtgaaaga gttggtgacg gtttagttgc tgcccacatt       240
attgccagag tccactctga agttgaaaac attttgccaa aggctccaca ggct             294

<210> SEQ ID NO 9
<211> LENGTH: 249
<212> TYPE: DNA
<213> ORGANISM: Artificial Sequence
<220> FEATURE:
<223> OTHER INFORMATION: CsoS4A nucleotide sequence
```

<400> SEQUENCE: 9
atgaagatca tgcaagttga aaagactttg gtttctacca acagaattgc tgatatgggt      60
cacaagccat tgttggttgt ttgggaaaaa cctggtgctc aagacaagt tgctgttgat      120 gctattggtt gtattccagg tgactgggtt ttgtgtgttg gttcttctgc tgccagagaa      180
gctgctggtt ccaagtctta cccatctgat ttgactatca tcggtattat tgaccaatgg      240
aacggtgaa                                                             249

<210> SEQ ID NO 10
<211> LENGTH: 297
<212> TYPE: DNA
<213> ORGANISM: Artificial Sequence
<220> FEATURE:
<223> OTHER INFORMATION: HO-H nuxleotide sequence

<400> SEQUENCE: 10
atggctgatg ctttgggtat gattgaagtt agaggtttcg ttggtatggt tgaagctgct      60
gatgctatgg ttaaggctgc taaagttgaa ttgatcggtt acgaaaaaac tggtggtggt      120
tatgttactg ctgttgttag aggtgatgtt gctgctgtaa aagctgctac tgaagctggt      180
caaagggctg ctgaaagagt tggagaagtt gttgctgttc atgttattcc aagaccacat      240
gttaatgttg atgctgcttt gccattgggt agaactccag gtatggataa gtctgct        297

<210> SEQ ID NO 11
<211> LENGTH: 288
<212> TYPE: DNA
<213> ORGANISM: Artificial Sequence
<220> FEATURE:
<223> OTHER INFORMATION: HO-P nucleotide sequence

<400> SEQUENCE: 11
atggttttag gtaaagttgt cggtactgtt gttgcatcaa gaaaggaacc aagaattgaa      60
ggtttatctt tattattggt tagagcttgt gatccagatg gtactccaac tggtggtgct      120
gttgtttgtg ctgatgctgt tggtgctggt gttggtgaag ttgtttttata tgcttctggt      180 tcttctgcta gacaaactga agttactaat aatagaccag ttgatgctac tattatggct      240
attgttgatt tggttgaaat gggtggtgat gttagattta gaaaagat                  288

<210> SEQ ID NO 12
<211> LENGTH: 615
<212> TYPE: DNA
<213> ORGANISM: Artificial Sequence
<220> FEATURE:
<223> OTHER INFORMATION: HO-T1 nucleotide sequence

<400> SEQUENCE: 12
atggatcatg ctccagaaag atttgatgct actcctccag ctggtgaacc agatagacca      60
gctttgggtg ttttggaatt gacttctatt gctagaggta ttaccgtttgc tgatgctgct      120 ttgaaaagag caccatcttt gttgttgatg tccagaccag tttcttccgg taaacatttg      180
ttgatgatga gaggtcaagt tgccgaagtt gaagaatcta tgattgctgc tagagaaatt      240
gctggtgctg ttctggtgc tttgttggat gaattggaat tgccatatgc tcacgaacaa      300
ctttggagat ttttggatgc tccagttgtt gcagatgctt gggaagaaga tactgaatcc      360
gttattatcg ttgaaaccgc tactgtttgt gctgctattg attctgctga tgcagcctta      420
aaaactgctc ctgttgtttt gagagatatg agattggcta ttggtattgc tggtaaggct      480

```
ttctttactt tgactggtga attggctgat gttgaagctg ctgctgaagt tgttagagaa        540
agatgtggtg ctagattgct agaattggct tgtattgcaa gaccagttga cgaattgaga        600
ggtaggttgt ttttc                                                         615
```

<210> SEQ ID NO 13
<211> LENGTH: 83
<212> TYPE: PRT
<213> ORGANISM: Artificial Sequence
<220> FEATURE:
<223> OTHER INFORMATION: Spycatcher tag amino acid sequence

<400> SEQUENCE: 13

```
Asp Ser Ala Thr His Ile Lys Phe Ser Lys Arg Asp Glu Asp Gly Lys
1               5                   10                  15

Glu Leu Ala Gly Ala Thr Met Glu Leu Arg Asp Ser Ser Gly Lys Thr
            20                  25                  30

Ile Ser Thr Trp Ile Ser Asp Gly Gln Val Lys Asp Phe Tyr Leu Tyr
        35                  40                  45

Pro Gly Lys Tyr Thr Phe Val Glu Thr Ala Ala Pro Asp Gly Tyr Glu
    50                  55                  60

Val Ala Thr Ala Ile Thr Phe Thr Val Asn Glu Gln Gly Gln Val Thr
65                  70                  75                  80

Val Asn Gly
```

<210> SEQ ID NO 14
<211> LENGTH: 249
<212> TYPE: DNA
<213> ORGANISM: Artificial Sequence
<220> FEATURE:
<223> OTHER INFORMATION: Spycatcher tag nucleotide sequence

<400> SEQUENCE: 14

```
gattctgcta ctcatattaa gttctccaag agggacgaag atggtaaaga attggctggt         60
gcaactatgg aattgagaga ttcttctggt aagaccattt ccacctggat ttctgatggt        120
caagttaagg atttctactt gtacccaggt aagtacactt tcgttgaaac tgctgctcca        180
gatggttatg aagttgctac tgctattact ttcaccgtca atgaacaagg tcaagtcact        240
gttaatggt                                                                249
```

<210> SEQ ID NO 15
<211> LENGTH: 13
<212> TYPE: PRT
<213> ORGANISM: Artificial Sequence
<220> FEATURE:
<223> OTHER INFORMATION: Spytag amino acid sequence

<400> SEQUENCE: 15

```
Ala His Ile Val Met Val Asp Ala Tyr Lys Pro Thr Lys
1               5                   10
```

<210> SEQ ID NO 16
<211> LENGTH: 39
<212> TYPE: DNA
<213> ORGANISM: Artificial Sequence
<220> FEATURE:
<223> OTHER INFORMATION: Spytag nucleotide sequence

<400> SEQUENCE: 16

```
gctcatatag ttatggttga tgcttacaag ccaacaaaa                                39
```

-continued

```
<210> SEQ ID NO 17
<211> LENGTH: 21
<212> TYPE: PRT
<213> ORGANISM: Artificial Sequence
<220> FEATURE:
<223> OTHER INFORMATION: CC-Di-A amino acid sequence

<400> SEQUENCE: 17

Glu Ile Ala Ala Leu Glu Lys Glu Asn Ala Ala Leu Glu Gln Glu Ile
1               5                   10                  15

Ala Ala Leu Glu Gln
            20

<210> SEQ ID NO 18
<211> LENGTH: 63
<212> TYPE: DNA
<213> ORGANISM: Artificial Sequence
<220> FEATURE:
<223> OTHER INFORMATION: CC-Di-A nucleotide sequence

<400> SEQUENCE: 18
gaaattgcag ctttggaaaa agaaaacgct gccttggaac aagaaattgc cgcattagaa      60
caa                                                                   63

<210> SEQ ID NO 19
<211> LENGTH: 21
<212> TYPE: PRT
<213> ORGANISM: Artificial Sequence
<220> FEATURE:
<223> OTHER INFORMATION: CC-Di-B amino acid sequemce

<400> SEQUENCE: 19

Lys Ile Ala Ala Leu Lys Lys Lys Asn Ala Ala Leu Lys Gln Lys Ile
1               5                   10                  15

Ala Ala Leu Lys Gln
            20

<210> SEQ ID NO 20
<211> LENGTH: 63
<212> TYPE: DNA
<213> ORGANISM: Artificial Sequence
<220> FEATURE:
<223> OTHER INFORMATION: CC-Di-B nucleotide sequence

<400> SEQUENCE: 20
aaaattgcag cattgaaaaa gaagaacgcc gccttgaaac aaaaaattgc tgccttaaaa      60
caa                                                                   63

<210> SEQ ID NO 21
<211> LENGTH: 8
<212> TYPE: PRT
<213> ORGANISM: Artificial Sequence
<220> FEATURE:
<223> OTHER INFORMATION: Strep-Tag II (SII) amino acid sequence

<400> SEQUENCE: 21

Trp Ser His Pro Gln Phe Glu Lys
1               5

<210> SEQ ID NO 22
<211> LENGTH: 24
<212> TYPE: DNA
<213> ORGANISM: Artificial Sequence
<220> FEATURE:
<223> OTHER INFORMATION: Strep-Tag II (SII) nucleotide sequence
```

<400> SEQUENCE: 22
tggtcacatc cacaatttga aaag                                                              24

<210> SEQ ID NO 23
<211> LENGTH: 1555
<212> TYPE: DNA
<213> ORGANISM: Artificial Sequence
<220> FEATURE:
<223> OTHER INFORMATION: Promoter PT7 nucleotide sequence

<400> SEQUENCE: 23
tcactgcccg ctttccagtc gggaaacctg tcgtgccagc tgcattaatg aatcggccaa      60
cgcgcgggga gaggcggttt gcgtattggg cgccagggtg gtttttcttt tcaccagtga     120
aacgggcaac agctgattgc ccttcaccgc ctggccctga gagagttgca gcaagcggtc     180
cacgctggtt tgccccagca ggcgaaaatc ctgtttgatg gtggttaacg cgggatata     240 acatgagctg tcttcggtat cgtcgtatcc cactaccgag atatccgcac caacgcgcag     300
cccggactcg gtaatggcgc gcattgcgcc cagcgccatc tgatcgttgg caaccagcat     360
cgcagtggga acgatgccct cattcagcat ttgcatggtt tgttgaaaac cggacatggc     420
actccagtcg ccttcccgtt ccgctatcgg ctgaatttga ttgcgagtga gatatttatg     480
ccagccagcc agacgcagac gcgccgagac agaacttaat gggcccgcta acagcgcgat     540
ttgctggtga cccaatgcga ccagatgctc cacgcccagt cgcgtaccgt cttcatggga     600
gaaaataata ctgttgatgg gtgtctggtc agagacatca agaaataacg ccggaacatt     660
agtgcaggca gcttccacag caatggcatc ctggtcatcc agcggatagt taatgatcag     720
cccactgacg cgttgcgcga agattgtg caccgccgct ttacaggctt cgacgccgct     780
tcgttctacc atcgacacca ccacgctggc acccagttga tcggcgcgag atttaatcgc     840
cgcgacaatt tgcgacggcg cgtgcaggc cagactggag gtggcaacgc caatcagcaa     900
cgactgtttg cccgccagtt gttgtgccac gcggttggga atgtaattca gctccgccat     960
cgccgcttcc acttttttcc gcgttttcgc agaaacgtgg ctggcctggt tcaccacgcg    1020
ggaaacggtc tgataagaga caccggcata ctctgcgaca tcgtataacg ttactggttt    1080
cacattcacc accctgaatt gactctcttc cgggcgctat catgccatac cgcgaaaggt    1140
tttgcgccat tcgatggtgt ccgggatctc gacgctctcc cttatcgac tcctgcatta    1200 ggaagcagcc cagtagtagg ttgaggccgt tgagcaccgc cgccgcaagg aatggtgcat    1260
gcaaggagat ggcgcccaac agtcccccgg ccacggggcc tgccaccata cccacgccga    1320
aacaagcgct catgagcccg aagtggcgag cccgatcttc cccatcggtg atgtcggcga    1380
tataggcgcc agcaaccgca cctgtggcgc cggtgatgcc ggccacgatg cgtccggcgt    1440
agaggatcga gatctcgatc ccgcgaaatt aatacgactc actataggg aattgtgagc    1500 ggataacaat tcccctctag aaataatttt gtttaacttt aagaaggaga tatac        1555

<210> SEQ ID NO 24
<211> LENGTH: 118
<212> TYPE: DNA
<213> ORGANISM: Artificial Sequence
<220> FEATURE:
<223> OTHER INFORMATION: Promoter PCON5 nucleotide sequence

<400> SEQUENCE: 24
ggcttcccaa ccttaccaga gggcgcccca gctggcaatt ccgacgtctt tatggctagc      60

```
tcagtcctag gtacaatgct agcgaattca aaagatcttt taagaaggag atatacat      118

<210> SEQ ID NO 25
<211> LENGTH: 500
<212> TYPE: DNA
<213> ORGANISM: Artificial Sequence
<220> FEATURE:
<223> OTHER INFORMATION: Promoter PTDH3 nucleotide sequence

<400> SEQUENCE: 25
acagtttatt cctggcatcc actaaatata atggagcccg ctttttaagc tggcatccag       60
aaaaaaaaag aatcccagca ccaaaatatt gttttcttca ccaaccatca gttcataggt      120
ccattctctt agcgcaacta cagagaacag gggcacaaac aggcaaaaaa cgggcacaac      180
ctcaatggag tgatgcaacc tgcctggagt aaatgatgac acaaggcaat tgacccacgc      240
atgtatctat ctcattttct tacaccttct attaccttct gctctctctg atttggaaaa      300
agctgaaaaa aaaggttgaa accagttccc tgaaattatt cccctacttg actaataagt      360
atataaagac ggtaggtatt gattgtaatt ctgtaaatct atttcttaaa cttcttaaat      420 tctacttta tagttagtct ttttttttagt tttaaaacac caagaactta gtttcgaata      480
aacacacata aacaaacaaa                                                  500

<210> SEQ ID NO 26
<211> LENGTH: 500
<212> TYPE: DNA
<213> ORGANISM: Artificial Sequence
<220> FEATURE:
<223> OTHER INFORMATION: Promoter PPYK1 nucleotide sequence

<400> SEQUENCE: 26
acagattggg agattttcat agtagaattc agcatgatag ctacgtaaat gtgttccgca       60
ccgtcacaaa gtgttttcta ctgttctttc ttctttcgtt cattcagttg agttgagtga      120
gtgctttgtt caatggatct tagctaaaat gcatattttt tctcttggta aatgaatgct      180
tgtgatgtct tccaagtgat ttcctttcct tcccatatga tgctaggtac ctttagtgtc      240
ttcctaaaaa aaaaaaaagg ctcgccatca aaacgatatt cgttggcttt tttttctgaa      300
ttataaatac tctttggtaa cttttcattt ccaagaacct cttttttcca gttatatcat      360
ggtccccttt caaagttatt ctctactctt tttcatattc attcttttttc atcctttggt      420 tttttattct taacttgttt attattctct cttgtttcta tttacaagac accaatcaaa      480
acaaataaaa catcatcaca                                                  500

<210> SEQ ID NO 27
<211> LENGTH: 500
<212> TYPE: DNA
<213> ORGANISM: Artificial Sequence
<220> FEATURE:
<223> OTHER INFORMATION: Promoter PYEF3 nucleotide sequence

<400> SEQUENCE: 27
attaaaaaaa caacttacaa tcattgttcg ccccttccat acttactgcc actcgcaaaa       60
gggcccaacc agggcaatta cgtatcaaaa aatcatgaca ggctgggtaa taaatattcg      120
tgaagaaaga agaaattaaa aaaagaaacg aagaagcaaa aaaaagaaaa gactccgttt      180
aatcactttc aaccgcggtt tatccggccc cacccatgca taaccctaaa ttattagatc      240
acttagcacg tgaaaagaa acgttttttaa tgtttttttt tttttttttct tttttctttt      300 ttgcgttggt gaaaatttt tcgcttcctc gagtataatt atctcatctc atctttcata      360
```

-continued

```
taagataaga agttttataa aaaccttttg catcaaaatt ttgtagaata tctctttttc    420
ttacgctctc tttctttcct taattgtttt ctaaagaacc gtgtattttt ctagttcgaa    480
tccatcgata acattaaaag                                                 500
```

<210> SEQ ID NO 28
<211> LENGTH: 3589
<212> TYPE: DNA
<213> ORGANISM: Artificial Sequence
<220> FEATURE:
<223> OTHER INFORMATION: HcKan_O-CmCherry plasmid

<400> SEQUENCE: 28

```
aagaaaggcc cacccgtgaa ggtgagccag tgagttgatt gcagtccagt tacgctggag     60
tccgtctcgg atgagagacc gaattcgcgg ccgcttctag agcaatacgc aaaccgcctc    120
tccccgcgcg ttggccgatt cattaatgca gctggcacga caggtttccc gactggaaag    180
cgggcagtga gcgcaacgca attaatgtga gttagctcac tcattaggca ccccaggctt    240
tacactttat gcttccggct cgtatgttgt gtggaattgt gagcggataa caatttcaca    300
catactagag aaagaggaga aatactagat ggcttcctcc gaagacgtta tcaaagagtt    360
catgcgtttc aaagttcgta tggaaggttc cgttaacggt cacgagttcg aaatcgaagg    420
tgaaggtgaa ggtcgtccgt acgaaggtac ccagaccgct aaactgaaag ttaccaaagg    480
tggtccgctg ccgttcgctt gggacatcct gtccccgcag ttccagtacg gttccaaagc    540
ttacgttaaa cacccggctg acatcccgga ctacctgaaa ctgtccttcc cggaaggttt    600
caaatgggaa cgtgttatga acttcgaaga cggtggtgtt gttaccgtta cccaggactc    660
ctccctgcaa gacggtgagt tcatctacaa agttaaactg cgtggtacca acttcccgtc    720
cgacggtccg gttatgcaga aaaaaccat gggttgggaa gcttccaccg aacgtatgta    780
cccggaagac ggtgctctga aggtgaaat caaaatgcgt ctgaaactga agacggtgg    840 tcactacgac gctgaagtta aaaccaccta catggctaaa aaaccggttc agctgccggg    900
tgcttacaaa accgacatca aactggacat cacctcccac aacgaagact acaccatcgt    960
tgaacagtac gaacgtgctg aaggtcgtca ctccaccggt gcttaataac gctgatagtg   1020
ctagtgtaga tcgctactag agccaggcat caaataaaac gaaaggctca gtcgaaagac   1080
tgggcctttc gttttatctg ttgtttgtcg gtgaacgctc tctactagag tcacactggc   1140
tcaccttcgg gtgggccttt ctgcgtttat atactagtag cggccgctgc agggtctctg   1200
gttcttctat ggtgagcaag ggcgaggagg ataacatggc catcatcaag gagttcatgc   1260
gcttcaaggt gcacatggag ggctccgtga acggccacga gttcgagatc gagggcgagg   1320 gcgaggccg cccctacgag ggcacccaga ccgccaagct gaaggtgacc aagggtggcc   1380
ccctgccctt cgcctgggac atcctgtccc ctcagttcat gtacggctcc aaggcctacg   1440
tgaagcaccc cgccgacatc cccgactact tgaagctgtc cttccccgag ggcttcaagt   1500
gggagcgcgt gatgaacttc gaggacggcg gcgtggtgac cgtgacccag gactcctccc   1560
tgcaggacgg cgagttcatc tacaaggtga agctgcgcgg caccaacttc ccctccgacg   1620
gccccgtaat gcagaagaag accatgggct gggaggcctc ctccgagcgg atgtaccccg   1680
aggacggcgc cctgaagggc gagatcaagc agaggctgaa gctgaaggac ggcggccact   1740
acgacgctga ggtcaagacc acctacaagg ccaagaagcc cgtgcagctg cccggcgcct   1800
acaacgtcaa catcaagttg gacatcacct cccacaacga ggactacacc atcgtggaac   1860
```

-continued

```
agtacgaacg cgccgagggc cgccactcca ccggcggcat ggacgagctg tacaagtagc    1920
cgagacgact gaccatttaa atcatacctg acctccatag cagaaagtca aaagcctccg    1980
accggaggct tttgacttga tcggcacgta agaggttcca actttcacca taatgaaata    2040
agatcactac cgggcgtatt ttttgagtta tcgagatttt caggagctaa ggaagctaaa    2100
atgagccata ttcaacggga aacgtcttgc tcgaggccgc gattaaattc caacatggat    2160
gctgatttat atgggtataa atgggctcgc gataatgtcg ggcaatcagg tgcgacaatc    2220
tatcgattgt atgggaagcc cgatgcgcca gagttgtttc tgaaacatgg caaaggtagc    2280
gttgccaatg atgttacaga tgagatggtc aggctaaact ggctgacgga atttatgcct    2340
cttccgacca tcaagcattt tatccgtact cctgatgatg catggttact caccactgcg    2400
atcccaggga aaacagcatt ccaggtatta gaagaatatc ctgattcagg tgaaaatatt    2460
gttgatgcgc tggcagtgtt cctgcgccgg ttgcattcga ttcctgtttg taattgtcct    2520
tttaacggcg atcgcgtatt tcgtctcgct caggcgcaat cacgaatgaa taacggtttg    2580
gttggtgcga gtgattttga tgacgagcgt aatggctggc ctgttgaaca agtctggaaa    2640
gaaatgcata agcttttgcc attctcaccg gattcagtcg tcactcatgg tgatttctca    2700
cttgataacc ttattttga cgaggggaaa ttaataggtt gtattgatgt tggacgagtc    2760
ggaatcgcag accgatacca ggatcttgcc atcctatgga actgcctcgg tgagttttct    2820
ccttcattac agaaacggct ttttcaaaaa tatggtattg ataatcctga tatgaataaa    2880
ttgcagtttc acttgatgct cgatgagttt ttctaatgag ggcccaaatg taatcacctg    2940
gctcaccttc gggtgggcct ttctgcgttg ctggcgtttt tccataggct ccgcccccct    3000
gacgagcatc acaaaaatcg atgctcaagt cagaggtggc gaaacccgac aggactataa    3060
agataccagg cgtttccccc tggaagctcc ctcgtgcgct ctcctgttcc gaccctgccg    3120
cttaccggat acctgtccgc ctttctccct tcgggaagcg tggcgctttc tcatagctca    3180
cgctgtaggt atctcagttc ggtgtaggtc gttcgctcca agctgggctg tgtgcacgaa    3240
ccccccgttc agcccgaccg ctgcgcctta tccggtaact atcgtcttga gtccaacccg    3300
gtaagacacg acttatcgcc actggcagca gccactggta acaggattag cagagcgagg    3360
tatgtaggcg gtgctacaga gttcttgaag tggtggccta actacggcta cactagaaga    3420
acagtatttg gtatctgcgc tctgctgaag ccagttacct cggaaaaaga gttggtagct    3480
cttgatccgg caaacaaacc accgctggta gcggtggttt ttttgtttgc aagcagcaga    3540
ttacgcgcag aaaaaaagga tctcaagaag atcctttgat tttctaccg                3589
```

```
<210> SEQ ID NO 29
<211> LENGTH: 708
<212> TYPE: DNA
<213> ORGANISM: Artificial Sequence
<220> FEATURE:
<223> OTHER INFORMATION: HcKan_O-CmCherry nucleotide sequence of key ORF

<400> SEQUENCE: 29
atggtgagca agggcgagga ggataacatg gccatcatca aggagttcat gcgcttcaag     60
gtgcacatgg agggctccgt gaacggccac gagttcgaga tcgagggcga gggcgagggc    120
cgcccctacg agggcaccca gaccgccaag ctgaaggtga ccaagggtgg ccccctgccc    180
ttcgcctggg acatcctgtc ccctcagttc atgtacggct ccaaggccta cgtgaagcac    240
cccgccgaca tccccgacta cttgaagctg tccttccccg agggcttcaa gtgggagcgc    300
gtgatgaact tcgaggacgg cggcgtggtg accgtgaccc aggactcctc cctgcaggac    360
```

```
ggcgagttca tctacaaggt gaagctgcgc ggcaccaact tcccctccga cggcccgta       420 atgcagaaga agaccatggg ctgggaggcc tcctccgagc ggatgtaccc cgaggacggc       480
gccctgaagg gcgagatcaa gcagaggctg aagctgaagg acggcggcca ctacgacgct       540
gaggtcaaga ccacctacaa ggccaagaag cccgtgcagc tgcccggcgc ctacaacgtc       600
aacatcaagt tggacatcac ctcccacaac gaggactaca ccatcgtgga acagtacgaa       660
cgcgccgagg ccgccactc caccggcggc atggacgagc tgtacaag                    708
```

<210> SEQ ID NO 30
<211> LENGTH: 236
<212> TYPE: PRT
<213> ORGANISM: Artificial Sequence
<220> FEATURE:
<223> OTHER INFORMATION: HcKan_O-CmCherry amino acid sequence of key ORF

<400> SEQUENCE: 30

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```

<210> SEQ ID NO 31
<211> LENGTH: 2905
<212> TYPE: DNA
<213> ORGANISM: Artificial Sequence
<220> FEATURE:
<223> OTHER INFORMATION: HcKan_O-CSII plasmid

<400> SEQUENCE: 31

```
aagaaaggcc cacccgtgaa ggtgagccag tgagttgatt gcagtccagt tacgctggag       60
```

-continued

```
tccgtctcgg atgagagacc gaattcgcgg ccgcttctag agcaatacgc aaaccgcctc    120
tccccgcgcg ttggccgatt cattaatgca gctggcacga caggtttccc gactggaaag    180
cgggcagtga gcgcaacgca attaatgtga gttagctcac tcattaggca ccccaggctt    240
tacactttat gcttccggct cgtatgttgt gtggaattgt gagcggataa caatttcaca    300
catactagag aaagaggaga aatactagat ggcttcctcc gaagacgtta tcaaagagtt    360
catgcgtttc aaagttcgta tggaaggttc cgttaacggt cacgagttcg aaatcgaagg    420
tgaaggtgaa ggtcgtccgt acgaaggtac ccagaccgct aaactgaaag ttaccaaagg    480
tggtccgctg ccgttcgctt gggacatcct gtccccgcag ttccagtacg gttccaaagc    540
ttacgttaaa cacccggctg acatcccgga ctacctgaaa ctgtccttcc cggaaggttt    600
caaatgggaa cgtgttatga acttcgaaga cggtggtgtt gttaccgtta cccaggactc    660
ctccctgcaa gacggtgagt tcatctacaa agttaaactg cgtggtacca acttcccgtc    720
cgacggtccg gttatgcaga aaaaaaccat gggttgggaa gcttccaccg aacgtatgta    780
cccggaagac ggtgctctga aaggtgaaat caaaatgcgt ctgaaactga agacggtgg    840 tcactacgac gctgaagtta aaaccaccta catggctaaa aaaccggttc agctgccggg    900
tgcttacaaa accgacatca aactggacat cacctcccac aacgaagact acaccatcgt    960
tgaacagtac gaacgtgctg aaggtcgtca ctccaccggt gcttaataac gctgatagtg   1020
ctagtgtaga tcgctactag agccaggcat caaataaaac gaaaggctca gtcgaaagac   1080
tgggcctttc gttttatctg ttgtttgtcg gtgaacgctc tctactagag tcacactggc   1140
tcaccttcgg gtgggccttt ctgcgtttat atactagtag cggccgctgc agggtctctg   1200
gttcttcttg gtcacatcca caatttgaaa agtagccgag acgactgacc atttaaatca   1260
tacctgacct ccatagcaga aagtcaaaag cctccgaccg gaggcttttg acttgatcgg   1320
cacgtaagag gttccaactt tcaccataat gaaataagat cactaccggg cgtatttttt   1380
gagttatcga gattttcagg agctaaggaa gctaaaatga gccatattca acgggaaacg   1440
tcttgctcga ggccgcgatt aaattccaac atggatgctg atttatatgg gtataaatgg   1500
gctcgcgata atgtcgggca atcaggtgcg acaatctatc gattgtatgg gaagcccgat   1560
gcgccagagt tgtttctgaa acatggcaaa ggtagcgttg ccaatgatgt tacagatgag   1620
atggtcaggc taaactggct gacggaattt atgcctcttc cgaccatcaa gcattttatc   1680
cgtactcctg atgatgcatg gttactcacc actgcgatcc cagggaaaac agcattccag   1740
gtattagaag aatatcctga ttcaggtgaa aatattgttg atgcgctggc agtgttcctg   1800
cgccggttgc attcgattcc tgtttgtaat gtcctttta acggcgatcg cgtatttcgt   1860
ctcgctcagg cgcaatcacg aatgaataac ggtttggttg gtgcgagtga ttttgatgac   1920
gagcgtaatg gctggcctgt tgaacaagtc tggaagaaa tgcataagct tttgccattc   1980
tcaccggatt cagtcgtcac tcatggtgat ttctcacttg ataaccttat ttttgacgag   2040
gggaaattaa taggttgtat tgatgttgga cgagtcggaa tcgcagaccg ataccaggat   2100
cttgccatcc tatggaactg cctcggtgag ttttctcctt cattacagaa acggcttttt   2160
caaaaatatg gtattgataa tcctgatatg aataaattgc agtttcactt gatgctcgat   2220
gagtttttct aatgagggcc caaatgtaat cacctggctc accttcgggt gggcctttct   2280
gcgttgctgg cgtttttcca taggctccgc cccctgacg agcatcacaa aaatcgatgc   2340
tcaagtcaga ggtggcgaaa cccgacagga ctataaagat accaggcgtt tccccctgga   2400
```

-continued

```
agctccctcg tgcgctctcc tgttccgacc ctgccgctta ccggatacct gtccgccttt      2460
ctcccttcgg gaagcgtggc gctttctcat agctcacgct gtaggtatct cagttcggtg      2520
taggtcgttc gctccaagct gggctgtgtg cacgaacccc ccgttcagcc cgaccgctgc      2580
gccttatccg gtaactatcg tcttgagtcc aacccggtaa gacacgactt atcgccactg      2640
gcagcagcca ctggtaacag gattagcaga gcgaggtatg taggcggtgc tacagagttc      2700
ttgaagtggt ggcctaacta cggctacact agaagaacag tatttggtat ctgcgctctg      2760
ctgaagccag ttacctcgga aaaagagttg gtagctcttg atccggcaaa caaaccaccg      2820
ctggtagcgg tggtttttttt gtttgcaagc agcagattac gcgcagaaaa aaaggatctc      2880
aagaagatcc tttgatttttc taccg                                          2905
```

```
<210> SEQ ID NO 32
<211> LENGTH: 2899
<212> TYPE: DNA
<213> ORGANISM: Artificial Sequence
<220> FEATURE:
<223> OTHER INFORMATION: HcKan_O-CHis6 plasmid

<400> SEQUENCE: 32
aagaaaggcc cacccgtgaa ggtgagccag tgagttgatt gcagtccagt tacgctggag       60
tccgtctcgg atgagagacc gaattcgcgg ccgcttctag agcaatacgc aaaccgcctc      120
tccccgcgcg ttggccgatt cattaatgca gctggcacga caggtttccc gactggaaag      180
cgggcagtga gcgcaacgca attaatgtga gttagctcac tcattaggca ccccaggctt      240
tacactttat gcttccggct cgtatgttgt gtggaattgt gagcggataa caatttcaca      300
catactagag aaagaggaga atactagat ggcttcctcc gaagacgtta tcaaagagtt      360
catgcgtttc aaagttcgta tggaaggttc cgttaacggt cacgagttcg aaatcgaagg      420
tgaaggtgaa ggtcgtccgt acgaaggtac ccagaccgct aaactgaaag ttaccaaagg      480
tggtccgctg ccgttcgctt gggacatcct gtccccgcag ttccagtacg gttccaaagc      540
ttacgttaaa cacccggctg acatcccgga ctacctgaaa ctgtccttcc cggaaggttt      600
caaatgggaa cgtgttatga acttcgaaga cggtggtgtt gttaccgtta cccaggactc      660
ctccctgcaa gacggtgagt tcatctacaa agttaaactg cgtggtacca acttcccgtc      720
cgacggtccg gttatgcaga aaaaaaccat gggttgggaa gcttccaccg aacgtatgta      780
cccggaagac ggtgctctga aaggtgaaat caaaatgcgt ctgaaactga agacggtgg      840 tcactacgac gctgaagtta aaaccaccta catggctaaa aaaccggttc agctgccggg      900
tgcttacaaa accgacatca aactggacat cacctcccac aacgaagact acaccatcgt      960
tgaacagtac gaacgtgctg aaggtcgtca ctccaccggt gcttaataac gctgatagtg     1020
ctagtgtaga tcgctactag agccaggcat caaataaaac gaaaggctca gtcgaaagac     1080
tgggcctttc gttttatctg ttgtttgtcg gtgaacgctc tctactagag tcacactggc     1140
tcaccttcgg gtgggccttt ctgcgtttat atactagtag cggccgctgc agggtctctg     1200
gttcttctca tcatcaccat caccattagc cgagacgact gaccatttaa atcatacctg     1260
acctccatag cagaaagtca aaagcctccg accggaggct tttgacttga tcggcacgta     1320
agaggttcca actttcacca taatgaaata agatcactac cgggcgtatt ttttgagtta     1380
tcgagatttt caggagctaa ggaagctaaa atgagccata ttcaacggga acgtcttgc     1440 tcgaggccgc gattaaattc caacatggat gctgatttat atgggtataa atgggctcgc     1500
gataatgtcg ggcaatcagg tgcgacaatc tatcgattgt atgggaagcc cgatgcgcca     1560
```

```
gagttgtttc tgaaacatgg caaaggtagc gttgccaatg atgttacaga tgagatggtc    1620
aggctaaact ggctgacgga atttatgcct cttccgacca tcaagcattt tatccgtact    1680
cctgatgatg catggttact caccactgcg atcccaggga aaacagcatt ccaggtatta    1740
gaagaatatc ctgattcagg tgaaaatatt gttgatgcgc tggcagtgtt cctgcgccgg    1800
ttgcattcga ttcctgtttg taattgtcct tttaacggcg atcgcgtatt tcgtctcgct    1860
caggcgcaat cacgaatgaa taacggtttg gttggtgcga gtgattttga tgacgagcgt    1920
aatggctggc ctgttgaaca agtctggaaa gaaatgcata agcttttgcc attctcaccg    1980
gattcagtcg tcactcatgg tgatttctca cttgataacc ttattttttga cgaggggaaa    2040 ttaataggtt gtattgatgt tggacgagtc ggaatcgcag accgatacca ggatcttgcc    2100
atcctatgga actgcctcgg tgagtttttct ccttcattac agaaacggct ttttcaaaaa    2160
tatggtattg ataatcctga tatgaataaa ttgcagtttc acttgatgct cgatgagttt    2220
ttctaatgag ggcccaaatg taatcacctg gctcaccttc gggtgggcct ttctgcgttg    2280
ctggcgtttt tccataggct ccgcccccct gacgagcatc acaaaaatcg atgctcaagt    2340
cagaggtggc gaaacccgac aggactataa agataccagg cgtttccccc tggaagctcc    2400
ctcgtgcgct ctcctgttcc gaccctgccg cttaccggat acctgtccgc ctttctccct    2460
tcgggaagcg tggcgctttc tcatagctca cgctgtaggt atctcagttc ggtgtaggtc    2520
gttcgctcca agctgggctg tgtgcacgaa ccccccgttc agcccgaccg ctgcgcctta    2580
tccggtaact atcgtcttga gtccaacccg gtaagacacg acttatcgcc actggcagca    2640
gccactggta acaggattag cagagcgagg tatgtaggcg gtgctacaga gttcttgaag    2700
tggtggccta actacggcta cactagaaga acagtatttg gtatctgcgc tctgctgaag    2760
ccagttacct cggaaaaaga gttggtagct cttgatccgg caaacaaacc accgctggta    2820
gcggtggttt ttttgtttgc aagcagcaga ttacgcgcag aaaaaaagga tctcaagaag    2880
atcctttgat tttctaccg                                                2899
```

```
<210> SEQ ID NO 33
<211> LENGTH: 18
<212> TYPE: DNA
<213> ORGANISM: Artificial Sequence
<220> FEATURE:
<223> OTHER INFORMATION: HcKan_O-CHis6 nucleotide sequence of key ORF

<400> SEQUENCE: 33
catcatcacc atcaccat                                                    18

<210> SEQ ID NO 34
<211> LENGTH: 6
<212> TYPE: PRT
<213> ORGANISM: Artificial Sequence
<220> FEATURE:
<223> OTHER INFORMATION: HcKan_O-CHis6 amino acid sequence of key ORF

<400> SEQUENCE: 34

His His His His His His
1               5

<210> SEQ ID NO 35
<211> LENGTH: 2983
<212> TYPE: DNA
<213> ORGANISM: Artificial Sequence
<220> FEATURE:
<223> OTHER INFORMATION: HcKan_O-CCCDiA plasmid
```

-continued

<400> SEQUENCE: 35

```
aagaaaggcc cacccgtgaa ggtgagccag tgagttgatt gcagtccagt tacgctggag    60
tccgtctcgg atgagagacc gaattcgcgg ccgcttctag agcaatacgc aaaccgcctc   120
tccccgcgcg ttggccgatt cattaatgca gctggcacga caggtttccc gactggaaag   180
cgggcagtga gcgcaacgca attaatgtga gttagctcac tcattaggca ccccaggctt   240
tacactttat gcttccggct cgtatgttgt gtggaattgt gagcggataa caatttcaca   300
catactagag aaagaggaga aatactagat ggcttcctcc gaagacgtta tcaaagagtt   360
catgcgtttc aaagttcgta tggaaggttc cgttaacggt cacgagttcg aaatcgaagg   420
tgaaggtgaa ggtcgtccgt acgaaggtac ccagaccgct aaactgaaag ttaccaaagg   480
tggtccgctg ccgttcgctt gggacatcct gtccccgcag ttccagtacg gttccaaagc   540
ttacgttaaa cacccggctg acatcccgga ctacctgaaa ctgtccttcc cggaaggttt   600
caaatgggaa cgtgttatga acttcgaaga cggtggtgtt gttaccgtta cccaggactc   660
ctccctgcaa gacggtgagt tcatctacaa agttaaactg cgtggtacca acttcccgtc   720
cgacggtccg gttatgcaga aaaaaaccat gggttgggaa gcttccaccg aacgtatgta   780
cccggaagac ggtgctctga aggtgaaat caaaatgcgt ctgaaactga agacggtgg    840 tcactacgac gctgaagtta aaaccaccta catggctaaa aaaccggttc agctgccggg   900
tgcttacaaa accgacatca aactggacat cacctcccac aacgaagact acaccatcgt   960
tgaacagtac gaacgtgctg aaggtcgtca ctccaccggt gcttaataac gctgatagtg   1020
ctagtgtaga tcgctactag agccaggcat caaataaaac gaaaggctca gtcgaaagac   1080
tgggcctttc gttttatctg ttgtttgtcg gtgaacgctc tctactagag tcacactggc   1140
tcaccttcgg gtgggccttt ctgcgtttat atactagtag cggccgctgc agggtctctg   1200
gttctggtgg tggttcaggt ggttctgaaa ttgcagcttt ggaaaaagaa aacgctgcct   1260
tggaacaaga aattgccgca ttagaacaag gtggtagtgg tggatctggt tagccgagac   1320
gactgaccat ttaaatcata cctgacctcc atagcagaaa gtcaaaagcc tccgaccgga   1380
ggcttttgac ttgatcggca cgtaagaggt tccaactttc accataatga aataagatca   1440
ctaccgggcg tattttttga gttatcgaga ttttcaggag ctaaggaagc taaaatgagc   1500
catattcaac gggaaacgtc ttgctcgagg ccgcgattaa attccaacat ggatgctgat   1560
ttatatgggt ataaatgggc tcgcgataat gtcgggcaat caggtgcgac aatctatcga   1620
ttgtatggga agcccgatgc gccagagttg tttctgaaac atggcaaagg tagcgttgcc   1680
aatgatgtta cagatgagat ggtcaggcta aactggctga cggaatttat gcctcttccg   1740
accatcaagc attttatccg tactcctgat gatgcatggt tactcaccac tgcgatccca   1800
gggaaaacag cattccaggt attagaagaa tatcctgatt caggtgaaaa tattgttgat   1860
gcgctggcag tgttcctgcg ccggttgcat tcgattcctg tttgtaattg tccttttaac   1920
ggcgatcgcg tatttcgtct cgcacaggcg caatcacgaa tgaataacgg tttggttggt   1980
gcgagtgatt ttgatgacga gcgtaatggc tggcctgttg aacaagtctg gaaagaaatg   2040
cataagcttt tgccattctc accggattca gtcgtcactc atggtgattt ctcacttgat   2100
aaccttattt ttgacgaggg gaaattaata ggttgtattg atgttggacg agtcggaatc   2160
gcagaccgat accaggatct tgccatccta tggaactgcc tcggtgagtt ttctccttca   2220
ttacagaaac ggctttttca aaaatatggt attgataatc ctgatatgaa taaattgcag   2280
```

```
tttcacttga tgctcgatga gttttttctaa tgagggccca aatgtaatca cctggctcac      2340
cttcgggtgg gcctttctgc gttgctggcg tttttccata ggctccgccc ccctgacgag      2400
catcacaaaa atcgatgctc aagtcagagg tggcgaaacc cgacaggact ataaagatac      2460
caggcgtttc ccctggaag ctccctcgtg cgctctcctg ttccgaccct gccgcttacc       2520
ggatacctgt ccgcctttct cccttcggga agcgtggcgc tttctcatag ctcacgctgt      2580
aggtatctca gttcggtgta ggtcgttcgc tccaagctgg gctgtgtgca cgaacccccc      2640
gttcagcccg accgctgcgc cttatccggt aactatcgtc ttgagtccaa cccggtaaga      2700
cacgacttat cgccactggc agcagccact ggtaacagga ttagcagagc gaggtatgta      2760
ggcggtgcta cagagttctt gaagtggtgg cctaactacg gctacactag aagaacagta      2820
tttggtatct gcgctctgct gaagccagtt acctcggaaa aagagttggt agctcttgat      2880
ccggcaaaca aaccaccgct ggtagcggtg gtttttttgt ttgcaagcag cagattacgc      2940
gcagaaaaaa aggatctcaa gaagatcctt tgatttttcta ccg                       2983
```

<210> SEQ ID NO 36
<211> LENGTH: 2983
<212> TYPE: DNA
<213> ORGANISM: Artificial Sequence
<220> FEATURE:
<223> OTHER INFORMATION: HcKan_O-CCCDiB plasmid

<400> SEQUENCE: 36

```
aagaaaggcc cacccgtgaa ggtgagccag tgagttgatt gcagtccagt tacgctggag        60
tccgtctcgg atgagagacc gaattcgcgg ccgcttctag agcaatacgc aaaccgcctc       120
tccccgcgcg ttggccgatt cattaatgca gctggcacga caggtttccc gactggaaag       180
cgggcagtga gcgcaacgca attaatgtga gttagctcac tcattaggca ccccaggctt       240
tacactttat gcttccggct cgtatgttgt gtggaattgt gagcggataa caatttcaca       300
catactagag aaagaggaga aatactagat ggcttcctcc gaagacgtta tcaaagagtt       360
catgcgtttc aaagttcgta tggaaggttc cgttaacggt cacgagttcg aaatcgaagg       420
tgaaggtgaa ggtcgtccgt acgaaggtac ccagaccgct aaactgaaag ttaccaaagg       480
tggtccgctg ccgttcgctt gggacatcct gtccccgcag ttccagtacg gttccaaagc       540
ttacgttaaa cacccggctg acatcccgga ctacctgaaa ctgtccttcc cggaaggttt       600
caaatgggaa cgtgttatga acttcgaaga cggtggtgtt gttaccgtta cccaggactc       660
ctccctgcaa gacggtgagt tcatctacaa agttaaactg cgtggtacca acttcccgtc       720
cgacggtccg gttatgcaga aaaaaaccat gggttgggaa gcttccaccg aacgtatgta       780
cccggaagac ggtgctctga aaggtgaaat caaaatgcgt ctgaaactga agacggtgg        840 tcactacgac gctgaagtta aaaccaccta catggctaaa aaaccggttc agctgccggg       900
tgcttacaaa accgacatca aactggacat cacctcccac aacgaagact acaccatcgt       960
tgaacagtac gaacgtgctg aaggtcgtca ctccaccggt gcttaataac gctgatagtg      1020
ctagtgtaga tcgctactag agccaggcat caaataaaac gaaaggctca gtcgaaagac      1080
tgggcctttc gttttatctg ttgtttgtcg gtgaacgctc tctactagag tcacactggc      1140
tcaccttcgg gtgggccttt ctgcgtttat atactagtag cggccgctgc agggtctctg      1200
gttctggtgg tggtagtggt ggttctaaa ttgcagcatt gaaaaagaag aacgccgcct       1260
tgaaacaaaa aattgctgcc ttaaaacaag gtggagtgg tggatctggt tagccgagac       1320
gactgaccat ttaaatcata cctgacctcc atagcagaaa gtcaaaagcc tccgaccgga      1380
```

-continued

```
ggcttttgac ttgatcggca cgtaagaggt tccaactttc accataatga aataagatca    1440
ctaccgggcg tattttttga gttatcgaga ttttcaggag ctaaggaagc taaaatgagc    1500
catattcaac gggaaacgtc ttgctcgagg ccgcgattaa attccaacat ggatgctgat    1560
ttatatgggt ataaatgggc tcgcgataat gtcgggcaat caggtgcgac aatctatcga    1620
ttgtatggga agcccgatgc gccagagttg tttctgaaac atggcaaagg tagcgttgcc    1680
aatgatgtta cagatgagat ggtcaggcta aactggctga cggaatttat gcctcttccg    1740
accatcaagc attttatccg tactcctgat gatgcatggt tactcaccac tgcgatccca    1800
gggaaaacag cattccaggt attagaagaa tatcctgatt caggtgaaaa tattgttgat    1860
gcgctggcag tgttcctgcg ccggttgcat tcgattcctg tttgtaattg tcctttaac    1920 ggcgatcgcg tatttcgtct cgcacaggcg caatcacgaa tgaataacgg tttggttggt    1980
gcgagtgatt ttgatgacga gcgtaatggc tggcctgttg aacaagtctg gaaagaaatg    2040
cataagcttt tgccattctc accggattca gtcgtcactc atggtgattt ctcacttgat    2100
aaccttattt ttgacgaggg gaaattaata ggttgtattg atgttggacg agtcggaatc    2160
gcagaccgat accaggatct tgccatccta tggaactgcc tcggtgagtt ttctccttca    2220
ttacagaaac ggctttttca aaaatatggt attgataatc ctgatatgaa taaattgcag    2280
tttcacttga tgctcgatga gtttttctaa tgagggccca aatgtaatca cctggctcac    2340
cttcgggtgg gcctttctgc gttgctggcg tttttccata ggctccgccc ccctgacgag    2400
catcacaaaa atcgatgctc aagtcagagg tggcgaaacc cgacaggact ataaagatac    2460
caggcgtttc cccctggaag ctccctcgtg cgctctcctg ttccgaccct gccgcttacc    2520
ggatacctgt ccgcctttct cccttcggga agcgtggcgc tttctcatag ctcacgctgt    2580
aggtatctca gttcggtgta ggtcgttcgc tccaagctgg gctgtgtgca cgaaccccccc    2640 gttcagcccg accgctgcgc cttatccggt aactatcgtc ttgagtccaa cccggtaaga    2700
cacgacttat cgccactggc agcagccact ggtaacagga ttagcagagc gaggtatgta    2760
ggcggtgcta cagagttctt gaagtggtgg cctaactacg ctacactag aagaacagta    2820 tttggtatct gcgctctgct gaagccagtt acctcggaaa aagagttggt agctcttgat    2880
ccggcaaaca aaccaccgct ggtagcggtg gtttttttgt ttgcaagcag cagattacgc    2940
gcagaaaaaa aggatctcaa gaagatcctt tgatttctta ccg    2983
```

```
<210> SEQ ID NO 37
<211> LENGTH: 3136
<212> TYPE: DNA
<213> ORGANISM: Artificial Sequence
<220> FEATURE:
<223> OTHER INFORMATION: HcKan_O-CSpyCatcher plasmid

<400> SEQUENCE: 37
```

```
aagaaaggcc cacccgtgaa ggtgagccag tgagttgatt gcagtccagt tacgctggag     60
tccgtctcgg atgagagacc gaattcgcgg ccgcttctag agcaatacgc aaaccgcctc    120
tccccgcgcg ttggccgatt cattaatgca gctggcacga caggtttccc gactggaaag    180
cgggcagtga gcgcaacgca attaatgtga gttagctcac tcattaggca ccccaggctt    240
tacactttat gcttccggct cgtatgttgt gtggaattgt gagcggataa caatttcaca    300
catactagag aaagaggaga aatactagat ggcttcctcc gaagacgtta tcaaagagtt    360
catgcgtttc aaagttcgta tggaaggttc cgttaacggt cacgagttcg aaatcgaagg    420
```

-continued

```
tgaaggtgaa ggtcgtccgt acgaaggtac ccagaccgct aaactgaaag ttaccaaagg    480
tggtccgctg ccgttcgctt gggacatcct gtccccgcag ttccagtacg gttccaaagc    540
ttacgttaaa cacccggctg acatcccgga ctacctgaaa ctgtccttcc cggaaggttt    600
caaatgggaa cgtgttatga acttcgaaga cggtggtgtt gttaccgtta cccaggactc    660
ctccctgcaa gacggtgagt tcatctacaa agttaaactg cgtggtacca acttcccgtc    720
cgacggtccg gttatgcaga aaaaaaccat gggttgggaa gcttccaccg aacgtatgta    780
cccggaagac ggtgctctga aaggtgaaat caaaatgcgt ctgaaactga agacggtgg    840 tcactacgac gctgaagtta aaaccaccta catggctaaa aaaccggttc agctgccggg    900
tgcttacaaa accgacatca aactggacat cacctcccac aacgaagact acaccatcgt    960
tgaacagtac gaacgtgctg aaggtcgtca ctccaccggt gcttaataac gctgatagtg    1020
ctagtgtaga tcgctactag agccaggcat caaataaaac gaaaggctca gtcgaaagac    1080
tgggcctttc gttttatctg ttgtttgtcg gtgaacgctc tctactagag tcacactggc    1140
tcaccttcgg gtgggccttt ctgcgtttat atactagtag cggccgctgc agggtctctg    1200
gttctggtgg ttctgattct gctactcata ttaagttctc caagagggac gaagatggta    1260
aagaattggc tggtgcaact atggaattga gagattcttc tggtaagacc atttccacct    1320
ggatttctga tggtcaagtt aaggatttct acttgtaccc aggtaagtac actttcgttg    1380
aaaactgctg tccagatggt tatgaagttg ctactgctat tactttcacc gtcaatgaac    1440
aaggtcaagt cactgttaat ggttagccga gacgactgac catttaaatc atacctgacc    1500
tccatagcag aaagtcaaaa gcctccgacc ggaggctttt gacttgatcg gcacgtaaga    1560
ggttccaact ttcaccataa tgaaataaga tcactaccgg gcgtattttt tgagttatcg    1620
agattttcag gagctaagga agctaaaatg agccatattc aacgggaaac gtcttgctcg    1680
aggccgcgat taaattccaa catggatgct gatttatatg ggtataaatg gctcgcgat    1740 aatgtcgggc aatcaggtgc gacaatctat cgattgtatg ggaagcccga tgcgccagag    1800
ttgtttctga aacatggcaa aggtagcgtt gccaatgatg ttacagatga gatggtcagg    1860
ctaaactggc tgacggaatt tatgcctctt ccgaccatca agcattttat ccgtactcct    1920
gatgatgcat ggttactcac cactgcgatc ccagggaaaa cagcattcca ggtattagaa    1980
gaatatcctg attcaggtga aaatattgtt gatgcgctgg cagtgttcct gcgccggttg    2040
cattcgattc ctgtttgtaa ttgtcctttt aacggcgatc gcgtatttcg tctcgctcag    2100
gcgcaatcac gaatgaataa cggtttggtt ggtgcgagtg attttgatga cgagcgtaat    2160
ggctggcctg ttgaacaagt ctggaaagaa atgcataagc ttttgccatt ctcaccggat    2220
tcagtcgtca ctcatggtga tttctcactt gataacctta tttttgacga ggggaaatta    2280
ataggttgta ttgatgttgg acgagtcgga atcgcagacc gataccagga tcttgccatc    2340
ctatggaact gcctcggtga gttttctcct tcattacaga aacggctttt tcaaaaatat    2400
ggtattgata atcctgatat gaataaattg cagtttcact tgatgctcga tgagttttc    2460 taatgagggc ccaaatgtaa tcacctggct caccttcggg tgggcctttc tgcgttgctg    2520
gcgtttttcc ataggctccg cccccctgac gagcatcaca aaaatcgatg ctcaagtcag    2580
aggtggcgaa acccgacagg actataaaga taccaggcgt ttccccctgg aagctccctc    2640
gtgcgctctc ctgttccgac cctgccgctt accggatacc tgtccgcctt tctcccttcg    2700
ggaagcgtgg cgctttctca tagctcacgc tgtaggtatc tcagttcggt gtaggtcgtt    2760
cgctccaagc tgggctgtgt gcacgaaccc cccgttcagc ccgaccgctg cgccttatcc    2820
```

```
ggtaactatc gtcttgagtc caacccggta agacacgact tatcgccact ggcagcagcc     2880
actggtaaca ggattagcag agcgaggtat gtaggcggtg ctacagagtt cttgaagtgg     2940
tggcctaact acggctacac tagaagaaca gtatttggta tctgcgctct gctgaagcca     3000
gttacctcgg aaaaagagtt ggtagctctt gatccggcaa acaaaccacc gctggtagcg     3060
gtggtttttt tgtttgcaag cagcagatta cgcgcagaaa aaaaggatct caagaagatc     3120
ctttgatttt ctaccg     3136

<210> SEQ ID NO 38
<211> LENGTH: 2926
<212> TYPE: DNA
<213> ORGANISM: Artificial Sequence
<220> FEATURE:
<223> OTHER INFORMATION: HcKan_O-CSpyTag plasmid

<400> SEQUENCE: 38
aagaaaggcc cacccgtgaa ggtgagccag tgagttgatt gcagtccagt tacgctggag       60
tccgtctcgg atgagagacc gaattcgcgg ccgcttctag agcaatacgc aaaccgcctc      120
tccccgcgcg ttggccgatt cattaatgca gctggcacga caggtttccc gactggaaag      180
cgggcagtga gcgcaacgca attaatgtga gttagctcac tcattaggca ccccaggctt      240
tacactttat gcttccggct cgtatgttgt gtggaattgt gagcggataa caatttcaca      300
catactagag aaagaggaga atactagat ggcttcctcc gaagacgtta tcaaagagtt      360
catgcgtttc aaagttcgta tggaaggttc cgttaacggt cacgagttcg aaatcgaagg      420
tgaaggtgaa ggtcgtccgt acgaaggtac ccagaccgct aaactgaaag ttaccaaagg      480
tggtccgctg ccgttcgctt gggacatcct gtccccgcag ttccagtacg gttccaaagc      540
ttacgttaaa cacccggctg acatcccgga ctacctgaaa ctgtccttcc cggaaggttt      600
caaatgggaa cgtgttatga acttcgaaga cggtggtgtt gttaccgtta cccaggactc      660
ctccctgcaa gacggtgagt tcatctacaa agttaaactg cgtggtacca acttcccgtc      720
cgacggtccg gttatgcaga aaaaaaccat gggttgggaa gcttccaccg aacgtatgta      780
cccggaagac ggtgctctga aaggtgaaat caaaatgcgt ctgaaactga aagacggtgg      840
tcactacgac gctgaagtta aaaccaccta catggctaaa aaaccggttc agctgccggg      900
tgcttacaaa accgacatca aactggacat cacctcccac aacgaagact acaccatcgt      960
tgaacagtac gaacgtgctg aaggtcgtca ctccaccggt gcttaataac gctgatagtg     1020
ctagtgtaga tcgctactag agccaggcat caaataaaac gaaaggctca gtcgaaagac     1080
tgggcctttc gttttatctg ttgtttgtcg gtgaacgctc tctactagag tcacactggc     1140
tcaccttcgg gtgggccttt ctgcgtttat atactagtag cggccgctgc agggtctctg     1200
gttctggtgg ttctgctcat atagttatgg ttgatgctta caagccaaca aaatagccga     1260
gacgactgac catttaaatc atacctgacc tccatagcag aaagtcaaaa gcctccgacc     1320
ggaggctttt gacttgatcg gcacgtaaga ggttccaact ttcaccataa tgaaataaga     1380
tcactaccgg gcgtattttt tgagttatcg agattttcag gagctaagga agctaaaatg     1440
agccatattc aacgggaaac gtcttgctcg aggccgcgat taaattccaa catggatgct     1500
gatttatatg ggtataaatg gctcgcgat aatgtcgggc aatcaggtgc gacaatctat     1560
cgattgtatg ggaagcccga tgcgccagag ttgtttctga acatggcaa aggtagcgtt     1620 gccaatgatg ttacagatga gatggtcagg ctaaactggc tgacggaatt tatgcctctt     1680
```

-continued

```
ccgaccatca agcattttat ccgtactcct gatgatgcat ggttactcac cactgcgatc      1740
ccagggaaaa cagcattcca ggtattagaa gaatatcctg attcaggtga aaatattgtt      1800
gatgcgctgg cagtgttcct gcgccggttg cattcgattc ctgtttgtaa ttgtcctttt      1860
aacggcgatc gcgtatttcg tctcgctcag gcgcaatcac gaatgaataa cggtttggtt      1920
ggtgcgagtg attttgatga cgagcgtaat ggctggcctg ttgaacaagt ctggaaagaa      1980
atgcataagc ttttgccatt ctcaccggat tcagtcgtca ctcatggtga tttctcactt      2040
gataacctta ttttttgacga ggggaaatta ataggttgta ttgatgttgg acgagtcgga      2100
atcgcagacc gataccagga tcttgccatc ctatggaact gcctcggtga gttttctcct      2160
tcattacaga aacggctttt tcaaaaatat ggtattgata atcctgatat gaataaattg      2220
cagtttcact tgatgctcga tgagtttttc taatgagggc ccaaatgtaa tcacctggct      2280
caccttcggg tgggcctttc tgcgttgctg gcgtttttcc ataggctccg cccccctgac      2340
gagcatcaca aaaatcgatg ctcaagtcag aggtggcgaa acccgacagg actataaaga      2400
taccaggcgt ttccccctgg aagctccctc gtgcgctctc ctgttccgac cctgccgctt      2460
accggatacc tgtccgcctt tctcccttcg ggaagcgtgg cgctttctca tagctcacgc      2520
tgtaggtatc tcagttcggt gtaggtcgtt cgctccaagc tgggctgtgt gcacgaaccc      2580
cccgttcagc ccgaccgctg cgccttatcc ggtaactatc gtcttgagtc caacccggta      2640
agacacgact tatcgccact ggcagcagcc actggtaaca ggattagcag agcgaggtat      2700
gtaggcggtg ctacagagtt cttgaagtgg tggcctaact acggctacac tagaagaaca      2760
gtatttggta tctgcgctct gctgaagcca gttacctcgg aaaaagagtt ggtagctctt      2820
gatccggcaa acaaaccacc gctggtagcg gtggtttttt tgtttgcaag cagcagatta      2880
cgcgcagaaa aaaaggatct caagaagatc ctttgatttt ctaccg                    2926
```

```
<210> SEQ ID NO 39
<211> LENGTH: 2944
<212> TYPE: DNA
<213> ORGANISM: Artificial Sequence
<220> FEATURE:
<223> OTHER INFORMATION: HcKan_O-S2CP plasmid

<400> SEQUENCE: 39
```

```
aagaaaggcc cacccgtgaa ggtgagccag tgagttgatt gcagtccagt tacgctggag        60
tccgtctcgg atgagagacc gaattcgcgg ccgcttctag agcaatacgc aaaccgcctc       120
tccccgcgcg ttggccgatt cattaatgca gctggcacga caggtttccc gactggaaag       180
cgggcagtga gcgcaacgca attaatgtga gttagctcac tcattaggca ccccaggctt       240
tacactttat gcttccggct cgtatgttgt gtggaattgt gagcggataa caatttcaca       300
catactagag aaagaggaga aatactagat ggcttcctcc gaagacgtta tcaaagagtt       360
catgcgtttc aaagttcgta tggaaggttc cgttaacggt cacgagttcg aaatcgaagg       420
tgaaggtgaa ggtcgtccgt acgaaggtac ccagaccgct aaactgaaag ttaccaaagg       480
tggtccgctg ccgttcgctt gggacatcct gtccccgcag ttccagtacg gttccaaagc       540
ttacgttaaa cacccggctg acatcccgga ctacctgaaa ctgtccttcc cggaaggttt       600
caaatgggaa cgtgttatga acttcgaaga cggtggtgtt gttaccgtta cccaggactc       660
ctccctgcaa gacggtgagt tcatctacaa agttaaactg cgtggtacca acttcccgtc       720
cgacggtccg gttatgcaga aaaaaaccat ggggttggga gcttccaccg aacgtatgta       780
cccggaagac ggtgctctga aaggtgaaat caaaatgcgt ctgaaactga agacggtgg       840
```

-continued

```
tcactacgac gctgaagtta aaaccaccta catggctaaa aaaccggttc agctgccggg      900
tgcttacaaa accgacatca aactggacat cacctcccac aacgaagact acaccatcgt      960
tgaacagtac gaacgtgctg aaggtcgtca ctccaccggt gcttaataac gctgatagtg     1020
ctagtgtaga tcgctactag agccaggcat caaataaaac gaaaggctca gtcgaaagac     1080
tgggcctttc gttttatctg ttgtttgtcg gtgaacgctc tctactagag tcacactggc     1140
tcaccttcgg gtgggccttt ctgcgtttat atactagtag cggccgctgc agggtctctt     1200
ctaagattac tggttcttct ggtaacgata cccaaggttc tttgattact tactctggtg     1260
gtgctagagg ttagccgaga cgactgacca tttaaatcat acctgacctc catagcagaa     1320
agtcaaaagc ctccgaccgg aggcttttga cttgatcggc acgtaagagg ttccaacttt     1380
caccataatg aaataagatc actaccgggc gtattttttg agttatcgag attttcagga     1440
gctaaggaag ctaaaatgag ccatattcaa cgggaaacgt cttgctcgag gccgcgatta     1500
aattccaaca tggatgctga tttatatggg tataaatggg ctcgcgataa tgtcgggcaa     1560
tcaggtgcga caatctatcg attgtatggg aagcccgatg cgccagagtt gtttctgaaa     1620
catggcaaag gtagcgttgc caatgatgtt acagatgaga tggtcaggct aaactggctg     1680
acggaattta tgcctcttcc gaccatcaag cattttatcc gtactcctga tgatgcatgg     1740
ttactcacca ctgcgatccc agggaaaaca gcattccagg tattagaaga atatcctgat     1800
tcaggtgaaa atattgttga tgcgctggca gtgttcctgc gccggttgca ttcgattcct     1860
gtttgtaatt gtcctttaa cggcgatcgc gtatttcgtc tcgctcaggc gcaatcacga     1920
atgaataacg gtttggttgg tgcgagtgat tttgatgacg agcgtaatgg ctggcctgtt     1980
gaacaagtct ggaaagaaat gcataagctt ttgccattct caccggattc agtcgtcact     2040
catggtgatt tctcacttga taaccttatt tttgacgagg ggaaattaat aggttgtatt     2100
gatgttggac gagtcggaat cgcagaccga taccaggatc ttgccatcct atggaactgc     2160
ctcggtgagt tttctccttc attacagaaa cggctttttc aaaaatatgg tattgataat     2220
cctgatatga ataaattgca gtttcacttg atgctcgatg agtttttcta atgagggccc     2280
aaatgtaatc acctggctca ccttcgggtg ggcctttctg cgttgctggc gtttttccat     2340
aggctccgcc cccctgacga gcatcacaaa aatcgatgct caagtcagag gtggcgaaac     2400
ccgacaggac tataaagata ccaggcgttt ccccctggaa gctccctcgt gcgctctcct     2460
gttccgaccc tgccgcttac cggatacctg tccgcctttc tcccttcggg aagcgtggcg     2520
ctttctcata gctcacgctg taggtatctc agttcggtgt aggtcgttcg ctccaagctg     2580
ggctgtgtgc acgaaccccc cgttcagccc gaccgctgcg ccttatccgg taactatcgt     2640
cttgagtcca acccggtaag acacgactta tcgccactgg cagcagccac tggtaacagg     2700
attagcagag cgaggtatgt aggcggtgct acagagttct tgaagtggtg gcctaactac     2760
ggctacacta agaacagt atttggtatc tgcgctctgc tgaagccagt tacctcggaa     2820
aaagagttgg tagctcttga tccggcaaac aaaccaccgc tggtagcggt ggtttttttg     2880
tttgcaagca gcagattacg cgcagaaaaa aaggatctca agaagatcct ttgatttttct     2940 accg                                                                  2944
```

```
<210> SEQ ID NO 40
<211> LENGTH: 1864
<212> TYPE: DNA
<213> ORGANISM: Artificial Sequence
<220> FEATURE:
```

<223> OTHER INFORMATION: HcKan_P-Pcon3 plasmid

<400> SEQUENCE: 40
aagaaaggcc cacccgtgaa ggtgagccag tgagttgatt gcagtccagt tacgctggag          60
tccgtctcgg gctggcttcc caaccttacc agagggcgcc ccagctggca attccgacgt         120
cctgacagct agctcagtcc taggtataat gctagcgaat tcaaaagatc ttttaagaag         180
gagatataca tgatgcgaga cgactgacca tttaaatcat acctgacctc catagcagaa         240
agtcaaaagc ctccgaccgg aggcttttga cttgatcggc acgtaagagg ttccaacttt         300
caccataatg aaataagatc actaccgggc gtattttttg agttatcgag attttcagga         360
gctaaggaag ctaaaatgag ccatattcaa cgggaaacgt cttgctcgag gccgcgatta         420
aattccaaca tggatgctga tttatatggg tataaatggg ctcgcgataa tgtcgggcaa         480
tcaggtgcga caatctatcg attgtatggg aagcccgatg cgccagagtt gtttctgaaa         540
catggcaaag gtagcgttgc caatgatgtt acagatgaga tggtcaggct aaactggctg         600
acggaattta tgcctcttcc gaccatcaag cattttatcc gtactcctga tgatgcatgg         660
ttactcacca ctgcgatccc agggaaaaca gcattccagg tattagaaga atatcctgat         720
tcaggtgaaa atattgttga tgcgctggca gtgttcctgc gccggttgca ttcgattcct         780
gtttgtaatt gtccttttaa cggcgatcgc gtatttcgtc tcgctcaggc gcaatcacga         840
atgaataacg gtttggttgg tgcgagtgat tttgatgacg agcgtaatgg ctggcctgtt         900
gaacaagtct ggaaagaaat gcataagctt ttgccattct caccggattc agtcgtcact         960
catggtgatt tctcacttga taaccttatt tttgacgagg ggaaattaat aggttgtatt        1020
gatgttggac gagtcggaat cgcagaccga taccaggatc ttgccatcct atggaactgc        1080
ctcggtgagt tttctccttc attacagaaa cggctttttc aaaaatatgg tattgataat        1140
cctgatatga ataaattgca gtttcacttg atgctcgatg agtttttcta atgagggccc        1200
aaatgtaatc acctggctca ccttcgggtg ggcctttctg cgttgctggc gttttttccat       1260 aggctccgcc cccctgacga gcatcacaaa aatcgatgct caagtcagag gtggcgaaac        1320
ccgacaggac tataaagata ccaggcgttt ccccctggaa gctccctcgt gcgctctcct        1380
gttccgaccc tgccgcttac cggatacctg tccgcctttc tcccttcggg aagcgtggcg        1440
ctttctcata gctcacgctg taggtatctc agttcggtgt aggtcgttcg ctccaagctg        1500
ggctgtgtgc acgaaccccc cgttcagccc gaccgctgcg ccttatccgg taactatcgt        1560
cttgagtcca acccggtaag acacgactta tcgccactgg cagcagccac tggtaacagg        1620
attagcagag cgaggtatgt aggcggtgct acagagttct tgaagtggtg gcctaactac        1680
ggctacacta agaagacagt atttggtatc tgcgctctgc tgaagccagt tacctcggaa        1740
aaagagttgg tagctcttga tccggcaaac aaaccaccgc tggtagcggt ggtttttttg        1800
tttgcaagca gcagattacg cgcagaaaaa aaggatctca agaagatcct ttgattttct        1860
accg                                                                     1864

<210> SEQ ID NO 41
<211> LENGTH: 1864
<212> TYPE: DNA
<213> ORGANISM: Artificial Sequence
<220> FEATURE:
<223> OTHER INFORMATION: HcKan_P-Pcon4 plasmid

<400> SEQUENCE: 41
aagaaaggcc cacccgtgaa ggtgagccag tgagttgatt gcagtccagt tacgctggag          60

-continued

```
tccgtctcgg gctggcttcc caaccttacc agagggcgcc ccagctggca attccgacgt     120
ctttacggct agctcagtcc taggtactat gctagcgaat tcaaaagatc ttttaagaag     180
gagatataca tgatgcgaga cgactgacca tttaaatcat acctgacctc catagcagaa     240
agtcaaaagc ctccgaccgg aggcttttga cttgatcggc acgtaagagg ttccaacttt     300
caccataatg aaataagatc actaccgggc gtattttttg agttatcgag attttcagga     360
gctaaggaag ctaaaatgag ccatattcaa cgggaaacgt cttgctcgag gccgcgatta     420
aattccaaca tggatgctga tttatatggg tataaatggg ctcgcgataa tgtcgggcaa     480
tcaggtgcga caatctatcg attgtatggg aagcccgatg cgccagagtt gtttctgaaa     540
catggcaaag gtagcgttgc caatgatgtt acagatgaga tggtcaggct aaactggctg     600
acggaattta tgcctcttcc gaccatcaag cattttatcc gtactcctga tgatgcatgg     660
ttactcacca ctgcgatccc agggaaaaca gcattccagg tattagaaga atatcctgat     720
tcaggtgaaa atattgttga tgcgctggca gtgttcctgc gccggttgca ttcgattcct     780
gtttgtaatt gtccttttaa cggcgatcgc gtatttcgtc tcgctcaggc gcaatcacga     840
atgaataacg gtttggttgg tgcgagtgat tttgatgacg agcgtaatgg ctggcctgtt     900
gaacaagtct ggaaagaaat gcataagctt ttgccattct caccggattc agtcgtcact     960
catggtgatt tctcacttga taaccttatt tttgacgagg ggaaattaat aggttgtatt    1020
gatgttggac gagtcggaat cgcagaccga taccaggatc ttgccatcct atggaactgc    1080
ctcggtgagt tttctccttc attacagaaa cggctttttc aaaaatatgg tattgataat    1140
cctgatatga ataaattgca gtttcacttg atgctcgatg agtttttcta atgagggccc    1200
aaatgtaatc acctggctca ccttcgggtg ggcctttctg cgttgctggc gtttttccat    1260
aggctccgcc cccctgacga gcatcacaaa aatcgatgct caagtcagag gtggcgaaac    1320
ccgacaggac tataaagata ccaggcgttt ccccctggaa gctccctcgt gcgctctcct    1380
gttccgaccc tgccgcttac cggatacctg tccgcctttc tcccttcggg aagcgtggcg    1440
ctttctcata gctcacgctg taggtatctc agttcggtgt aggtcgttcg ctccaagctg    1500
ggctgtgtgc acgaaccccc cgttcagccc gaccgctgcg ccttatccgg taactatcgt    1560
cttgagtcca acccggtaag acacgactta tcgccactgg cagcagccac tggtaacagg    1620
attagcagag cgaggtatgt aggcggtgct acagagttct tgaagtggtg gcctaactac    1680
ggctacacta agaacagt atttggtatc tgcgctctgc tgaagccagt tacctcggaa       1740
aaagagttgg tagctcttga tccggcaaac aaaccaccgc tggtagcggt ggtttttttg    1800
tttgcaagca gcagattacg cgcagaaaaa aaggatctca agaagatcct ttgatttct      1860 accg                                                                 1864
```

<210> SEQ ID NO 42
<211> LENGTH: 1864
<212> TYPE: DNA
<213> ORGANISM: Artificial Sequence
<220> FEATURE:
<223> OTHER INFORMATION: HcKan_P-Pcon5 plasmid

<400> SEQUENCE: 42

```
aagaaaggcc cacccgtgaa ggtgagccag tgagttgatt gcagtccagt tacgctggag      60
tccgtctcgg gctggcttcc caaccttacc agagggcgcc ccagctggca attccgacgt     120
ctttatggct agctcagtcc taggtacaat gctagcgaat tcaaaagatc ttttaagaag     180
```

-continued

```
gagatataca tgatgcgaga cgactgacca tttaaatcat acctgacctc catagcagaa     240
agtcaaaagc ctccgaccgg aggcttttga cttgatcggc acgtaagagg ttccaacttt     300
caccataatg aaataagatc actaccgggc gtatttttg agttatcgag attttcagga      360
gctaaggaag ctaaaatgag ccatattcaa cgggaaacgt cttgctcgag gccgcgatta     420
aattccaaca tggatgctga tttatatggg tataaatggg ctcgcgataa tgtcgggcaa     480
tcaggtgcga caatctatcg attgtatggg aagcccgatg cgccagagtt gtttctgaaa     540
catggcaaag gtagcgttgc caatgatgtt acagatgaga tggtcaggct aaactggctg     600
acggaattta tgcctcttcc gaccatcaag cattttatcc gtactcctga tgatgcatgg     660
ttactcacca ctgcgatccc agggaaaaca gcattccagg tattagaaga atatcctgat     720
tcaggtgaaa atattgttga tgcgctggca gtgttcctgc gccggttgca ttcgattcct     780
gtttgtaatt gtccttttaa cggcgatcgc gtatttcgtc tcgctcaggc gcaatcacga     840
atgaataacg gtttggttgg tgcgagtgat tttgatgacg agcgtaatgg ctggcctgtt     900
gaacaagtct ggaaagaaat gcataagctt ttgccattct caccggattc agtcgtcact     960
catggtgatt tctcacttga taaccttatt tttgacgagg ggaaattaat aggttgtatt    1020
gatgttggac gagtcggaat cgcagaccga taccaggatc ttgccatcct atggaactgc    1080
ctcggtgagt tttctccttc attacagaaa cggctttttc aaaaatatgg tattgataat    1140
cctgatatga ataaattgca gtttcacttg atgctcgatg agtttttcta atgagggccc    1200
aaatgtaatc acctggctca ccttcgggtg ggcctttctg cgttgctggc gtttttccat    1260
aggctccgcc cccctgacga gcatcacaaa aatcgatgct caagtcagag gtggcgaaac    1320
ccgacaggac tataaagata ccaggcgttt cccctggaa gctccctcgt gcgctctcct     1380
gttccgaccc tgccgcttac cggatacctg tccgcctttc tcccttcggg aagcgtggcg    1440
ctttctcata gctcacgctg taggtatctc agttcggtgt aggtcgttcg ctccaagctg    1500
ggctgtgtgc acgaacccccc cgttcagccc gaccgctgcg ccttatccgg taactatcgt    1560
cttgagtcca acccggtaag acacgactta tcgccactgg cagcagccac tggtaacagg    1620
attagcagag cgaggtatgt aggcggtgct acagagttct tgaagtggtg gcctaactac    1680
ggctacacta gaagaacagt atttggtatc tgcgctctgc tgaagccagt tacctcggaa    1740
aaagagttgg tagctcttga tccggcaaac aaaccaccgc tggtagcggt ggtttttttg    1800
tttgcaagca gcagattacg cgcagaaaaa aaggatctca agaagatcct ttgatttttct   1860 accg                                                                 1864
```

```
<210> SEQ ID NO 43
<211> LENGTH: 3301
<212> TYPE: DNA
<213> ORGANISM: Artificial Sequence
<220> FEATURE:
<223> OTHER INFORMATION: HcKan_P-LacI+PT7 plasmid

<400> SEQUENCE: 43
```

```
aagaaaggcc cacccgtgaa ggtgagccag tgagttgatt gcagtccagt tacgctggag      60
tccgtctcgg gcttcactgc ccgctttcca gtcgggaaac ctgtcgtgcc agctgcatta     120
atgaatcggc caacgcgcgg ggagaggcgg tttgcgtatt gggcgccagg gtggtttttc     180
ttttcaccag tgaaacggc aacagctgat tgcccttcac cgcctggccc tgagagagtt      240
gcagcaagcg gtccacgctg gtttgcccca gcaggcgaaa atcctgtttg atggtggtta     300
acggcgggat ataacatgag ctgtcttcgg tatcgtcgta tcccactacc gagatatccg     360
```

-continued

```
caccaacgcg cagcccggac tcggtaatgg cgcgcattgc gcccagcgcc atctgatcgt       420
tggcaaccag catcgcagtg ggaacgatgc cctcattcag catttgcatg gtttgttgaa       480
aaccggacat ggcactccag tcgccttccc gttccgctat cggctgaatt tgattgcgag       540
tgagatattt atgccagcca gccagacgca gacgcgccga gacagaactt aatgggcccg       600
ctaacagcgc gatttgctgg tgacccaatg cgaccagatg ctccacgccc agtcgcgtac       660
cgtcttcatg ggagaaaata atactgttga tgggtgtctg gtcagagaca tcaagaaata       720
acgccggaac attagtgcag gcagcttcca cagcaatggc atcctggtca tccagcggat       780
agttaatgat cagcccactg acgcgttgcg cgagaagatt gtgcaccgcc gctttacagg       840
cttcgacgcc gcttcgttct accatcgaca ccaccacgct ggcacccagt tgatcggcgc       900
gagatttaat cgccgcgaca atttgcgacg gcgcgtgcag ggccagactg gaggtggcaa       960
cgccaatcag caacgactgt ttgcccgcca gttgttgtgc cacgcggttg ggaatgtaat      1020
tcagctccgc catcgccgct tccactttt cccgcgtttt cgcagaaacg tggctggcct       1080
ggttcaccac gcgggaaacg gtctgataag agacaccggc atactctgcg acatcgtata      1140
acgttactgg tttcacattc accaccctga attgactctc ttccgggcgc tatcatgcca      1200
taccgcgaaa ggttttgcgc cattcgatgg tgtccgggat ctcgacgctc tcccttatgc      1260
gactcctgca ttaggaagca gcccagtagt aggttgaggc cgttgagcac cgccgccgca      1320
aggaatggtg catgcaagga gatggcgccc aacagtcccc cggccacggg gcctgccacc      1380
atacccacgc cgaaacaagc gctcatgagc ccgaagtggc gagcccgatc ttccccatcg      1440
gtgatgtcgg cgatataggc gccagcaacc gcacctgtgg cgccggtgat gccggccacg      1500
atgcgtccgg cgtagaggat cgagatctcg atcccgcgaa attaatacga ctcactatag      1560
gggaattgtg agcggataac aattccctc tagaaataat tttgtttaac tttaagaagg      1620
agatatacga tgcgagacga ctgaccattt aaatcatacc tgacctccat agcagaaagt      1680
caaaagcctc cgaccggagg cttttgactt gatcggcacg taagaggttc caactttcac      1740
cataatgaaa taagatcact accgggcgta ttttttgagt tatcgagatt ttcaggagct      1800
aaggaagcta aaatgagcca tattcaacgg gaaacgtctt gctcgaggcc gcgattaaat      1860
tccaacatgg atgctgattt atatgggtat aaatgggctc gcgataatgt cgggcaatca      1920
ggtgcgacaa tctatcgatt gtatgggaag cccgatgcgc cagagttgtt tctgaaacat      1980
ggcaaaggta gcgttgccaa tgatgttaca gatgagatgg tcaggctaaa ctggctgacg      2040
gaatttatgc ctcttccgac catcaagcat tttatccgta ctcctgatga tgcatggtta      2100
ctcaccactg cgatcccagg gaaaacagca ttccaggtat tagaagaata tcctgattca      2160
ggtgaaaata ttgttgatgc gctggcagtg ttcctgcgcc ggttgcattc gattcctgtt      2220
tgtaattgtc cttttaacgg cgatcgcgta tttcgtctcg ctcaggcgca atcacgaatg      2280
aataacggtt tggttggtgc gagtgatttt gatgacgagc gtaatggctg cctgttgaa       2340 caagtctgga aagaaatgca taagcttttg ccattctcac cggattcagt cgtcactcat      2400
ggtgatttct cacttgataa ccttattttt gacgagggga attaataggt tgtattgat       2460 gttggacgag tcggaatcgc agaccgatac caggatcttg ccatcctatg gaactgcctc      2520
ggtgagtttt ctccttcatt acagaaacgg ctttttcaaa aatatggtat tgataatcct      2580
gatatgaata aattgcagtt tcacttgatg ctcgatgagt ttttctaatg agggcccaaa      2640
tgtaatcacc tggctcacct tcgggtgggc ctttctgcgt tgctggcgtt tttccatagg      2700
```

```
ctccgccccc ctgacgagca tcacaaaaat cgatgctcaa gtcagaggtg gcgaaacccg    2760
acaggactat aaagatacca ggcgtttccc cctggaagct ccctcgtgcg ctctcctgtt    2820
ccgaccctgc cgcttaccgg atacctgtcc gcctttctcc cttcgggaag cgtggcgctt    2880
tctcatagct cacgctgtag gtatctcagt tcggtgtagg tcgttcgctc caagctgggc    2940
tgtgtgcacg aacccccgt tcagcccgac cgctgcgcct tatccggtaa ctatcgtctt    3000
gagtccaacc cggtaagaca cgacttatcg ccactggcag cagccactgg taacaggatt    3060
agcagagcga ggtatgtagg cggtgctaca gagttcttga agtggtggcc taactacggc    3120
tacactagaa gaacagtatt tggtatctgc gctctgctga agccagttac ctcggaaaaa    3180
gagttggtag ctcttgatcc ggcaaacaaa ccaccgctgg tagcggtggt ttttttgttt    3240
gcaagcagca gattacgcgc agaaaaaaag gatctcaaga agatcctttg attttctacc    3300
g                                                                    3301

<210> SEQ ID NO 44
<211> LENGTH: 2499
<212> TYPE: DNA
<213> ORGANISM: Artificial Sequence
<220> FEATURE:
<223> OTHER INFORMATION: HcKan_O-His6-meGFP plasmid

<400> SEQUENCE: 44
aagaaaggcc cacccgtgaa ggtgagccag tgagttgatt gcagtccagt tacgctggag      60
tccgtctcgg atgggttctt ctcatcatca ccatcaccat tcttctggga tgtctaaagg     120
tgaagaatta ttcactggtg ttgtcccaat tttggttgaa ttagatggtg atgttaatgg     180
tcacaaattt tctgtctccg gtgaaggtga aggtgatgct acttacggta aattgacctt     240
aaaatttatt tgtactactg gtaaattgcc agttccatgg ccaaccttag tcactacttt     300
aacttatggt gttcaatgtt tttctagata cccagatcat atgaaacaac atgacttttt     360
caagtctgcc atgccagaag ttatgttca agaaagaact atttttttca agatgacgg      420 taactacaag accagagctg aagtcaagtt tgaaggtgat accttagtta atagaatcga     480
attaaaaggt attgatttta agaagatgg taacattta ggtcacaaat tggaatacaa     540
ctataactct cacaatgttt acatcatggc tgacaaacaa aagaatggta tcaaagttaa     600
cttcaaaatt agacacaaca ttgaagatgg ttctgttcaa ttagctgacc attatcaaca     660
aaatactcca attggtgatg gtccagtctt gttaccagac aaccattact tatccactca     720
atctaaatta tccaaagatc aaacgaaaa gagagatcac atggtcttgt tagaatttgt     780
tactgctgct ggtattaccc atggtatgga tgaattgtac aaataatagc cgagacgact     840
gaccatttaa atcatacctg acctccatag cagaaagtca aaagcctccg accggaggct     900
tttgacttga tcggcacgta gaggttccaa ctttcacca taatgaaata agatcactac     960
cgggcgtatt ttttgagtta tcgagatttt caggagctaa ggaagctaaa atgagccata    1020
ttcaacggga aacgtcttgc tcgaggccgc gattaaattc caacatggat gctgatttat    1080
atgggtataa atgggctcgc gataatgtcg ggcaatcagg tgcgacaatc tatcgattgt    1140
atgggaagcc cgatgcgcca gagttgtttc tgaaacatgg caaaggtagc gttgccaatg    1200
atgttacaga tgagatggtc aggctaaact ggctgacgga atttatgcct cttccgacca    1260
tcaagcattt tatccgtact cctgatgatg catggttact caccactgcg atcccaggga    1320
aaacagcatt ccaggtatta gaagaatatc ctgattcagg tgaaatatt gttgatgcgc    1380 tggcagtgtt cctgcgccgg ttgcattcga ttcctgtttg taattgtcct tttaacggcg    1440
```

```
atcgcgtatt tcgtctcgct caggcgcaat cacgaatgaa taacggtttg gttggtgcga      1500
gtgattttga tgacgagcgt aatggctggc ctgttgaaca agtctggaaa gaaatgcata      1560
agcttttgcc attctcaccg gattcagtcg tcactcatgg tgatttctca cttgataacc      1620
ttatttttga cgaggggaaa ttaataggtt gtattgatgt tggacgagtc ggaatcgcag      1680
accgatacca ggatcttgcc atcctatgga actgcctcgg tgagttttct ccttcattac      1740
agaaacggct ttttcaaaaa tatggtattg ataatcctga tatgaataaa ttgcagtttc      1800
acttgatgct cgatgagttt ttctaatgag ggcccaaatg taatcacctg gctcaccttc      1860
gggtgggcct ttctgcgttg ctggcgtttt tccataggct ccgcccccct gacgagcatc      1920
acaaaaatcg atgctcaagt cagaggtggc gaaacccgac aggactataa agataccagg      1980
cgtttccccc tggaagctcc ctcgtgcgct ctcctgttcc gaccctgccg cttaccggat      2040
acctgtccgc ctttctccct tcgggaagcg tggcgctttc tcatagctca cgctgtaggt      2100
atctcagttc ggtgtaggtc gttcgctcca agctgggctg tgtgcacgaa ccccccgttc      2160
agcccgaccg ctgcgcctta tccggtaact atcgtcttga gtccaacccg gtaagacacg      2220
acttatcgcc actggcagca gccactggta acaggattag cagagcgagg tatgtaggcg      2280
gtgctacaga gttcttgaag tggtggccta actacggcta cactagaaga acagtatttg      2340
gtatctgcgc tctgctgaag ccagttacct cggaaaaaga gttggtagct cttgatccgg      2400
caaacaaacc accgctggta gcggtggttt ttttgtttgc aagcagcaga ttacgcgcag      2460
aaaaaaagga tctcaagaag atcctttgat tttctaccg                              2499
```

```
<210> SEQ ID NO 45
<211> LENGTH: 753
<212> TYPE: DNA
<213> ORGANISM: Artificial Sequence
<220> FEATURE:
<223> OTHER INFORMATION: HcKan_O-His6-meGFP nucleotide sequence of key
      ORF

<400> SEQUENCE: 45
atgggttctt ctcatcatca ccatcaccat tcttctggga tgtctaaagg tgaagaatta       60
ttcactggtg ttgtcccaat tttggttgaa ttagatggtg atgttaatgg tcacaaattt      120
tctgtctccg gtgaaggtga aggtgatgct acttacggta aattgacctt aaaatttatt      180
tgtactactg gtaaattgcc agttccatgg ccaaccttag tcactacttt aacttatggt      240
gttcaatgtt tttctagata cccagatcat atgaaacaac atgacttttt caagtctgcc      300
atgccagaag gttatgttca agaaagaact atttttttca agatgacggt aactacaag       360 accagagctg aagtcaagtt tgaaggtgat accttagtta atagaatcga attaaaaggt      420 attgattta aagaagatgg taacatttta ggtcacaaat tggaatacaa ctataactct       480
cacaatgttt acatcatggc tgacaaacaa aagaatggta tcaaagttaa cttcaaaatt      540
agacacaaca ttgaagatgg ttctgttcaa ttagctgacc attatcaaca aaatactcca      600
attggtgatg gtccagtctt gttaccagac aaccattact tatccactca atctaaatta      660 tccaagatc caaacgaaaa gagagatcac atggtcttgt tagaatttgt tactgctgct       720
ggtattaccc atggtatgga tgaattgtac aaa                                    753
```

```
<210> SEQ ID NO 46
<211> LENGTH: 251
<212> TYPE: PRT
<213> ORGANISM: Artificial Sequence
```

<220> FEATURE:
<223> OTHER INFORMATION: HcKan_O-His6-meGFP amino acid sequence of key
      ORF

<400> SEQUENCE: 46

Met Gly Ser Ser His His His His His His Ser Ser Gly Met Ser Lys
1               5                   10                  15

Gly Glu Glu Leu Phe Thr Gly Val Val Pro Ile Leu Val Glu Leu Asp
            20                  25                  30

Gly Asp Val Asn Gly His Lys Phe Ser Val Ser Gly Glu Gly Glu Gly
        35                  40                  45

Asp Ala Thr Tyr Gly Lys Leu Thr Leu Lys Phe Ile Cys Thr Thr Gly
    50                  55                  60

Lys Leu Pro Val Pro Trp Pro Thr Leu Val Thr Thr Leu Thr Tyr Gly
65                  70                  75                  80

Val Gln Cys Phe Ser Arg Tyr Pro Asp His Met Lys Gln His Asp Phe
                85                  90                  95

Phe Lys Ser Ala Met Pro Glu Gly Tyr Val Gln Glu Arg Thr Ile Phe
            100                 105                 110

Phe Lys Asp Asp Gly Asn Tyr Lys Thr Arg Ala Glu Val Lys Phe Glu
        115                 120                 125

Gly Asp Thr Leu Val Asn Arg Ile Glu Leu Lys Gly Ile Asp Phe Lys
    130                 135                 140

Glu Asp Gly Asn Ile Leu Gly His Lys Leu Glu Tyr Asn Tyr Asn Ser
145                 150                 155                 160

His Asn Val Tyr Ile Met Ala Asp Lys Gln Lys Asn Gly Ile Lys Val
                165                 170                 175

Asn Phe Lys Ile Arg His Asn Ile Glu Asp Gly Ser Val Gln Leu Ala
            180                 185                 190

Asp His Tyr Gln Gln Asn Thr Pro Ile Gly Asp Gly Pro Val Leu Leu
        195                 200                 205

Pro Asp Asn His Tyr Leu Ser Thr Gln Ser Lys Leu Ser Lys Asp Pro
    210                 215                 220

Asn Glu Lys Arg Asp His Met Val Leu Leu Glu Phe Val Thr Ala Ala
225                 230                 235                 240

Gly Ile Thr His Gly Met Asp Glu Leu Tyr Lys
                245                 250

<210> SEQ ID NO 47
<211> LENGTH: 2658
<212> TYPE: DNA
<213> ORGANISM: Artificial Sequence
<220> FEATURE:
<223> OTHER INFORMATION: HcKan_O-UmuD1-40-meGFP-S2CP plasmid

<400> SEQUENCE: 47
aagaaaggcc cacccgtgaa ggtgagccag tgagttgatt gcagtccagt tacgctggag      60
tccgtctcgg atgctgttta tcaaacctgc cgatctgcgt gaaattgtta cctttccgct     120
gtttagcgat ctggttcagt gtggtttttcc gagtccggca gcagattatg ttgaacagcg     180
tattgatctg agcagcggta tgtctaaagg tgaagaatta ttcactggtg ttgtcccaat     240
tttggttgaa ttagatggtg atgttaatgg tcacaaattt tctgtctccg gtgaaggtga     300
aggtgatgct acttacggta aattgacctt aaaatttatt tgtactactg gtaaattgcc     360
agttccatgg ccaaccttag tcactacttt aacttatggt gttcaatgtt tttctagata     420
cccagatcat atgaaacaac atgacttttt caagtctgcc atgccagaag ttatgttca     480

-continued

```
agaaagaact attttttttca aagatgacgg taactacaag accagagctg aagtcaagtt      540
tgaaggtgat accttagtta atagaatcga attaaaaggt attgatttta aagaagatgg      600
taacatttta ggtcacaaat tggaatacaa ctataactct cacaatgttt acatcatggc      660
tgacaaacaa aagaatggta tcaaagttaa cttcaaaatt agacacaaca ttgaagatgg      720
ttctgttcaa ttagctgacc attatcaaca aaatactcca attggtgatg gtccagtctt      780
gttaccagac aaccattact tatccactca atctaaatta tccaaagatc caaacgaaaa      840
gagagatcac atggtcttgt tagaatttgt tactgctgct ggtattaccc atggtatgga      900
tgaattgtac aaatctaaga ttactggttc ttctggtaac gatacccaag gttctttgat      960
tacttactct ggtggtgcta gaggttagcc gagacgactg accatttaaa tcatacctga     1020
cctccatagc agaaagtcaa aagcctccga ccgggaggctt ttgacttgat cggcacgtaa     1080
gaggttccaa ctttcaccat aatgaaataa gatcactacc gggcgtattt tttgagttat     1140
cgagattttc aggagctaag gaagctaaaa tgagccatat tcaacgggaa acgtcttgct     1200
cgaggccgcg attaaattcc aacatggatg ctgatttata tgggtataaa tgggctcgcg     1260
ataatgtcgg gcaatcaggt gcgacaatct atcgattgta tgggaagccc gatgcgccag     1320
agttgtttct gaaacatggc aaaggtagcg ttgccaatga tgttacagat gagatggtca     1380
ggctaaactg gctgacggaa tttatgcctc ttccgaccat caagcatttt atccgtactc     1440
ctgatgatgc atggttactc accactgcga tcccagggaa aacagcattc caggtattag     1500
aagaatatcc tgattcaggt gaaaatattg ttgatgcgct ggcagtgttc ctgcgccggt     1560
tgcattcgat tcctgtttgt aattgtcctt ttaacggcga tcgcgtattt cgtctcgctc     1620
aggcgcaatc acgaatgaat aacggtttgg ttggtgcgag tgattttgat gacgagcgta     1680
atggctggcc tgttgaacaa gtctggaaag aaatgcataa gcttttgcca ttctcaccgg     1740
attcagtcgt cactcatggt gatttctcac ttgataacct tattttttgac gaggggaaat     1800 taataggttg tattgatgtt ggacgagtcg gaatcgcaga ccgataccag gatcttgcca     1860
tcctatggaa ctgcctcggt gagttttctc cttcattaca gaaacggctt tttcaaaaat     1920
atggtattga taatcctgat atgaataaat tgcagtttca cttgatgctc gatgagtttt     1980
tctaatgagg gcccaaatgt aatcacctgg ctcaccttcg ggtgggcctt tctgcgttgc     2040
tggcgttttt ccataggctc cgcccccctg acgagcatca caaaaatcga tgctcaagtc     2100
agaggtggcg aaacccgaca ggactataaa gataccaggc gtttccccct ggaagctccc     2160
tcgtgcgctc tcctgttccg accctgccgc ttaccggata cctgtccgcc tttctccctt     2220
cgggaagcgt ggcgctttct catagctcac gctgtaggta tctcagttcg gtgtaggtcg     2280
ttcgctccaa gctgggctgt gtgcacgaac cccccgttca gcccgaccgc tgcgccttat     2340
ccggtaacta tcgtcttgag tccaacccgg taagacacga cttatcgcca ctggcagcag     2400
ccactggtaa caggattagc agagcgaggt atgtaggcgg tgctacagag ttcttgaagt     2460
ggtggcctaa ctacggctac actagaagaa cagtatttgg tatctgcgct ctgctgaagc     2520
cagttacctc ggaaaaagag ttggtagctc ttgatccggc aaacaaacca ccgctggtag     2580
cggtggtttt tttgtttgca agcagcagat tacgcgcaga aaaaaaggat ctcaagaaga     2640
tcctttgatt ttctaccg                                                   2658
```

<210> SEQ ID NO 48
<211> LENGTH: 915
<212> TYPE: DNA

-continued

<213> ORGANISM: Artificial Sequence
<220> FEATURE:
<223> OTHER INFORMATION: HcKan_O-UmuD1-40-meGFP-S2CP nucl;eotide
      sequence of key ORF

<400> SEQUENCE: 48

```
atgctgttta tcaaacctgc cgatctgcgt gaaattgtta cctttccgct gtttagcgat       60
ctggttcagt gtggttttcc gagtccggca gcagattatg ttgaacagcg tattgatctg      120
agcagcggta tgtctaaagg tgaagaatta ttcactggtg ttgtcccaat tttggttgaa      180
ttagatggtg atgttaatgg tcacaaattt tctgtctccg gtgaaggtga aggtgatgct      240
acttacggta aattgacctt aaaatttatt tgtactactg gtaaattgcc agttccatgg      300
ccaaccttag tcactacttt aacttatggt gttcaatgtt tttctagata cccagatcat      360
atgaaacaac atgacttttt caagtctgcc atgccagaag ttatgttca agaaagaact      420 attttttca aagatgacgg taactacaag accagagctg aagtcaagtt tgaaggtgat      480
accttagtta atagaatcga attaaaaggt attgatttta agaagatgg taacattta      540 ggtcacaaat tggaatacaa ctataactct cacaatgttt acatcatggc tgacaaacaa      600
aagaatggta tcaaagttaa cttcaaaatt agacacaaca ttgaagatgg ttctgttcaa      660
ttagctgacc attatcaaca aaatactcca attggtgatg tccagtctt gttaccagac      720 aaccattact tatccactca atctaaatta tccaaagatc aaacgaaaa gagagatcac      780 atggtcttgt tagaatttgt tactgctgct ggtattaccc atggtatgga tgaattgtac      840
aaatctaaga ttactggttc ttctggtaac gatacccaag gttctttgat tacttactct      900
ggtggtgcta gaggt                                                      915
```

<210> SEQ ID NO 49
<211> LENGTH: 305
<212> TYPE: PRT
<213> ORGANISM: Artificial Sequence
<220> FEATURE:
<223> OTHER INFORMATION: HcKan_O-UmuD1-40-meGFP-S2CP amino acid sequence
      of key ORF

<400> SEQUENCE: 49

```
Met Leu Phe Ile Lys Pro Ala Asp Leu Arg Glu Ile Val Thr Phe Pro
1               5                   10                  15

Leu Phe Ser Asp Leu Val Gln Cys Gly Phe Pro Ser Pro Ala Ala Asp
            20                  25                  30

Tyr Val Glu Gln Arg Ile Asp Leu Ser Ser Gly Met Ser Lys Gly Glu
        35                  40                  45

Glu Leu Phe Thr Gly Val Val Pro Ile Leu Val Glu Leu Asp Gly Asp
    50                  55                  60

Val Asn Gly His Lys Phe Ser Val Ser Gly Glu Gly Glu Gly Asp Ala
65                  70                  75                  80

Thr Tyr Gly Lys Leu Thr Leu Lys Phe Ile Cys Thr Thr Gly Lys Leu
                85                  90                  95

Pro Val Pro Trp Pro Thr Leu Val Thr Thr Leu Thr Tyr Gly Val Gln
            100                 105                 110

Cys Phe Ser Arg Tyr Pro Asp His Met Lys Gln His Asp Phe Phe Lys
        115                 120                 125

Ser Ala Met Pro Glu Gly Tyr Val Gln Glu Arg Thr Ile Phe Phe Lys
    130                 135                 140

Asp Asp Gly Asn Tyr Lys Thr Arg Ala Glu Val Lys Phe Glu Gly Asp
145                 150                 155                 160
```

```
Thr Leu Val Asn Arg Ile Glu Leu Lys Gly Ile Asp Phe Lys Glu Asp
            165                 170                 175

Gly Asn Ile Leu Gly His Lys Leu Glu Tyr Asn Tyr Asn Ser His Asn
            180                 185                 190

Val Tyr Ile Met Ala Asp Lys Gln Lys Asn Gly Ile Lys Val Asn Phe
            195                 200                 205

Lys Ile Arg His Asn Ile Glu Asp Gly Ser Val Gln Leu Ala Asp His
    210                 215                 220

Tyr Gln Gln Asn Thr Pro Ile Gly Asp Gly Pro Val Leu Leu Pro Asp
225                 230                 235                 240

Asn His Tyr Leu Ser Thr Gln Ser Lys Leu Ser Lys Asp Pro Asn Glu
            245                 250                 255

Lys Arg Asp His Met Val Leu Leu Glu Phe Val Thr Ala Ala Gly Ile
            260                 265                 270

Thr His Gly Met Asp Glu Leu Tyr Lys Ser Lys Ile Thr Gly Ser Ser
            275                 280                 285

Gly Asn Asp Thr Gln Gly Ser Leu Ile Thr Tyr Ser Gly Gly Ala Arg
    290                 295                 300

Gly
305
```

```
<210> SEQ ID NO 50
<211> LENGTH: 2586
<212> TYPE: DNA
<213> ORGANISM: Artificial Sequence
<220> FEATURE:
<223> OTHER INFORMATION: HcKan_O-UmuD1-40-meGFP plasmid

<400> SEQUENCE: 50
aagaaaggcc cacccgtgaa ggtgagccag tgagttgatt gcagtccagt tacgctggag     60
tccgtctcgg atgctgttta tcaaacctgc cgatctgcgt gaaattgtta cctttccgct    120
gtttagcgat ctggttcagt gtggttttcc gagtccggca gcagattatg ttgaacagcg    180
tattgatctg agcagcggta tgtctaaagg tgaagaatta ttcactggtg ttgtcccaat    240
tttggttgaa ttagatggtg atgttaatgg tcacaaattt tctgtctccg gtgaaggtga    300
aggtgatgct acttacggta aattgacctt aaaatttatt tgtactactg gtaaattgcc    360
agttccatgg ccaaccttag tcactacttt aacttatggt gttcaatgtt tttctagata    420
cccagatcat atgaaacaac atgacttttt caagtctgcc atgccagaag gttatgttca    480
agaaagaact atttttttca agatgacgg taactacaag accagagctg aagtcaagtt    540
tgaaggtgat accttagtta atagaatcga attaaaaggt attgatttta agaagatgg    600 taacatttta ggtcacaaat tggaatacaa ctataactct cacaatgttt acatcatggc    660
tgacaaacaa aagaatggta tcaaagttaa cttcaaaatt agacacaaca ttgaagatgg    720
ttctgttcaa ttagctgacc attatcaaca aaatactcca attggtgatg tccagtctt    780 gttaccagac aaccattact tatccactca atctaaatta tccaaagatc caaacgaaaa    840
gagagatcac atggtcttgt tagaatttgt tactgctgct ggtattaccc atggtatgga    900
tgaattgtac aaatagccga gacgactgac catttaaatc atacctgacc tccatagcag    960
aaagtcaaaa gcctccgacc ggaggctttt gacttgatcg gcacgtaaga ggttccaact   1020
ttcaccataa tgaaataaga tcactaccgg gcgtattttt tgagttatcg agatttcag    1080 gagctaagga agctaaaatg agccatattc aacgggaaac gtcttgctcg aggccgcgat   1140
```

-continued

```
taaattccaa catggatgct gatttatatg ggtataaatg ggctcgcgat aatgtcgggc    1200
aatcaggtgc gacaatctat cgattgtatg ggaagcccga tgcgccagag ttgtttctga    1260
aacatggcaa aggtagcgtt gccaatgatg ttacagatga gatggtcagg ctaaactggc    1320
tgacggaatt tatgcctctt ccgaccatca agcattttat ccgtactcct gatgatgcat    1380
ggttactcac cactgcgatc ccagggaaaa cagcattcca ggtattagaa gaatatcctg    1440
attcaggtga aaatattgtt gatgcgctgg cagtgttcct gcgccggttg cattcgattc    1500
ctgtttgtaa ttgtcctttt aacggcgatc gcgtatttcg tctcgctcag gcgcaatcac    1560
gaatgaataa cggtttggtt ggtgcgagtg attttgatga cgagcgtaat ggctggcctg    1620
ttgaacaagt ctggaaagaa atgcataagc ttttgccatt ctcaccggat tcagtcgtca    1680
ctcatggtga tttctcactt gataacctta ttttttgacga ggggaaatta ataggttgta    1740
ttgatgttgg acgagtcgga atcgcagacc gataccagga tcttgccatc ctatggaact    1800
gcctcggtga gttttctcct tcattacaga aacggctttt tcaaaaatat ggtattgata    1860
atcctgatat gaataaattg cagtttcact tgatgctcga tgagtttttc taatgagggc    1920
ccaaatgtaa tcacctggct caccttcggg tgggcctttc tgcgttgctg gcgtttttcc    1980
ataggctccg ccccctgac gagcatcaca aaaatcgatg ctcaagtcag aggtggcgaa    2040
acccgacagg actataaaga taccaggcgt ttcccctgg aagctccctc gtgcgctctc    2100
ctgttccgac cctgccgctt accggatacc tgtccgcctt tctcccttcg ggaagcgtgg    2160
cgctttctca tagctcacgc tgtaggtatc tcagttcggt gtaggtcgtt cgctccaagc    2220
tgggctgtgt gcacgaaccc cccgttcagc ccgaccgctg cgccttatcc ggtaactatc    2280
gtcttgagtc caacccggta agacacgact tatcgccact ggcagcagcc actggtaaca    2340
ggattagcag agcgaggtat gtaggcggtg ctacagagtt cttgaagtgg tggcctaact    2400
acggctacac tagaagaaca gtatttggta tctgcgctct gctgaagcca gttacctcgg    2460
aaaaagagtt ggtagctctt gatccggcaa acaaaccacc gctggtagcg gtggtttttt    2520
tgtttgcaag cagcagatta cgcgcagaaa aaaaggatct caagaagatc ctttgatttt    2580
ctaccg                                                                  2586
```

```
<210> SEQ ID NO 51
<211> LENGTH: 843
<212> TYPE: DNA
<213> ORGANISM: Artificial Sequence
<220> FEATURE:
<223> OTHER INFORMATION: HcKan_O-UmuD1-40-meGFP nucleotide sequence of
      key ORF

<400> SEQUENCE: 51
atgctgttta tcaaacctgc cgatctgcgt gaaattgtta cctttccgct gtttagcgat     60
ctggttcagt gtggtttttcc gagtccggca gcagattatg ttgaacagcg tattgatctg    120
agcagcggta tgtctaaagg tgaagaatta ttcactggtt ttgtcccaat tttggttgaa    180
ttagatggtg atgttaatgg tcacaaattt tctgtctccg gtgaaggtga aggtgatgct    240
acttacggta aattgacctt aaaatttatt tgtactactg gtaaattgcc agttccatgg    300
ccaaccttag tcactacttt aacttatggt gttcaatgtt tttctagata cccagatcat    360
atgaaacaac atgacttttt caagtctgcc atgccagaag ttatgttca gaaagaact     420 attttttttca aagatgacgg taactacaag accagagctg aagtcaagtt tgaaggtgat    480
accttagtta atagaatcga attaaaaggt attgatttta agaagatgg taacatttta    540
```

-continued ggtcacaaat tggaatacaa ctataactct cacaatgttt acatcatggc tgacaaacaa          600
aagaatggta tcaaagttaa cttcaaaatt agacacaaca ttgaagatgg ttctgttcaa          660
ttagctgacc attatcaaca aaatactcca attggtgatg tccagtctt gttaccagac           720 aaccattact tatccactca atctaaatta tccaaagatc caaacgaaaa gagagatcac          780
atggtcttgt tagaatttgt tactgctgct ggtattaccc atggtatgga tgaattgtac          840
aaa                                                                        843

<210> SEQ ID NO 52
<211> LENGTH: 281
<212> TYPE: PRT
<213> ORGANISM: Artificial Sequence
<220> FEATURE:
<223> OTHER INFORMATION: HcKan_O-UmuD1-40-meGFP amino acid sequence of
      key ORF

<400> SEQUENCE: 52

Met Leu Phe Ile Lys Pro Ala Asp Leu Arg Glu Ile Val Thr Phe Pro
1               5                   10                  15

Leu Phe Ser Asp Leu Val Gln Cys Gly Phe Pro Ser Pro Ala Ala Asp
            20                  25                  30

Tyr Val Glu Gln Arg Ile Asp Leu Ser Ser Gly Met Ser Lys Gly Glu
        35                  40                  45

Glu Leu Phe Thr Gly Val Val Pro Ile Leu Val Glu Leu Asp Gly Asp
    50                  55                  60

Val Asn Gly His Lys Phe Ser Val Ser Gly Glu Gly Glu Gly Asp Ala
65                  70                  75                  80

Thr Tyr Gly Lys Leu Thr Leu Lys Phe Ile Cys Thr Thr Gly Lys Leu
                85                  90                  95

Pro Val Pro Trp Pro Thr Leu Val Thr Thr Leu Thr Tyr Gly Val Gln
            100                 105                 110

Cys Phe Ser Arg Tyr Pro Asp His Met Lys Gln His Asp Phe Phe Lys
        115                 120                 125

Ser Ala Met Pro Glu Gly Tyr Val Gln Glu Arg Thr Ile Phe Phe Lys
    130                 135                 140

Asp Asp Gly Asn Tyr Lys Thr Arg Ala Glu Val Lys Phe Glu Gly Asp
145                 150                 155                 160

Thr Leu Val Asn Arg Ile Glu Leu Lys Gly Ile Asp Phe Lys Glu Asp
                165                 170                 175

Gly Asn Ile Leu Gly His Lys Leu Glu Tyr Asn Tyr Asn Ser His Asn
            180                 185                 190

Val Tyr Ile Met Ala Asp Lys Gln Lys Asn Gly Ile Lys Val Asn Phe
        195                 200                 205

Lys Ile Arg His Asn Ile Glu Asp Gly Ser Val Gln Leu Ala Asp His
    210                 215                 220

Tyr Gln Gln Asn Thr Pro Ile Gly Asp Gly Pro Val Leu Leu Pro Asp
225                 230                 235                 240

Asn His Tyr Leu Ser Thr Gln Ser Lys Leu Ser Lys Asp Pro Asn Glu
                245                 250                 255

Lys Arg Asp His Met Val Leu Leu Glu Phe Val Thr Ala Ala Gly Ile
            260                 265                 270

Thr His Gly Met Asp Glu Leu Tyr Lys
        275                 280

<210> SEQ ID NO 53

-continued

```
<211> LENGTH: 2037
<212> TYPE: DNA
<213> ORGANISM: Artificial Sequence
<220> FEATURE:
<223> OTHER INFORMATION: HcKan_O-CsoS1A plasmid

<400> SEQUENCE: 53
aagaaaggcc cacccgtgaa ggtgagccag tgagttgatt gcagtccagt tacgctggag      60
tccgtctcgg atggctgatg ttactggtat tgctttgggt atgattgaaa ctagaggttt     120
ggttccagct atcgaagctg ctgacgctat gaccaaggcc gctgaagtca gattggtcgg     180
tagacaattt gttggaggtg gttacgtcac tgtttttggt cgtggtgaaa ccggtgccgt     240
taacgctgct gttagagctg gtgctgatgc ttgtgaaaga gttggtgacg gtttagttgc     300
tgcccacatt attgccagag tccactctga agttgaaaac attttgccaa aggctccaca     360
ggcttagccg agacgactga ccatttaaat catacctgac ctccatagca gaaagtcaaa     420
agcctccgac cggaggcttt tgacttgatc ggcacgtaag aggttccaac tttcaccata     480
atgaaataag atcactaccg ggcgtatttt ttgagttatc gagattttca ggagctaagg     540
aagctaaaat gagccatatt caacgggaaa cgtcttgctc gaggccgcga ttaaattcca     600
acatggatgc tgatttatat gggtataaat gggctcgcga taatgtcggg caatcaggtg     660
cgacaatcta tcgattgtat gggaagcccg atgcgccaga gttgtttctg aaacatggca     720
aaggtagcgt tgccaatgat gttacagatg agatggtcag gctaaactgg ctgacggaat     780
ttatgcctct tccgaccatc aagcatttta tccgtactcc tgatgatgca tggttactca     840
ccactgcgat cccagggaaa acagcattcc aggtattaga agaatatcct gattcaggtg     900
aaaatattgt tgatgcgctg gcagtgttcc tgcgccggtt gcattcgatt cctgtttgta     960
attgtccttt aacggcgat cgcgtatttc gtctcgctca ggcgcaatca cgaatgaata    1020
acggtttggt tggtgcgagt gattttgatg acgagcgtaa tggctggcct gttgaacaag    1080
tctggaaaga aatgcataag cttttgccat tctcaccgga ttcagtcgtc actcatggtg    1140
atttctcact tgataacctt attttttgacg aggggaaatt aataggttgt attgatgttg    1200
gacgagtcgg aatcgcagac cgataccagg atcttgccat cctatggaac tgcctcggtg    1260
agttttctcc ttcattacag aaacggcttt ttcaaaaata tggtattgat aatcctgata    1320
tgaataaatt gcagtttcac ttgatgctcg atgagttttt ctaatgaggg cccaaatgta    1380
atcacctggc tcaccttcgg gtgggccttt ctgcgttgct ggcgtttttc cataggctcc    1440
gcccccctga cgagcatcac aaaaatcgat gctcaagtca gaggtggcga acccgacag    1500 gactataaag ataccaggcg tttccccctg gaagctccct cgtgcgctct cctgttccga    1560
ccctgccgct taccggatac ctgtccgcct ttctcccttc gggaagcgtg gcgctttctc    1620
atagctcacg ctgtaggtat ctcagttcgg tgtaggtcgt tcgctccaag ctgggctgtg    1680
tgcacgaacc ccccgttcag cccgaccgct gcgccttatc cggtaactat cgtcttgagt    1740
ccaacccggt aagacacgac ttatcgccac tggcagcagc cactggtaac aggattagca    1800
gagcgaggta tgtaggcggt gctacagagt tcttgaagtg gtggcctaac tacggctaca    1860
ctagaagaac agtatttggt atctgcgctc tgctgaagcc agttacctcg gaaaaagagt    1920
tggtagctct tgatccggca acaaaccac cgctggtagc ggtggttttt ttgtttgcaa    1980
gcagcagatt acgcgcagaa aaaaaggatc tcaagaagat cctttgattt tctaccg      2037
```

```
<210> SEQ ID NO 54
<211> LENGTH: 1992
```

```
<212> TYPE: DNA
<213> ORGANISM: Artificial Sequence
<220> FEATURE:
<223> OTHER INFORMATION: HcKan_O-CsoS4A plasmid

<400> SEQUENCE: 54
aagaaaggcc cacccgtgaa ggtgagccag tgagttgatt gcagtccagt tacgctggag        60
tccgtctcgg atgaagatca tgcaagttga aaagactttg gtttctacca acagaattgc       120
tgatatgggt cacaagccat tgttggttgt ttgggaaaaa cctggtgctc caagacaagt       180
tgctgttgat gctattggtt gtattccagg tgactgggtt ttgtgtgttg gttcttctgc       240
tgccagagaa gctgctggtt ccaagtctta cccatctgat ttgactatca tcggtattat       300
tgaccaatgg aacggtgaat agccgagacg actgaccatt taaatcatac ctgacctcca       360
tagcagaaag tcaaaagcct ccgaccggag gcttttgact tgatcggcac gtaagaggtt       420
ccaactttca ccataatgaa ataagatcac taccgggcgt attttttgag ttatcgagat       480
tttcaggagc taaggaagct aaaatgagcc atattcaacg ggaaacgtct tgctcgaggc       540
cgcgattaaa ttccaacatg gatgctgatt tatatgggta taaatgggct cgcgataatg       600
tcgggcaatc aggtgcgaca atctatcgat tgtatgggaa gcccgatgcg ccagagttgt       660
ttctgaaaca tggcaaaggt agcgttgcca atgatgttac agatgagatg gtcaggctaa       720
actggctgac ggaatttatg cctcttccga ccatcaagca ttttatccgt actcctgatg       780
atgcatggtt actcaccact gcgatcccag ggaaaacagc attccaggta ttagaagaat       840
atcctgattc aggtgaaaat attgttgatg cgctggcagt gttcctgcgc cggttgcatt       900
cgattcctgt ttgtaattgt ccttttaacg gcgatcgcgt atttcgtctc gctcaggcgc       960
aatcacgaat gaataacggt ttggttggtg cgagtgattt tgatgacgag cgtaatggct      1020
ggcctgttga acaagtctgg aaagaaatgc ataagctttt gccattctca ccggattcag      1080
tcgtcactca tggtgatttc tcacttgata accttatttt tgacgagggg aaattaatag      1140
gttgtattga tgttggacga gtcggaatcg cagaccgata ccaggatctt gccatcctat      1200
ggaactgcct cggtgagttt tctccttcat tacagaaacg ctttttcaa aaatatggta      1260 ttgataatcc tgatatgaat aaattgcagt ttcacttgat gctcgatgag ttttttctaat     1320 gagggcccaa atgtaatcac ctggctcacc ttcgggtggg cctttctgcg ttgctggcgt      1380
ttttccatag gctccgcccc cctgacgagc atcacaaaaa tcgatgctca agtcagaggt      1440
ggcgaaaccc gacaggacta taaagatacc aggcgtttcc ccctggaagc tccctcgtgc      1500
gctctcctgt tccgaccctg ccgcttaccg gatacctgtc cgcctttctc ccttcgggaa      1560
gcgtggcgct ttctcatagc tcacgctgta ggtatctcag ttcggtgtag tcgttcgct       1620 ccaagctggg ctgtgtgcac gaaccccccg ttcagcccga ccgctgcgcc ttatccggta      1680
actatcgtct tgagtccaac ccggtaagac acgacttatc gccactggca gcagccactg      1740
gtaacaggat tagcagagcg aggtatgtag gcggtgctac agagttcttg aagtggtggc      1800
ctaactacgg ctacactaga agaacagtat ttggtatctg cgctctgctg aagccagtta      1860
cctcggaaaa agagttggta gctcttgatc cggcaaacaa accaccgctg gtagcggtgg      1920
tttttttgtt tgcaagcagc agattacgcg cagaaaaaaa ggatctcaag aagatccttt      1980
gattttctac cg                                                           1992

<210> SEQ ID NO 55
<211> LENGTH: 1896
<212> TYPE: DNA
```

<213> ORGANISM: Artificial Sequence
<220> FEATURE:
<223> OTHER INFORMATION: HcKan_T-TT7 plasmid

<400> SEQUENCE: 55
aagaaaggcc cacccgtgaa ggtgagccag tgagttgatt gcagtccagt tacgctggag        60
tccgtctcgt agctaacaaa gcccgaaagg aagctgagtt ggctgctgcc accgctgagc       120
aataactagc ataacccctt ggggcctcta aacgggtctt gaggggtttt ttgctgaaag       180
gaggaactat atccggatat cccgcaagag gcccggcagt acccctccga gacgactgac       240
catttaaatc atacctgacc tccatagcag aaagtcaaaa gcctccgacc ggaggctttt       300
gacttgatcg gcacgtaaga ggttccaact ttcaccataa tgaaataaga tcactaccgg       360
gcgtattttt tgagttatcg agattttcag gagctaagga agctaaaatg agccatattc       420
aacgggaaac gtcttgctcg aggccgcgat taaattccaa catggatgct gatttatatg       480
ggtataaatg gctcgcgat aatgtcgggc aatcaggtgc gacaatctat cgattgtatg       540
ggaagcccga tgcgccagag ttgtttctga acatggcaa aggtagcgtt gccaatgatg       600
ttacagatga gatggtcagg ctaaactggc tgacggaatt tatgcctctt ccgaccatca       660
agcattttat ccgtactcct gatgatgcat ggttactcac cactgcgatc ccagggaaaa       720
cagcattcca ggtattagaa gaatatcctg attcaggtga aaatattgtt gatgcgctgg       780
cagtgttcct gcgccggttg cattcgattc ctgtttgtaa ttgtcctttt aacggcgatc       840
gcgtatttcg tctcgctcag gcgcaatcac gaatgaataa cggtttggtt ggtgcgagtg       900
attttgatga cgagcgtaat ggctggcctg ttgaacaagt ctggaaagaa atgcataagc       960
ttttgccatt ctcaccggat tcagtcgtca ctcatggtga tttctcactt gataacctta      1020
tttttgacga ggggaaatta ataggttgta ttgatgttgg acgagtcgga atcgcagacc      1080
gataccagga tcttgccatc ctatggaact gcctcggtga gtttct cct tcattacaga      1140 aacggctttt tcaaaaatat ggtattgata atcctgatat gaataaattg cagtttcact      1200
tgatgctcga tgagtttttc taatgagggc ccaaatgtaa tcacctggct caccttcggg      1260
tgggcctttc tgcgttgctg gcgtttttcc ataggctccg ccccc ctgac gagcatcaca      1320 aaaatcgatg ctcaagtcag aggtggcgaa acccgacagg actataaaga taccaggcgt      1380 ttcccctgg aagctccctc gtgcgctctc ctgttccgac cctgccgctt accggatacc      1440
tgtccgcctt tctcccttcg ggaagcgtgg cgctttctca tagctcacgc tgtaggtatc      1500
tcagttcggt gtaggtcgtt cgctccaagc tgggctgtgt gcacgaaccc cccgttcagc      1560
ccgaccgctg cgccttatcc ggtaactatc gtcttgagtc caacccggta agacacgact      1620
tatcgccact ggcagcagcc actggtaaca ggattagcag agcgaggtat gtaggcggtg      1680
ctacagagtt cttgaagtgg tggcctaact acggctacac tagaagaaca gtatttggta      1740
tctgcgctct gctgaagcca gttacctcgg aaaaagagtt ggtagctctt gatccggcaa      1800
acaaaccacc gctggtagcg gtggtttttt tgtttgcaag cagcagatta cgcgcagaaa      1860
aaaaggatct caagaagatc ctttgatttt ctaccg                                1896

<210> SEQ ID NO 56
<211> LENGTH: 2943
<212> TYPE: DNA
<213> ORGANISM: Artificial Sequence
<220> FEATURE:
<223> OTHER INFORMATION: pES1 plasmid

<400> SEQUENCE: 56

-continued

```
agagacccaa gacactgcgg ctttgtatgt gtccgcagcg cccgccgcag tctcacgccc        60
ggagcgtagc gaccgagtga gctagctatt tgtttatttt tctaaataca ttcaaatatg       120
tatccgctca tgagacaata accctgataa atgcttcaat aatattgaaa aaggaagagt       180
atgagggaag cggtgatcgc cgaagtatcg actcaactat cagaggtagt tggcgtcatc       240
gagcgccatc tcgaaccgac gttgctggcc gtacatttgt acggctccgc agtggatggc       300
ggcctgaagc cacacagtga tattgatttg ctggttacgg tgaccgtaag gcttgatgaa       360
acaacgcggc gagctttgat caacgacctt ttggaaactt cggcttcccc tggagagagc       420
gagattctcc gcgctgtaga agtcaccatt gttgtgcacg acgacatcat tccgtggcgt       480
tatccagcta agcgcgaact gcaatttgga gaatggcagc gcaatgacat tcttgcaggt       540
atcttcgagc cagccacgat cgacattgat ctggctatct tgctgacaaa agcaagagaa       600
catagcgttg ccttggtagg tccagcggcg gaggaactct ttgatccggt tcctgaacag       660
gatctatttg aggcgctaaa tgaaacctta acgctatgga actcgccgcc cgactgggct       720
ggcgatgagc gaaatgtagt gcttacgttg tcccgcattt ggtacagcgc agtaaccggc       780
aaaatcgcgc cgaaggatgt cgctgccgac tgggcaatgg agcgcctgcc ggcccagtat       840
cagcccgtca tacttgaagc tagacaggct tatcttggac aagaagaaga tcgcttggcc       900
tcgcgcgcag atcagttgga agaatttgtc cactacgtga aaggcgagat caccaaggta       960
gtcggcaaat aatgtctaac aattcgttca agccgagggg ccgcaagatc cggccacgat      1020
gacccggtcg tcggttcagg gcagggtcgt taaatagccg cttatgtcta ttgctggttt      1080
accggtttat tgactaccgg aagcagtgtg accgtgtgct tctcaaatgc ctgaggtttc      1140
agcaaaaaac ccctcaagac ccgtttagag gccccaaggg gttatgctag ttattgctca      1200
gcggcgtcag accccgtaga aaagatcaaa ggatcttctt gagatccttt ttttctgcgc      1260
gtaatctgct gcttgcaaac aaaaaaacca ccgctaccag cggtggtttg tttgccggat      1320
caagagctac caactctttt tccgaaggta actggcttca gcagagcgca gataccaaat      1380
actgtccttc tagtgtagcc gtagttaggc caccacttca agaactctgt agcaccgcct      1440
acatacctcg ctctgctaat cctgttacca gtggctgctg ccagtggcga taagtcgtgt      1500
cttaccgggt tggactcaag acgatagtta ccggataagg cgcagcggtc gggctgaacg      1560 ggggggttcgt gcacacagcc cagcttggag cgaacgacct acaccgaact gagatacct a   1620 cagcgtgagc tatgagaaag cgccacgctt cccgaaggga gaaaggcgga caggtatccg      1680
gtaagcggca gggtcggaac aggagagcgc acgagggagc ttccagggg g aaacgcctgg     1740 tatctttata gtcctgtcgg gtttcgccac ctctgacttg agcgtcgatt tttgtgatgc      1800
tcgtcagggg ggcggagcct atggaaaaac gccagcaacg cggcctttt t acggttcctg     1860 gccgttggca gtgactcggt ctctacctgg ctagagacgg caatacgcaa accgcctctc      1920
cccgcgcgtt ggccgattca ttaatgcagc tggcacgaca ggtttcccga ctggaaagcg      1980
ggcagtgagc gcaacgcaat taatgtgagt tagctcactc attaggcacc ccaggcttta      2040
cactttatgc ttccggctcg tatgttgtgt ggaattgtga gcggataaca atttcacaca      2100
tactagagaa agaggagaaa tactagatgg cttcctccga gacgttatc aaagagttca       2160 tgcgtttcaa agttcgtatg gaaggttccg ttaacggtca cgagttcgaa atcgaaggtg      2220
aaggtgaagg tcgtccgtac gaaggtaccc agaccgctaa actgaaagtt accaaaggtg      2280
gtccgctgcc gttcgcttgg gacatcctgt ccccgcagtt ccagtacggt tccaaagctt      2340
```

```
acgttaaaca cccggctgac atcccggact acctgaaact gtccttcccg gaaggtttca      2400
aatgggaacg tgttatgaac ttcgaagacg gtggtgttgt taccgttacc caggactcct      2460
ccctgcaaga cggtgagttc atctacaaag ttaaactgcg tggtaccaac ttcccgtccg      2520
acggtccggt tatgcagaaa aaaccatggt gttgggaagc ttccaccgaa cgtatgtacc      2580
cggaagacgg tgctctgaaa ggtgaaatca aaatgcgtct gaaactgaaa gacggtggtc      2640
actacgacgc tgaagttaaa accacctaca tggctaaaaa accggttcag ctgccgggtg      2700
cttacaaaac cgacatcaaa ctggacatca cctcccacaa cgaagactac accatcgttg      2760
aacagtacga acgtgctgaa ggtcgtcact ccaccggtgc ttaataacgc tgatagtgct      2820
agtgtagatc gctactagag ccaggcatca aataaaacga aaggctcagt cgaaagactg      2880
ggcctttcgt tttatctgtt gtttgtcggt gaacgctctc tactagagcg tctcacctct      2940
gag                                                                    2943

<210> SEQ ID NO 57
<211> LENGTH: 2943
<212> TYPE: DNA
<213> ORGANISM: Artificial Sequence
<220> FEATURE:
<223> OTHER INFORMATION: pES2 plasmid

<400> SEQUENCE: 57
agagacccaa gacactgcgg ctttgtatgt gtccgcagcg cccgccgcag tctcacgccc        60
ggagcgtagc gaccgagtga gctagctatt tgtttatttt tctaaataca ttcaaatatg       120
tatccgctca tgagacaata accctgataa atgcttcaat aatattgaaa aaggaagagt       180
atgagggaag cggtgatcgc cgaagtatcg actcaactat cagaggtagt tggcgtcatc       240
gagcgccatc tcgaaccgac gttgctggcc gtacatttgt acggctccgc agtggatggc       300
ggcctgaagc cacacagtga tattgatttg ctggttacgg tgaccgtaag gcttgatgaa       360
acaacgcggc gagctttgat caacgacctt ttggaaactt cggcttcccc tggagagagc       420
gagattctcc gcgctgtaga agtcaccatt gttgtgcacg acgacatcat tccgtggcgt       480
tatccagcta agcgcgaact gcaatttgga gaatggcagc gcaatgacat tcttgcaggt       540
atcttcgagc cagccacgat cgacattgat ctggctatct tgctgacaaa agcaagagaa       600
catacgcttg ccttggtagg tccagcggcg gaggaactct ttgatccggt tcctgaacag       660
gatctatttg aggcgctaaa tgaaacctta acgctatgga actcgccgcc cgactgggct       720
ggcgatgagc gaaatgtagt gcttacgttg tcccgcattt ggtacagcgc agtaaccggc       780
aaaatcgcgc cgaaggatgt cgctgccgac tgggcaatgg agcgcctgcc ggcccagtat       840
cagcccgtca tacttgaagc tagacaggct tatcttggac aagaagaaga tcgcttggcc       900
tcgcgcgcag atcagttgga agaatttgtc cactacgtga aaggcgagat caccaaggta       960
gtcggcaaat aatgtctaac aattcgttca agccgagggg ccgcaagatc cggccacgat      1020
gacccggtcg tcggttcagg gcagggtcgt taaatagccg cttatgtcta ttgctggttt      1080
accggtttat tgactaccgg aagcagtgtg accgtgtgct tctcaaatgc ctgaggtttc      1140
agcaaaaaac ccctcaagac ccgtttagag gccccagggg gttatgctag ttattgctca      1200
gcggcgtcag accccgtaga aaagatcaaa ggatcttctt gagatccttt ttttctgcgc      1260
gtaatctgct gcttgcaaac aaaaaaacca ccgctaccag cggtggtttg tttgccggat      1320
caagagctac caactctttt tccgaaggta actggcttca gcagagcgca gataccaaat      1380
actgtccttc tagtgtagcc gtagttaggc caccacttca agaactctgt agcaccgcct      1440
```

-continued

```
acatacctcg ctctgctaat cctgttacca gtggctgctg ccagtggcga taagtcgtgt    1500
cttaccgggt tggactcaag acgatagtta ccggataagg cgcagcggtc gggctgaacg    1560
gggggttcgt gcacacagcc cagcttggag cgaacgacct acaccgaact gagataccta    1620
cagcgtgagc tatgagaaag cgccacgctt cccgaaggga gaaaggcgga caggtatccg    1680
gtaagcggca gggtcggaac aggagagcgc acgagggagc ttccaggggg aaacgcctgg    1740
tatctttata gtcctgtcgg gtttcgccac ctctgacttg agcgtcgatt tttgtgatgc    1800
tcgtcagggg ggcggagcct atggaaaaac gccagcaacg cggccttttt acggttcctg    1860
gccgttggca gtgactcggt ctctacctgg ctagagacgg caatacgcaa accgcctctc    1920
cccgcgcgtt ggccgattca ttaatgcagc tggcacgaca ggtttcccga ctggaaagcg    1980
ggcagtgagc gcaacgcaat taatgtgagt tagctcactc attaggcacc ccaggcttta    2040
cactttatgc ttccggctcg tatgttgtgt ggaattgtga gcggataaca atttcacaca    2100
tactagagaa agaggagaaa tactagatgg cttcctccga agacgttatc aaagagttca    2160
tgcgtttcaa agttcgtatg gaaggttccg ttaacggtca cgagttcgaa atcgaaggtg    2220
aaggtgaagg tcgtccgtac gaaggtaccc agaccgctaa actgaaagtt accaaaggtg    2280
gtccgctgcc gttcgcttgg gacatcctgt ccccgcagtt ccagtacggt tccaaagctt    2340
acgttaaaca cccggctgac atcccggact acctgaaact gtccttcccg gaaggtttca    2400
aatgggaacg tgttatgaac ttcgaagacg gtggtgttgt taccgttacc caggactcct    2460
ccctgcaaga cggtgagttc atctacaaag ttaaactgcg tggtaccaac ttcccgtccg    2520
acggtccggt tatgcagaaa aaaaccatgg gttgggaagc ttccaccgaa cgtatgtacc    2580
cggaagacgg tgctctgaaa ggtgaaatca aaatgcgtct gaaactgaaa gacggtggtc    2640
actacgacgc tgaagttaaa accacctaca tggctaaaaa accggttcag ctgccgggtg    2700
cttacaaaac cgacatcaaa ctggacatca cctcccacaa cgaagactac accatcgttg    2760
aacagtacga acgtgctgaa ggtcgtcact ccaccggtgc ttaataacgc tgatagtgct    2820
agtgtagatc gctactagag ccaggcatca aataaaacga aaggctcagt cgaaagactg    2880
ggcctttcgt tttatctgtt gtttgtcggt gaacgctctc tactagagcg tctcacctca    2940
ggc                                                                  2943
```

<210> SEQ ID NO 58
<211> LENGTH: 2943
<212> TYPE: DNA
<213> ORGANISM: Artificial Sequence
<220> FEATURE:
<223> OTHER INFORMATION: pES3 plasmid
<400> SEQUENCE: 58

```
agagacccaa gacactgcgg ctttgtatgt gtccgcagcg cccgccgcag tctcacgccc      60
ggagcgtagc gaccgagtga gctagctatt tgtttatttt tctaaataca ttcaaatatg     120
tatccgctca tgagacaata accctgataa atgcttcaat aatattgaaa aaggaagagt     180
atgagggaag cggtgatcgc cgaagtatcg actcaactat cagaggtagt tggcgtcatc     240
gagcgccatc tcgaaccgac gttgctggcc gtacatttgt acggctccgc agtggatggc     300
ggcctgaagc cacacagtga tattgatttg ctggttacgg tgaccgtaag gcttgatgaa     360
acaacgcggc gagctttgat caacgacctt ttggaaactt cggcttcccc tggagagagc     420
gagattctcc gcgctgtaga agtcaccatt gttgtgcacg acgacatcat tccgtggcgt     480
```

-continued

```
tatccagcta agcgcgaact gcaatttgga gaatggcagc gcaatgacat tcttgcaggt    540
atcttcgagc cagccacgat cgacattgat ctggctatct tgctgacaaa agcaagagaa    600
catagcgttg ccttggtagg tccagcggcg gaggaactct ttgatccggt tcctgaacag    660
gatctatttg aggcgctaaa tgaaacctta acgctatgga actcgccgcc cgactgggct    720
ggcgatgagc gaaatgtagt gcttacgttg tcccgcattt ggtacagcgc agtaaccggc    780
aaaatcgcgc cgaaggatgt cgctgccgac tgggcaatgg agcgcctgcc ggcccagtat    840
cagcccgtca tacttgaagc tagacaggct tatcttggac aagaagaaga tcgcttggcc    900
tcgcgcgcag atcagttgga agaatttgtc cactacgtga aaggcgagat caccaaggta    960
gtcggcaaat aatgtctaac aattcgttca agccgagggg ccgcaagatc cggccacgat   1020
gacccggtcg tcggttcagg gcagggtcgt taaatagccg cttatgtcta ttgctggttt   1080
accggtttat tgactaccgg aagcagtgtg accgtgtgct tctcaaatgc ctgaggtttc   1140
agcaaaaaac ccctcaagac ccgtttagag gccccaaggg gttatgctag ttattgctca   1200
gcggcgtcag accccgtaga aaagatcaaa ggatcttctt gagatccttt ttttctgcgc   1260
gtaatctgct gcttgcaaac aaaaaaacca ccgctaccag cggtggtttg tttgccggat   1320
caagagctac caactctttt tccgaaggta actggcttca gcagagcgca gataccaaat   1380
actgtccttc tagtgtagcc gtagttaggc caccacttca agaactctgt agcaccgcct   1440
acatacctcg ctctgctaat cctgttacca gtggctgctg ccagtggcga taagtcgtgt   1500
cttaccgggt tggactcaag acgatagtta ccggataagg cgcagcggtc gggctgaacg   1560 ggggggttcgt gcacacagcc cagcttggag cgaacgacct acaccgaact gagatacccta  1620 cagcgtgagc tatgagaaag cgccacgctt cccgaaggga gaaaggcgga caggtatccg   1680
gtaagcggca gggtcggaac aggagagcgc acgagggagc ttccaggggg aaacgcctgg   1740
tatctttata gtcctgtcgg gtttcgccac ctctgacttg agcgtcgatt tttgtgatgc   1800
tcgtcagggg ggcggagcct atggaaaaac gccagcaacg cggcctttttt acggttcctg   1860 gccgttggca gtgactcggt ctctaggcgg ctagagacgg caatacgcaa accgcctcta   1920
gccgcgcgtt ggccgattca ttaatgcagc tggcacgaca ggtttcccga ctggaaagcg   1980
ggcagtgagc gcaacgcaat taatgtgagt tagctcactc attaggcacc ccaggcttta   2040
cactttatgc ttccggctcg tatgttgtgt ggaattgtga gcggataaca atttcacaca   2100
tactagagaa agaggagaaa tactagatgg cttcctccga agacgttatc aaagagttca   2160
tgcgtttcaa agttcgtatg gaaggttccg ttaacggtca cgagttcgaa atcgaaggtg   2220
aaggtgaagg tcgtccgtac gaaggtaccc agaccgctaa actgaaagtt accaaaggtg   2280
gtccgctgcc gttcgcttgg gacatcctgt ccccgcagtt ccagtacggt tccaaagctt   2340
acgttaaaca cccggctgac atcccggact acctgaaact gtccttcccg gaaggtttca   2400
aatgggaacg tgttatgaac ttcgaagacg gtggtgttgt taccgttacc caggactcct   2460
ccctgcaaga cggtgagttc atctacaaag ttaaactgcg tggtaccaac ttcccgtccg   2520
acggtccggt tatgcagaaa aaaaccatgg gttgggaagc ttccaccgaa cgtatgtacc   2580
cggaagacgg tgctctgaaa ggtgaaatca aaatgcgtct gaaactgaaa gacggtggtc   2640
actacgacgc tgaagttaaa accacctaca tggctaaaaa accggttcag ctgccgggtg   2700
cttacaaaac cgacatcaaa ctggacatca cctcccacaa cgaagactac accatcgttg   2760
aacagtacga acgtgctgaa ggtcgtcact ccaccggtgc ttaataacgc tgatagtgct   2820
agtgtagatc gctactagag ccaggcatca aataaaacga aaggctcagt cgaaagactg   2880
```

-continued

```
ggcctttcgt tttatctgtt gtttgtcggt gaacgctctc tactagagcg tctcacctct    2940
gag                                                                   2943

<210> SEQ ID NO 59
<211> LENGTH: 2943
<212> TYPE: DNA
<213> ORGANISM: Artificial Sequence
<220> FEATURE:
<223> OTHER INFORMATION: pES4 plasmid

<400> SEQUENCE: 59
agagacccaa gacactgcgg ctttgtatgt gtccgcagcg cccgccgcag tctcacgccc      60
ggagcgtagc gaccgagtga gctagctatt tgtttatttt tctaaataca ttcaaatatg     120
tatccgctca tgagacaata accctgataa atgcttcaat aatattgaaa aaggaagagt     180
atgagggaag cggtgatcgc cgaagtatcg actcaactat cagaggtagt tggcgtcatc     240
gagcgccatc tcgaaccgac gttgctggcc gtacatttgt acggctccgc agtggatggc     300
ggcctgaagc cacacagtga tattgatttg ctggttacgg tgaccgtaag gcttgatgaa     360
acaacgcggc gagctttgat caacgacctt ttggaaactt cggcttcccc tggagagagc     420
gagattctcc gcgctgtaga agtcaccatt gttgtgcacg acgacatcat tccgtggcgt     480
tatccagcta agcgcgaact gcaatttgga gaatggcagc gcaatgacat tcttgcaggt     540
atcttcgagc cagccacgat cgacattgat ctggctatct tgctgacaaa agcaagagaa     600
catagcgttg ccttggtagg tccagcggcg gaggaactct ttgatccggt tcctgaacag     660
gatctatttg aggcgctaaa tgaaacctta acgctatgga actcgccgcc cgactgggct     720
ggcgatgagc gaaatgtagt gcttacgttg tcccgcattt ggtacagcgc agtaaccggc     780
aaaatcgcgc cgaaggatgt cgctgccgac tgggcaatgg agcgcctgcc ggcccagtat     840
cagcccgtca tacttgaagc tagacaggct tatcttggac aagaagaaga tcgcttggcc     900
tcgcgcgcag atcagttgga agaatttgtc cactacgtga aaggcgagat caccaaggta     960
gtcggcaaat aatgtctaac aattcgttca agccgagggg ccgcaagatc cggccacgat    1020
gacccggtcg tcggttcagg gcagggtcgt taaatagccg cttatgtcta ttgctggttt    1080
accggtttat tgactaccgg aagcagtgtg accgtgtgct tctcaaatgc ctgaggtttc    1140
agcaaaaaac ccctcaagac ccgtttagag gccccaaggg gttatgctag ttattgctca    1200
gcggcgtcag accccgtaga aaagatcaaa ggatcttctt gagatccttt ttttctgcgc    1260
gtaatctgct gcttgcaaac aaaaaaacca ccgctaccag cggtggtttg tttgccggat    1320
caagagctac caactctttt tccgaaggta actggcttca gcagagcgca gataccaaat    1380
actgtccttc tagtgtagcc gtagttaggc caccacttca agaactctgt agcaccgcct    1440
acatacctcg ctctgctaat cctgttacca gtggctgctg ccagtggcga taagtcgtgt    1500
cttaccgggt tggactcaag acgatagtta ccggataagg cgcagcggtc gggctgaacg    1560
gggggttcgt gcacacagcc cagcttggag cgaacgacct acaccgaact gagatacctta   1620 cagcgtgagc tatgagaaag cgccacgctt cccgaaggga gaaaggcgga caggtatccg    1680
gtaagcggca gggtcggaac aggagagcgc acgagggagc ttccaggggg aaacgcctgg    1740
tatctttata gtcctgtcgg gtttcgccac ctctgacttg agcgtcgatt tttgtgatgc    1800
tcgtcagggg ggcggagcct atggaaaaac gccagcaacg cggccttttt acggttcctg    1860
gccgttggca gtgactcggt ctctaggcgg ctagagacgg caatacgcaa accgcctcta    1920
```

-continued

```
gccgcgcgtt ggccgattca ttaatgcagc tggcacgaca ggtttcccga ctggaaagcg      1980
ggcagtgagc gcaacgcaat taatgtgagt tagctcactc attaggcacc ccaggcttta      2040
cactttatgc ttccggctcg tatgttgtgt ggaattgtga gcggataaca atttcacaca      2100
tactagagaa agaggagaaa tactagatgg cttcctccga agacgttatc aaagagttca      2160
tgcgtttcaa agttcgtatg gaaggttccg ttaacggtca cgagttcgaa atcgaaggtg      2220
aaggtgaagg tcgtccgtac gaaggtaccc agaccgctaa actgaaagtt accaaaggtg      2280
gtccgctgcc gttcgcttgg gacatcctgt ccccgcagtt ccagtacggt tccaaagctt      2340
acgttaaaca cccggctgac atcccggact acctgaaact gtccttcccg gaaggtttca      2400
aatgggaacg tgttatgaac ttcgaagacg gtggtgttgt taccgttacc caggactcct      2460
ccctgcaaga cggtgagttc atctacaaag ttaaactgcg tggtaccaac ttcccgtccg      2520
acggtccggt tatgcagaaa aaaaccatgg gttgggaagc ttccaccgaa cgtatgtacc      2580
cggaagacgg tgctctgaaa ggtgaaatca aaatgcgtct gaaactgaaa gacggtggtc      2640
actacgacgc tgaagttaaa accacctaca tggctaaaaa accggttcag ctgccgggtg      2700
cttacaaaac cgacatcaaa ctggacatca cctcccacaa cgaagactac accatcgttg      2760
aacagtacga acgtgctgaa ggtcgtcact ccaccggtgc ttaataacgc tgatagtgct      2820
agtgtagatc gctactagag ccaggcatca aataaaacga aaggctcagt cgaaagactg      2880
ggcctttcgt tttatctgtt gtttgtcggt gaacgctctc tactagagcg tctcacctct      2940
gcc                                                                    2943

<210> SEQ ID NO 60
<211> LENGTH: 2943
<212> TYPE: DNA
<213> ORGANISM: Artificial Sequence
<220> FEATURE:
<223> OTHER INFORMATION: pES5 plasmid

<400> SEQUENCE: 60
agagacccaa gacactgcgg ctttgtatgt gtccgcagcg cccgccgcag tctcacgccc        60
ggagcgtagc gaccgagtga gctagctatt tgtttatttt tctaaataca ttcaaatatg       120
tatccgctca tgagacaata accctgataa atgcttcaat aatattgaaa aaggaagagt       180
atgagggaag cggtgatcgc cgaagtatcg actcaactat cagaggtagt tggcgtcatc       240
gagcgccatc tcgaaccgac gttgctggcc gtacatttgt acggctccgc agtggatggc       300
ggcctgaagc cacacagtga tattgatttg ctggttacgg tgaccgtaag gcttgatgaa       360
acaacgcggc gagctttgat caacgacctt ttggaaactt cggcttcccc tggagagagc       420
gagattctcc gcgctgtaga agtcaccatt gttgtgcacg acgacatcat ccgtggcgt        480 tatccagcta agcgcgaact gcaatttgga gaatggcagc gcaatgacat tcttgcaggt       540
atcttcgagc cagccacgat cgacattgat ctggctatct tgctgacaaa gcaagagaa        600 catagcgttg ccttggtagg tccagcggcg gaggaactct ttgatccggt tcctgaacag       660
gatctatttg aggcgctaaa tgaaacctta acgctatgga actcgccgcc cgactgggct       720
ggcgatgagc gaaatgtagt gcttacgttg tcccgcattt ggtacagcgc agtaaccggc       780
aaaatcgcgc cgaaggatgt cgctgccgac tgggcaatgg agcgcctgcc ggcccagtat       840
cagcccgtca tacttgaagc tagacaggct tatcttggac aagaagaaga tcgcttggcc       900
tcgcgcgcag atcagttgga agaatttgtc cactacgtga aaggcgagat caccaaggta       960
gtcggcaaat aatgtctaac aattcgttca agccgagggg ccgcaagatc cggccacgat      1020
```

-continued

```
gacccggtcg tcggttcagg gcagggtcgt taaatagccg cttatgtcta ttgctggttt      1080
accggtttat tgactaccgg aagcagtgtg accgtgtgct tctcaaatgc ctgaggtttc      1140
agcaaaaaac ccctcaagac ccgtttagag gccccaaggg gttatgctag ttattgctca      1200
gcggcgtcag acccgtaga aaagatcaaa ggatcttctt gagatccttt ttttctgcgc       1260
gtaatctgct gcttgcaaac aaaaaaacca ccgctaccag cggtggtttg tttgccggat      1320
caagagctac caactctttt tccgaaggta actggcttca gcagagcgca gataccaaat      1380
actgtccttc tagtgtagcc gtagttaggc caccacttca agaactctgt agcaccgcct      1440
acatacctcg ctctgctaat cctgttacca gtggctgctg ccagtggcga taagtcgtgt      1500
cttaccgggt tggactcaag acgatagtta ccggataagg cgcagcggtc gggctgaacg      1560
gggggttcgt gcacacagcc cagcttggag cgaacgacct acaccgaact gagataccta      1620
cagcgtgagc tatgagaaag cgccacgctt cccgaaggga gaaaggcgga caggtatccg      1680
gtaagcggca gggtcggaac aggagagcgc acgagggagc ttccaggggg aaacgcctgg      1740
tatctttata gtcctgtcgg gtttcgccac ctctgacttg agcgtcgatt tttgtgatgc      1800
tcgtcagggg ggcggagcct atggaaaaac gccagcaacg cggcctttt acggttcctg       1860 gccgttggca gtgactcggt ctcttgccgg ctagagacgg caatacgcaa accgcctcta      1920
gccgcgcgtt ggccgattca ttaatgcagc tggcacgaca ggtttcccga ctggaaagcg      1980
ggcagtgagc gcaacgcaat taatgtgagt tagctcactc attaggcacc ccaggcttta      2040
cactttatgc ttccggctcg tatgttgtgt ggaattgtga gcggataaca atttcacaca      2100
tactagagaa agaggagaaa tactagatgg cttcctccga agacgttatc aaagagttca      2160
tgcgtttcaa agttcgtatg gaaggttccg ttaacggtca cgagttcgaa atcgaaggtg      2220
aaggtgaagg tcgtccgtac gaaggtaccc agaccgctaa actgaaagtt accaaaggtg      2280
gtccgctgcc gttcgcttgg gacatcctgt ccccgcagtt ccagtacggt tccaaagctt      2340
acgttaaaca cccggctgac atcccggact acctgaaact gtccttcccg gaaggtttca      2400
aatgggaacg tgttatgaac ttcgaagacg gtggtgttgt taccgttacc caggactcct      2460
ccctgcaaga cggtgagttc atctacaaag ttaaactgcg tggtaccaac ttcccgtccg      2520
acggtccggt tatgcagaaa aaaaccatgg gttgggaagc ttccaccgaa cgtatgtacc      2580
cggaagacgg tgctctgaaa ggtgaaatca aaatgcgtct gaaactgaaa gacggtggtc      2640
actacgacgc tgaagttaaa accacctaca tggctaaaaa accggttcag ctgccgggtg      2700
cttacaaaac cgacatcaaa ctggacatca cctcccacaa cgaagactac accatcgttg      2760
aacagtacga acgtgctgaa ggtcgtcact ccaccggtgc ttaataacgc tgatagtgct      2820
agtgtagatc gctactagag ccaggcatca aataaaacga aaggctcagt cgaaagactg      2880
ggcctttcgt tttatctgtt gtttgtcggt gaacgctctc tactagagcg tctcacctct      2940
gag                                                                      2943
```

```
<210> SEQ ID NO 61
<211> LENGTH: 2943
<212> TYPE: DNA
<213> ORGANISM: Artificial Sequence
<220> FEATURE:
<223> OTHER INFORMATION: pES6 plasmid

<400> SEQUENCE: 61
agagacccaa gacactgcgg ctttgtatgt gtccgcagcg cccgccgcag tctcacgccc        60
```

-continued

```
ggagcgtagc gaccgagtga gctagctatt tgtttatttt tctaaataca ttcaaatatg      120
tatccgctca tgagacaata accctgataa atgcttcaat aatattgaaa aaggaagagt      180
atgagggaag cggtgatcgc cgaagtatcg actcaactat cagaggtagt tggcgtcatc      240
gagcgccatc tcgaaccgac gttgctggcc gtacatttgt acggctccgc agtggatggc      300
ggcctgaagc cacacagtga tattgatttg ctggttacgg tgaccgtaag gcttgatgaa      360
acaacgcggc gagctttgat caacgacctt ttggaaactt cggcttcccc tggagagagc      420
gagattctcc gcgctgtaga agtcaccatt gttgtgcacg acgacatcat tccgtggcgt      480
tatccagcta agcgcgaact gcaatttgga gaatggcagc gcaatgacat tcttgcaggt      540
atcttcgagc cagccacgat cgacattgat ctggctatct tgctgacaaa agcaagagaa      600
catagcgttg ccttggtagg tccagcggcg gaggaactct ttgatccggt tcctgaacag      660
gatctatttg aggcgctaaa tgaaacctta acgctatgga actcgccgcc cgactgggct      720
ggcgatgagc gaaatgtagt gcttacgttg tcccgcattt ggtacagcgc agtaaccggc      780
aaaatcgcgc cgaaggatgt cgctgccgac tgggcaatgg agcgcctgcc ggcccagtat      840
cagcccgtca tacttgaagc tagacaggct tatcttggac aagaagaaga tcgcttggcc      900
tcgcgcgcag atcagttgga agaatttgtc cactacgtga aaggcgagat caccaaggta      960
gtcggcaaat aatgtctaac aattcgttca agccgagggg ccgcaagatc cggccacgat     1020
gacccggtcg tcggttcagg gcagggtcgt taaatagccg cttatgtcta ttgctggttt     1080
accggtttat tgactaccgg aagcagtgtg accgtgtgct tctcaaatgc ctgaggtttc     1140
agcaaaaaac ccctcaagac ccgtttagag gccccaaggg gttatgctag ttattgctca     1200
gcggcgtcag acccgtaga aaagatcaaa ggatcttctt gagatccttt ttttctgcgc     1260
gtaatctgct gcttgcaaac aaaaaaacca ccgctaccag cggtggtttg tttgccggat     1320
caagagctac caactctttt tccgaaggta actggcttca gcagagcgca gataccaaat     1380
actgtccttc tagtgtagcc gtagttaggc caccacttca agaactctgt agcaccgcct     1440
acatacctcg ctctgctaat cctgttacca gtggctgctg ccagtggcga taagtcgtgt     1500
cttaccgggt tggactcaag acgatagtta ccggataagg cgcagcggtc gggctgaacg     1560
gggggttcgt gcacacagcc cagcttggag cgaacgacct acaccgaact gagatacctta     1620 cagcgtgagc tatgagaaag cgccacgctt cccgaaggga gaaaggcgga caggtatccg     1680
gtaagcggca gggtcggaac aggagagcgc acgagggagc ttccaggggg aaacgcctgg     1740
tatctttata gtcctgtcgg gtttcgccac ctctgacttg agcgtcgatt tttgtgatgc     1800
tcgtcagggg ggcggagcct atggaaaaac gccagcaacg cggcctttt acggttcctg     1860 gccgttggca gtgactcggt ctcttgccgg ctagagacgg caatacgcaa accgcctctc     1920
cccgcgcgtt ggccgattca ttaatgcagc tggcacgaca ggtttcccga ctggaaagcg     1980
ggcagtgagc gcaacgcaat taatgtgagt tagctcactc attaggcacc ccaggcttta     2040
cactttatgc ttccggctcg tatgttgtgt ggaattgtga gcggataaca atttcacaca     2100
tactagagaa agaggagaaa tactagatgg cttcctccga agacgttatc aaagagttca     2160
tgcgtttcaa agttcgtatg gaaggttccg ttaacggtca cgagttcgaa atcgaaggtg     2220
aaggtgaagg tcgtccgtac gaaggtaccc agaccgctaa actgaaagtt accaaaggtg     2280
gtccgctgcc gttcgcttgg gacatcctgt ccccgcagtt ccagtacggt tccaaagctt     2340
acgttaaaca cccggctgac atcccggact acctgaaact gtccttcccg gaaggtttca     2400
aatgggaacg tgttatgaac ttcgaagacg gtggtgttgt taccgttacc caggactcct     2460
```

```
ccctgcaaga cggtgagttc atctacaaag ttaaactgcg tggtaccaac ttcccgtccg       2520
acggtccggt tatgcagaaa aaaaccatgg gttgggaagc ttccaccgaa cgtatgtacc       2580
cggaagacgg tgctctgaaa ggtgaaatca aaatgcgtct gaaactgaaa gacggtggtc       2640
actacgacgc tgaagttaaa accacctaca tggctaaaaa accggttcag ctgccgggtg       2700
cttacaaaac cgacatcaaa ctggacatca cctcccacaa cgaagactac accatcgttg       2760
aacagtacga acgtgctgaa ggtcgtcact ccaccggtgc ttaataacgc tgatagtgct       2820
agtgtagatc gctactagag ccaggcatca aataaaacga aaggctcagt cgaaagactg       2880
ggcctttcgt tttatctgtt gtttgtcggt gaacgctctc tactagagcg tctcacctcc       2940
act                                                                     2943

<210> SEQ ID NO 62
<211> LENGTH: 2942
<212> TYPE: DNA
<213> ORGANISM: Artificial Sequence
<220> FEATURE:
<223> OTHER INFORMATION: pES7 plasmid

<400> SEQUENCE: 62
agagacccaa gacactgcgg ctttgtatgt gtccgcagcg cccgccgcag tctcacgccc         60
ggagcgtagc gaccgagtga gctagctatt tgtttatttt tctaaataca ttcaaatatg        120
tatccgctca tgagacaata accctgataa atgcttcaat aatattgaaa aaggaagagt        180
atgagggaag cggtgatcgc cgaagtatcg actcaactat cagaggtagt tggcgtcatc        240
gagcgccatc tcgaaccgac gttgctggcc gtacatttgt acggctccgc agtggatggc        300
ggcctgaagc cacacagtga tattgatttg ctggttacgg tgaccgtaag gcttgatgaa        360
acaacgcggc gagctttgat caacgacctt ttggaaactt cggcttcccc tggagagagc        420
gagattctcc gcgctgtaga agtcaccatt gttgtgcacg acgacatcat tccgtggcgt        480
tatccagcta agcgcgaact gcaatttgga gaatggcagc gcaatgacat tcttgcaggt        540
atcttcgagc cagccacgat cgacattgat ctggctatct tgctgacaaa agcaagagaa        600
catagcgttg ccttggtagg tccagcggcg gaggaactct ttgatccggt tcctgaacag        660
gatctatttg aggcgctaaa tgaaacctta cgctatgga actcgccgcc cgactgggct         720
ggcgatgagc gaaatgtagt gcttacgttg tcccgcattt ggtacagcgc agtaaccggc        780
aaaatcgcgc cgaaggatgt cgctgccgac tgggcaatgg agcgcctgcc ggcccagtat        840
cagcccgtca tacttgaagc tagacaggct tatcttggac aagaagaaga tcgcttggcc        900
tcgcgcgcag atcagttgga agaatttgtc cactacgtga aaggcgagat caccaaggta        960
gtcggcaaat aatgtctaac aattcgttca agccgagggg ccgcaagatc cggccacgat       1020
gacccggtcg tcggttcagg gcagggtcgt taaatagccg cttatgtcta ttgctggttt       1080
accggtttat tgactaccgg aagcagtgtg accgtgtgct tctcaaatgc ctgaggtttc       1140
agcaaaaaac ccctcaagac ccgtttagag gccccaaggg gttatgctag ttattgctca       1200
gcggcgtcag accccgtaga aaagatcaaa ggatcttctt gagatccttt ttttctgcgc       1260
gtaatctgct gcttgcaaac aaaaaaacca ccgctaccag cggtggtttg tttgccggat       1320
caagagctac caactctttt tccgaaggta actggcttca gcagagcgca gataccaaat       1380
actgtccttc tagtgtagcc gtagttaggc caccacttca agaactctgt agcaccgcct       1440
acatacctcg ctctgctaat cctgttacca gtggctgctg ccagtggcga taagtcgtgt       1500
```

-continued

```
cttaccgggt tggactcaag acgatagtta ccggataagg cgcagcggtc gggctgaacg    1560 ggggggttcgt gcacacagcc cagcttggag cgaacgacct acaccgaact gagataccta    1620
cagcgtgagc tatgagaaag cgccacgctt cccgaaggga gaaaggcgga caggtatccg    1680
gtaagcggca gggtcggaac aggagagcgc acgagggagc ttccagggg aaacgcctgg    1740 tatctttata gtcctgtcgg gtttcgccac ctctgacttg agcgtcgatt tttgtgatgc    1800
tcgtcagggg ggcggagcct atggaaaaac gccagcaacg cggcctttt acggttcctg    1860 gccgttggca gtgactcggt ctctcactgg ctagagacgg caatacgcaa accgcctcta    1920
gccgcgcgtt ggccgattca ttaatgcagc tggcacgaca ggtttcccga ctggaaagcg    1980
ggcagtgagc gcaacgcaat taatgtgagt tagctcactc attaggcacc ccaggcttta    2040
cactttatgc ttccggctcg tatgttgtgt ggaattgtga gcggataaca atttcacaca    2100
tactagagaa agaggagaaa tactagatgg cttcctccga agacgttatc aaagagttca    2160
tgcgtttcaa agttcgtatg gaaggttccg ttaacggtca cgagttcgaa atcgaaggtg    2220
aaggtgaagg tcgtccgtac gaaggtaccc agaccgctaa actgaaagtt accaaaggtg    2280
gtccgctgcc gttcgcttgg gacatcctgt ccccgcagtt ccagtacggt tccaaagctt    2340
acgttaaaca cccggctgac atcccggact acctgaaact gtccttcccg gaaggtttca    2400
aatgggaacg tgttatgaac ttcgaagacg gtggtgttgt taccgttacc caggactcct    2460
ccctgcaaga cggtgagttc atctacaaag ttaaactgcg tggtaccaac ttcccgtccg    2520
acggtccggt tatgcagaaa aaaaccatgg gttgggaagc ttccaccgaa cgtatgtacc    2580
cggaagacgg tgctctgaaa ggtgaaatca aaatgcgtct gaaactgaaa gacggtggtc    2640
actacgacgc tgaagttaaa accacctaca tggctaaaaa accggttcag ctgccgggtg    2700
cttacaaaac cgacatcaaa ctggacatca cctcccacaa cgaagactac accatcgttg    2760
aacagtacga acgtgctgaa ggtcgtcact ccaccggtgc ttaataacgc tgatagtgct    2820
agtgtagatc gctactagag ccaggcatca aataaaacga aaggctcagt cgaaagactg    2880
ggcctttcgt tttatctgtt gtttgtcggt gaacgctctc tactagacgt ctcacctctg    2940
ag                                                                   2942
```

<210> SEQ ID NO 63
<211> LENGTH: 4498
<212> TYPE: DNA
<213> ORGANISM: Artificial Sequence
<220> FEATURE:
<223> OTHER INFORMATION: pCKH plasmid

<400> SEQUENCE: 63

```
actcctccct gcaagacggt gagttcatct acaaagttaa actgcgtggt accaacttcc      60
cgtccgacgg tccggttatg cagaaaaaaa ccatgggttg ggaagcttcc accgaacgta     120
tgtacccgga agacggtgct ctgaaaggtg aaatcaaaat gcgtctgaaa ctgaaagacg     180
gtggtcacta cgacgctgaa gttaaaacca cctacatggc taaaaaaccg gttcagctgc     240
cgggtgctta caaaaccgac atcaaactgg acatcacctc ccacaacgaa gactacacca     300
tcgttgaaca gtacgaacgt gctgaaggtc gtcactccac cggtgcttaa taacgctgat     360
agtgctagtg tagatcgcta ctagagccag gcatcaaata aaacgaaagg ctcagtcgaa     420
agactgggcc tttcgtttta tctgttgttt gtcggtgaac gctctctact agagtggtct     480
catgagcgag acgtccggca tccgcttaca gacaagctgt gacagtctcc gggagctgca     540
tgtgtcagag gttttcaccg tcatcaccga aacgcgcgag actaaagggc ctcgtgatac     600
```

```
gcctattttt ataggttaat gtcatgataa taatggtttc ttaggacgga tcgcttgcct    660
gtaacttaca cgcgcctcgt atcttttaat gatggaataa tttgggaatt tactctgtgt    720
ttatttattt ttatgttttg tatttggatt ttagaaagta aataaagaag gtagaagagt    780
tacggaatga agaaaaaaaa ataaacaaag gtttaaaaaa tttcaacaaa aagcgtactt    840
tacatatata tttattagac aagaaaagca gattaaatag atatacattc gattaacgat    900
aagtaaaatg taaaatcaca ggattttcgt gtgtggtctt ctacacagac aagatgaaac    960
aattcggcat taatacctga gagcaggaag agcaagataa aaggtagtat ttgttggcga   1020 tcccctaga gtcttttaca tcttcggaaa acaaaaacta ttttttcttt aatttctttt   1080
tttactttct atttttaatt tatatattta tattaaaaaa tttaaattat aattatttt   1140 atagcacgtg atgaaaagga cccaggtggc attgacttga tcggcacgta agaggttcca   1200
actttcacca taatgaaata agatcactac cgggcgtatt ttttgagtta tcgagatttt   1260
caggagctaa ggaagctaaa atgagccata ttcaacggga aacgtcttgc tcgaggccgc   1320
gattaaattc caacatggat gctgatttat atgggtataa atgggctcgc gataatgtcg   1380
ggcaatcagg tgcgacaatc tatcgattgt atgggaagcc cgatgcgcca gagttgtttc   1440
tgaaacatgg caaaggtagc gttgccaatg atgttacaga tgagatggtc aggctaaact   1500
ggctgacgga atttatgcct cttccgacca tcaagcattt tatccgtact cctgatgatg   1560
catggttact caccactgcg atcccaggga aaacagcatt ccaggtatta gaagaatatc   1620
ctgattcagg tgaaaatatt gttgatgcgc tggcagtgtt cctgcgccgg ttgcattcga   1680
ttcctgtttg taattgtcct tttaacggcg atcgcgtatt tcgtctcgca caggcgcaat   1740
cacgaatgaa taacggtttg gttggtgcga gtgattttga tgacgagcgt aatggctggc   1800
ctgttgaaca agtctggaaa gaaatgcata agcttttgcc attctcaccg gattcagtcg   1860
tcactcatgg tgatttctca cttgataacc ttatttttga cgaggggaaa ttaataggtt   1920
gtattgatgt tggacgagtc ggaatcgcag accgatacca ggatcttgcc atcctatgga   1980
actgcctcgg tgagttttct ccttcattac agaaacggct ttttcaaaaa tatggtattg   2040
ataatcctga tatgaataaa ttgcagtttc acttgatgct cgatgagttt ttctaatgag   2100
ggcccaaatg taatcacctg gctcaccttc gggtgggcct ttctgcgttg ctggcgtttt   2160
tccataggct ccgcccccct gacgagcatc acaaaaatcg atgctcaagt cagaggtggc   2220
gaaacccgac aggactataa agataccagg cgtttccccc tggaagctcc ctcgtgcgct   2280
ctcctgttcc gaccctgccg cttaccggat acctgtccgc ctttctccct tcgggaagcg   2340
tggcgctttc tcatagctca cgctgtaggt atctcagttc ggtgtaggtc gttcgctcca   2400
agctgggctg tgtgcacgaa ccccccgttc agcccgaccc ctgcgcctta ccggtaact   2460 atcgtcttga gtccaacccg gtaagacacg acttatcgcc actggcagca gccactggta   2520
acaggattag cagagcgagg tatgtaggcg gtgctacaga gttcttgaag tggtggccta   2580
actacggcta cactagaaga acagtatttg gtatctgcgc tctgctgaag ccagttacct   2640
cggaaaaaga gttggtagct cttgatccgg caaacaaacc accgctggta gcggtggttt   2700
ttttgtttgc aagcagcaga ttacgcgcag aaaaaaagga tctcaagaag atcctttgat   2760
tttctaccga actgtgcggt atttcacacc gcatagatcc gtcgagttca agagaaaaaa   2820
aaagaaaaag caaaaagaaa aaaggaaagc gcgcctcgtt cagaatgaca cgtatagaat   2880
gatgcattac cttgtcatct tcagtatcat actgttcgta tacatactta ctgacattca   2940
```

-continued

```
taggtataca tatatacaca tgtatatata tcgtatgctg cagctttaaa taatcggtgt      3000
cactacataa gaacaccttt ggtggaggga acatcgttgg taccattggg cgaggtggct      3060
tctcttatgg caaccgcaag agccttgaac gcactctcac tacggtgatg atcattcttg      3120
cctcgcagac aatcaacgtg gagggtaatt ctgctagcct ctgcaaagct ttcaagaaaa      3180
tgcgggatca tctcgcaaga gagatctcct actttctccc tttgcaaacc aagttcgaca      3240
actgcgtacg gcctgttcga aagatctacc accgctctgg aaagtgcctc atccaaaggc      3300
gcaaatcctg atccaaacct ttttactcca cgcacggccc ctagggcctc tttaaaagct      3360
tgaccgagag caatcccgca gtcttcagtg gtgtgatggt cgtctatgtg taagtcacca      3420
atgcactcaa cgattagcga ccagccggaa tgcttggcca gagcatgtat catatggtcc      3480
agaaacccta tacctgtgtg gacgttaatc acttgcgatt gtgtggcctg ttctgctact      3540
gcttctgcct ctttttctgg gaagatcgag tgctctatcg ctaggggacc acccttttaaa     3600 gagatcgcaa tctgaatctt ggtttcattt gtaatacgct ttactagggc tttctgctct      3660
gtcatctttg ccttcgttta tcttgcctgc tcattttta gtatattctt cgaagaaatc       3720
acattacttt atataatgta taattcatta tgtgataatg ccaatcgcta agaaaaaaaa      3780
agagtcatcc gctaggtgga aaaaaaaaaa tgaaaatcat taccgaggca taaaaaaata      3840
tagagtgtac tagaggaggc caagagtaat agaaaaagaa aattgcggga aaggactgtg      3900
ttatgacttc cctgactaat gccgacgtct cgacctcgag accgcaatac gcaaaccgcc      3960
tctccccgcg cgttggccga ttcattaatg cagctggcac gacaggtttc ccgactggaa      4020
agcgggcagt gagcgcaacg caattaatgt gagttagctc actcattagg caccccaggc      4080
tttacacttt atgcttccgg ctcgtatgtt gtgtggaatt gtgagcggat aacaatttca      4140
cacatactag agaaagagga gaaatactag atggcttcct ccgaagacgt tatcaaagag      4200
ttcatgcgtt tcaaagttcg tatggaaggt tccgttaacg gtcacgagtt cgaaatcgaa      4260
ggtgaaggtg aaggtcgtcc gtacgaaggt acccagaccg ctaaactgaa agttaccaaa      4320
ggtggtccgc tgccgttcgc ttgggacatc ctgtccccgc agttccagta cggttccaaa      4380
gcttacgtta aacacccggc tgacatcccg gactacctga aactgtcctt cccggaaggt      4440
ttcaaatggg aacgtgttat gaacttcgaa gacggtggtg ttgttaccgt tacccagg       4498
```

```
<210> SEQ ID NO 64
<211> LENGTH: 6033
<212> TYPE: DNA
<213> ORGANISM: Artificial Sequence
<220> FEATURE:
<223> OTHER INFORMATION: pCKH-Cso-BMC plasmid

<400> SEQUENCE: 64
tgagcgagac gtccggcatc cgcttacaga caagctgtga cagtctccgg gagctgcatg       60
tgtcagaggt tttcaccgtc atcaccgaaa cgcgcgagac taaagggcct cgtgatacgc       120 ctattttttat aggttaatgt catgataata atggtttctt aggacggatc gcttgcctgt      180
aacttacacg cgcctcgtat cttttaatga tggaataatt tgggaattta ctctgtgttt       240
atttattttt atgtttgta tttggatttt agaaagtaaa taaagaaggt agaagagtta       300
cggaatgaag aaaaaaaat aaacaaaggt ttaaaaaatt tcaacaaaaa gcgtacttta       360
catatatatt tattagacaa gaaaagcaga ttaaatagat atacattcga ttaacgataa       420
gtaaaatgta aaatcacagg attttcgtgt gtggtcttct acacagacaa gatgaaacaa       480
ttcggcatta atacctgaga gcaggaagag caagataaaa ggtagtattt gttggcgatc       540
```

```
cccctagagt cttttacatc ttcggaaaac aaaaactatt ttttctttaa tttctttttt      600
tactttctat ttttaatta tatatttata ttaaaaaatt taaattataa ttatttttat       660
agcacgtgat gaaaaggacc caggtggcat tgacttgatc ggcacgtaag aggttccaac      720
tttcaccata atgaaataag atcactaccg ggcgtatttt ttgagttatc gagattttca      780
ggagctaagg aagctaaaat gagccatatt caacgggaaa cgtcttgctc gaggccgcga      840
ttaaattcca acatggatgc tgatttatat gggtataaat gggctcgcga taatgtcggg      900
caatcaggtg cgacaatcta tcgattgtat gggaagcccg atgcgccaga gttgtttctg      960
aaacatggca aaggtagcgt tgccaatgat gttacagatg agatggtcag gctaaactgg     1020
ctgacggaat ttatgcctct tccgaccatc aagcatttta tccgtactcc tgatgatgca     1080
tggttactca ccactgcgat cccagggaaa acagcattcc aggtattaga agaatatcct     1140
gattcaggtg aaaatattgt tgatgcgctg gcagtgttcc tgcgccggtt gcattcgatt     1200
cctgtttgta attgtccttt taacggcgat cgcgtatttc gtctcgcaca ggcgcaatca     1260
cgaatgaata acggtttggt tggtgcgagt gattttgatg acgagcgtaa tggctggcct     1320
gttgaacaag tctggaaaga aatgcataag cttttgccat tctcaccgga ttcagtcgtc     1380
actcatggtg atttctcact tgataacctt attttttgacg aggggaaatt aataggttgt    1440
attgatgttg gacgagtcgg aatcgcagac cgataccagg atcttgccat cctatggaac     1500
tgcctcggtg agttttctcc ttcattacag aaacggcttt ttcaaaaata tggtattgat     1560
aatcctgata tgaataaatt gcagtttcac ttgatgctcg atgagttttt ctaatgaggg     1620
cccaaatgta atcacctggc tcaccttcgg gtgggccttt ctgcgttgct ggcgtttttc     1680
cataggctcc gccccctga cgagcatcac aaaaatcgat gctcaagtca gaggtggcga      1740
aacccgacag gactataaag ataccaggcg tttccccctg gaagctccct cgtgcgctct     1800
cctgttccga ccctgccgct taccggatac ctgtccgcct ttctcccttc gggaagcgtg     1860
gcgctttctc atagctcacg ctgtaggtat ctcagttcgg tgtaggtcgt tcgctccaag     1920
ctgggctgtg tgcacgaacc ccccgttcag cccgaccgct gcgccttatc cggtaactat     1980
cgtcttgagt ccaacccggt aagacacgac ttatcgccac tggcagcagc cactggtaac     2040
aggattagca gagcgaggta tgtaggcggt gctacagagt tcttgaagtg gtggcctaac     2100
tacggctaca ctagaagaac agtatttggt atctgcgctc tgctgaagcc agttacctcg     2160
gaaaaagagt tggtagctct tgatccggca acaaaccac cgctggtagc ggtggttttt      2220
ttgtttgcaa gcagcagatt acgcgcagaa aaaaaggatc tcaagaagat cctttgattt     2280
tctaccgaac tgtgcggtat ttcacaccgc atagatccgt cgagttcaag agaaaaaaaa     2340
agaaaaagca aaagaaaaa aggaaagcgc gcctcgttca gaatgacacg tatagaatga     2400
tgcattacct tgtcatcttc agtatcatac tgttcgtata catacttact gacattcata     2460
ggtatacata tatacacatg tatatatatc gtatgctgca gctttaaata atcggtgtca     2520
ctacataaga acacctttgg tggagggaac atcgttggta ccattgggcg aggtggcttc     2580
tcttatggca accgcaagag ccttgaacgc actctcacta cggtgatgat cattcttgcc     2640
tcgcagacaa tcaacgtgga gggtaattct gctagcctct gcaaagcttt caagaaaatg     2700
cgggatcatc tcgcaagaga gatctcctac tttctccctt tgcaaaccaa gttcgacaac     2760
tgcgtacggc ctgttcgaaa gatctaccac cgctctggaa agtgcctcat ccaaaggcgc     2820
aaatcctgat ccaaaccttt ttactccacg cacggcccct agggcctctt taaaagcttg     2880
```

-continued

```
accgagagca atcccgcagt cttcagtggt gtgatggtcg tctatgtgta agtcaccaat      2940
gcactcaacg attagcgacc agccggaatg cttggccaga gcatgtatca tatggtccag      3000
aaaccctata cctgtgtgga cgttaatcac ttgcgattgt gtggcctgtt ctgctactgc      3060
ttctgcctct tttctgggga agatcgagtg ctctatcgct aggggaccac cctttaaaga      3120
gatcgcaatc tgaatcttgg tttcatttgt aatacgcttt actagggctt tctgctctgt      3180
catctttgcc ttcgtttatc ttgcctgctc atttttttagt atattcttcg aagaaatcac      3240
attactttat ataatgtata attcattatg tgataatgcc aatcgctaag aaaaaaaaag      3300
agtcatccgc taggtggaaa aaaaaaaatg aaaatcatta ccgaggcata aaaaaatata      3360
gagtgtacta gaggaggcca agagtaatag aaaaagaaaa ttgcgggaaa ggactgtgtt      3420
atgacttccc tgactaatgc cgacgtctcg acctggctgg cttcccaacc ttaccagagg      3480
gcgccccagc tggcaattcc gacgtcttta tggctagctc agtcctaggt acaatgctag      3540
cgaattcaaa agatctttta agaaggagat atacatgatg aagatcatgc aagttgaaaa      3600
gactttggtt tctaccaaca gaattgctga tatgggtcac aagccattgt tggttgtttg      3660
ggaaaaacct ggtgctccaa gacaagttgc tgttgatgct attggttgta ttccaggtga      3720
ctgggttttg tgtgttggtt cttctgctgc cagagaagct gctggttcca agtcttaccc      3780
atctgatttg actatcatcg gtattattga ccaatggaac ggtgaaggtt cttcttggtc      3840
acatccacaa tttgaaaagt agctaacaaa gcccgaaagg aagctgagtt ggctgctgcc      3900
accgctgagc aataactagc ataaccccctt ggggcctcta aacgggtctt gaggggtttt      3960
ttgctgaaag gaggaactat atccggatat cccgcaagag gccggcagt accccctcagg      4020 cggcttcact gcccgctttc cagtcgggaa acctgtcgtg ccagctgcat taatgaatcg      4080
gccaacgcgc ggggagaggc ggtttgcgta ttgggcgcca gggtggtttt cttttttcacc      4140 agtgaaacgg gcaacagctg attgcccttc accgcctggc cctgagagag ttgcagcaag      4200
cggtccacgc tggtttgccc cagcaggcga aaatcctgtt tgatggtggt taacggcggg      4260
atataacatg agctgtcttc ggtatcgtcg tatcccacta ccgagatatc cgcaccaacg      4320
cgcagcccgg actcggtaat ggcgcgcatt gcgcccagcg ccatctgatc gttggcaacc      4380
agcatcgcag tgggaacgat gccctcattc agcatttgca tggtttgttg aaaaccggac      4440
atggcactcc agtcgccttc ccgttccgct atcggctgaa tttgattgcg agtgagatat      4500
ttatgccagc cagccagacg cagacgcgcc gagacagaac ttaatgggcc cgctaacagc      4560
gcgatttgct ggtgacccaa tgcgaccaga tgctccacgc ccagtcgcgt accgtcttca      4620
tgggagaaaa taatactgtt gatgggtgtc tggtcagaga catcaagaaa taacgccgga      4680
acattagtgc aggcagcttc cacagcaatg gcatcctggt catccagcgg atagttaatg      4740
atcagcccac tgacgcgttg cgcgagaaga ttgtgcaccg ccgctttaca ggcttcgacg      4800
ccgcttcgtt ctaccatcga caccaccacg ctggcaccca gttgatcggc gcgagattta      4860
atcgccgcga caatttgcga cggcgcgtgc agggccagac tggaggtggc aacgccaatc      4920
agcaacgact gtttgcccgc cagttgttgt gccacgcggt tgggaatgta attcagctcc      4980
gccatcgccg cttccacttt ttcccgcgtt ttcgcagaaa cgtggctggc ctggttcacc      5040
acgcgggaaa cggtctgata agagacaccg gcatactctg cgacatcgta taacgttact      5100
ggtttcacat tcaccaccct gaattgactc tcttccgggc gctatcatgc cataccgcga      5160
aaggttttgc gccattcgat ggtgtccggg atctcgacgc tctcccttat gcgactcctg      5220
cattaggaag cagcccagta gtaggttgag gccgttgagc accgccgccg caaggaatgg      5280
```

-continued

```
tgcatgcaag gagatggcgc ccaacagtcc cccggccacg gggcctgcca ccatacccac    5340
gccgaaacaa gcgctcatga gcccgaagtg gcgagcccga tcttccccat cggtgatgtc    5400
ggcgatatag gcgccagcaa ccgcacctgt ggcgccggtg atgccggcca cgatgcgtcc    5460
ggcgtagagg atcgagatct cgatcccgcg aaattaatac gactcactat agggggaattg    5520 tgagcggata acaattcccc tctagaaata attttgttta actttaagaa ggagatatac    5580
gatggctgat gttactggta ttgctttggg tatgattgaa actagaggtt tggttccagc    5640
tatcgaagct gctgacgcta tgaccaaggc cgctgaagtc agattggtcg gtagacaatt    5700
tgttggaggt ggttacgtca ctgttttggt tcgtggtgaa accggtgccg ttaacgctgc    5760
tgttagagct ggtgctgatg cttgtgaaag agttggtgac ggtttagttg ctgcccacat    5820
tattgccaga gtccactctg aagttgaaaa cattttgcca aaggctccac aggcttagct    5880
aacaaagccc gaaaggaagc tgagttggct gctgccaccg ctgagcaata actagcataa    5940
ccccttgggg cctctaaacg ggtcttgagg ggttttttgc tgaaaggagg aactatatcc    6000
ggatatcccg caagaggccc ggcagtaccc ctc                                 6033
```

```
<210> SEQ ID NO 65
<211> LENGTH: 2246
<212> TYPE: DNA
<213> ORGANISM: Artificial Sequence
<220> FEATURE:
<223> OTHER INFORMATION: HcKan_P-TDH3 plasmid

<400> SEQUENCE: 65
```

```
aagaaaggcc cacccgtgaa ggtgagccag tgagttgatt gcagtccagt tacgctggag      60
tccgtctcgg gctacagttt attcctggca tccactaaat ataatggagc ccgcttttta     120
agctggcatc cagaaaaaaa aagaatccca gcaccaaaat attgttttct tcaccaacca     180
tcagttcata ggtccattct cttagcgcaa ctacagagaa caggggcaca aacaggcaaa     240
aaacgggcac aacctcaatg gagtgatgca acctgcctgg agtaaatgat gacacaaggc     300
aattgaccca cgcatgtatc tatctcattt tcttacacct tctattacct tctgctctct     360
ctgatttgga aaaagctgaa aaaaaggtt gaaaccagtt ccctgaaatt attcccctac      420
ttgactaata gtatataaa gacggtaggt attgattgta attctgtaaa tctatttctt     480
aaacttctta aattctactt ttatagttag tctttttttt agtttaaaa caccaagaac      540 ttagtttcga ataaacacac ataaacaaac aaagatgcga gacgactgac catttaaatc     600
atacctgacc tccatagcag aaagtcaaaa gcctccgacc ggaggctttt gacttgatcg     660
gcacgtaaga ggttccaact ttcaccataa tgaaataaga tcactaccgg gcgtattttt     720
tgagttatcg agattttcag gagctaagga agctaaaatg agccatattc aacgggaaac     780
gtcttgctcg aggccgcgat taaattccaa catggatgct gatttatatg ggtataaatg     840
ggctcgcgat aatgtcgggc aatcaggtgc gacaatctat cgattgtatg ggaagcccga     900
tgcgccagag ttgtttctga acatggcaa aggtagcgtt gccaatgatg ttacagatga     960
gatggtcagg ctaaactggc tgacggaatt tatgcctctt ccgaccatca agcattttat    1020
ccgtactcct gatgatgcat ggttactcac cactgcgatc ccagggaaaa cagcattcca    1080
ggtattagaa gaatatcctg attcaggtga aaatattgtt gatgcgctgg cagtgttcct    1140
gcgccggttg cattcgattc ctgtttgtaa ttgtcctttt aacggcgatc gcgtatttcg    1200
tctcgctcag gcgcaatcac gaatgaataa cggtttggtt ggtgcgagtg attttgatga    1260
```

```
cgagcgtaat ggctggcctg ttgaacaagt ctggaaagaa atgcataagc tttttgccatt    1320 ctcaccggat tcagtcgtca ctcatggtga tttctcactt gataacctta ttttttgacga    1380 ggggaaatta ataggttgta ttgatgttgg acgagtcgga atcgcagacc gataccagga    1440
tcttgccatc ctatggaact gcctcggtga gttttctcct tcattacaga aacggctttt    1500
tcaaaaatat ggtattgata atcctgatat gaataaattg cagtttcact tgatgctcga    1560 tgagttttc taatgagggc ccaaatgtaa tcacctggct caccttcggg tgggcctttc     1620
tgcgttgctg gcgtttttcc ataggctccg ccccctgac gagcatcaca aaaatcgatg     1680
ctcaagtcag aggtggcgaa acccgacagg actataaaga taccaggcgt ttcccctgg     1740 aagctccctc gtgcgctctc ctgttccgac cctgccgctt accggatacc tgtccgcctt     1800
tctcccttcg ggaagcgtgg cgctttctca tagctcacgc tgtaggtatc tcagttcggt     1860
gtaggtcgtt cgctccaagc tgggctgtgt gcacgaaccc cccgttcagc ccgaccgctg     1920
cgccttatcc ggtaactatc gtcttgagtc caacccggta agacacgact tatcgccact     1980
ggcagcagcc actggtaaca ggattagcag agcgaggtat gtaggcggtg ctacagagtt     2040
cttgaagtgg tggcctaact acggctacac tagaagaaca gtatttggta tctgcgctct     2100
gctgaagcca gttacctcgg aaaaagagtt ggtagctctt gatccggcaa acaaaccacc     2160
gctggtagcg gtggtttttt tgtttgcaag cagcagatta cgcgcagaaa aaaggatct      2220 caagaagatc ctttgatttt ctaccg                                          2246

<210> SEQ ID NO 66
<211> LENGTH: 2246
<212> TYPE: DNA
<213> ORGANISM: Artificial Sequence
<220> FEATURE:
<223> OTHER INFORMATION: HcKan_P-YEF3 plasmid

<400> SEQUENCE: 66
aagaaaggcc cacccgtgaa ggtgagccag tgagttgatt gcagtccagt tacgctggag       60
tccgtctcgg gctattaaaa aaacaactta caatcattgt tcgccccttc catacttact      120
gccactcgca aaagggccca accagggcaa ttacgtatca aaaaatcatg acaggctggg      180
taataaatat tcgtgaagaa agaagaaatt aaaaaaagaa acgaagaagc aaaaaaaaga      240
aaagactccg tttaatcact ttcaaccgcg gtttatccgg ccccacccat gcataaccct      300
aaattattag atcacttagc acgtgaaaaa gaaacgtttt taatgttttt tttttttttt      360 tcttttttctt tttttgcgtt ggtgaaaatt ttttcgcttc ctcgagtata attatctcat     420
ctcatctttc atataagata agaagtttta taaaaacctt ttgcatcaaa attttgtaga      480
atatctcttt ttcttacgct ctctttcttt ccttaattgt tttctaaaga accgtgtatt     540
tttctagttc gaatccatcg ataacattaa aaggatgcga gacgactgac catttaaatc     600
atacctgacc tccatagcag aaagtcaaaa gcctccgacc ggaggctttt gacttgatcg     660
gcacgtaaga ggttccaact ttcaccataa tgaaataaga tcactaccgg cgtatttttt     720
tgagttatcg agattttcag gagctaagga agctaaaatg agccatattc aacgggaaac     780
gtcttgctcg aggccgcgat taaattccaa catggatgct gatttatatg ggtataaatg     840
ggctcgcgat aatgtcgggc aatcaggtgc gacaatctat cgattgtatg ggaagcccga     900
tgcgccagag ttgtttctga aacatggcaa aggtagcgtt gccaatgatg ttacagatga     960
gatggtcagg ctaaactggc tgacggaatt tatgcctctt ccgaccatca agcattttat    1020
ccgtactcct gatgatgcat ggttactcac cactgcgatc ccagggaaaa cagcattcca    1080
```

-continued

```
ggtattagaa gaatatcctg attcaggtga aaatattgtt gatgcgctgg cagtgttcct    1140
gcgccggttg cattcgattc ctgtttgtaa ttgtcctttt aacggcgatc gcgtatttcg    1200
tctcgctcag gcgcaatcac gaatgaataa cggtttggtt ggtgcgagtg attttgatga    1260
cgagcgtaat ggctggcctg ttgaacaagt ctggaaagaa atgcataagc ttttgccatt    1320
ctcaccggat tcagtcgtca ctcatggtga tttctcactt gataacctta tttttgacga    1380
ggggaaatta ataggttgta ttgatgttgg acgagtcgga atcgcagacc gataccagga    1440
tcttgccatc ctatggaact gcctcggtga gttttctcct tcattacaga aacggctttt    1500
tcaaaaatat ggtattgata atcctgatat gaataaattg cagtttcact tgatgctcga    1560 tgagttttc taatgagggc ccaaatgtaa tcacctggct caccttcggg tgggcctttc    1620
tgcgttgctg gcgtttttcc ataggctccg ccccctgac gagcatcaca aaaatcgatg    1680
ctcaagtcag aggtggcgaa acccgacagg actataaaga taccaggcgt ttcccctgg    1740 aagctccctc gtgcgctctc ctgttccgac cctgccgctt accggatacc tgtccgcctt    1800
tctcccttcg ggaagcgtgg cgctttctca tagctcacgc tgtaggtatc tcagttcggt    1860
gtaggtcgtt cgctccaagc tgggctgtgt gcacgaaccc cccgttcagc ccgaccgctg    1920
cgccttatcc ggtaactatc gtcttgagtc caacccggta agacacgact tatcgccact    1980
ggcagcagcc actggtaaca ggattagcag agcgaggtat gtaggcggtg ctacagagtt    2040
cttgaagtgg tggcctaact acggctacac tagaagaaca gtatttggta tctgcgctct    2100
gctgaagcca gttacctcgg aaaaagagtt ggtagctctt gatccggcaa acaaaccacc    2160
gctggtagcg gtggtttttt tgtttgcaag cagcagatta cgcgcagaaa aaaaggatct    2220
caagaagatc ctttgatttt ctaccg                                        2246
```

<210> SEQ ID NO 67
<211> LENGTH: 2246
<212> TYPE: DNA
<213> ORGANISM: Artificial Sequence
<220> FEATURE:
<223> OTHER INFORMATION: HcKan_P-PYK1 plasmid

<400> SEQUENCE: 67

```
aagaaaggcc cacccgtgaa ggtgagccag tgagttgatt gcagtccagt tacgctggag     60
tccgtctcgg gctacagatt gggagatttt catagtagaa ttcagcatga tagctacgta    120
aatgtgttcc gcaccgtcac aaagtgtttt ctactgttct ttcttctttc gttcattcag    180
ttgagttgag tgagtgcttt gttcaatgga tcttagctaa aatgcatatt ttttctcttg    240
gtaaatgaat gcttgtgatg tcttccaagt gatttccttt ccttcccata tgatgctagg    300
tacctttagt gtcttcctaa aaaaaaaaaa aggctcgcca tcaaaacgat attcgttggc    360
ttttttttct gaattataaa tactctttgg taacttttca tttccaagaa cctctttttt    420
ccagttatat catggtcccc tttcaaagtt attctctact cttttcata ttcattcttt    480 ttcatccttt ggttttttat tcttaacttg tttattattc tctcttgttt ctatttacaa    540
gacaccaatc aaaacaaata aaacatcatc acagatgcga gacgactgac catttaaatc    600
atacctgacc tccatagcag aaagtcaaaa gcctccgacc ggaggctttt gacttgatcg    660
gcacgtaaga ggttccaact ttcaccataa tgaaataaga tcactaccgg gcgtattttt    720
tgagttatcg agattttcag gagctaagga agctaaaatg agccatattc aacgggaaac    780
gtcttgctcg aggccgcgat taaattccaa catggatgct gatttatatg ggtataaatg    840
```

-continued

```
ggctcgcgat aatgtcgggc aatcaggtgc gacaatctat cgattgtatg ggaagcccga      900
tgcgccagag ttgtttctga aacatggcaa aggtagcgtt gccaatgatg ttacagatga      960
gatggtcagg ctaaactggc tgacggaatt tatgcctctt ccgaccatca agcattttat     1020
ccgtactcct gatgatgcat ggttactcac cactgcgatc ccagggaaaa cagcattcca     1080
ggtattagaa gaatatcctg attcaggtga aaatattgtt gatgcgctgg cagtgttcct     1140
gcgccggttg cattcgattc ctgtttgtaa ttgtcctttt aacggcgatc gcgtatttcg     1200
tctcgctcag gcgcaatcac gaatgaataa cggtttggtt ggtgcgagtg attttgatga     1260
cgagcgtaat ggctggcctg ttgaacaagt ctggaaagaa atgcataagc ttttgccatt     1320
ctcaccggat tcagtcgtca ctcatggtga tttctcactt gataacctta tttttgacga     1380
ggggaaatta ataggttgta ttgatgttgg acgagtcgga atcgcagacc gataccagga     1440
tcttgccatc ctatggaact gcctcggtga gttttctcct tcattacaga aacggctttt     1500
tcaaaaatat ggtattgata atcctgatat gaataaattg cagtttcact tgatgctcga     1560
tgagtttttc taatgagggc ccaaatgtaa tcacctggct caccttcggg tgggcctttc     1620
tgcgttgctg gcgtttttcc ataggctccg cccccctgac gagcatcaca aaaatcgatg     1680
ctcaagtcag aggtggcgaa acccgacagg actataaaga taccaggcgt ttccccctgg     1740
aagctccctc gtgcgctctc ctgttccgac cctgccgctt accggatacc tgtccgcctt     1800
tctcccttcg ggaagcgtgg cgctttctca tagctcacgc tgtaggtatc tcagttcggt     1860
gtaggtcgtt cgctccaagc tgggctgtgt gcacgaaccc cccgttcagc ccgaccgctg     1920
cgccttatcc ggtaactatc gtcttgagtc caacccggta agacacgact tatcgccact     1980
ggcagcagcc actggtaaca ggattagcag agcgaggtat gtaggcggtg ctacagagtt     2040
cttgaagtgg tggcctaact acggctacac tagaagaaca gtatttggta tctgcgctct     2100
gctgaagcca gttacctcgg aaaaagagtt ggtagctctt gatccggcaa acaaaccacc     2160
gctggtagcg gtggtttttt tgtttgcaag cagcagatta cgcgcagaaa aaaggatct     2220 caagaagatc ctttgatttt ctaccg                                          2246
```

<210> SEQ ID NO 68
<211> LENGTH: 2040
<212> TYPE: DNA
<213> ORGANISM: Artificial Sequence
<220> FEATURE:
<223> OTHER INFORMATION: HcKan_O-HO-H plasmid

<400> SEQUENCE: 68

```
aagaaaggcc cacccgtgaa ggtgagccag tgagttgatt gcagtccagt tacgctggag       60
tccgtctcgg atggctgatg ctttgggtat gattgaagtt agaggtttcg ttggtatggt      120
tgaagctgct gatgctatgg ttaaggctgc taaagttgaa ttgatcggtt acgaaaaaac      180
tggtggtggt tatgttactg ctgttgttag aggtgatgtg gctgctgtaa aagctgctac      240
tgaagctggt caaagggctg ctgaaagagt tggagaagtt gttgctgttc atgttattcc      300
aagaccacat gttaatgttg atgctgcttt gccattgggt agaactccag gtatggataa      360
gtctgcttag ccgagacgac tgaccattta aatcatacct gacctccata gcagaaagtc      420
aaaagcctcc gaccggaggc ttttgacttg atcggcacgt aagaggttcc aactttcacc      480
ataatgaaat aagatcacta ccgggcgtat ttttttgagtt atcgagattt tcaggagcta      540
aggaagctaa aatgagccat attcaacggg aaacgtcttg ctcgaggccg cgattaaatt      600
ccaacatgga tgctgattta tatgggtata aatgggctcg cgataatgtc gggcaatcag      660
```

```
gtgcgacaat ctatcgattg tatgggaagc ccgatgcgcc agagttgttt ctgaaacatg    720
gcaaaggtag cgttgccaat gatgttacag atgagatggt caggctaaac tggctgacgg    780
aatttatgcc tcttccgacc atcaagcatt ttatccgtac tcctgatgat gcatggttac    840
tcaccactgc gatcccaggg aaaacagcat tccaggtatt agaagaatat cctgattcag    900
gtgaaaatat tgttgatgcg ctggcagtgt tcctgcgccg gttgcattcg attcctgttt    960
gtaattgtcc ttttaacggc gatcgcgtat ttcgtctcgc tcaggcgcaa tcacgaatga   1020
ataacggttt ggttggtgcg agtgattttg atgacgagcg taatggctgg cctgttgaac   1080
aagtctggaa agaaatgcat aagctttgc cattctcacc ggattcagtc gtcactcatg    1140
gtgatttctc acttgataac cttattttg acgaggggaa attaataggt tgtattgatg    1200
ttggacgagt cggaatcgca gaccgatacc aggatcttgc catcctatgg aactgcctcg   1260
gtgagttttc tccttcatta cagaaacggc tttttcaaaa atatggtatt gataatcctg   1320
atatgaataa attgcagttt cacttgatgc tcgatgagtt tttctaatga gggcccaaat   1380
gtaatcacct ggctcacctt cgggtgggcc tttctgcgtt gctggcgttt ttccataggc   1440 tccgccccc tgacgagcat cacaaaaatc gatgctcaag tcagaggtgg cgaaacccga   1500
caggactata aagataccag gcgtttcccc ctggaagctc cctcgtgcgc tctcctgttc   1560
cgaccctgcc gcttaccgga tacctgtccg cctttctccc ttcgggaagc gtggcgcttt   1620
ctcatagctc acgctgtagg tatctcagtt cggtgtaggt cgttcgctcc aagctgggct   1680
gtgtgcacga accccccgtt cagcccgacc gctgcgcctt atccggtaac tatcgtcttg   1740
agtccaaccc ggtaagacac gacttatcgc cactggcagc agccactggt aacaggatta   1800
gcagagcgag gtatgtaggc ggtgctacag agttcttgaa gtggtggcct aactacggct   1860
acactagaag aacagtattt ggtatctgcg ctctgctgaa gccagttacc tcggaaaaag   1920
agttggtagc tcttgatccg gcaaacaaac caccgctggt agcggtggtt ttttttgtttg   1980 caagcagcag attacgcgca gaaaaaaagg atctcaagaa gatcctttga ttttctaccg   2040
```

<210> SEQ ID NO 69
<211> LENGTH: 2031
<212> TYPE: DNA
<213> ORGANISM: Artificial Sequence
<220> FEATURE:
<223> OTHER INFORMATION: HcKan_O-HO-P plasmid

<400> SEQUENCE: 69

```
aagaaaggcc cacccgtgaa ggtgagccag tgagttgatt gcagtccagt tacgctggag     60
tccgtctcgg atggttttag gtaaagttgt cggtactgtt gttgcatcaa gaaaggaacc    120
aagaattgaa ggtttatctt tattattggt tagagcttgt gatccagatg gtactccaac    180
tggtggtgct gttgtttgtg ctgatgctgt tggtgctggt gttggtgaag ttgtttttata   240 tgcttctggt tcttctgcta gacaaactga agttactaat aatagaccag ttgatgctac    300
tattatggct attgttgatt tggttgaaat gggtggtgat gttagattta gaaaagatta    360
gccgagacga ctgaccattt aaatcatacc tgacctccat agcagaaagt caaaagcctc    420
cgaccggagg cttttgactt gatcggcacg taagaggttc caactttcac cataatgaaa    480
taagatcact accgggcgta ttttttgagt tatcgagatt ttcaggagct aaggaagcta    540
aaatgagcca tattcaacgg gaaacgtctt gctcgaggcc gcgattaaat tccaacatgg    600
atgctgattt atatgggtat aaatgggctc gcgataatgt cgggcaatca ggtgcgacaa    660
```

```
tctatcgatt gtatgggaag cccgatgcgc cagagttgtt tctgaaacat ggcaaaggta        720
gcgttgccaa tgatgttaca gatgagatgg tcaggctaaa ctggctgacg gaatttatgc        780
ctcttccgac catcaagcat tttatccgta ctcctgatga tgcatggtta ctcaccactg        840
cgatcccagg gaaaacagca ttccaggtat tagaagaata tcctgattca ggtgaaaata        900
ttgttgatgc gctggcagtg ttcctgcgcc ggttgcattc gattcctgtt tgtaattgtc        960
cttttaacgg cgatcgcgta tttcgtctcg ctcaggcgca atcacgaatg aataacggtt       1020
tggttggtgc gagtgatttt gatgacgagc gtaatggctg gcctgttgaa caagtctgga       1080
aagaaatgca taagcttttg ccattctcac cggattcagt cgtcactcat ggtgatttct       1140
cacttgataa ccttatttttt gacgagggga aattaatagg ttgtattgat gttggacgag       1200
tcggaatcgc agaccgatac caggatcttg ccatcctatg gaactgcctc ggtgagtttt       1260
ctccttcatt acagaaacgg cttttttcaaa aatatggtat tgataatcct gatatgaata       1320
aattgcagtt tcacttgatg ctcgatgagt ttttctaatg agggcccaaa tgtaatcacc       1380
tggctcacct tcgggtgggc ctttctgcgt tgctggcgtt tttccatagg ctccgccccc       1440
ctgacgagca tcacaaaaat cgatgctcaa gtcagaggtg gcgaaacccg acaggactat       1500
aaagatacca ggcgtttccc cctggaagct ccctcgtgcg ctctcctgtt ccgaccctgc       1560
cgcttaccgg atacctgtcc gcctttctcc cttcgggaag cgtggcgctt tctcatagct       1620
cacgctgtag gtatctcagt tcggtgtagg tcgttcgctc caagctgggc tgtgtgcacg       1680
aaccccccgt tcagcccgac cgctgcgcct tatccggtaa ctatcgtctt gagtccaacc       1740
cggtaagaca cgacttatcg ccactggcag cagccactgg taacaggatt agcagagcga       1800
ggtatgtagg cggtgctaca gagttcttga agtggtggcc taactacggc tacactagaa       1860
gaacagtatt tggtatctgc gctctgctga agccagttac ctcggaaaaa gagttggtag       1920
ctcttgatcc ggcaaacaaa ccaccgctgg tagcggtggt ttttttgttt gcaagcagca       1980
gattacgcgc agaaaaaaag gatctcaaga agatcctttg atttttctacc g              2031
```

```
<210> SEQ ID NO 70
<211> LENGTH: 2358
<212> TYPE: DNA
<213> ORGANISM: Artificial Sequence
<220> FEATURE:
<223> OTHER INFORMATION: HcKan_O-HO-T1 plasmid

<400> SEQUENCE: 70
aagaaaggcc cacccgtgaa ggtgagccag tgagttgatt gcagtccagt tacgctggag         60
tccgtctcgg atggatcatg ctccagaaag atttgatgct actcctccag ctggtgaacc        120
agatagacca gctttgggtg ttttggaatt gacttctatt gctagaggta ttaccgttgc        180
tgatgctgct ttgaaaagag caccatcttt gttgttgatg tccagaccag tttcttccgg        240
taaacatttg ttgatgatga gaggtcaagt tgccgaagtt gaagaatcta tgattgctgc        300
tagagaaatt gctggtgctg ttctggtgc tttgttggat gaattggaat tgccatatgc        360
tcacgaacaa ctttggagat ttttggatgc tccagttgtt gcagatgctt gggaagaaga        420
tactgaatcc gttattatcg ttgaaaccgc tactgtttgt gctgctattg attctgctga        480
tgcagcctta aaaactgctc ctgttgtttt gagagatatg agattggcta ttggtattgc        540
tggtaaggct ttctttactt tgactggtga attggctgat gttgaagctg ctgctgaagt        600
tgttagagaa agatgtggtg ctagattgct agaattggct tgtattgcaa gaccagttga        660
cgaattgaga ggtaggttgt ttttctagcc gagacgactg accatttaaa tcatacctga        720
```

-continued

```
cctccatagc agaaagtcaa aagcctccga ccggaggctt ttgacttgat cggcacgtaa      780
gaggttccaa ctttcaccat aatgaaataa gatcactacc gggcgtattt tttgagttat      840
cgagattttc aggagctaag gaagctaaaa tgagccatat tcaacgggaa acgtcttgct      900
cgaggccgcg attaaattcc aacatggatg ctgatttata tgggtataaa tgggctcgcg      960
ataatgtcgg gcaatcaggt gcgacaatct atcgattgta tgggaagccc gatgcgccag     1020
agttgtttct gaaacatggc aaaggtagcg ttgccaatga tgttacagat gagatggtca     1080
ggctaaactg gctgacggaa tttatgcctc ttccgaccat caagcatttt atccgtactc     1140
ctgatgatgc atggttactc accactgcga tcccagggaa aacagcattc caggtattag     1200
aagaatatcc tgattcaggt gaaaatattg ttgatgcgct ggcagtgttc ctgcgccggt     1260
tgcattcgat tcctgtttgt aattgtcctt ttaacggcga tcgcgtattt cgtctcgctc     1320
aggcgcaatc acgaatgaat aacggtttgg ttggtgcgag tgattttgat gacgagcgta     1380
atggctggcc tgttgaacaa gtctggaaag aaatgcataa gcttttgcca ttctcaccgg     1440
attcagtcgt cactcatggt gatttctcac ttgataacct tatttttgac gaggggaaat     1500
taataggttg tattgatgtt ggacgagtcg gaatcgcaga ccgataccag gatcttgcca     1560
tcctatggaa ctgcctcggt gagttttctc cttcattaca gaaacggctt tttcaaaaat     1620
atggtattga taatcctgat atgaataaat tgcagtttca cttgatgctc gatgagtttt     1680
tctaatgagg gcccaaatgt aatcacctgg ctcaccttcg ggtgggcctt tctgcgttgc     1740
tggcgttttt ccataggctc cgccccctg acgagcatca caaaaatcga tgctcaagtc      1800
agaggtggcg aaacccgaca ggactataaa gataccaggc gtttccccct ggaagctccc     1860
tcgtgcgctc tcctgttccg accctgccgc ttaccggata cctgtccgcc tttctccctt     1920
cgggaagcgt ggcgctttct catagctcac gctgtaggta tctcagttcg gtgtaggtcg     1980
ttcgctccaa gctgggctgt gtgcacgaac cccccgttca gcccgaccgc tgcgccttat     2040
ccggtaacta tcgtcttgag tccaacccgg taagacacga cttatcgcca ctggcagcag     2100
ccactggtaa caggattagc agagcgaggt atgtaggcgg tgctacagag ttcttgaagt     2160
ggtggcctaa ctacggctac actagaagaa cagtatttgg tatctgcgct ctgctgaagc     2220
cagttacctc ggaaaaagag ttggtagctc ttgatccggc aaacaaacca ccgctggtag     2280
cggtggtttt tttgtttgca agcagcagat tacgcgcaga aaaaaaggat ctcaagaaga     2340
tcctttgatt ttctaccg                                                   2358
```

```
<210> SEQ ID NO 71
<211> LENGTH: 2201
<212> TYPE: DNA
<213> ORGANISM: Artificial Sequence
<220> FEATURE:
<223> OTHER INFORMATION: HcKan_T-RPL41B plasmid

<400> SEQUENCE: 71
```

```
aagaaaggcc cacccgtgaa ggtgagccag tgagttgatt gcagtccagt tacgctggag       60
tccgtctcgt agcgcggatt gagagcaaat cgttaagttc aggtcaagta aaaattgatt      120
tcgaaaacta atttctctta tacaatcctt tgattggacc gtcatccttt cgaatataag      180
attttgttaa gaatatttta gacagagatc tactttatat ttaatatcta gatattacat      240
aatttcctct ctaataaaat atcattaata aaataaaaat gaagcgattt gattttgtgt      300
tgtcaactta gtttgccgct atgcctcttg ggtaatgcta ttattgaatc gaagggcttt      360
```

```
attatattac cctttagctt attctgaggt ttctgtggcg tgcaaagtga tgaaccgggc      420 gggtttaag gataaaatca aaaagtgaaa aaatgaacgg aaaatggaat acctgtgaaa      480
tggagaatga taatgaatct ttctgtcgtg cttgaaagat tttcggctcc tccgagacga      540
ctgaccattt aaatcatacc tgacctccat agcagaaagt caaaagcctc cgaccggagg      600
cttttgactt gatcggcacg taagaggttc caactttcac cataatgaaa taagatcact      660
accgggcgta ttttttgagt tatcgagatt ttcaggagct aaggaagcta aaatgagcca      720
tattcaacgg gaaacgtctt gctcgaggcc gcgattaaat tccaacatgg atgctgattt      780
atatgggtat aaatgggctc gcgataatgt cgggcaatca ggtgcgacaa tctatcgatt      840
gtatgggaag cccgatgcgc cagagttgtt tctgaaacat ggcaaaggta gcgttgccaa      900
tgatgttaca gatgagatgg tcaggctaaa ctggctgacg gaatttatgc ctcttccgac      960
catcaagcat tttatccgta ctcctgatga tgcatggtta ctcaccactg cgatcccagg     1020
gaaaacagca ttccaggtat tagaagaata tcctgattca ggtgaaaata ttgttgatgc     1080
gctggcagtg ttcctgcgcc ggttgcattc gattcctgtt tgtaattgtc cttttaacgg     1140
cgatcgcgta tttcgtctcg ctcaggcgca atcacgaatg aataacggtt tggttggtgc     1200
gagtgatttt gatgacgagc gtaatggctg gcctgttgaa caagtctgga agaaatgca     1260 taagctttg ccattctcac cggattcagt cgtcactcat ggtgatttct cacttgataa     1320
ccttattttt gacgagggga aattaatagg ttgtattgat gttggacgag tcggaatcgc     1380
agaccgatac caggatcttg ccatcctatg gaactgcctc ggtgagtttt ctccttcatt     1440
acagaaacgg cttttccaaa aatatggtat tgataatcct gatatgaata aattgcagtt     1500
tcacttgatg ctcgatgagt ttttctaatg agggcccaaa tgtaatcacc tggctcacct     1560
tcgggtgggc ctttctgcgt tgctggcgtt tttccatagg ctccgccccc ctgacgagca     1620
tcacaaaaat cgatgctcaa gtcagaggtg gcgaaacccg acaggactat aaagatacca     1680
ggcgtttccc cctggaagct ccctcgtgcg ctctcctgtt ccgaccctgc cgcttaccgg     1740
atacctgtcc gcctttctcc cttcgggaag cgtggcgctt tctcatagct cacgctgtag     1800
gtatctcagt tcggtgtagg tcgttcgctc caagctgggc tgtgtgcacg aaccccccgt     1860
tcagcccgac cgctgcgcct tatccggtaa ctatcgtctt gagtccaacc cggtaagaca     1920
cgacttatcg ccactggcag cagccactgg taacaggatt agcagagcga ggtatgtagg     1980
cggtgctaca gagttcttga agtggtggcc taactacggc tacactagaa gaacagtatt     2040
tggtatctgc gctctgctga agccagttac ctcggaaaaa gagttggtag ctcttgatcc     2100
ggcaaacaaa ccaccgctgg tagcggtggt ttttttgttt gcaagcagca gattacgcgc     2160
agaaaaaaag gatctcaaga agatcctttg attttctacc g                          2201
```

<210> SEQ ID NO 72
<211> LENGTH: 2172
<212> TYPE: DNA
<213> ORGANISM: Artificial Sequence
<220> FEATURE:
<223> OTHER INFORMATION: HcKan_T-HBT1 plasmid

<400> SEQUENCE: 72

```
aagaaaggcc cacccgtgaa ggtgagccag tgagttgatt gcagtccagt tacgctggag       60
tccgtctcgt agcacacttc tcgattaaca aattcccagt attctttgaa atctattttt      120
cttcctcaat tgaatttgaa taactgtcta cgcggactcc tcctatctac aactacaaca      180
aattttaacc actttattac cactttcctc tttcatttat ttttgtcttt tatgttgtca      240
```

```
atttactagt attttttttt ttttcattta cgttcaaggt tttttatact catttaactt          300
gtcttaggtt atttatatat atacctatat atttatatat atatatatat atgtatgtat          360
atattattat caccaaatga gaaataatag ctaatttgat ttttgattat ttaaaatatt          420
ggtttgttct ttctgcaaac atctcgtttg gtacgatatt agtgaaaaac gatgtaatta          480
tcaacacgtg cattacccac ctccgagacg actgaccatt taaatcatac ctgacctcca          540
tagcagaaag tcaaaagcct ccgaccggag gcttttgact tgatcggcac gtaagaggtt          600
ccaactttca ccataatgaa ataagatcac taccgggcgt attttttgag ttatcgagat          660
tttcaggagc taaggaagct aaaatgagcc atattcaacg ggaaacgtct tgctcgaggc          720
cgcgattaaa ttccaacatg gatgctgatt tatatgggta taaatgggct cgcgataatg          780
tcgggcaatc aggtgcgaca atctatcgat tgtatgggaa gcccgatgcg ccagagttgt          840
ttctgaaaca tggcaaaggt agcgttgcca atgatgttac agatgagatg gtcaggctaa          900
actggctgac ggaatttatg cctcttccga ccatcaagca ttttatccgt actcctgatg          960
atgcatggtt actcaccact gcgatcccag ggaaaacagc attccaggta ttagaagaat         1020
atcctgattc aggtgaaaat attgttgatg cgctggcagt gttcctgcgc cggttgcatt         1080
cgattcctgt ttgtaattgt ccttttaacg gcgatcgcgt atttcgtctc gctcaggcgc         1140
aatcacgaat gaataacggt ttggttggtg cgagtgattt tgatgacgag cgtaatggct         1200
ggcctgttga acaagtctgg aaagaaatgc ataagctttt gccattctca ccggattcag         1260
tcgtcactca tggtgatttc tcacttgata accttatttt tgacgagggg aaattaatag         1320
gttgtattga tgttggacga gtcggaatcg cagaccgata ccaggatctt gccatcctat         1380
ggaactgcct cggtgagttt ctccttcat tacagaaacg ctttttcaa aaatatggta          1440 ttgataatcc tgatatgaat aaattgcagt ttcacttgat gctcgatgag ttttttctaat        1500 gagggcccaa atgtaatcac ctggctcacc ttcgggtggg cctttctgcg ttgctggcgt         1560
ttttccatag gctccgcccc cctgacgagc atcacaaaaa tcgatgctca agtcagaggt         1620
ggcgaaaccc gacaggacta taaagatacc aggcgtttcc ccctggaagc tccctcgtgc         1680
gctctcctgt tccgaccctg ccgcttaccg gatacctgtc cgcctttctc ccttcgggaa         1740
gcgtggcgct ttctcatagc tcacgctgta ggtatctcag ttcggtgtag gtcgttcgct         1800
ccaagctggg ctgtgtgcac gaacccccg ttcagcccga ccgctgcgcc ttatccggta         1860
actatcgtct tgagtccaac ccggtaagac acgacttatc gccactggca gcagccactg         1920
gtaacaggat tagcagagcg aggtatgtag gcggtgctac agagttcttg aagtggtggc         1980
ctaactacgg ctacactaga agaacagtat ttggtatctg cgctctgctg aagccagtta         2040
cctcggaaaa agagttggta gctcttgatc cggcaaacaa accaccgctg gtagcggtgg         2100
tttttttgtt tgcaagcagc agattacgcg cagaaaaaaa ggatctcaag aagatccttt         2160
gattttctac cg                                                              2172
```

```
<210> SEQ ID NO 73
<211> LENGTH: 2200
<212> TYPE: DNA
<213> ORGANISM: Artificial Sequence
<220> FEATURE:
<223> OTHER INFORMATION: HcKan_T-RPS20 plasmid

<400> SEQUENCE: 73
aagaaaggcc cacccgtgaa ggtgagccag tgagttgatt gcagtccagt tacgctggag           60
```

```
tccgtctcgt agcaactaag ctggttctaa ctggaaataa tttccattag attcctcttt      120
ttctcgtcca ttaaccaaaa tatattattg aattcagcgg ttccttttt ctcattttcg       180 catatagctg cactattaga atcagcccac tctaggtaaa cacagttcct cgatatacct      240
ctgtcttact atcagtggtt aaaccttatg caaatataat atatatatat atatatatat      300
ctcatacttt tgttgattct tgtgtaatta ttggaaaaga caaaacaaag caagcgtttc      360
tattcatcat atttacaagt attttttatga aaaactattt cttaattttc ccaccggcgg     420
ctttgaataa ggcaatgtca ttgtcctgca taatatattg tttgcctgca cgtttgataa      480
gtcccttaga ttttagtaaa gactcattta gcggtggttc catcttccct ccgagacgac      540
tgaccattta aatcatacct gacctccata gcagaaagtc aaaagcctcc gaccggaggc      600
ttttgacttg atcggcacgt aagaggttcc aactttcacc ataatgaaat aagatcacta      660
ccgggcgtat tttttgagtt atcgagattt tcaggagcta aggaagctaa aatgagccat      720
attcaacggg aaacgtcttg ctcgaggccg cgattaaatt ccaacatgga tgctgattta      780
tatgggtata aatgggctcg cgataatgtc gggcaatcag gtgcgacaat ctatcgattg      840
tatgggaagc ccgatgcgcc agagttgttt ctgaaacatg gcaaaggtag cgttgccaat      900
gatgttacag atgagatggt caggctaaac tggctgacgg aatttatgcc tcttccgacc      960
atcaagcatt ttatccgtac tcctgatgat gcatggttac tcaccactgc gatcccaggg     1020
aaaacagcat tccaggtatt agaagaatat cctgattcag gtgaaaatat tgttgatgcg     1080
ctggcagtgt tcctgcgccg gttgcattcg attcctgttt gtaattgtcc ttttaacggc     1140
gatcgcgtat ttcgtctcgc tcaggcgcaa tcacgaatga ataacggttt ggttggtgcg     1200
agtgattttg atgacgagcg taatggctgg cctgttgaac aagtctggaa agaaatgcat     1260
aagcttttgc cattctcacc ggattcagtc gtcactcatg gtgatttctc acttgataac     1320
cttatttttg acgaggggaa attaataggt tgtattgatg ttggacgagt cggaatcgca     1380
gaccgatacc aggatcttgc catcctatgg aactgcctcg gtgagttttc tccttcatta     1440
cagaaacggc ttttttcaaaa atatggtatt gataatcctg atatgaataa attgcagttt     1500
cacttgatgc tcgatgagtt tttctaatga gggcccaaat gtaatcacct ggctcacctt     1560
cgggtgggcc tttctgcgtt gctggcgttt ttccataggc tccgcccccc tgacgagcat     1620
cacaaaaatc gatgctcaag tcagaggtgg cgaaacccga caggactata aagataccag     1680
gcgtttcccc ctggaagctc cctcgtgcgc tctcctgttc cgaccctgcc gcttaccgga     1740
tacctgtccg cctttctccc ttcgggaagc gtggcgcttt ctcatagctc acgctgtagg     1800
tatctcagtt cggtgtaggt cgttcgctcc aagctgggct gtgtgcacga accccccgtt     1860
cagcccgacc gctgcgcctt atccggtaac tatcgtcttg agtccaaccc ggtaagacac     1920
gacttatcgc cactggcagc agccactggt aacaggatta gcagagcgag gtatgtaggc     1980
ggtgctacag agttcttgaa gtggtggcct aactacggct acactagaag aacagtattt     2040
ggtatctgcg ctctgctgaa gccagttacc tcggaaaaag agttggtagc tcttgatccg     2100
gcaaacaaac caccgctggt agcggtggtt tttttgtttg caagcagcag attacgcgca     2160
gaaaaaaagg atctcaagaa gatcctttga ttttctaccg                          2200
```

<210> SEQ ID NO 74
<211> LENGTH: 4531
<212> TYPE: DNA
<213> ORGANISM: Artificial Sequence
<220> FEATURE:
<223> OTHER INFORMATION: pCKU plasmid

<400> SEQUENCE: 74

```
actcctccct gcaagacggt gagttcatct acaaagttaa actgcgtggt accaacttcc     60
cgtccgacgg tccggttatg cagaaaaaaa ccatgggttg ggaagcttcc accgaacgta    120
tgtacccgga agacggtgct ctgaaaggtg aaatcaaaat gcgtctgaaa ctgaaagacg    180
gtggtcacta cgacgctgaa gttaaaacca cctacatggc taaaaaaccg gttcagctgc    240
cgggtgctta caaaaccgac atcaaactgg acatcacctc ccacaacgaa gactacacca    300
tcgttgaaca gtacgaacgt gctgaaggtc gtcactccac cggtgcttaa taacgctgat    360
agtgctagtg tagatcgcta ctagagccag gcatcaaata aaacgaaagg ctcagtcgaa    420
agactgggcc tttcgtttta tctgttgttt gtcggtgaac gctctctact agagtggtct    480
catgagcgag acgtccggca tccgcttaca gacaagctgt gacaatctcc gggagctgca    540
tgtgtcagag gttttcaccg tcatcaccga aacgcgcgag attaaagggc ctcgtgatac    600 gcctatttt  ataggttaat gtcatgataa taatggtttc ttagacggat cgcttgcctg    660
taacttacac gcgcctcgta tcttttaatg atggaataat ttgggaattt actctgtgtt    720
tatttatttt tatgttttgt atttggattt tagaaagtaa ataaagaagg tagaagagtt    780
acggaatgaa gaaaaaaaaa taaacaaagg tttaaaaaat ttcaacaaaa agcgtacttt    840
acatatatat ttattagaca agaaaagcag attaaataga tatacattcg attaacgata    900
agtaaaatgt aaaatcacag gattttcgtg tgtggtcttc tacacagaca agatgaaaca    960
attcggcatt aatacctgag agcaggaaga gcaagataaa aggtagtatt tgttggcgat   1020
ccccctagag tcttttacat cttcggaaaa caaaaactat tttttcttta atttctttt    1080 ttactttcta tttttaattt atatatttat attaaaaaat ttaaattata attatttta    1140 tagcacgtga tgaaaaggac ccaggtggca ttgacttgat cggcacgtaa gaggttccaa   1200
ctttcaccat aatgaaataa gatcactacc gggcgtattt tttgagttat cgagattttc   1260
aggagctaag gaagctaaaa tgagccatat tcaacgggaa acgtcttgct cgaggccgcg   1320
attaaattcc aacatggatg ctgatttata tgggtataaa tgggctcgcg ataatgtcgg   1380
gcaatcaggt gcgacaatct atcgattgta tgggaagccc gatgcgccag agttgtttct   1440
gaaacatggc aaaggtagcg ttgccaatga tgttacagat gagatggtca ggctaaactg   1500
gctgacggaa tttatgcctc ttccgaccat caagcatttt atccgtactc ctgatgatgc   1560
atggttactc accactgcga tcccagggaa aacagcattc caggtattag aagaatatcc   1620
tgattcaggt gaaaatattg ttgatgcgct ggcagtgttc ctgcgccggt tgcattcgat   1680
tcctgtttgt aattgtcctt ttaacggcga tcgcgtattt cgtctcgcac aggcgcaatc   1740
acgaatgaat aacggtttgg ttggtgcgag tgattttgat gacgagcgta atggctggcc   1800
tgttgaacaa gtctggaaag aaatgcataa gcttttgcca ttctcaccgg attcagtcgt   1860
cactcatggt gatttctcac ttgataacct tattttgac  gaggggaaat taataggttg   1920
tattgatgtt ggacgagtcg gaatcgcaga ccgataccag gatcttgcca tcctatggaa   1980
ctgcctcggt gagttttctc cttcattaca gaaacggctt tttcaaaaat atggtattga   2040
taatcctgat atgaataaat tgcagtttca cttgatgctc gatgagtttt ctaatgagg    2100 gcccaaatgt aatcacctgg ctcaccttcg ggtgggcctt tctgcgttgc tggcgttttt   2160
ccataggctc cgcccccctg acgagcatca caaaaatcga tgctcaagtc agaggtggcg   2220
aaacccgaca ggactataaa gataccaggc gtttccccct ggaagctccc tcgtgcgctc   2280
```

-continued

```
tcctgttccg accctgccgc ttaccggata cctgtccgcc tttctccctt cgggaagcgt   2340
ggcgctttct catagctcac gctgtaggta tctcagttcg gtgtaggtcg ttcgctccaa   2400
gctgggctgt gtgcacgaac cccccgttca gcccgaccgc tgcgccttat ccggtaacta   2460
tcgtcttgag tccaacccgg taagacacga cttatcgcca ctggcagcag ccactggtaa   2520
caggattagc agagcgaggt atgtaggcgg tgctacagag ttcttgaagt ggtggcctaa   2580
ctacggctac actagaagaa cagtatttgg tatctgcgct ctgctgaagc cagttacctc   2640
ggaaaaagag ttggtagctc ttgatccggc aaacaaacca ccgctggtag cggtggtttt   2700
tttgtttgca agcagcagat tacgcgcaga aaaaaaggat ctcaagaaga tcctttgatt   2760
ttctaccgaa cgtttacaat ttcctgatgc ggtattttct ccttacgcat ctgtgcggta   2820
tttcacaccg catagggtaa taactgatat aattaaattg aagctctaat ttgtgagttt   2880
agtatacatg catttactta taatacagtt ttttagtttt gctggccgca tcttctcaaa   2940
tatgcttccc agcctgcttt tctgtaacgt tcaccctcta ccttagcatc ccttcccttt   3000
gcaaatagtc ctcttccaac aataataatg tcagatcctg tagacaccac atcatccacg   3060
gttctatact gttgacccaa tgcgtcaccc ttgtcatcta aacccacacc gggtgtcata   3120
atcaaccaat cgtaaccttc atctcttcca cccatgtctc tttgagcaat aaagccgata   3180
acaaaatctt tgtcgctctt cgcaatgtca acagtaccct tagtatattc tccagtagat   3240
agggagccct tgcatgacaa ttctgctaac atcaaaaggc ctctaggttc ctttgttact   3300
tcttctgccg cctgcttcaa accgctaaca atacctgggc ccaccacacc gtgtgcattc   3360
gtaatgtctg cccattctgc tattctgtat acacccgcag agtactgcaa tttgactgta   3420
ttaccaatgt cagcaaattt tctgtcttcg aagagtaaaa aattgtactt ggcggataat   3480
gcctttagcg gcttaactgt gccctccatg gaaaaatcag tcaagatatc cacatgtgtt   3540
tttagtaaac aaattttggg acctaatgct tcaactaact ccagtaattc cttggtggta   3600
cgaacatcca atgaagcaca caagtttgtt tgcttttcgt gcatgatatt aaatagcttg   3660
gcagcaacag gactaggatg agtagcagca cgttccttat atgtagcttt cgacatgatt   3720
tatcttcgtt tcctgcaggt ttttgttctg tgcagttggg ttaagaatac tgggcaattt   3780
catgtttctt caacactaca tatgcgtata tataccaatc taagtctgtg ctccttcctt   3840
cgttcttcct tctgttcgga gattaccgaa tcaaaaaaat ttcaaagaaa ccgaaatcaa   3900 aaaaagaat aaaaaaaaaa tgatgaattg aattgaaaag ctgtggtatg gtgcactacg   3960
tctcgacctc gagaccgcaa tacgcaaacc gcctctcccc gcgcgttggc cgattcatta   4020
atgcagctgg cacgacaggt ttcccgactg gaaagcgggc agtgagcgca acgcaattaa   4080
tgtgagttag ctcactcatt aggcacccca ggctttacac tttatgcttc cggctcgtat   4140
gttgtgtgga attgtgagcg gataacaatt tcacacatac tagagaaaga ggagaaatac   4200
tagatggctt cctccgaaga cgttatcaaa gagttcatgc gtttcaaagt tcgtatggaa   4260
ggttccgtta acggtcacga gttcgaaatc gaaggtgaag gtgaaggtcg tccgtacgaa   4320
ggtacccaga ccgctaaact gaaagttacc aaaggtggtc cgctgccgtt cgcttgggac   4380
atcctgtccc cgcagttcca gtacggttcc aaagcttacg ttaaacaccc ggctgacatc   4440
ccggactacc tgaaactgtc cttcccggaa ggtttcaaat gggaacgtgt tatgaacttc   4500
gaagacggtg gtgttgttac cgttacccag g                                   4531
```

```
<210> SEQ ID NO 75
<211> LENGTH: 6441
```

<212> TYPE: DNA
<213> ORGANISM: Artificial Sequence
<220> FEATURE:
<223> OTHER INFORMATION: pGAU-YMRW?15 plasmid

<400> SEQUENCE: 75

```
gcaaaaggcc aggaaccgta aaaaggccgc gttgctggcg ttttttccata ggctccgccc     60 ccctgacgag catcacaaaa atcgacgctc aagtcagagg tggcgaaacc cgacaggact    120
ataaagatac caggcgtttc cccctggaag ctccctcgtg cgctctcctg ttccgaccct    180
gccgcttacc ggatacctgt ccgcctttct cccttcggga agcgtggcgc tttctcatag    240
ctcacgctgt aggtatctca gttcggtgta ggtcgttcgc tccaagctgg gctgtgtgca    300
cgaacccccc gttcagcccg accgctgcgc cttatccggt aactatcgtc ttgagtccaa    360
cccggtaaga cacgacttat cgccactggc agcagccact ggtaacagga ttagcagagc    420
gaggtatgta ggcggtgcta cagagttctt gaagtggtgg cctaactacg gctacactag    480
aaggacagta tttggtatct gcgctctgct gaagccagtt accttcggaa aaagagttgg    540
tagctcttga tccggcaaac aaaccaccgc tggtagcggt ggtttttttg tttgcaagca    600
gcagattacg cgcagaaaaa aaggatctca agaagatcct ttgatctttt ctacggggtc    660
tgacgctcag tggaacgaaa actcacgtta agggattttg gtcatgagat tatcaaaaag    720
gatcttcacc tagatccttt taaattaaaa atgaagtttt aaatcaatct aaagtatata    780
tgagtaaact tggtctgaca gttaccaatg cttaatcagt gaggcaccta tctcagcgat    840
ctgtctattt cgttcatcca tagttgcctg actccccgtc gtgtagataa ctacgatacg    900
ggagggctta ccatctggcc ccagtgctgc aatgataccg cggctccac gctcaccggc    960 tccagattta tcagcaataa accagccagc cggaagggcc gagcgcagaa gtggtcctgc   1020
aactttatcc gcctccatcc agtctattaa ttgttgccgg gaagctagag taagtagttc   1080
gccagttaat agtttgcgca acgttgttgc cattgctaca ggcatcgtgg tgtcacgctc   1140
gtcgtttggt atggcttcat tcagctccgg ttcccaacga tcaaggcgag ttacatgatc   1200
ccccatgttg tgcaaaaaag cggttagctc cttcggtcct ccgatcgttg tcagaagtaa   1260
gttggccgca gtgttatcac tcatggttat ggcagcactg cataattctc ttactgtcat   1320
gccatccgta agatgctttt ctgtgactgg tgagtactca accaagtcat tctgagaata   1380
gtgtatgcgg cgaccgagtt gctcttgccc ggcgtcaata cgggataata ccgcgccaca   1440
tagcagaact ttaaaagtgc tcatcattgg aaaacgttct tcggggcgaa aactctcaag   1500
gatcttaccg ctgttgagat ccagttcgat gtaacccact cgtgcaccca actgatcttc   1560
agcatctttt actttcacca gcgtttctgg gtgagcaaaa acaggaaggc aaaatgccgc   1620
aaaaaaggga ataagggcga cacgaaatg ttgaatactc atactcttcc tttttcaata   1680
ttattgaagc atttatcagg gttattgtct catgagcgga tacatatttg aatgtattta   1740
gaaaaataaa caaatagggg ttccgcgcac atttccccga aaagtgccac ggtctctgtc   1800
atcaatcaaa gcaacccaca aatcctaggc tgaatcatga tatcgatgga agcaatcaac   1860
aattttatca agaccgcacc aaagcacgac tatctgacag gcggagttca tcattctggt   1920
aatgtagacg tgttacaatt aagcggcaat aaagaagatg gtagtttagt atggaaccat   1980
acttttgttg atgtagacaa caatgtggta gctaagtttg aagacgctct cgaaaaactt   2040
gaaagtttgc accggcgctc atcctcatcc acaggcaatg aagaacacgc taacgtttaa   2100
ccgaggggag tcacttcata atgatgtgag aaataagtga atattgtaat aattgttggg   2160
```

-continued

```
actccattgt caacaaaagc tataatgtag gtatacagta tatactagaa gttctcctcg    2220
aggatcttgg aatccacaaa agggagtcga taaatctata taataaaaat tactttatct    2280
tctttcgttt tatacgttgt cgtttattat cctattacgt tatcaatctt cgcatttcag    2340
ctttcattag atttgatgac tgtttctcaa actttatgtc attttcttac accgctctct    2400
acctggctcg aagcacgcta gtaacatcag ctaacgaaag agttagaggc tcgctaaatc    2460
gcactgtcgg ggtcccttgg gtattttaca ctagcgtcag gacgactagc atgtgtcttt    2520
ccttccaggg gtatgcgggt gcgtggacaa atgagcagca tacgtattta ctcggcgtgc    2580
ctgctctctc gtatttctcc tggagatcaa ggaaatgttt catgtccaag cgaaaagccg    2640
ctctacggaa tggatctacg ttactgcctg cataaggaaa ccggtgtagc caaggacgaa    2700
agcgacccta ggttctaacc atcgactttg gcggaaaggt ttcactcagg aagcagacac    2760
tgattgacac ggtttagcag aacgtttgag gactaggtca aattgagtgg tttaatatcg    2820
gcatgtctgg ctttaaaatt cagtatagtg cgctgatcgg aaacgaatta aaaacacgag    2880
ttcccaaaac caggcgggct cgccacgcta atcgggatgc ataccacagc ttttcaattc    2940
aattcatcat ttttttttta ttcttttttt tgatttcggt ttctttgaaa tttttttgat    3000
tcggtaatct ccgaacagaa ggaagaacga aggaaggagc acagacttag attggtatat    3060
atacgcatat gtagtgttga agaaacatga aattgcccag tattcttaac ccaactgcac    3120
agaacaaaaa cctgcaggaa acgaagataa atcatgtcga aagctacata taggaacgt     3180 gctgctactc atcctagtcc tgttgctgcc aagctattta atatcatgca cgaaaagcaa    3240
acaaacttgt gtgcttcatt ggatgttcgt accaccaagg aattactgga gttagttgaa    3300
gcattaggtc ccaaaatttg tttactaaaa acacatgtgg atatcttgac tgattttttcc   3360 atggagggca cagttaagcc gctaaaggca ttatccgcca agtacaattt tttactcttc    3420
gaagacagaa aatttgctga cattggtaat acagtcaaat tgcagtactc tgcgggtgta    3480
tacagaatag cagaatgggc agacattacg aatgcacacg gtgtggtggg cccaggtatt    3540
gttagcggtt tgaagcaggc ggcagaagaa gtaacaaagg aacctagagg ccttttgatg    3600
ttagcagaat tgtcatgcaa gggctcccta tctactggag aatatactaa gggtactgtt    3660
gacattgcga agagcgacaa agattttgtt atcggcttta ttgctcaaag agacatgggt    3720
ggaagagatg aaggttacga ttggttgatt atgacacccg gtgtgggttt agatgacaag    3780
ggtgacgcat tgggtcaaca gtatagaacc gtggatgatg tggtgtctac aggatctgac    3840
attattattg ttggaagagg actatttgca aagggaaggg atgctaaggt agagggtgaa    3900
cgttacagaa aagcaggctg ggaagcatat ttgagaagat gcggccagca aaactaaaaa    3960
actgtattat aagtaaatgc atgtatacta aactcacaaa ttagagcttc aatttaatta    4020
tatcagttat taccctatgc ggtgtgaaat accgcacaga tgcgtaagga gaaaataccg    4080
catcaggtag ccgctagtaa catcagctaa cgaaagagtt agaggctcgc taaatcgcac    4140
tgtcggggtc ccttgggtat tttacactag cgtcaggacg actagcatgt gtctttcctt    4200
ccaggggtat gcgggtgcgt ggacaaatga gcagcatacg tatttactcg gcgtgcctgc    4260
tctctcgtat ttctcctgga gatcaaggaa atgtttcatg tccaagcgaa aagccgctct    4320
acggaatgga tctacgttac tgcctgcata aggaaaccgg tgtagccaag gacgaaagcg    4380
accctaggtt ctaaccatcg actttggcgg aaaggtttca ctcaggaagc agacactgat    4440
tgacacggtt tagcagaacg tttgaggact aggtcaaatt gagtggttta atatcggcat    4500
gtctggcttt aaaattcagt atagtgcgct gatcggaaac gaattaaaaa cacgagttcc    4560
```

-continued

```
caaaaccagg cgggctcgcc acgctaatcg gtgcaccacc tcaggcagag aacctagaga    4620
cggcaatacg caaaccgcct ctccccgcgc gttggccgat tcattaatgc agctggcacg    4680
acaggtttcc cgactggaaa gcgggcagtg agcgcaacgc aattaatgtg agttagctca    4740
ctcattaggc accccaggct ttacacttta tgcttccggc tcgtatgttg tgtggaattg    4800
tgagcggata acaatttcac acatactaga gaaagaggag aaatactaga tggcttcctc    4860
cgaagacgtt atcaaagagt tcatgcgttt caaagttcgt atggaaggtt ccgttaacgg    4920
tcacgagttc gaaatcgaag gtgaaggtga aggtcgtccg tacgaaggta cccagaccgc    4980
taaactgaaa gttaccaaag gtggtccgct gccgttcgct tgggcatcc tgtccccgca     5040 gttccagtac ggttccaaag cttacgttaa acacccggct gacatcccgg actacctgaa    5100
actgtccttc ccggaaggtt tcaaatggga acgtgttatg aacttcgaag acggtggtgt    5160
tgttaccgtt acccaggact cctccctgca agacggtgag ttcatctaca agttaaact     5220 gcgtggtacc aacttcccgt ccgacggtcc ggttatgcag aaaaaaacca tgggttggga    5280
agcttccacc gaacgtatgt acccggaaga cggtgctctg aaaggtgaaa tcaaaatgcg    5340
tctgaaactg aaagacggtg gtcactacga cgctgaagtt aaaaccacct acatggctaa    5400
aaaaccggtt cagctgccgg gtgcttacaa aaccgacatc aaactggaca tcacctccca    5460
caacgaagac tacaccatcg ttgaacagta cgaacgtgct gaaggtcgtc actccaccgg    5520
tgcttaataa cgctgatagt gctagtgtag atcgctacta gagccaggca tcaaataaaa    5580
cgaaaggctc agtcgaaaga ctgggccttt cgttttatct gttgtttgtc ggtgaacgct    5640
ctctactaga gtcacactgg ctccgtctca tgagcgctca tggaaaatgc aaccgataaa    5700
ccattataaa tcttcgcggt tatctggcat tgttattaac caaaaaaatg ccggcctatt    5760
acaagctact gttcaataaa tattgttgta atgaagacgg tccaactgta caaatacagc    5820
aaactgtcat atataaggag tcttatgtga cagcacttgc gttattgtca gccggagtat    5880
gtctttgtcg cattctgggc ttttttacttt ctgctcagaa ggaagtacga acaagaaaaa    5940
aaaatcacca atgcttccct tttcagtatt agtttcatat ttgtttacgt tcaaactcgt    6000
cgtttgcgcg ataacctcta aaaaagtcaa ttacgtaact atatcaatca gagaatgcaa    6060
aaagcactat cataaaaatg tgtctagggg atgtgagaca tgtcaattat aagaagtgat    6120
ggtgtcatag tatatatatc ataaaagatt atcaaagttt caatcctttg tattttctag    6180
tttagcgcca acttttgaca aaacctaaac tttagataat catcattctt acaattttta    6240
tctggatggc aataatctcc tatataaagc ccagataaac tgtaaaaaga atccatcact    6300
atttgaaaaa aagtcatctg gcacgtttaa ttatcagagc agaaatgatg aagggtgtta    6360
gcgccgtcca ctgatgtgcc tggtagtcat gatttacgta taactaacac atcatgagga    6420
cggcggctcg gagagaccga t                                             6441
```

<210> SEQ ID NO 76
<211> LENGTH: 7606
<212> TYPE: DNA
<213> ORGANISM: Artificial Sequence
<220> FEATURE:
<223> OTHER INFORMATION: pGAU-YMRW?15-HO-BMC plasmid

<400> SEQUENCE: 76

```
tgagcgagac gtccggcatc cgcttacaga caagctgtga caatctccgg gagctgcatg        60
tgtcagaggt tttcaccgtc atcaccgaaa cgcgcgagat taaagggcct cgtgatacgc       120
```

-continued

```
ctattttttat aggttaatgt catgataata atggtttctt agacggatcg cttgcctgta      180
acttacacgc gcctcgtatc tttttaatgat ggaataattt gggaatttac tctgtgttta      240
tttattttta tgttttgtat ttggatttta gaaagtaaat aaagaaggta gaagagttac      300
ggaatgaaga aaaaaaaata aacaaaggtt taaaaaattt caacaaaaag cgtactttac      360
atatatattt attagacaag aaaagcagat taaatagata tacattcgat taacgataag      420
taaaatgtaa aatcacagga ttttcgtgtg tggtcttcta cacagacaag atgaaacaat      480
tcggcattaa tacctgagag caggaagagc aagataaaag gtagtatttg ttggcgatcc      540
ccctagagtc ttttacatct tcggaaaaca aaaactattt tttctttaat ttctttttttt      600 actttctatt tttaatttat atatttatat taaaaaattt aaattataat tatttttata      660
gcacgtgatg aaaaggaccc aggtggcatt gacttgatcg gcacgtaaga ggttccaact      720
ttcaccataa tgaaataaga tcactaccgg gcgtattttt tgagttatcg agattttcag      780
gagctaagga agctaaaatg agccatattc aacgggaaac gtcttgctcg aggccgcgat      840
taaattccaa catggatgct gatttatatg ggtataaatg ggctcgcgat aatgtcgggc      900
aatcaggtgc gacaatctat cgattgtatg ggaagcccga tgcgccagag ttgtttctga      960
aacatggcaa aggtagcgtt gccaatgatg ttacagatga gatggtcagg ctaaactggc     1020
tgacggaatt tatgcctctt ccgaccatca agcattttat ccgtactcct gatgatgcat     1080
ggttactcac cactgcgatc ccagggaaaa cagcattcca ggtattagaa gaatatcctg     1140
attcaggtga aaatattgtt gatgcgctgg cagtgttcct gcgccggttg cattcgattc     1200
ctgtttgtaa ttgtcctttt aacggcgatc gcgtatttcg tctcgcacag cgcaatcac     1260 gaatgaataa cggtttggtt ggtgcgagtg attttgatga cgagcgtaat ggctggcctg     1320
ttgaacaagt ctggaaagaa atgcataagc ttttgccatt ctcaccggat tcagtcgtca     1380
ctcatggtga tttctcactt gataacctta tttttgacga ggggaaatta ataggttgta     1440
ttgatgttgg acgagtcgga atcgcagacc gataccagga tcttgccatc ctatggaact     1500
gcctcggtga gtttttctcct tcattacaga aacggctttt tcaaaaatat ggtattgata     1560
atcctgatat gaataaattg cagtttcact tgatgctcga tgagtttttc taatgagggc     1620
ccaaatgtaa tcacctggct caccttcggg tgggcctttc tgcgttgctg gcgtttttcc     1680
ataggctccg cccccctgac gagcatcaca aaaatcgatg ctcaagtcag aggtggcgaa     1740
acccgacagg actataaaga taccaggcgt ttcccctgg aagctccctc gtgcgctctc     1800
ctgttccgac cctgccgctt accggatacc tgtccgcctt tctcccttcg ggaagcgtgg     1860
cgctttctca tagctcacgc tgtaggtatc tcagttcggt gtaggtcgtt cgctccaagc     1920
tgggctgtgt gcacgaaccc cccgttcagc ccgaccgctg cgccttatcc ggtaactatc     1980
gtcttgagtc caacccggta agacacgact tatcgccact ggcagcagcc actggtaaca     2040
ggattagcag agcgaggtat gtaggcggtg ctacagagtt cttgaagtgg tggcctaact     2100
acggctacac tagaagaaca gtatttggta tctgcgctct gctgaagcca gttacctcgg     2160
aaaaagagtt ggtagctctt gatccggcaa acaaaccacc gctggtagcg gtggtttttt     2220
tgtttgcaag cagcagatta cgcgcagaaa aaaaggatct caagaagatc ctttgatttt     2280
ctaccgaacg tttacaattt cctgatgcgg tattttctcc ttacgcatct gtgcggtatt     2340
tcacaccgca tagggtaata actgatataa ttaaattgaa gctctaattt gtgagtttag     2400
tatacatgca tttacttata atacagtttt ttagtttttgc tggccgcatc ttctcaaata     2460
tgcttcccag cctgcttttc tgtaacgttc accctctacc ttagcatccc ttccctttgc     2520
```

-continued

```
aaatagtcct cttccaacaa taataatgtc agatcctgta gacaccacat catccacggt    2580
tctatactgt tgacccaatg cgtcaccctt gtcatctaaa cccacaccgg gtgtcataat    2640
caaccaatcg taaccttcat ctcttccacc catgtctctt tgagcaataa agccgataac    2700
aaaatctttg tcgctcttcg caatgtcaac agtaccctta gtatattctc cagtagatag    2760
ggagcccttg catgacaatt ctgctaacat caaaaggcct ctaggttcct ttgttacttc    2820
ttctgccgcc tgcttcaaac cgctaacaat acctgggccc accacaccgt gtgcattcgt    2880
aatgtctgcc cattctgcta ttctgtatac acccgcagag tactgcaatt tgactgtatt    2940
accaatgtca gcaaattttc tgtcttcgaa gagtaaaaaa ttgtacttgg cggataatgc    3000
ctttagcggc ttaactgtgc cctccatgga aaaatcagtc aagatatcca catgtgtttt    3060
tagtaaacaa attttgggac ctaatgcttc aactaactcc agtaattcct tggtggtacg    3120
aacatccaat gaagcacaca agtttgtttg cttttcgtgc atgatattaa atagcttggc    3180
agcaacagga ctaggatgag tagcagcacg ttccttatat gtagctttcg acatgattta    3240
tcttcgtttc ctgcaggttt ttgttctgtg cagttgggtt aagaatactg ggcaatttca    3300
tgtttcttca acactacata tgcgtatata taccaatcta agtctgtgct ccttccttcg    3360
ttcttccttc tgttcggaga ttaccgaatc aaaaaaattt caaagaaacc gaaatcaaaa    3420
aaaagaataa aaaaaaaatg atgaattgaa ttgaaaagct gtggtatggt gcactacgtc    3480
tcgacctggc tacagtttat tcctggcatc cactaaatat aatggagccc gctttttaag    3540
ctggcatcca gaaaaaaaaa gaatcccagc accaaaatat tgttttcttc accaaccatc    3600
agttcatagg tccattctct tagcgcaact acagagaaca ggggcacaaa caggcaaaaa    3660
acgggcacaa cctcaatgga gtgatgcaac ctgcctggag taaatgatga cacaaggcaa    3720
ttgacccacg catgtatcta tctcattttc ttacaccttc tattaccttc tgctctctct    3780
gatttggaaa aagctgaaaa aaaaggttga aaccagttcc ctgaaattat tcccctactt    3840
gactaataag tatataaaga cggtaggtat tgattgtaat tctgtaaatc tatttcttaa    3900
acttcttaaa ttctactttt atagttagtc tttttttttag ttttaaaaca ccaagaactt    3960
agtttcgaat aaacacacat aaacaaacaa agatggctga tgctttgggt atgattgaag    4020
ttagaggttt cgttggtatg gttgaagctg ctgatgctat ggttaaggct gctaaagttg    4080
aattgatcgg ttacgaaaaa actggtggtg gttatgttac tgctgttgtt agaggtgatg    4140
ttgctgctgt aaaagctgct actgaagctg tcaaagggc tgctgaaaga gttggagaag    4200
ttgttgctgt tcatgttatt ccaagaccac atgttaatgt tgatgctgct ttgccattgg    4260
gtagaactcc aggtatggat aagtctgctt agcgcggatt gagagcaaat cgttaagttc    4320
aggtcaagta aaaattgatt tcgaaaacta atttctctta tacaatcctt tgattggacc    4380
gtcatccttt cgaatataag attttgttaa gaatatttta gacagagatc tactttatat    4440
ttaatatcta gatattacat aatttcctct ctaataaaat atcattaata aaataaaaat    4500
gaagcgattt gattttgtgt tgtcaactta gtttgccgct atgcctcttg ggtaatgcta    4560
ttattgaatc gaagggcttt attatattac cctttagctt attctgaggt ttctgtggcg    4620
tgcaaagtga tgaaccgggc gggttttaag gataaaatca aaaagtgaaa aaatgaacgg    4680
aaaatggaat acctgtgaaa tggagaatga taatgaatct ttctgtcgtg cttgaaagat    4740
tttcggctcc tcaggcggct attaaaaaaa caacttacaa tcattgttcg ccccttccat    4800
acttactgcc actcgcaaaa gggcccaacc agggcaatta cgtatcaaaa aatcatgaca    4860
```

-continued

```
ggctgggtaa taaatattcg tgaagaaaga agaaattaaa aaaagaaacg aagaagcaaa    4920
aaaaagaaaa gactccgttt aatcactttc aaccgcggtt tatccggccc cacccatgca    4980
taaccctaaa ttattagatc acttagcacg tgaaaaagaa acgttttaa tgtttttttt    5040 ttttttttct ttttctttt ttgcgttggt gaaaattttt tcgcttcctc gagtataatt    5100
atctcatctc atctttcata taagataaga agttttataa aaaccttttg catcaaaatt    5160
ttgtagaata tctctttttc ttacgctctc tttctttcct taattgtttt ctaaagaacc    5220
gtgtattttt ctagttcgaa tccatcgata acattaaaag gatggatcat gctccagaaa    5280
gatttgatgc tactcctcca gctggtgaac cagatagacc agctttgggt gttttggaat    5340
tgacttctat tgctagaggt attaccgttg ctgatgctgc tttgaaaaga gcaccatctt    5400
tgttgttgat gtccagacca gtttcttccg gtaaacattt gttgatgatg agaggtcaag    5460
ttgccgaagt tgaagaatct atgattgctg ctagagaaat tgctggtgct ggttctggtg    5520
ctttgttgga tgaattggaa ttgccatatg ctcacgaaca actttggaga ttttttggatg    5580 ctccagttgt tgcagatgct tgggaagaag atactgaatc cgttattatc gttgaaaccg    5640
ctactgtttg tgctgctatt gattctgctg atgcagcctt aaaaactgct cctgttgttt    5700
tgagagatat gagattggct attggtattg ctggtaaggc tttctttact ttgactggtg    5760
aattggctga tgttgaagct gctgctgaag ttgttagaga aagatgtggt gctagattgc    5820
tagaattggc ttgtattgca agaccagttg acgaattgag aggtaggttg ttttttctagc    5880 acacttctcg attaacaaat tcccagtatt ctttgaaatc tatttttctt cctcaattga    5940
atttgaataa ctgtctacgc ggactcctcc tatctacaac tacaacaaat tttaaccact    6000
ttattaccac tttcctcttt catttatttt tgtctttat gttgtcaatt tactagtatt    6060
tttttttttt tcatttacgt tcaaggtttt ttatactcat ttaacttgtc ttaggttatt    6120
tatatatata cctatatatt tatatatata tatatatg tatgtatata ttattatcac    6180
caaatgagaa ataatagcta atttgatttt tgattattta aaatattggt ttgttctttc    6240
tgcaaacatc tcgtttggta cgatattagt gaaaaacgat gtaattatca acacgtgcat    6300
tacccacctc tgccggctac agattgggag attttcatag tagaattcag catgatagct    6360
acgtaaatgt gttccgcacc gtcacaaagt gttttctact gttctttctt ctttcgttca    6420
ttcagttgag ttgagtgagt gctttgttca atggatctta gctaaaatgc atatttttc    6480 tcttggtaaa tgaatgcttg tgatgtcttc caagtgattt cctttccttc ccatatgatg    6540
ctaggtacct ttagtgtctt cctaaaaaaa aaaaaaggct cgccatcaaa acgatattcg    6600
ttggcttttt tttctgaatt ataaatactc tttggtaact tttcatttcc aagaacctct    6660
tttttccagt tatatcatgg tcccctttca aagttattct ctactctttt tcatattcat    6720 tcttttttcat cctttggttt tttattctta acttgtttat tattctctct tgtttctatt    6780
tacaagacac caatcaaaac aaataaaaca tcatcacaga tggtttttagg taaagttgtc    6840 ggtactgttg ttgcatcaag aaaggaacca agaattgaag gtttatcttt attattggtt    6900
agagcttgtg atccagatgg tactccaact ggtggtgctg ttgtttgtgc tgatgctgtt    6960
ggtgctggtg ttggtgaagt tgtttttatat gcttctggtt cttctgctag acaaactgaa    7020
gttactaata atagaccagt tgatgctact attatggcta ttgttgattt ggttgaaatg    7080
ggtggtgatg ttagatttag aaaagatggt tcttcttggt cacatccaca atttgaaaag    7140
tagcaactaa gctggttcta actggaaata atttccatta gattcctctt tttctcgtcc    7200
attaaccaaa atatattatt gaattcagcg gttccttttt tctcatttttc gcatatagct    7260
```

-continued

```
gcactattag aatcagccca ctctaggtaa acacagttcc tcgatatacc tctgtcttac      7320
tatcagtggt taaaccttat gcaaatataa tatatatata tatatatata tatatatctc      7380
atacttttgt tgattcttgt gtaattattg gaaaagacaa aacaaagcaa gcgtttctat      7440
tcatatttac aagtattttt tatgacaaac tatttcttaa ttttcccacc ggcggctttg      7500
aataaggcaa tgtcattgtc ctgcataata tattgtttgc ctgcacgttt gataagtccc      7560
ttagatttta gtaaagactc atttagcggt ggttccatct tccctc                     7606

<210> SEQ ID NO 77
<211> LENGTH: 122
<212> TYPE: DNA
<213> ORGANISM: Artificial Sequence
<220> FEATURE:
<223> OTHER INFORMATION: Promoter Pcon3 nucleotide sequence

<400> SEQUENCE: 77
ggctggcttc ccaaccttac cagagggcgc cccagctggc aattccgacg tcctgacagc        60
tagctcagtc ctaggtataa tgctagcgaa ttcaaaagat cttttaagaa ggagatatac       120
at                                                                      122

<210> SEQ ID NO 78
<211> LENGTH: 122
<212> TYPE: DNA
<213> ORGANISM: Artificial Sequence
<220> FEATURE:
<223> OTHER INFORMATION: Promoter Pcon4 nucleotide sequence

<400> SEQUENCE: 78
ggctggcttc ccaaccttac cagagggcgc cccagctggc aattccgacg tctttacggc        60
tagctcagtc ctaggtacta tgctagcgaa ttcaaaagat cttttaagaa ggagatatac       120
at                                                                      122

<210> SEQ ID NO 79
<211> LENGTH: 154
<212> TYPE: DNA
<213> ORGANISM: Artificial Sequence
<220> FEATURE:
<223> OTHER INFORMATION: Promoter TT7 nucleotide sequence

<400> SEQUENCE: 79
tagctaacaa agcccgaaag gaagctgagt tggctgctgc caccgctgag caataactag        60
cataacccct tggggcctct aaacgggtct tgaggggttt tttgctgaaa ggaggaacta       120
tatccggata tcccgcaaga ggcccggcag tacc                                   154

<210> SEQ ID NO 80
<211> LENGTH: 459
<212> TYPE: DNA
<213> ORGANISM: Artificial Sequence
<220> FEATURE:
<223> OTHER INFORMATION: Yeast transcriptional terminator TRPL41B

<400> SEQUENCE: 80
tagcgcggat tgagagcaaa tcgttaagtt caggtcaagt aaaaattgat ttcgaaaact        60
aatttctctt atacaatcct ttgattggac cgtcatcctt tcgaatataa gatttttgtta      120 agaatatttt agacagagat ctactttata tttaatatct agatattaca taatttcctc       180
tctaataaaa tatcattaat aaaataaaaa tgaagcgatt tgattttgtg ttgtcaactt       240
```

-continued

```
agtttgccgc tatgcctctt gggtaatgct attattgaat cgaagggctt tattatatta      300
ccctttagct tattctgagg tttctgtggc gtgcaaagtg atgaaccggg cgggttttaa      360
ggataaaatc aaaaagtgaa aaaatgaacg gaaaatggaa tacctgtgaa atggagaatg      420
ataatgaatc tttctgtcgt gcttgaaaga ttttcggct                             459

<210> SEQ ID NO 81
<211> LENGTH: 430
<212> TYPE: DNA
<213> ORGANISM: Artificial Sequence
<220> FEATURE:
<223> OTHER INFORMATION: Yeast transcriptional terminator THBT1

<400> SEQUENCE: 81
tagcacactt ctcgattaac aaattcccag tattctttga aatctatttt tcttcctcaa       60
ttgaatttga ataactgtct acgcggactc ctcctatcta caactacaac aaattttaac      120
cactttatta ccactttcct ctttcattta tttttgtctt ttatgttgtc aatttactag      180
tatttttttt tttttcattt acgttcaagg tttttttatac tcatttaact tgtcttaggt      240
tatttatata tatacctata tatttatata tatatatata tatgtatgta tatattatta      300
tcaccaaatg agaaataata gctaatttga tttttgatta tttaaaatat tggtttgttc      360
tttctgcaaa catctcgttt ggtacgatat tagtgaaaaa cgatgtaatt atcaacacgt      420
gcattaccca                                                             430

<210> SEQ ID NO 82
<211> LENGTH: 458
<212> TYPE: DNA
<213> ORGANISM: Artificial Sequence
<220> FEATURE:
<223> OTHER INFORMATION: Yeast transcriptional terminator TRPS20

<400> SEQUENCE: 82
tagcaactaa gctggttcta actggaaata atttccatta gattcctctt tttctcgtcc       60
attaaccaaa atatattatt gaattcagcg gttcctttttt tctcattttc gcatatagct      120
gcactattag aatcagccca ctctaggtaa acacagttcc tcgatatacc tctgtcttac      180
tatcagtggt taaaccttat gcaaatataa tatatatata tatatatata tctcatactt      240
ttgttgattc ttgtgtaatt attggaaaag acaaaacaaa gcaagcgttt ctattcatca      300
tatttacaag tattttttatg aaaaactatt tcttaatttt cccaccggcg gctttgaata      360
aggcaatgtc attgtcctgc ataatatatt gtttgcctgc acgtttgata agtcccttag      420
attttagtaa agactcattt agcggtggtt ccatcttc                              458

<210> SEQ ID NO 83
<211> LENGTH: 1864
<212> TYPE: DNA
<213> ORGANISM: Artificial Sequence
<220> FEATURE:
<223> OTHER INFORMATION: HcKan_P-Pcon2 plasmid

<400> SEQUENCE: 83
aagaaaggcc cacccgtgaa ggtgagccag tgagttgatt gcagtccagt tacgctggag       60
tccgtctcgg gctggcttcc caaccttacc agagggcgcc ccagctggca attccgacgt      120
cttgacggct agctcagtcc taggtacagt gctagcgaat tcaaaagatc ttttaagaag      180
gagatataca tgatgcgaga cgactgacca tttaaatcat acctgacctc catagcagaa      240
agtcaaaagc ctccgaccgg aggcttttga cttgatcggc acgtaagagg ttccaacttt      300
```

-continued

```
caccataatg aaataagatc actaccgggc gtattttttg agttatcgag attttcagga     360
gctaaggaag ctaaaatgag ccatattcaa cgggaaacgt cttgctcgag gccgcgatta     420
aattccaaca tggatgctga tttatatggg tataaatggg ctcgcgataa tgtcgggcaa     480
tcaggtgcga caatctatcg attgtatggg aagcccgatg cgccagagtt gtttctgaaa     540
catggcaaag gtagcgttgc caatgatgtt acagatgaga tggtcaggct aaactggctg     600
acggaattta tgcctcttcc gaccatcaag cattttatcc gtactcctga tgatgcatgg     660
ttactcacca ctgcgatccc agggaaaaca gcattccagg tattagaaga atatcctgat     720
tcaggtgaaa atattgttga tgcgctggca gtgttcctgc gccggttgca ttcgattcct     780
gtttgtaatt gtccttttaa cggcgatcgc gtatttcgtc tcgctcaggc gcaatcacga     840
atgaataacg gtttggttgg tgcgagtgat tttgatgacg agcgtaatgg ctggcctgtt     900
gaacaagtct ggaaagaaat gcataagctt ttgccattct caccggattc agtcgtcact     960
catggtgatt tctcacttga taaccttatt tttgacgagg ggaaattaat aggttgtatt    1020
gatgttggac gagtcggaat cgcagaccga taccaggatc ttgccatcct atggaactgc    1080
ctcggtgagt tttctccttc attacagaaa cggctttttc aaaaatatgg tattgataat    1140
cctgatatga ataaattgca gtttcacttg atgctcgatg agtttttcta atgagggccc    1200
aaatgtaatc acctggctca ccttcgggtg ggcctttctg cgttctggc gttttttccat    1260 aggctccgcc ccctgacga gcatcacaaa aatcgatgct caagtcagag gtggcgaaac    1320
ccgacaggac tataaagata ccaggcgttt cccctggaa gctccctcgt gcgctctcct    1380
gttccgaccc tgccgcttac cggatacctg tccgcctttc tcccttcggg aagcgtggcg    1440
ctttctcata gctcacgctg taggtatctc agttcggtgt aggtcgttcg ctccaagctg    1500
ggctgtgtgc acgaaccccc cgttcagccc gaccgctgcg ccttatccgg taactatcgt    1560
cttgagtcca acccggtaag acacgactta tcgccactgg cagcagccac tggtaacagg    1620
attagcagag cgaggtatgt aggcggtgct acagagttct tgaagtggtg gcctaactac    1680
ggctacacta gaagaacagt atttggtatc tgcgctctgc tgaagccagt tacctcggaa    1740
aaagagttgg tagctcttga tccggcaaac aaaccaccgc tggtagcggt ggtttttttg    1800
tttgcaagca gcagattacg cgcagaaaaa aaggatctca agaagatcct ttgatttttct    1860 accg                                                                  1864
```

```
<210> SEQ ID NO 84
<211> LENGTH: 122
<212> TYPE: DNA
<213> ORGANISM: Artificial Sequence
<220> FEATURE:
<223> OTHER INFORMATION: Promoter Pcon2 nucleotide sequence

<400> SEQUENCE: 84
ggctggcttc ccaaccttac cagagggcgc cccagctggc aattccgacg tcttgacggc      60
tagctcagtc ctaggtacag tgctagcgaa ttcaaaagat cttttaagaa ggagatatac     120
at                                                                    122
```

```
<210> SEQ ID NO 85
<211> LENGTH: 20
<212> TYPE: DNA
<213> ORGANISM: Artificial Sequence
<220> FEATURE:
<223> OTHER INFORMATION: HcKan_chc_F' forward primer
```

-continued

```
<400> SEQUENCE: 85
gatcctttga ttttctaccg                                                      20

<210> SEQ ID NO 86
<211> LENGTH: 21
<212> TYPE: DNA
<213> ORGANISM: Artificial Sequence
<220> FEATURE:
<223> OTHER INFORMATION: HcKan_chc_R' reverse primer

<400> SEQUENCE: 86
ctcgataact caaaaaatac g                                                    21

<210> SEQ ID NO 87
<211> LENGTH: 20
<212> TYPE: DNA
<213> ORGANISM: Artificial Sequence
<220> FEATURE:
<223> OTHER INFORMATION: pES_Chc_F' forward primer

<400> SEQUENCE: 87
cggagcctat ggaaaaacgc                                                      20

<210> SEQ ID NO 88
<211> LENGTH: 20
<212> TYPE: DNA
<213> ORGANISM: Artificial Sequence
<220> FEATURE:
<223> OTHER INFORMATION: pES_Chc_R' reverse primer

<400> SEQUENCE: 88
ccgcagtgtc ttgggtctct                                                      20

<210> SEQ ID NO 89
<211> LENGTH: 23
<212> TYPE: DNA
<213> ORGANISM: Artificial Sequence
<220> FEATURE:
<223> OTHER INFORMATION: His_chc_F' forward primer

<400> SEQUENCE: 89
tagagtgtac tagaggaggc caa                                                  23

<210> SEQ ID NO 90
<211> LENGTH: 20
<212> TYPE: DNA
<213> ORGANISM: Artificial Sequence
<220> FEATURE:
<223> OTHER INFORMATION: CEN_chc_R' reverse primer

<400> SEQUENCE: 90
ggtgatgacg gtgaaaacct                                                      20

<210> SEQ ID NO 91
<211> LENGTH: 24
<212> TYPE: DNA
<213> ORGANISM: Artificial Sequence
<220> FEATURE:
<223> OTHER INFORMATION: Ura_chc_F' forward primer

<400> SEQUENCE: 91
tctgttcgga gattaccgaa tcaa                                                 24

<210> SEQ ID NO 92
<211> LENGTH: 20
```

<212> TYPE: DNA
<213> ORGANISM: Artificial Sequence
<220> FEATURE:
<223> OTHER INFORMATION: pGau_chc_F' forward primer

<400> SEQUENCE: 92
ccacctcagg cagagaacct                                                                    20

<210> SEQ ID NO 93
<211> LENGTH: 19
<212> TYPE: DNA
<213> ORGANISM: Artificial Sequence
<220> FEATURE:
<223> OTHER INFORMATION: pGau_chc_R' reverse primer

<400> SEQUENCE: 93
ggaaaaacgc cagcaacgc                                                                     19

<210> SEQ ID NO 94
<211> LENGTH: 30
<212> TYPE: PRT
<213> ORGANISM: Artificial Sequence
<220> FEATURE:
<223> OTHER INFORMATION: S2CP(30) amino acid sequence

<400> SEQUENCE: 94

Lys Pro Glu Lys Pro Gly Ser Lys Ile Thr Gly Ser Ser Gly Asn Asp
1               5                   10                  15

Thr Gln Gly Ser Leu Ile Thr Tyr Ser Gly Gly Ala Arg Gly
            20                  25                  30

<210> SEQ ID NO 95
<211> LENGTH: 90
<212> TYPE: DNA
<213> ORGANISM: Artificial Sequence
<220> FEATURE:
<223> OTHER INFORMATION: S2CP(30) nucleotide sequence

<400> SEQUENCE: 95
aaaccggaaa aaccaggtag caaaattacc ggtagcagcg gcaatgatac ccagggtagc         60
ctgattacct atagcggtgg tgcacgtggt                                                         90

<210> SEQ ID NO 96
<211> LENGTH: 229
<212> TYPE: PRT
<213> ORGANISM: Artificial Sequence
<220> FEATURE:
<223> OTHER INFORMATION: HO-T1-SpyTag amino acid sequence

<400> SEQUENCE: 96

Met Asp His Ala Pro Glu Arg Phe Asp Ala Thr Pro Pro Ala Gly Glu
1               5                   10                  15

Pro Asp Arg Pro Ala Leu Gly Val Leu Glu Leu Thr Ser Ile Ala Arg
            20                  25                  30

Gly Ile Thr Val Ala Asp Ala Ala Leu Lys Arg Ala Pro Ser Leu Leu
            35                  40                  45

Leu Met Ser Arg Pro Val Ser Ser Gly Lys His Leu Leu Met Met Arg
        50                  55                  60

Gly Gln Val Ala Glu Val Glu Glu Ser Met Ile Ala Ala Arg Glu Ile
65                  70                  75                  80

Ala Gly Ala Gly Gly Gly Ser Gly Gly Ser Ala His Ile Val Met Val
                85                  90                  95

```
Asp Ala Tyr Lys Pro Thr Lys Gly Gly Ser Gly Gly Ser Gly Ala Leu
            100                 105                 110

Leu Asp Glu Leu Glu Leu Pro Tyr Ala His Glu Gln Leu Trp Arg Phe
        115                 120                 125

Leu Asp Ala Pro Val Val Ala Asp Ala Trp Glu Glu Asp Thr Glu Ser
    130                 135                 140

Val Ile Ile Val Glu Thr Ala Thr Val Cys Ala Ala Ile Asp Ser Ala
145                 150                 155                 160

Asp Ala Ala Leu Lys Thr Ala Pro Val Val Leu Arg Asp Met Arg Leu
                165                 170                 175

Ala Ile Gly Ile Ala Gly Lys Ala Phe Phe Thr Leu Thr Gly Glu Leu
            180                 185                 190

Ala Asp Val Glu Ala Ala Ala Glu Val Val Arg Glu Arg Cys Gly Ala
        195                 200                 205

Arg Leu Leu Glu Leu Ala Cys Ile Ala Arg Pro Val Asp Glu Leu Arg
    210                 215                 220

Gly Arg Leu Phe Phe
225
```

<210> SEQ ID NO 97
<211> LENGTH: 687
<212> TYPE: DNA
<213> ORGANISM: Artificial Sequence
<220> FEATURE:
<223> OTHER INFORMATION: HO-T1-SpyTag nucleotide sequence

<400> SEQUENCE: 97

```
atggatcatg ctccagaaag atttgatgct actcctccag ctggtgaacc agatagacca      60
gctttgggtg ttttggaatt gacttctatt gctagaggta ttaccgttgc tgatgctgct     120
ttgaaaagag caccatcttt gttgttgatg tccagaccag tttcttccgg taaacatttg     180
ttgatgatga gaggtcaagt tgccgaagtt gaagaatcta tgattgctgc tagagaaatt     240
gctggtgctg gtggtggttc aggtggttct gctcatatag ttatggttga tgcttacaag     300
ccaacaaaag gtggtagtgg tggatctggt gctttgttgg atgaattgga attgccatat     360
gctcacgaac aactttggag attttttggat gctccagttg ttgcagatgc ttgggaagaa     420
gatactgaat ccgttattat cgttgaaacc gctactgttt gtgctgctat tgattctgct     480
gatgcagcct taaaaactgc tcctgttgtt ttgagagata tgagattggc tattggtatt     540
gctggtaagg ctttctttac tttgactggt gaattggctg atgttgaagc tgctgctgaa     600
gttgttagag aaagatgtgg tgctagattg ctagaattgg catgtattgc aagaccagtt     660
gacgaattga gaggtaggtt gtttttc                                         687
```

<210> SEQ ID NO 98
<211> LENGTH: 339
<212> TYPE: PRT
<213> ORGANISM: Artificial Sequence
<220> FEATURE:
<223> OTHER INFORMATION: GFP-SpyCatcher amino acid sequence

<400> SEQUENCE: 98

```
Met Gly Ser Ser His His His His His His Ser Ser Gly Met Ser Lys
1               5                   10                  15

Gly Glu Glu Leu Phe Thr Gly Val Val Pro Ile Leu Val Glu Leu Asp
            20                  25                  30

Gly Asp Val Asn Gly His Lys Phe Ser Val Ser Gly Glu Gly Glu Gly
        35                  40                  45
```

```
Asp Ala Thr Tyr Gly Lys Leu Thr Leu Lys Phe Ile Cys Thr Thr Gly
    50                  55                  60

Lys Leu Pro Val Pro Trp Pro Thr Leu Val Thr Thr Leu Thr Tyr Gly
65                  70                  75                  80

Val Gln Cys Phe Ser Arg Tyr Pro Asp His Met Lys Gln His Asp Phe
                85                  90                  95

Phe Lys Ser Ala Met Pro Glu Gly Tyr Val Gln Glu Arg Thr Ile Phe
                100                 105                 110

Phe Lys Asp Asp Gly Asn Tyr Lys Thr Arg Ala Glu Val Lys Phe Glu
                115                 120                 125

Gly Asp Thr Leu Val Asn Arg Ile Glu Leu Lys Gly Ile Asp Phe Lys
    130                 135                 140

Glu Asp Gly Asn Ile Leu Gly His Lys Leu Glu Tyr Asn Tyr Asn Ser
145                 150                 155                 160

His Asn Val Tyr Ile Met Ala Asp Lys Gln Lys Asn Gly Ile Lys Val
                165                 170                 175

Asn Phe Lys Ile Arg His Asn Ile Glu Asp Gly Ser Val Gln Leu Ala
                180                 185                 190

Asp His Tyr Gln Gln Asn Thr Pro Ile Gly Asp Gly Pro Val Leu Leu
                195                 200                 205

Pro Asp Asn His Tyr Leu Ser Thr Gln Ser Lys Leu Ser Lys Asp Pro
    210                 215                 220

Asn Glu Lys Arg Asp His Met Val Leu Leu Glu Phe Val Thr Ala Ala
225                 230                 235                 240

Gly Ile Thr His Gly Met Asp Glu Leu Tyr Lys Gly Ser Gly Gly Ser
                245                 250                 255

Asp Ser Ala Thr His Ile Lys Phe Ser Lys Arg Asp Glu Asp Gly Lys
                260                 265                 270

Glu Leu Ala Gly Ala Thr Met Glu Leu Arg Asp Ser Ser Gly Lys Thr
                275                 280                 285

Ile Ser Thr Trp Ile Ser Asp Gly Gln Val Lys Asp Phe Tyr Leu Tyr
    290                 295                 300

Pro Gly Lys Tyr Thr Phe Val Glu Thr Ala Ala Pro Asp Gly Tyr Glu
305                 310                 315                 320

Val Ala Thr Ala Ile Thr Phe Thr Val Asn Glu Gln Gly Gln Val Thr
                325                 330                 335

Val Asn Gly
```

<210> SEQ ID NO 99
<211> LENGTH: 1017
<212> TYPE: DNA
<213> ORGANISM: Artificial Sequence
<220> FEATURE:
<223> OTHER INFORMATION: GFP-SpyCatcher nucleotide sequence

<400> SEQUENCE: 99

```
atgggttctt ctcatcatca ccatcaccat tcttctggga tgtctaaagg tgaagaatta         60
ttcactggtg ttgtcccaat tttggttgaa ttagatggtg atgttaatgg tcacaaattt        120
tctgtctccg gtgaaggtga aggtgatgct acttacggta aattgacctt aaaatttatt        180
tgtactactg gtaaattgcc agttccatgg ccaaccttag tcactacttt aacttatggt        240
gttcaatgtt tttctagata cccagatcat atgaaacaac atgacttttt caagtctgcc        300
atgccagaag gttatgttca agaaagaact atttttttca aagatgacgg taactacaag        360
```

```
accagagctg aagtcaagtt tgaaggtgat accttagtta atagaatcga attaaaaggt    420
attgatttta aagaagatgg taacatttta ggtcacaaat tggaatacaa ctataactct    480
cacaatgttt acatcatggc tgacaaacaa aagaatggta tcaaagttaa cttcaaaatt    540
agacacaaca ttgaagatgg ttctgttcaa ttagctgacc attatcaaca aaatactcca    600
attggtgatg tccagtctt gttaccagac aaccattact tatccactca atctaaatta    660
tccaaagatc caaacgaaaa gagagatcac atggtcttgt tagaatttgt tactgctgct    720
ggtattaccc atggtatgga tgaattgtac aaaggttctg gtggttctga ttctgctact    780
catattaagt tctccaagag ggacgaagat ggtaaagaat tggctggtgc aactatggaa    840
ttgagagatt cttctggtaa gaccatttcc acctggattt ctgatggtca agttaaggat    900
ttctacttgt acccaggtaa gtacactttc gttgaaactg ctgctccaga tggttatgaa    960
gttgctactg ctattacttt caccgtcaat gaacaaggtc aagtcactgt taatggt    1017
```

```
<210> SEQ ID NO 100
<211> LENGTH: 296
<212> TYPE: PRT
<213> ORGANISM: Artificial Sequence
<220> FEATURE:
<223> OTHER INFORMATION: APEX2-S2CP(30) amino acid sequence

<400> SEQUENCE: 100

Met Gly Ser Ser His His His His His His Ser Ser Gly Met Gly Lys
1               5                   10                  15

Ser Tyr Pro Thr Val Ser Ala Asp Tyr Gln Asp Ala Val Glu Lys Ala
            20                  25                  30

Lys Lys Lys Leu Arg Gly Phe Ile Ala Glu Lys Arg Cys Ala Pro Leu
        35                  40                  45

Met Leu Arg Leu Ala Phe His Ser Ala Gly Thr Phe Asp Lys Gly Thr
    50                  55                  60

Lys Thr Gly Gly Pro Phe Gly Thr Ile Lys His Pro Ala Glu Leu Ala
65                  70                  75                  80

His Ser Ala Asn Asn Gly Leu Asp Ile Ala Val Arg Leu Leu Glu Pro
                85                  90                  95

Leu Lys Ala Glu Phe Pro Ile Leu Ser Tyr Ala Asp Phe Tyr Gln Leu
            100                 105                 110

Ala Gly Val Val Ala Val Glu Val Thr Gly Gly Pro Lys Val Pro Phe
        115                 120                 125

His Pro Gly Arg Glu Asp Lys Pro Glu Pro Pro Glu Gly Arg Leu
    130                 135                 140

Pro Asp Pro Thr Lys Gly Ser Asp His Leu Arg Asp Val Phe Gly Lys
145                 150                 155                 160

Ala Met Gly Leu Thr Asp Gln Asp Ile Val Ala Leu Ser Gly Gly His
                165                 170                 175

Thr Ile Gly Ala Ala His Lys Glu Arg Ser Gly Phe Glu Gly Pro Trp
            180                 185                 190

Thr Ser Asn Pro Leu Ile Phe Asp Asn Ser Tyr Phe Thr Glu Leu Leu
        195                 200                 205

Ser Gly Glu Lys Glu Gly Leu Leu Gln Leu Pro Ser Asp Lys Ala Leu
    210                 215                 220

Leu Ser Asp Pro Val Phe Arg Pro Leu Val Asp Lys Tyr Ala Ala Asp
225                 230                 235                 240

Glu Asp Ala Phe Phe Ala Asp Tyr Ala Glu Ala His Gln Lys Leu Ser
                245                 250                 255
```

-continued

```
Glu Leu Gly Phe Ala Asp Ala Gly Ser Ser Lys Pro Glu Lys Pro Gly
            260                 265                 270

Ser Lys Ile Thr Gly Ser Ser Gly Asn Asp Thr Gln Gly Ser Leu Ile
        275                 280                 285

Thr Tyr Ser Gly Gly Ala Arg Gly
    290                 295

<210> SEQ ID NO 101
<211> LENGTH: 888
<212> TYPE: DNA
<213> ORGANISM: Artificial Sequence
<220> FEATURE:
<223> OTHER INFORMATION: APEX2-S2CP(30) nucleotide sequence

<400> SEQUENCE: 101
atgggttctt ctcatcatca ccatcaccat tcttctggga tgggtaagtc ttacccaact        60
gtttctgctg attatcaaga tgctgttgaa aaggccaaga agaagttgag aggtttcatt       120
gctgaaaaaa gatgcgctcc attgatgttg agattggctt ttcattctgc tggtactttc       180
gataagggta caaaaactgg tggtccattc ggtactatca acatccagc tgaattggct        240 cattcagcta acaatggttt ggatattgct gtcagattgc tggaaccatt gaaagccgaa       300
tttccaattt tgtcctacgc cgattttttac caattggctg gtgttgttgc agttgaagtt       360
acaggtggtc caaaagttcc atttcatcca ggtagagaag ataagccaga accaccacca       420
gaaggtagat tgccagatcc aacaaaaggt tctgatcact tgagagatgt tttcggtaaa       480
gctatgggtt tgactgatca agatattgtc gctttgtctg gtggtcatac aattggtgct       540
gctcacaaag aaagatcagg ttttgaaggt ccttggactt ctaacccatt gatctttgat       600
aactcttact tcaccgagtt gttgtccggt gaaaaagaag gtttgttgca attgccatct       660
gataaggctt gttgtctga tccagttttc agaccattgg ttgataagta tgctgctgat       720
gaagatgctt tctttgctga ttacgctgaa gctcatcaaa agttgtctga attgggtttt       780
gctgatgctg gttcttctaa accggaaaaa ccaggtagca aaattaccgg tagcagcggc       840
aatgataccc agggtagcct gattacctat agcggtggtg cacgtggt                   888

<210> SEQ ID NO 102
<211> LENGTH: 1070
<212> TYPE: PRT
<213> ORGANISM: Artificial Sequence
<220> FEATURE:
<223> OTHER INFORMATION: LacZ-S2CP(30) amino acid sequence

<400> SEQUENCE: 102

Met Gly Ser Ser His His His His His His Ser Ser Gly Met Thr Met
1               5                   10                  15

Ile Thr Asp Ser Leu Ala Val Val Leu Gln Arg Arg Asp Trp Glu Asn
            20                  25                  30

Pro Gly Val Thr Gln Leu Asn Arg Leu Ala Ala His Pro Pro Phe Ala
        35                  40                  45

Ser Trp Arg Asn Ser Glu Glu Ala Arg Thr Asp Arg Pro Ser Gln Gln
    50                  55                  60

Leu Arg Ser Leu Asn Gly Glu Trp Arg Phe Ala Trp Phe Pro Ala Pro
65                  70                  75                  80

Glu Ala Val Pro Glu Ser Trp Leu Glu Cys Asp Leu Pro Glu Ala Asp
                85                  90                  95

Thr Val Val Val Pro Ser Asn Trp Gln Met His Gly Tyr Asp Ala Pro
```

-continued

```
                100               105               110

Ile Tyr Thr Asn Val Thr Tyr Pro Ile Thr Val Asn Pro Pro Phe Val
        115               120               125

Pro Thr Glu Asn Pro Thr Gly Cys Tyr Ser Leu Thr Phe Asn Val Asp
    130               135               140

Glu Ser Trp Leu Gln Glu Gly Gln Thr Arg Ile Ile Phe Asp Gly Val
145               150               155               160

Asn Ser Ala Phe His Leu Trp Cys Asn Gly Arg Trp Val Gly Tyr Gly
                165               170               175

Gln Asp Ser Arg Leu Pro Ser Glu Phe Asp Leu Ser Ala Phe Leu Arg
            180               185               190

Ala Gly Glu Asn Arg Leu Ala Val Met Val Leu Arg Trp Ser Asp Gly
            195               200               205

Ser Tyr Leu Glu Asp Gln Asp Met Trp Arg Met Ser Gly Ile Phe Arg
    210               215               220

Asp Val Ser Leu Leu His Lys Pro Thr Thr Gln Ile Ser Asp Phe His
225               230               235               240

Val Ala Thr Arg Phe Asn Asp Asp Phe Ser Arg Ala Val Leu Glu Ala
            245               250               255

Glu Val Gln Met Cys Gly Glu Leu Arg Asp Tyr Leu Arg Val Thr Val
            260               265               270

Ser Leu Trp Gln Gly Glu Thr Gln Val Ala Ser Gly Thr Ala Pro Phe
    275               280               285

Gly Gly Glu Ile Ile Asp Glu Arg Gly Gly Tyr Ala Asp Arg Val Thr
    290               295               300

Leu Arg Leu Asn Val Glu Asn Pro Lys Leu Trp Ser Ala Glu Ile Pro
305               310               315               320

Asn Leu Tyr Arg Ala Val Val Glu Leu His Thr Ala Asp Gly Thr Leu
            325               330               335

Ile Glu Ala Glu Ala Cys Asp Val Gly Phe Arg Glu Val Arg Ile Glu
            340               345               350

Asn Gly Leu Leu Leu Leu Asn Gly Lys Pro Leu Leu Ile Arg Gly Val
            355               360               365

Asn Arg His Glu His His Pro Leu His Gly Gln Val Met Asp Glu Gln
    370               375               380

Thr Met Val Gln Asp Ile Leu Leu Met Lys Gln Asn Asn Phe Asn Ala
385               390               395               400

Val Arg Cys Ser His Tyr Pro Asn His Pro Leu Trp Tyr Thr Leu Cys
            405               410               415

Asp Arg Tyr Gly Leu Tyr Val Val Asp Glu Ala Asn Ile Glu Thr His
            420               425               430

Gly Met Val Pro Met Asn Arg Leu Thr Asp Asp Pro Arg Trp Leu Pro
            435               440               445

Ala Met Ser Glu Arg Val Thr Arg Met Val Gln Arg Asp Arg Asn His
    450               455               460

Pro Ser Val Ile Ile Trp Ser Leu Gly Asn Glu Ser Gly His Gly Ala
465               470               475               480

Asn His Asp Ala Leu Tyr Arg Trp Ile Lys Ser Val Asp Pro Ser Arg
            485               490               495

Pro Val Gln Tyr Glu Gly Gly Gly Ala Asp Thr Thr Ala Thr Asp Ile
            500               505               510

Ile Cys Pro Met Tyr Ala Arg Val Asp Glu Asp Gln Pro Phe Pro Ala
            515               520               525
```

-continued

```
Val Pro Lys Trp Ser Ile Lys Lys Trp Leu Ser Leu Pro Gly Glu Thr
    530             535             540

Arg Pro Leu Ile Leu Cys Glu Tyr Ala His Ala Met Gly Asn Ser Leu
545             550             555             560

Gly Gly Phe Ala Lys Tyr Trp Gln Ala Phe Arg Gln Tyr Pro Arg Leu
            565             570             575

Gln Gly Gly Phe Val Trp Asp Trp Val Asp Gln Ser Leu Ile Lys Tyr
            580             585             590

Asp Glu Asn Gly Asn Pro Trp Ser Ala Tyr Gly Gly Asp Phe Gly Asp
            595             600             605

Thr Pro Asn Asp Arg Gln Phe Cys Met Asn Gly Leu Val Phe Ala Asp
    610             615             620

Arg Thr Pro His Pro Ala Leu Thr Glu Ala Lys His Gln Gln Gln Phe
625             630             635             640

Phe Gln Phe Arg Leu Ser Gly Gln Thr Ile Glu Val Thr Ser Glu Tyr
            645             650             655

Leu Phe Arg His Ser Asp Asn Glu Leu Leu His Trp Met Val Ala Leu
            660             665             670

Asp Gly Lys Pro Leu Ala Ser Gly Glu Val Pro Leu Asp Val Ala Pro
            675             680             685

Gln Gly Lys Gln Leu Ile Glu Leu Pro Glu Leu Pro Gln Pro Glu Ser
    690             695             700

Ala Gly Gln Leu Trp Leu Thr Val Arg Val Val Gln Pro Asn Ala Thr
705             710             715             720

Ala Trp Ser Glu Ala Gly His Ile Ser Ala Trp Gln Gln Trp Arg Leu
            725             730             735

Ala Glu Asn Leu Ser Val Thr Leu Pro Ala Ala Ser His Ala Ile Pro
            740             745             750

His Leu Thr Thr Ser Glu Met Asp Phe Cys Ile Glu Leu Gly Asn Lys
            755             760             765

Arg Trp Gln Phe Asn Arg Gln Ser Gly Phe Leu Ser Gln Met Trp Ile
    770             775             780

Gly Asp Lys Lys Gln Leu Leu Thr Pro Leu Arg Asp Gln Phe Thr Arg
785             790             795             800

Ala Pro Leu Asp Asn Asp Ile Gly Val Ser Glu Ala Thr Arg Ile Asp
            805             810             815

Pro Asn Ala Trp Val Glu Arg Trp Lys Ala Ala Gly His Tyr Gln Ala
            820             825             830

Glu Ala Ala Leu Leu Gln Cys Thr Ala Asp Thr Leu Ala Asp Ala Val
            835             840             845

Leu Ile Thr Thr Ala His Ala Trp Gln His Gly Lys Thr Leu Phe
    850             855             860

Ile Ser Arg Lys Thr Tyr Arg Ile Asp Gly Ser Gly Gln Met Ala Ile
865             870             875             880

Thr Val Asp Val Glu Val Ala Ser Asp Thr Pro His Pro Ala Arg Ile
            885             890             895

Gly Leu Asn Cys Gln Leu Ala Gln Val Ala Glu Arg Val Asn Trp Leu
            900             905             910

Gly Leu Gly Pro Gln Glu Asn Tyr Pro Asp Arg Leu Thr Ala Ala Cys
            915             920             925

Phe Asp Arg Trp Asp Leu Pro Leu Ser Asp Met Tyr Thr Pro Tyr Val
    930             935             940
```

-continued

```
Phe Pro Ser Glu Asn Gly Leu Arg Cys Gly Thr Arg Glu Leu Asn Tyr
945                 950                 955                 960

Gly Pro His Gln Trp Arg Gly Asp Phe Gln Phe Asn Ile Ser Arg Tyr
                965                 970                 975

Ser Gln Gln Gln Leu Met Glu Thr Ser His Arg His Leu Leu His Ala
                980                 985                 990

Glu Glu Gly Thr Trp Leu Asn Ile  Asp Gly Phe His Met  Gly Ile Gly
        995                 1000                1005

Gly Asp  Asp Ser Trp Ser Pro  Ser Val Ser Ala Glu  Phe Gln Leu
    1010                1015                1020

Ser Ala  Gly Arg Tyr His Tyr  Gln Leu Val Trp Cys  Gln Lys Gly
    1025                1030                1035

Ser Ser  Lys Pro Glu Lys Pro  Gly Ser Lys Ile Thr  Gly Ser Ser
    1040                1045                1050

Gly Asn  Asp Thr Gln Gly Ser  Leu Ile Thr Tyr Ser  Gly Gly Ala
    1055                1060                1065

Arg Gly
    1070

<210> SEQ ID NO 103
<211> LENGTH: 3210
<212> TYPE: DNA
<213> ORGANISM: Artificial Sequence
<220> FEATURE:
<223> OTHER INFORMATION: LacZ-S2CP(30) nucleotide sequence

<400> SEQUENCE: 103
atgggttctt ctcatcatca ccatcaccat tcttctggga tgaccatgat tacggattca      60
ctggccgtcg ttttacaacg tcgtgactgg gaaaaccctg gcgttaccca acttaatcgc     120
cttgcagcac atccccctttt cgccagctgg cgtaatagcg aagaggcccg caccgatcgc     180
ccttcccaac agttgcgcag cctgaatggc gaatggcgct ttgcctggtt ccggcacca     240 gaagcggtgc cggaaagctg gctggagtgc gatcttcctg aggccgatac tgtcgtcgtc     300
ccctcaaact ggcagatgca cggttacgat gcgcccatct acaccaacgt gacctatccc     360
attacggtca atccgccgtt tgttcccacg gagaatccga cgggttgtta ctcgctcaca     420
tttaatgttg atgaaagctg gctacaggaa ggccagacgc gaattatttt tgatggcgtt     480
aactcggcgt ttcatctgtg gtgcaacggg cgctgggtcg gttacggcca ggacagtcgt     540
ttgccgtctg aatttgacct gagcgcattt ttacgcgccg gagaaaaccg cctcgcggtg     600
atggtgctgc gctggagtga cggcagttat ctggaagatc aggatatgtg cggatgagc     660 ggcattttcc gtgatgtctc gttgctgcat aaaccgacta cacaaatcag cgatttccat     720
gttgccactc gctttaatga tgatttcagc cgcgctgtac tggaggctga agttcagatg     780
tgcggcgagt tgcgtgacta cctacgggta acagtttctt tatggcaggg tgaaacgcag     840
gtcgccagcg gcaccgcgcc tttcggcggt gaaattatcg atgagcgtgg tggttatgcc     900
gatcgcgtca cactacgtct gaacgtcgaa aacccgaaac tgtggagcgc cgaaatcccg     960
aatctctatc gtgcggtggt tgaactgcac accgccgacg gcacgctgat tgaagcagaa    1020
gcctgcgatg tcggtttccg cgaggtgcgg attgaaaatg gtctgctgct gctgaacggc    1080
aagccgttgc tgattcgagg cgttaaccgt cacgagcatc atcctctgca tggtcaggtc    1140
atggatgagc agacgatggt gcaggatatc ctgctgatga agcagaacaa ctttaacgcc    1200
gtgcgctgtt cgcattatcc gaaccatccg ctgtggtaca cgctgtgcga ccgctacggc    1260
```

-continued

```
ctgtatgtgg tggatgaagc caatattgaa acccacggca tggtgccaat gaatcgtctg    1320
accgatgatc cgcgctggct accggcgatg agcgaacgcg taacgcgaat ggtgcagcgc    1380
gatcgtaatc acccgagtgt gatcatctgg tcgctgggga atgaatcagg ccacggcgct    1440
aatcacgacg cgctgtatcg ctggatcaaa tctgtcgatc cttcccgccc ggtgcagtat    1500
gaaggcggcg gagccgacac cacggccacc gatattattt gcccgatgta cgcgcgcgtg    1560
gatgaagacc agcccttccc ggctgtgccg aaatggtcca tcaaaaaatg gctttcgcta    1620
cctggagaaa cgcgcccgct gatcctttgc gaatacgccc acgcgatggg taacagtctt    1680
ggcggtttcg ctaaatactg gcaggcgttt cgtcagtatc cccgtttaca gggcggcttc    1740
gtctgggact gggtggatca gtcgctgatt aaatatgatg aaaacggcaa cccgtggtcg    1800
gcttacggcg gtgattttgg cgatacgccg aacgatcgcc agttctgtat gaacggtctg    1860
gtctttgccg accgcacgcc gcatccagcg ctgacggaag caaaacacca gcagcagttt    1920
ttccagttcc gtttatccgg gcaaaccatc gaagtgacca gcgaatacct gttccgtcat    1980
agcgataacg agctcctgca ctggatggtg gcgctggatg gtaagccgct ggcaagcggt    2040
gaagtgcctc tggatgtcgc tccacaaggt aaacagttga ttgaactgcc tgaactaccg    2100
cagccggaga gcgccgggca actctggctc acagtacgcg tagtgcaacc gaacgcgacc    2160
gcatggtcag aagccggaca catcagcgcc tggcagcagt ggcgtctggc tgaaaacctc    2220
agcgtgacac tccccgccgc gtcccacgcc atcccgcatc tgaccaccag cgaaatggat    2280
ttttgcatcg agctgggtaa taagcgttgg caatttaacc gccagtcagg ctttctttca    2340
cagatgtgga ttggcgataa aaaacaactg ctgacgccgc tgcgcgatca gttcacccgt    2400
gcaccgctgg ataacgacat tggcgtaagt gaagcgaccc gcattgaccc taacgcctgg    2460
gtcgaacgct ggaaggcggc gggccattac caggccgaag cagcgttgtt gcagtgcacg    2520
gcagatacac ttgctgatgc ggtgctgatt acgaccgctc acgcgtggca gcatcagggg    2580
aaaaccttat ttatcagccg gaaaacctac cggattgatg gtagtggtca aatggcgatt    2640
accgttgatg ttgaagtggc gagcgataca ccgcatccgg cgcggattgg cctgaactgc    2700
cagctggcgc aggtagcaga gcgggtaaac tggctcggat tagggccgca agaaaactat    2760
cccgaccgcc ttactgccgc ctgtttgac cgctgggatc tgccattgtc agacatgtat    2820
accccgtacg tcttcccgag cgaaaacggt ctgcgctgcg ggacgcgcga attgaattat    2880
ggcccacacc agtggcgcgg cgacttccag ttcaacatca gccgctacag tcaacagcaa    2940
ctgatggaaa ccagccatcg ccatctgctg cacgcggaag aaggcacatg gctgaatatc    3000
gacggtttcc atatggggat tggtggcgac gactcctgga gcccgtcagt atcggcggaa    3060
ttccagctga gcgccggtcg ctaccattac cagttggtct ggtgtcaaaa aggttcttct    3120
aaaccggaaa aaccaggtag caaaattacc ggtagcagcg gcaatgatac ccagggtagc    3180
ctgattacct atagcggtgg tgcacgtggt                                     3210
```

<210> SEQ ID NO 104
<211> LENGTH: 453
<212> TYPE: DNA
<213> ORGANISM: Artificial Sequence
<220> FEATURE:
<223> OTHER INFORMATION: Promoter PGPM1 nucleotide sequence

<400> SEQUENCE: 104

```
gtgatgtcta agtaaccttt atggtatatt tcttaatgtg gaaagatact agcgcgcgca      60
cccacacaca agcttcgtct tttcttgaag aaaagaggaa gctcgctaaa tgggattcca     120
```

-continued

```
ctttccgttc cctgccagct gatggaaaaa ggttagtgga acgatgaaga ataaaaagag      180
agatccactg aggtgaaatt tcagctgaca gcgagtttca tgatcgtgat gaacaatggt      240
aacgagttgt ggctgttgcc agggagggtg gttctcaact tttaatgtat ggccaaatcg      300
ctacttgggt ttgttatata acaaagaaga aataatgaac tgattctctt cctccttctt      360
gtcctttctt aattctgttg taattacctt cctttgtaat ttttttttgta attattcttc      420 ttaataatcc aaacaaacac acatattaca ata                                    453

<210> SEQ ID NO 105
<211> LENGTH: 432
<212> TYPE: DNA
<213> ORGANISM: Artificial Sequence
<220> FEATURE:
<223> OTHER INFORMATION: Yeast transcriptional terminator TYPT31

<400> SEQUENCE: 105
gagatatttt gcagcagttg cgcacttgca tgtgaatgac tcttctcccc tttaattctg       60
tgctatattt ttacaatttt ctgctgacat atagtttata tacatataga acgcatatag      120
gaaattgaag taaacagaat acacaagtag aggccggtat gtacgacatt ttgcttacta      180
ctctttaaaa tcatcgtctt cttcgtcttc atcgtcttct tcttttttcac catatcctac      240 atcatcttta gagcctgtgc taggttcctt cttgtctaat tcttctgcag tcttttttata      300 gtcaattact ttgccgcgtg ttcttcttcc ggatgtgatg atattagagg tatcaatttc      360
tgccaaatcg tcctcttctt cttctccctc atttcccatc aatgcgtcta acttggcatc      420
gtccatatca ga                                                          432

<210> SEQ ID NO 106
<211> LENGTH: 2971
<212> TYPE: DNA
<213> ORGANISM: Artificial Sequence
<220> FEATURE:
<223> OTHER INFORMATION: HcKan_O-S2CP(30) plasmid

<400> SEQUENCE: 106
aagaaaggcc cacccgtgaa ggtgagccag tgagttgatt gcagtccagt tacgctggag       60
tccgtctcgg atgagagacc gaattcgcgg ccgcttctag agcaatacgc aaaccgcctc      120
tccccgcgcg ttggccgatt cattaatgca gctggcacga caggtttccc gactggaaag      180
cgggcagtga gcgcaacgca attaatgtga gttagctcac tcattaggca ccccaggctt      240
tacactttat gcttccggct cgtatgttgt gtggaattgt gagcggataa caatttcaca      300
catactagag aaagaggaga aatactagat ggcttcctcc gaagacgtta tcaaagagtt      360
catgcgtttc aaagttcgta tggaaggttc cgttaacggt cacgagttcg aaatcgaagg      420
tgaaggtgaa ggtcgtccgt acgaaggtac ccagaccgct aaactgaaag ttaccaaagg      480
tggtccgctg ccgttcgctt gggacatcct gtccccgcag ttccagtacg gttccaaagc      540
ttacgttaaa cacccggctg acatcccgga ctacctgaaa ctgtccttcc cggaaggttt      600
caaatgggaa cgtgttatga acttcgaaga cggtggtgtt gttaccgtta cccaggactc      660
ctccctgcaa gacggtgagt catctacaa agttaaactg cgtggtacca acttcccgtc      720
cgacggtccg gttatgcaga aaaaaaccat gggttgggaa gcttccaccg aacgtatgta      780
cccggaagac ggtgctctga aaggtgaaat caaaatgcgt ctgaaactga agacggtgg      840 tcactacgac gctgaagtta aaaccaccta catggctaaa aaaccggttc agctgccggg      900
```

```
tgcttacaaa accgacatca aactggacat cacctcccac aacgaagact acaccatcgt      960
tgaacagtac gaacgtgctg aaggtcgtca ctccaccggt gcttaataac gctgatagtg     1020
ctagtgtaga tcgctactag agccaggcat caaataaaac gaaaggctca gtcgaaagac     1080
tgggcctttc gttttatctg ttgtttgtcg gtgaacgctc tctactagag tcacactggc     1140
tcaccttcgg gtgggccttt ctgcgtttat atactagtag cggccgctgc agggtctctg     1200
gttcttctaa accggaaaaa ccaggtagca aaattaccgg tagcagcggc aatgataccc     1260
agggtagcct gattacctat agcggtggtg cacgtggtta gccgagacga ctgaccattt     1320
aaatcatacc tgacctccat agcagaaagt caaaagcctc cgaccggagg cttttgactt     1380
gatcggcacg taagaggttc caactttcac cataatgaaa taagatcact accgggcgta     1440 tttttttgagt tatcgagatt ttcaggagct aaggaagcta aaatgagcca tattcaacgg     1500
gaaacgtctt gctcgaggcc gcgattaaat tccaacatgg atgctgattt atatgggtat     1560
aaatgggctc gcgataatgt cgggcaatca ggtgcgacaa tctatcgatt gtatgggaag     1620
cccgatgcgc cagagttgtt tctgaaacat ggcaaaggta gcgttgccaa tgatgttaca     1680
gatgagatgg tcaggctaaa ctggctgacg gaatttatgc ctcttccgac catcaagcat     1740
tttatccgta ctcctgatga tgcatggtta ctcaccactg cgatcccagg gaaaacagca     1800
ttccaggtat tagaagaata tcctgattca ggtgaaaata ttgttgatgc gctggcagtg     1860
ttcctgcgcc ggttgcattc gattcctgtt tgtaattgtc cttttaacgg cgatcgcgta     1920
tttcgtctcg ctcaggcgca atcacgaatg aataacggtt tggttggtgc gagtgatttt     1980
gatgacgagc gtaatggctg gcctgttgaa caagtctgga aagaaatgca taagcttttg     2040
ccattctcac cggattcagt cgtcactcat ggtgatttct cacttgataa ccttattttt     2100
gacgagggga aattaatagg ttgtattgat gttggacgag tcggaatcgc agaccgatac     2160
caggatcttg ccatcctatg gaactgcctc ggtgagtttt ctccttcatt acagaaacgg     2220 cttttttcaaa aatatggtat tgataatcct gatatgaata aattgcagtt tcacttgatg     2280
ctcgatgagt ttttctaatg agggcccaaa tgtaatcacc tggctcacct tcgggtgggc     2340
ctttctgcgt tgctggcgtt tttccatagg ctccgccccc ctgacgagca tcacaaaaat     2400
cgatgctcaa gtcagaggtg gcgaaacccg acaggactat aaagatacca ggcgtttccc     2460
cctggaagct ccctcgtgcg ctctcctgtt ccgaccctgc cgcttaccgg atacctgtcc     2520
gcctttctcc cttcgggaag cgtggcgctt tctcatagct cacgctgtag gtatctcagt     2580
tcggtgtagg tcgttcgctc caagctgggc tgtgtgcacg aacccccgt tcagcccgac      2640 cgctgcgcct tatccggtaa ctatcgtctt gagtccaacc cggtaagaca cgacttatcg     2700
ccactggcag cagccactgg taacaggatt agcagagcga ggtatgtagg cggtgctaca     2760
gagttcttga agtggtggcc taactacggc tacactagaa gaacagtatt tggtatctgc     2820
gctctgctga agccagttac ctcggaaaaa gagttggtag ctcttgatcc ggcaaacaaa     2880
ccaccgctgg tagcggtggt ttttttgttt gcaagcagca gattacgcgc agaaaaaaag     2940
gatctcaaga agatcctttg attttctacc g                                    2971
```

<210> SEQ ID NO 107
<211> LENGTH: 90
<212> TYPE: DNA
<213> ORGANISM: Artificial Sequence
<220> FEATURE:
<223> OTHER INFORMATION: HcKan_O-S2CP(30) nucleotide sequence of key ORF

<400> SEQUENCE: 107

```
aaaccggaaa aaccaggtag caaaattacc ggtagcagcg gcaatgatac ccagggtagc        60
ctgattacct atagcggtgg tgcacgtggt                                         90

<210> SEQ ID NO 108
<211> LENGTH: 36
<212> TYPE: PRT
<213> ORGANISM: Artificial Sequence
<220> FEATURE:
<223> OTHER INFORMATION: HcKan_O-S2CP(30) amino acid sequence of key ORF

<400> SEQUENCE: 108

Lys Pro Glu Lys Pro Gly Lys Pro Glu Lys Pro Gly Ser Lys Ile Thr
1               5                   10                  15

Gly Ser Ser Gly Asn Asp Thr Gln Gly Ser Leu Ile Thr Tyr Ser Gly
            20                  25                  30

Gly Ala Arg Gly
        35

<210> SEQ ID NO 109
<211> LENGTH: 2631
<212> TYPE: DNA
<213> ORGANISM: Artificial Sequence
<220> FEATURE:
<223> OTHER INFORMATION: HcKan_O-APEX2-S2CP(30) plasmid

<400> SEQUENCE: 109
aagaaaggcc cacccgtgaa ggtgagccag tgagttgatt gcagtccagt tacgctggag        60
tccgtctcgg atgggttctt ctcatcatca ccatcaccat tcttctggga tgggtaagtc       120
ttacccaact gtttctgctg attatcaaga tgctgttgaa aaggccaaga agaagttgag       180
aggtttcatt gctgaaaaaa gatgcgctcc attgatgttg agattggctt ttcattctgc       240
tggtactttc gataagggta caaaaactgg tggtccattc ggtactatca aacatccagc       300
tgaattggct cattcagcta caatggtttt ggatattgct gtcagattgc tggaaccatt       360
gaaagccgaa tttccaattt tgtcctacgc cgattttac caattggctg gtgttgttgc        420
agttgaagtt acaggtggtc caaaagttcc atttcatcca ggtagagaag ataagccaga       480
accaccacca gaaggtagat tgccagatcc aacaaaaggt tctgatcact tgagagatgt       540
tttcggtaaa gctatgggtt tgactgatca agatattgtc gctttgtctg gtggtcatac       600
aattggtgct gctcacaaag aaagatcagg ttttgaaggt ccttggactt ctaacccatt       660
gatctttgat aactcttact tcaccgagtt gttgtccggt gaaaaagaag gtttgttgca       720
attgccatct gataaggctt gttgtctga tccagttttc agaccattgg ttgataagta       780
tgctgctgat gaagatgctt tctttgctga ttacgctgaa gctcatcaaa agttgtctga       840
attgggtttt gctgatgctg gttcttctaa accggaaaaa ccaggtagca aaattaccgg       900
tagcagcggc aatgataccc agggtagcct gattacctat agcggtggtg cacgtggtta       960
gccgagacga ctgaccattt aaatcatacc tgacctccat agcagaaagt caaaagcctc      1020
cgaccggagg cttttgactt gatcggcacg taagaggttc caactttcac cataatgaaa      1080
taagatcact accgggcgta ttttttgagt tatcgagatt ttcaggagct aaggaagcta      1140
aaatgagcca tattcaacgg gaaacgtctt gctcgaggcc gcgattaaat tccaacatgg      1200
atgctgattt atatgggtat aaatgggctc gcgataatgt cggcaatca ggtgcgacaa       1260 tctatcgatt gtatgggaag cccgatgcgc cagagttgtt tctgaaacat ggcaaaggta      1320
gcgttgccaa tgatgttaca gatgagatgg tcaggctaaa ctggctgacg gaatttatgc      1380
```

-continued

```
ctcttccgac catcaagcat tttatccgta ctcctgatga tgcatggtta ctcaccactg    1440
cgatcccagg gaaaacagca ttccaggtat tagaagaata tcctgattca ggtgaaaata    1500
ttgttgatgc gctggcagtg ttcctgcgcc ggttgcattc gattcctgtt tgtaattgtc    1560
cttttaacgg cgatcgcgta tttcgtctcg ctcaggcgca atcacgaatg aataacggtt    1620
tggttggtgc gagtgatttt gatgacgagc gtaatggctg gcctgttgaa caagtctgga    1680
aagaaatgca taagcttttg ccattctcac cggattcagt cgtcactcat ggtgatttct    1740
cacttgataa ccttattttt gacgagggga aattaatagg ttgtattgat gttggacgag    1800
tcggaatcgc agaccgatac caggatcttg ccatcctatg gaactgcctc ggtgagtttt    1860
ctccttcatt acagaaacgg ctttttcaaa aatatggtat tgataatcct gatatgaata    1920
aattgcagtt tcacttgatg ctcgatgagt ttttctaatg agggcccaaa tgtaatcacc    1980
tggctcacct tcgggtgggc ctttctgcgt tgctggcgtt tttccatagg ctccgccccc    2040
ctgacgagca tcacaaaaat cgatgctcaa gtcagaggtg gcgaaacccg acaggactat    2100
aaagatacca ggcgtttccc cctggaagct ccctcgtgcg ctctcctgtt ccgaccctgc    2160
cgcttaccgg atacctgtcc gcctttctcc cttcgggaag cgtggcgctt tctcatagct    2220
cacgctgtag gtatctcagt tcggtgtagg tcgttcgctc caagctgggc tgtgtgcacg    2280
aaccccccgt tcagcccgac cgctgcgcct tatccggtaa ctatcgtctt gagtccaacc    2340
cggtaagaca cgacttatcg ccactggcag cagccactgg taacaggatt agcagagcga    2400
ggtatgtagg cggtgctaca gagttcttga agtggtggcc taactacggc tacactagaa    2460
gaacagtatt tggtatctgc gctctgctga agccagttac ctcggaaaaa gagttggtag    2520
ctcttgatcc ggcaaacaaa ccaccgctgg tagcggtggt ttttttgttt gcaagcagca    2580
gattacgcgc agaaaaaaag gatctcaaga agatcctttg attttctacc g             2631
```

<210> SEQ ID NO 110
<211> LENGTH: 888
<212> TYPE: DNA
<213> ORGANISM: Artificial Sequence
<220> FEATURE:
<223> OTHER INFORMATION: HcKan_O-APEX2-S2CP(30) nucleotide sequence of
     key ORF

<400> SEQUENCE: 110

```
atgggttctt ctcatcatca ccatcaccat tcttctggga tgggtaagtc ttacccaact     60
gtttctgctg attatcaaga tgctgttgaa aaggccaaga agaagttgag aggtttcatt    120
gctgaaaaaa gatgcgctcc attgatgttg agattggctt tcattctgc tggtactttc     180 gataagggta caaaaactgg tggtccattc ggtactatca aacatccagc tgaattggct    240
cattcagcta acaatggttt ggatattgct gtcagattgc tggaaccatt gaaagccgaa    300
tttccaattt tgtcctacgc cgattttac caattggctg gtgttgttgc agttgaagtt     360
acaggtggtc caaagttcc atttcatcca ggtagagaag ataagccaga accaccacca     420
gaaggtagat tgccagatcc aacaaaaggt tctgatcact tgagagatgt tttcggtaaa    480
gctatgggtt tgactgatca agatattgtc gctttgtctg tggtcatac aattggtgct     540 gctcacaaag aaagatcagg ttttgaaggt ccttggactt ctaacccatt gatctttgat    600
aactcttact tcaccgagtt gttgtccggt gaaaagaag gtttgttgca attgccatct     660
gataaggctt gttgtctga tccagttttc agaccattgg ttgataagta tgctgctgat    720
gaagatgctt tctttgctga ttacgctgaa gctcatcaaa agttgtctga attgggtttt    780
```

```
gctgatgctg gttcttctaa accggaaaaa ccaggtagca aaattaccgg tagcagcggc        840
aatgataccc agggtagcct gattacctat agcggtggtg cacgtggt                     888
```

```
<210> SEQ ID NO 111
<211> LENGTH: 296
<212> TYPE: PRT
<213> ORGANISM: Artificial Sequence
<220> FEATURE:
<223> OTHER INFORMATION: HcKan_O-APEX2-S2CP(30) amino acid sequence of
      key ORF

<400> SEQUENCE: 111

Met Gly Ser Ser His His His His His His Ser Ser Gly Met Gly Lys
1               5                   10                  15

Ser Tyr Pro Thr Val Ser Ala Asp Tyr Gln Asp Ala Val Glu Lys Ala
            20                  25                  30

Lys Lys Lys Leu Arg Gly Phe Ile Ala Glu Lys Arg Cys Ala Pro Leu
        35                  40                  45

Met Leu Arg Leu Ala Phe His Ser Ala Gly Thr Phe Asp Lys Gly Thr
    50                  55                  60

Lys Thr Gly Gly Pro Phe Gly Thr Ile Lys His Pro Ala Glu Leu Ala
65                  70                  75                  80

His Ser Ala Asn Asn Gly Leu Asp Ile Ala Val Arg Leu Leu Glu Pro
                85                  90                  95

Leu Lys Ala Glu Phe Pro Ile Leu Ser Tyr Ala Asp Phe Tyr Gln Leu
            100                 105                 110

Ala Gly Val Val Ala Val Glu Val Thr Gly Gly Pro Lys Val Pro Phe
            115                 120                 125

His Pro Gly Arg Glu Asp Lys Pro Glu Pro Pro Glu Gly Arg Leu
    130                 135                 140

Pro Asp Pro Thr Lys Gly Ser Asp His Leu Arg Asp Val Phe Gly Lys
145                 150                 155                 160

Ala Met Gly Leu Thr Asp Gln Asp Ile Val Ala Leu Ser Gly Gly His
                165                 170                 175

Thr Ile Gly Ala Ala His Lys Glu Arg Ser Gly Phe Glu Gly Pro Trp
            180                 185                 190

Thr Ser Asn Pro Leu Ile Phe Asp Asn Ser Tyr Phe Thr Glu Leu Leu
            195                 200                 205

Ser Gly Glu Lys Glu Gly Leu Leu Gln Leu Pro Ser Asp Lys Ala Leu
    210                 215                 220

Leu Ser Asp Pro Val Phe Arg Pro Leu Val Asp Lys Tyr Ala Ala Asp
225                 230                 235                 240

Glu Asp Ala Phe Phe Ala Asp Tyr Ala Glu Ala His Gln Lys Leu Ser
                245                 250                 255

Glu Leu Gly Phe Ala Asp Ala Gly Ser Ser Lys Pro Glu Lys Pro Gly
            260                 265                 270

Ser Lys Ile Thr Gly Ser Ser Gly Asn Asp Thr Gln Gly Ser Leu Ile
        275                 280                 285

Thr Tyr Ser Gly Gly Ala Arg Gly
    290                 295
```

```
<210> SEQ ID NO 112
<211> LENGTH: 4953
<212> TYPE: DNA
<213> ORGANISM: Artificial Sequence
<220> FEATURE:
```

<223> OTHER INFORMATION: HcKan_O-LacZ-S2CTP plasmid

<400> SEQUENCE: 112

```
aagaaaggcc cacccgtgaa ggtgagccag tgagttgatt gcagtccagt tacgctggag      60
tccgtctcgg atgggttctt ctcatcatca ccatcaccat tcttctggga tgaccatgat     120
tacggattca ctggccgtcg ttttacaacg tcgtgactgg gaaaaccctg gcgttaccca     180
acttaatcgc cttgcagcac atcccccttt cgccagctgg cgtaatagcg aagaggcccg     240
caccgatcgc ccttcccaac agttgcgcag cctgaatggc gaatggcgct ttgcctggtt     300
tccggcacca gaagcggtgc cggaaagctg gctggagtgc gatcttcctg aggccgatac     360
tgtcgtcgtc ccctcaaact ggcagatgca cggttacgat gcgcccatct acaccaacgt     420
gacctatccc attacggtca atccgccgtt tgttcccacg gagaatccga cgggttgtta     480
ctcgctcaca tttaatgttg atgaaagctg gctacaggaa ggccagacgc gaattatttt     540
tgatggcgtt aactcggcgt ttcatctgtg gtgcaacggg cgctgggtcg gttacggcca     600
ggacagtcgt ttgccgtctg aatttgacct gagcgcattt ttacgcgccg gagaaaaccg     660
cctcgcggtg atggtgctgc ctggagtga cggcagttat ctggaagatc aggatatgtg     720
gcggatgagc ggcattttcc gtgatgtctc gttgctgcat aaaccgacta cacaaatcag     780
cgatttccat gttgccactc gctttaatga tgatttcagc cgcgctgtac tggaggctga     840
agttcagatg tgcggcgagt tgcgtgacta cctacgggta acagtttctt tatggcaggg     900
tgaaacgcag tcgccagcg gcaccgcgcc tttcggcggt gaaattatcg atgagcgtgg     960
tggttatgcc gatcgcgtca cactacgtct gaacgtcgaa aacccgaaac tgtggagcgc    1020
cgaaatcccg aatctctatc gtgcggtggt tgaactgcac accgccgacg gcacgctgat    1080
tgaagcagaa gcctgcgatg tcggtttccg cgaggtgcgg attgaaaatg gtctgctgct    1140
gctgaacggc aagccgttgc tgattcgagg cgttaaccgt cacgagcatc atcctctgca    1200
tggtcaggtc atggatgagc agacgatggt gcaggatatc ctgctgatga agcagaacaa    1260
ctttaacgcc gtgcgctgtt cgcattatcc gaaccatccg ctgtggtaca cgctgtgcga    1320
ccgctacggc ctgtatgtgg tggatgaagc caatattgaa acccacggca tggtgccaat    1380
gaatcgtctg accgatgatc cgcgctggct accggcgatg agcgaacgcg taacgcgaat    1440
ggtgcagcgc gatcgtaatc acccgagtgt gatcatctgg tcgctgggga atgaatcagg    1500
ccacggcgct aatcacgacg cgctgtatcg ctggatcaaa tctgtcgatc cttcccgccc    1560
ggtgcagtat gaaggcggcg gagccgacac cacggccacc gatattattt gcccgatgta    1620
cgcgcgcgtg gatgaagacc agcccttccc ggctgtgccg aaatggtcca tcaaaaaatg    1680
gctttcgcta cctggagaaa cgcgcccgct gatcctttgc gaatacgccc acgcgatggg    1740
taacagtctt ggcggtttcg ctaaatactg gcaggcgttt cgtcagtatc ccgtttaca    1800 gggcggcttc gtctgggact gggtggatca gtcgctgatt aaatatgatg aaaacggcaa    1860
cccgtggtcg gcttacggcg gtgattttgg cgatacgccg aacgatcgcc agttctgtat    1920
gaacggtctg gtctttgccg accgcacgcc gcatccagcg ctgacggaag caaaacacca    1980
gcagcagttt ttccagttcc gtttatccgg caaaccatc gaagtgacca gcgaatacct    2040
gttccgtcat agcgataacg agctcctgca ctggatggtg gcgctggatg gtaagccgct    2100
ggcaagcggt gaagtgcctc tggatgtcgc tccacaaggt aaacagttga ttgaactgcc    2160
tgaactaccg cagccggaga gcgccgggca actctggctc acagtacgcg tagtgcaacc    2220
gaacgcgacc gcatggtcag aagccggaca catcagcgcc tggcagcagt ggcgtctggc    2280
```

```
tgaaaacctc agcgtgacac tccccgccgc gtcccacgcc atcccgcatc tgaccaccag    2340
cgaaatggat ttttgcatcg agctgggtaa taagcgttgg caatttaacc gccagtcagg    2400
ctttctttca cagatgtgga ttggcgataa aaaacaactg ctgacgccgc tgcgcgatca    2460
gttcacccgt gcaccgctgg ataacgacat tggcgtaagt gaagcgaccc gcattgaccc    2520
taacgcctgg gtcgaacgct ggaaggcggc gggccattac caggccgaag cagcgttgtt    2580
gcagtgcacg gcagatacac ttgctgatgc ggtgctgatt acgaccgctc acgcgtggca    2640
gcatcagggg aaaaccttat ttatcagccg gaaaacctac cggattgatg gtagtggtca    2700
aatggcgatt accgttgatg ttgaagtggc gagcgataca ccgcatccgg cgcggattgg    2760
cctgaactgc cagctggcgc aggtagcaga gcgggtaaac tggctcggat tagggccgca    2820
agaaaactat cccgaccgcc ttactgccgc ctgttttgac cgctgggatc tgccattgtc    2880
agacatgtat accccgtacg tcttcccgag cgaaaacggt ctgcgctgcg ggacgcgcga    2940
attgaattat ggcccacacc agtggcgcgg cgacttccag ttcaacatca gccgctacag    3000
tcaacagcaa ctgatggaaa ccagccatcg ccatctgctg cacgcggaag aaggcacatg    3060
gctgaatatc gacggtttcc atatggggat tggtggcgac gactcctgga gcccgtcagt    3120
atcggcggaa ttccagctga gcgccggtcg ctaccattac cagttggtct ggtgtcaaaa    3180
aggttcttct aaaccggaaa aaccaggtag caaaattacc ggtagcagcg gcaatgatac    3240
ccagggtagc ctgattacct atagcggtgg tgcacgtggt tagccgagac gactgaccat    3300
ttaaatcata cctgacctcc atagcagaaa gtcaaaagcc tccgaccgga ggcttttgac    3360
ttgatcggca cgtaagaggt tccaactttc accataatga aataagatca ctaccgggcg    3420
tattttttga gttatcgaga ttttcaggag ctaaggaagc taaaatgagc catattcaac    3480
gggaaacgtc ttgctcgagg ccgcgattaa attccaacat ggatgctgat ttatatgggt    3540
ataaatgggc tcgcgataat gtcgggcaat caggtgcgac aatctatcga ttgtatggga    3600
agcccgatgc gccagagttg tttctgaaac atggcaaagg tagcgttgcc aatgatgtta    3660
cagatgagat ggtcaggcta aactggctga cggaatttat gcctcttccg accatcaagc    3720
attttatccg tactcctgat gatgcatggt tactcaccac tgcgatccca gggaaaacag    3780
cattccaggt attagaagaa tatcctgatt caggtgaaaa tattgttgat gcgctggcag    3840
tgttcctgcg ccggttgcat tcgattcctg tttgtaattg tccttttaac ggcgatcgcg    3900
tatttcgtct cgctcaggcg caatcacgaa tgaataacgg tttggttggt gcgagtgatt    3960
ttgatgacga gcgtaatggc tggcctgttg aacaagtctg gaaagaaatg cataagcttt    4020
tgccattctc accggattca gtcgtcactc atggtgattt ctcacttgat aaccttattt    4080
ttgacgaggg gaaattaata ggttgtattg atgttggacg agtcggaatc gcagaccgat    4140
accaggatct tgccatccta tggaactgcc tcggtgagtt ttctccttca ttacagaaac    4200
ggctttttca aaaatatggt attgataatc ctgatatgaa taaattgcag tttcacttga    4260
tgctcgatga gttttttctaa tgagggccca aatgtaatca cctggctcac cttcgggtgg    4320
gcctttctgc gttgctggcg tttttccata ggctccgccc ccctgacgag catcacaaaa    4380
atcgatgctc aagtcagagg tggcgaaacc cgacaggact ataaagatac caggcgtttc    4440
cccctggaag ctccctcgtg cgctctcctg ttccgaccct gccgcttacc ggatacctgt    4500
ccgcctttct cccttcggga agcgtggcgc tttctcatag ctcacgctgt aggtatctca    4560
gttcggtgta ggtcgttcgc tccaagctgg gctgtgtgca cgaacccccc gttcagcccg    4620
```

```
accgctgcgc cttatccggt aactatcgtc ttgagtccaa cccggtaaga cacgacttat    4680
cgccactggc agcagccact ggtaacagga ttagcagagc gaggtatgta ggcggtgcta    4740
cagagttctt gaagtggtgg cctaactacg gctacactag aagaacagta tttggtatct    4800
gcgctctgct gaagccagtt acctcggaaa aagagttggt agctcttgat ccggcaaaca    4860
aaccaccgct ggtagcggtg gtttttttgt ttgcaagcag cagattacgc gcagaaaaaa    4920
aggatctcaa gaagatcctt tgatttttcta ccg                                4953
```

```
<210> SEQ ID NO 113
<211> LENGTH: 3210
<212> TYPE: DNA
<213> ORGANISM: Artificial Sequence
<220> FEATURE:
<223> OTHER INFORMATION: HcKan_O-LacZ-S2CTP nucleotid sequence of key
      ORF

<400> SEQUENCE: 113
atgggttctt ctcatcatca ccatcaccat tcttctggga tgaccatgat tacggattca      60
ctggccgtcg ttttacaacg tcgtgactgg gaaaaccctg gcgttaccca acttaatcgc     120
cttgcagcac atcccccttt cgccagctgg cgtaatagcg aagaggcccg caccgatcgc     180
ccttcccaac agttgcgcag cctgaatggc gaatggcgct ttgcctggtt ccggcacca     240 gaagcggtgc cggaaagctg gctggagtgc gatcttcctg aggccgatac tgtcgtcgtc     300
ccctcaaact ggcagatgca cggttacgat gcgcccatct acaccaacgt gacctatccc     360
attacggtca atccgccgtt tgttcccacg gagaatccga cgggttgtta ctcgctcaca     420
tttaatgttg atgaaagctg gctacaggaa ggccagacgc gaattatttt tgatggcgtt     480
aactcggcgt ttcatctgtg gtgcaacggg cgctgggtcg ttacggcca ggacagtcgt      540 ttgccgtctg aatttgacct gagcgcattt ttacgcgccg gagaaaaccg cctcgcggtg     600
atggtgctgc gctggagtga cggcagttat ctggaagatc aggatatgtg gcggatgagc     660
ggcattttcc gtgatgtctc gttgctgcat aaaccgacta cacaaatcag cgatttccat     720
gttgccactc gctttaatga tgatttcagc cgcgctgtac tggaggctga agttcagatg     780
tgcggcgagt tgcgtgacta cctacgggta acagtttctt tatggcaggg tgaaacgcag     840
gtcgccagcg gcaccgcgcc tttcggcggt gaaattatcg atgagcgtgg tggttatgcc     900
gatcgcgtca cactacgtct gaacgtcgaa aacccgaaac tgtggagcgc cgaaatcccg     960
aatctctatc gtgcggtggt tgaactgcac accgccgacg gcacgctgat tgaagcagaa    1020
gcctgcgatg tcggtttccg cgaggtgcgg attgaaaatg gtctgctgct gctgaacggc    1080
aagccgttgc tgattcgagg cgttaaccgt cacgagcatc atcctctgca tggtcaggtc    1140
atggatgagc agacgatggt gcaggatatc ctgctgatga agcagaacaa ctttaacgcc    1200
gtgcgctgtt cgcattatcc gaaccatccg ctgtggtaca cgctgtgcga ccgctacggc    1260
ctgtatgtgg tggatgaagc caatattgaa acccacggca tggtgccaat gaatcgtctg    1320
accgatgatc cgcgctggct accggcgatg agcgaacgcg taacgcgaat ggtgcagcgc    1380
gatcgtaatc acccgagtgt gatcatctgg tcgctgggga atgaatcagg ccacggcgct    1440
aatcacgacg cgctgtatcg ctggatcaaa tctgtcgatc cttcccgccc ggtgcagtat    1500
gaaggcggcg gagccgacac cacggccacc gatattattt gcccgatgta cgcgcgcgtg    1560
gatgaagacc agcccttccc ggctgtgccg aaatggtcca tcaaaaaatg ctttcgcta     1620 cctggagaaa cgcgcccgct gatcctttgc gaatacgccc acgcgatggg taacagtctt    1680
```

-continued

```
ggcggtttcg ctaaatactg gcaggcgttt cgtcagtatc cccgtttaca gggcggcttc      1740
gtctgggact gggtggatca gtcgctgatt aaatatgatg aaaacggcaa cccgtggtcg      1800
gcttacggcg gtgatttggg cgatacgccg aacgatcgcc agttctgtat gaacggtctg      1860
gtctttgccg accgcacgcc gcatccagcg ctgacggaag caaaacacca gcagcagttt      1920
ttccagttcc gtttatccgg gcaaaccatc gaagtgacca gcgaatacct gttccgtcat      1980
agcgataacg agctcctgca ctggatggtg gcgctggatg gtaagccgct ggcaagcggt      2040
gaagtgcctc tggatgtcgc tccacaaggt aaacagttga ttgaactgcc tgaactaccg      2100
cagccggaga gcgccgggca actctggctc acagtacgcg tagtgcaacc gaacgcgacc      2160
gcatggtcag aagccggaca catcagcgcc tggcagcagt ggcgtctggc tgaaaacctc      2220
agcgtgacac tccccgccgc gtcccacgcc atcccgcatc tgaccaccag cgaaatggat      2280
ttttgcatcg agctgggtaa taagcgttgg caatttaacc gccagtcagg ctttctttca      2340
cagatgtgga ttggcgataa aaaacaactg ctgacgccgc tgcgcgatca gttcacccgt      2400
gcaccgctgg ataacgacat tggcgtaagt gaagcgaccc gcattgaccc taacgcctgg      2460
gtcgaacgct ggaaggcggc gggccattac caggccgaag cagcgttgtt gcagtgcacg      2520
gcagatacac ttgctgatgc ggtgctgatt acgaccgctc acgcgtggca gcatcagggg      2580
aaaaccttat ttatcagccg gaaaacctac cggattgatg gtagtggtca aatggcgatt      2640
accgttgatg ttgaagtggc gagcgataca ccgcatccgg cgcggattgg cctgaactgc      2700
cagctggcgc aggtagcaga gcgggtaaac tggctcggat tagggccgca agaaaactat      2760
cccgaccgcc ttactgccgc ctgtttttgac cgctgggatc tgccattgtc agacatgtat      2820
accccgtacg tcttcccgag cgaaaacggt ctgcgctgcg ggacgcgcga attgaattat      2880
ggcccacacc agtggcgcgg cgacttccag ttcaacatca gccgctacag tcaacagcaa      2940
ctgatggaaa ccagccatcg ccatctgctg cacgcggaag aaggcacatg gctgaatatc      3000
gacggtttcc atatggggat tggtggcgac gactcctgga gcccgtcagt atcggcggaa      3060
ttccagctga gcgccggtcg ctaccattac cagttggtct ggtgtcaaaa aggttcttct      3120
aaaccggaaa aaccaggtag caaaattacc ggtagcagcg caatgatac ccagggtagc      3180 ctgattacct atagcggtgg tgcacgtggt      3210
```

```
<210> SEQ ID NO 114
<211> LENGTH: 1070
<212> TYPE: PRT
<213> ORGANISM: Artificial Sequence
<220> FEATURE:
<223> OTHER INFORMATION: HcKan_O-LacZ-S2CTP amino acid sequence of key
      ORF

<400> SEQUENCE: 114

Met Gly Ser Ser His His His His His His Ser Ser Gly Met Thr Met
1               5                   10                  15

Ile Thr Asp Ser Leu Ala Val Val Leu Gln Arg Arg Asp Trp Glu Asn
            20                  25                  30

Pro Gly Val Thr Gln Leu Asn Arg Leu Ala Ala His Pro Pro Phe Ala
        35                  40                  45

Ser Trp Arg Asn Ser Glu Glu Ala Arg Thr Asp Arg Pro Ser Gln Gln
    50                  55                  60

Leu Arg Ser Leu Asn Gly Glu Trp Arg Phe Ala Trp Phe Pro Ala Pro
65                  70                  75                  80

Glu Ala Val Pro Glu Ser Trp Leu Glu Cys Asp Leu Pro Glu Ala Asp
```

```
                    85                90                95
Thr Val Val Val Pro Ser Asn Trp Gln Met His Gly Tyr Asp Ala Pro
                100              105              110

Ile Tyr Thr Asn Val Thr Tyr Pro Ile Thr Val Asn Pro Pro Phe Val
            115              120              125

Pro Thr Glu Asn Pro Thr Gly Cys Tyr Ser Leu Thr Phe Asn Val Asp
        130              135              140

Glu Ser Trp Leu Gln Glu Gly Gln Thr Arg Ile Ile Phe Asp Gly Val
145              150              155              160

Asn Ser Ala Phe His Leu Trp Cys Asn Gly Arg Trp Val Gly Tyr Gly
            165              170              175

Gln Asp Ser Arg Leu Pro Ser Glu Phe Asp Leu Ser Ala Phe Leu Arg
            180              185              190

Ala Gly Glu Asn Arg Leu Ala Val Met Val Leu Arg Trp Ser Asp Gly
            195              200              205

Ser Tyr Leu Glu Asp Gln Asp Met Trp Arg Met Ser Gly Ile Phe Arg
        210              215              220

Asp Val Ser Leu Leu His Lys Pro Thr Thr Gln Ile Ser Asp Phe His
225              230              235              240

Val Ala Thr Arg Phe Asn Asp Asp Phe Ser Arg Ala Val Leu Glu Ala
            245              250              255

Glu Val Gln Met Cys Gly Glu Leu Arg Asp Tyr Leu Arg Val Thr Val
            260              265              270

Ser Leu Trp Gln Gly Glu Thr Gln Val Ala Ser Gly Thr Ala Pro Phe
        275              280              285

Gly Gly Glu Ile Ile Asp Glu Arg Gly Gly Tyr Ala Asp Arg Val Thr
        290              295              300

Leu Arg Leu Asn Val Glu Asn Pro Lys Leu Trp Ser Ala Glu Ile Pro
305              310              315              320

Asn Leu Tyr Arg Ala Val Val Glu Leu His Thr Ala Asp Gly Thr Leu
            325              330              335

Ile Glu Ala Glu Ala Cys Asp Val Gly Phe Arg Glu Val Arg Ile Glu
            340              345              350

Asn Gly Leu Leu Leu Leu Asn Gly Lys Pro Leu Leu Ile Arg Gly Val
            355              360              365

Asn Arg His Glu His His Pro Leu His Gly Gln Val Met Asp Glu Gln
        370              375              380

Thr Met Val Gln Asp Ile Leu Leu Met Lys Gln Asn Asn Phe Asn Ala
385              390              395              400

Val Arg Cys Ser His Tyr Pro Asn His Pro Leu Trp Tyr Thr Leu Cys
            405              410              415

Asp Arg Tyr Gly Leu Tyr Val Val Asp Glu Ala Asn Ile Glu Thr His
            420              425              430

Gly Met Val Pro Met Asn Arg Leu Thr Asp Asp Pro Arg Trp Leu Pro
            435              440              445

Ala Met Ser Glu Arg Val Thr Arg Met Val Gln Arg Asp Arg Asn His
        450              455              460

Pro Ser Val Ile Ile Trp Ser Leu Gly Asn Glu Ser Gly His Gly Ala
465              470              475              480

Asn His Asp Ala Leu Tyr Arg Trp Ile Lys Ser Val Asp Pro Ser Arg
            485              490              495

Pro Val Gln Tyr Glu Gly Gly Gly Ala Asp Thr Thr Ala Thr Asp Ile
        500              505              510
```

-continued

```
Ile Cys Pro Met Tyr Ala Arg Val Asp Glu Asp Gln Pro Phe Pro Ala
        515                 520                 525

Val Pro Lys Trp Ser Ile Lys Lys Trp Leu Ser Leu Pro Gly Glu Thr
    530                 535                 540

Arg Pro Leu Ile Leu Cys Glu Tyr Ala His Ala Met Gly Asn Ser Leu
545                 550                 555                 560

Gly Gly Phe Ala Lys Tyr Trp Gln Ala Phe Arg Gln Tyr Pro Arg Leu
            565                 570                 575

Gln Gly Gly Phe Val Trp Asp Trp Val Asp Gln Ser Leu Ile Lys Tyr
            580                 585                 590

Asp Glu Asn Gly Asn Pro Trp Ser Ala Tyr Gly Gly Asp Phe Gly Asp
            595                 600                 605

Thr Pro Asn Asp Arg Gln Phe Cys Met Asn Gly Leu Val Phe Ala Asp
    610                 615                 620

Arg Thr Pro His Pro Ala Leu Thr Glu Ala Lys His Gln Gln Gln Phe
625                 630                 635                 640

Phe Gln Phe Arg Leu Ser Gly Gln Thr Ile Glu Val Thr Ser Glu Tyr
            645                 650                 655

Leu Phe Arg His Ser Asp Asn Glu Leu Leu His Trp Met Val Ala Leu
            660                 665                 670

Asp Gly Lys Pro Leu Ala Ser Gly Glu Val Pro Leu Asp Val Ala Pro
            675                 680                 685

Gln Gly Lys Gln Leu Ile Glu Leu Pro Glu Leu Pro Gln Pro Glu Ser
    690                 695                 700

Ala Gly Gln Leu Trp Leu Thr Val Arg Val Val Gln Pro Asn Ala Thr
705                 710                 715                 720

Ala Trp Ser Glu Ala Gly His Ile Ser Ala Trp Gln Gln Trp Arg Leu
            725                 730                 735

Ala Glu Asn Leu Ser Val Thr Leu Pro Ala Ala Ser His Ala Ile Pro
            740                 745                 750

His Leu Thr Thr Ser Glu Met Asp Phe Cys Ile Glu Leu Gly Asn Lys
            755                 760                 765

Arg Trp Gln Phe Asn Arg Gln Ser Gly Phe Leu Ser Gln Met Trp Ile
    770                 775                 780

Gly Asp Lys Lys Gln Leu Leu Thr Pro Leu Arg Asp Gln Phe Thr Arg
785                 790                 795                 800

Ala Pro Leu Asp Asn Asp Ile Gly Val Ser Glu Ala Thr Arg Ile Asp
            805                 810                 815

Pro Asn Ala Trp Val Glu Arg Trp Lys Ala Ala Gly His Tyr Gln Ala
            820                 825                 830

Glu Ala Ala Leu Leu Gln Cys Thr Ala Asp Thr Leu Ala Asp Ala Val
            835                 840                 845

Leu Ile Thr Thr Ala His Ala Trp Gln His Gln Gly Lys Thr Leu Phe
    850                 855                 860

Ile Ser Arg Lys Thr Tyr Arg Ile Asp Gly Ser Gly Gln Met Ala Ile
865                 870                 875                 880

Thr Val Asp Val Glu Val Ala Ser Asp Thr Pro His Pro Ala Arg Ile
            885                 890                 895

Gly Leu Asn Cys Gln Leu Ala Gln Val Ala Glu Arg Val Asn Trp Leu
            900                 905                 910

Gly Leu Gly Pro Gln Glu Asn Tyr Pro Asp Arg Leu Thr Ala Ala Cys
            915                 920                 925
```

```
Phe Asp Arg Trp Asp Leu Pro Leu Ser Asp Met Tyr Thr Pro Tyr Val
    930             935             940

Phe Pro Ser Glu Asn Gly Leu Arg Cys Gly Thr Arg Glu Leu Asn Tyr
945             950             955             960

Gly Pro His Gln Trp Arg Gly Asp Phe Gln Phe Asn Ile Ser Arg Tyr
            965             970             975

Ser Gln Gln Gln Leu Met Glu Thr Ser His Arg His Leu Leu His Ala
            980             985             990

Glu Glu Gly Thr Trp Leu Asn Ile Asp Gly Phe His Met Gly Ile Gly
            995             1000            1005

Gly Asp Asp Ser Trp Ser Pro Ser Val Ser Ala Glu Phe Gln Leu
    1010            1015            1020

Ser Ala Gly Arg Tyr His Tyr Gln Leu Val Trp Cys Gln Lys Gly
    1025            1030            1035

Ser Ser Lys Pro Glu Lys Pro Gly Ser Lys Ile Thr Gly Ser Ser
    1040            1045            1050

Gly Asn Asp Thr Gln Gly Ser Leu Ile Thr Tyr Ser Gly Gly Ala
    1055            1060            1065

Arg Gly
    1070
```

<210> SEQ ID NO 115
<211> LENGTH: 2199
<212> TYPE: DNA
<213> ORGANISM: Artificial Sequence
<220> FEATURE:
<223> OTHER INFORMATION: HcKan_P-GPM1 plasmid

<400> SEQUENCE: 115

```
aagaaaggcc cacccgtgaa ggtgagccag tgagttgatt gcagtccagt tacgctggag      60
tccgtctcgg gctgtgatgt ctaagtaacc tttatggtat atttcttaat gtggaaagat     120
actagcgcgc gcacccacac acaagcttcg tcttttcttg aagaaaagag gaagctcgct     180
aaatgggatt ccactttccg ttccctgcca gctgatggaa aaaggttagt ggaacgatga     240
agaataaaaa gagagatcca ctgaggtgaa atttcagctg acagcgagtt tcatgatcgt     300
gatgaacaat ggtaacgagt tgtggctgtt gccagggagg gtggttctca acttttaatg     360
tatggccaaa tcgctacttg ggtttgttat ataacaaaga agaaataatg aactgattct     420
cttcctcctt cttgtccttt cttaattctg ttgtaattac cttcctttgt aatttttttt     480
gtaattattc ttcttaataa tccaaacaaa cacacatatt acaatagatg cgagacgact     540
gaccatttaa atcatacctg acctccatag cagaaagtca aaagcctccg accggaggct     600
tttgacttga tcggcacgta agaggttcca actttcacca taatgaaata agatcactac     660
cgggcgtatt ttttgagtta tcgagatttt caggagctaa ggaagctaaa atgagccata     720
ttcaacggga aacgtcttgc tcgaggccgc gattaaattc caacatggat gctgatttat     780
atgggtataa atgggctcgc gataatgtcg ggcaatcagg tgcgacaatc tatcgattgt     840
atgggaagcc cgatgcgcca gagttgtttc tgaaacatgg caaaggtagc gttgccaatg     900
atgttacaga tgagatggtc aggctaaact ggctgacgga atttatgcct cttccgacca     960
tcaagcattt tatccgtact cctgatgatg catggttact caccactgcg atcccaggga    1020
aaacagcatt ccaggtatta gaagaatatc ctgattcagg tgaaatatt gttgatcgcgc    1080 tggcagtgtt cctgcgccgg ttgcattcga ttcctgtttg taattgtcct tttaacggcg    1140
atcgcgtatt tcgtctcgct caggcgcaat cacgaatgaa taacggtttg gttggtgcga    1200
```

```
gtgattttga tgacgagcgt aatggctggc ctgttgaaca agtctggaaa gaaatgcata    1260
agcttttgcc attctcaccg gattcagtcg tcactcatgg tgatttctca cttgataacc    1320 ttattttga cgaggggaaa ttaataggtt gtattgatgt tggacgagtc ggaatcgcag     1380
accgatacca ggatcttgcc atcctatgga actgcctcgg tgagttttct ccttcattac    1440
agaaacggct ttttcaaaaa tatggtattg ataatcctga tatgaataaa ttgcagtttc    1500
acttgatgct cgatgagttt ttctaatgag ggcccaaatg taatcacctg gctcaccttc    1560
gggtgggcct ttctgcgttg ctggcgtttt tccataggct ccgcccccct gacgagcatc    1620
acaaaaatcg atgctcaagt cagaggtggc gaaacccgac aggactataa agataccagg    1680
cgtttccccc tggaagctcc ctcgtgcgct ctcctgttcc gaccctgccg cttaccggat    1740
acctgtccgc ctttctccct cgggaagcg tggcgctttc tcatagctca cgctgtaggt     1800
atctcagttc ggtgtaggtc gttcgctcca agctgggctg tgtgcacgaa ccccccgttc    1860
agcccgaccg ctgcgcctta ccggtaact atcgtcttga gtccaacccg gtaagacacg     1920
acttatcgcc actggcagca gccactggta acaggattag cagagcgagg tatgtaggcg    1980
gtgctacaga gttcttgaag tggtggccta actacggcta cactagaaga acagtatttg    2040
gtatctgcgc tctgctgaag ccagttacct cggaaaaaga gttggtagct cttgatccgg    2100
caaacaaacc accgctggta gcggtggttt ttttgtttgc aagcagcaga ttacgcgcag    2160
aaaaaaagga tctcaagaag atcctttgat tttctaccg                           2199
```

```
<210> SEQ ID NO 116
<211> LENGTH: 2430
<212> TYPE: DNA
<213> ORGANISM: Artificial Sequence
<220> FEATURE:
<223> OTHER INFORMATION: HcKan_O-HO-T1-SpyTag plasmid

<400> SEQUENCE: 116
aagaaaggcc cacccgtgaa ggtgagccag tgagttgatt gcagtccagt tacgctggag      60
tccgtctcgg atggatcatg ctccagaaag atttgatgct actcctccag ctggtgaacc     120
agatagacca gctttgggtg ttttggaatt gacttctatt gctagaggta ttaccgttgc     180
tgatgctgct ttgaaaagag caccatcttt gttgttgatg tccagaccag tttcttccgg     240
taaacatttg ttgatgatga gaggtcaagt tgccgaagtt gaagaatcta tgattgctgc     300
tagagaaatt gctggtgctg gtggtggttc aggtggttct gctcatatag ttatggttga     360
tgcttacaag ccaacaaaag gtggtagtgg tggatctggt gctttgttgg atgaattgga     420
attgccatat gctcacgaac aactttggag atttttggat gctccagttg ttgcagatgc     480
ttgggaagaa gatactgaat ccgttattat cgttgaaacc gctactgttt gtgctgctat     540
tgattctgct gatgcagcct aaaaaactgc tcctgttgtt ttgagagata tgagattggc     600
tattggtatt gctggtaagg ctttctttac tttgactggt gaattggctg atgttgaagc     660
tgctgctgaa gttgttagag aaagatgtgg tgctagattg ctagaattgg catgtattgc     720
aagaccagtt gacgaattga gaggtaggtt gtttttctag ccgagacgac tgaccattta     780
aatcatacct gacctccata gcagaaagtc aaaagcctcc gaccggaggc ttttgacttg     840
atcggcacgt aagaggttcc aactttcacc ataatgaaat aagatcacta ccgggcgtat     900
tttttgagtt atcgagattt tcaggagcta aggaagctaa aatgagccat attcaacggg     960
aaacgtcttg ctcgaggccg cgattaaatt ccaacatgga tgctgattta tatgggtata    1020
```

-continued

```
aatgggctcg cgataatgtc gggcaatcag gtgcgacaat ctatcgattg tatgggaagc     1080
ccgatgcgcc agagttgttt ctgaaacatg gcaaaggtag cgttgccaat gatgttacag     1140
atgagatggt caggctaaac tggctgacgg aatttatgcc tcttccgacc atcaagcatt     1200
ttatccgtac tcctgatgat gcatggttac tcaccactgc gatcccaggg aaaacagcat     1260
tccaggtatt agaagaatat cctgattcag gtgaaaatat tgttgatgcg ctggcagtgt     1320
tcctgcgccg gttgcattcg attcctgttt gtaattgtcc ttttaacggc gatcgcgtat     1380
ttcgtctcgc acaggcgcaa tcacgaatga ataacggttt ggttggtgcg agtgattttg     1440
atgacgagcg taatggctgg cctgttgaac aagtctggaa agaaatgcat aagctttttgc     1500 cattctcacc ggattcagtc gtcactcatg gtgatttctc acttgataac cttattttttg     1560 acgaggggaa attaataggt tgtattgatg ttggacgagt cggaatcgca gaccgatacc     1620
aggatcttgc catcctatgg aactgcctcg gtgagttttc tccttcatta cagaaacggc     1680 ttttttcaaaa atatggtatt gataatcctg atatgaataa attgcagttt cacttgatgc     1740
tcgatgagtt tttctaatga gggcccaaat gtaatcacct ggctcacctt cgggtgggcc     1800
tttctgcgtt gctggcgttt ttccataggc tccgcccccc tgacgagcat cacaaaaatc     1860
gatgctcaag tcagaggtgg cgaaacccga caggactata aagataccag gcgtttcccc     1920
ctggaagctc cctcgtgcgc tctcctgttc cgaccctgcc gcttaccgga tacctgtccg     1980
cctttctccc ttcgggaagc gtggcgcttt ctcatagctc acgctgtagg tatctcagtt     2040
cggtgtaggt cgttcgctcc aagctgggct gtgtgcacga accccccgtt cagcccgacc     2100
gctgcgcctt atccggtaac tatcgtcttg agtccaaccc ggtaagacac gacttatcgc     2160
cactggcagc agccactggt aacaggatta gcagagcgag gtatgtaggc ggtgctacag     2220
agttcttgaa gtggtggcct aactacggct acactagaag aacagtattt ggtatctgcg     2280
ctctgctgaa gccagttacc tcggaaaaag agttggtagc tcttgatccg gcaaacaaac     2340
caccgctggt agcggtggtt ttttgtttg caagcagcag attacgcgca gaaaaaaagg     2400
atctcaagaa gatcctttga ttttctaccg                                      2430
```

<210> SEQ ID NO 117
<211> LENGTH: 687
<212> TYPE: DNA
<213> ORGANISM: Artificial Sequence
<220> FEATURE:
<223> OTHER INFORMATION: HcKan_O-HO-T1-SpyTag nucleotide sequence of key
     ORF

<400> SEQUENCE: 117

```
atggatcatg ctccagaaag atttgatgct actcctccag ctggtgaacc agatagacca      60
gctttgggtg ttttggaatt gacttctatt gctagaggta ttaccgttgc tgatgctgct     120
ttgaaaagag caccatcttt gttgttgatg tccagaccag tttcttccgg taaacatttg     180
ttgatgatga gaggtcaagt tgccgaagtt gaagaatcta tgattgctgc tagagaaatt     240
gctggtgctg gtggtggttc aggtggttct gctcatatag ttatggttga tgcttacaag     300
ccaacaaaag gtggtagtgg tggatctggt gctttgttgg atgaattgga attgccatat     360
gctcacgaac aactttggag attttttggat gctccagttt ttgcagatgc ttgggaagaa     420
gatactgaat ccgttattat cgttgaaacc gctactgttt gtgctgctat tgattctgct     480
gatgcagcct aaaaaactgc tcctgttgtt ttgagagata tgagattggc tattggtatt     540
gctggtaagg ctttctttac tttgactggt gaattggctg atgttgaagc tgctgctgaa     600
```

```
gttgttagag aaagatgtgg tgctagattg ctagaattgg catgtattgc aagaccagtt      660
gacgaattga gaggtaggtt gtttttc                                          687
```

<210> SEQ ID NO 118
<211> LENGTH: 229
<212> TYPE: PRT
<213> ORGANISM: Artificial Sequence
<220> FEATURE:
<223> OTHER INFORMATION: HcKan_O-HO-T1-SpyTag amino acid sequence of key
     ORF

<400> SEQUENCE: 118

```
Met Asp His Ala Pro Glu Arg Phe Asp Ala Thr Pro Pro Ala Gly Glu
1               5                   10                  15

Pro Asp Arg Pro Ala Leu Gly Val Leu Glu Leu Thr Ser Ile Ala Arg
            20                  25                  30

Gly Ile Thr Val Ala Asp Ala Ala Leu Lys Arg Ala Pro Ser Leu Leu
        35                  40                  45

Leu Met Ser Arg Pro Val Ser Ser Gly Lys His Leu Leu Met Met Arg
    50                  55                  60

Gly Gln Val Ala Glu Val Glu Glu Ser Met Ile Ala Ala Arg Glu Ile
65                  70                  75                  80

Ala Gly Ala Gly Gly Gly Ser Gly Gly Ser Ala His Ile Val Met Val
                85                  90                  95

Asp Ala Tyr Lys Pro Thr Lys Gly Gly Ser Gly Gly Ser Gly Ala Leu
            100                 105                 110

Leu Asp Glu Leu Glu Leu Pro Tyr Ala His Glu Gln Leu Trp Arg Phe
        115                 120                 125

Leu Asp Ala Pro Val Val Ala Asp Ala Trp Glu Glu Asp Thr Glu Ser
    130                 135                 140

Val Ile Ile Val Glu Thr Ala Thr Val Cys Ala Ala Ile Asp Ser Ala
145                 150                 155                 160

Asp Ala Ala Leu Lys Thr Ala Pro Val Val Leu Arg Asp Met Arg Leu
                165                 170                 175

Ala Ile Gly Ile Ala Gly Lys Ala Phe Phe Thr Leu Thr Gly Glu Leu
            180                 185                 190

Ala Asp Val Glu Ala Ala Ala Glu Val Val Arg Glu Arg Cys Gly Ala
        195                 200                 205

Arg Leu Leu Glu Leu Ala Cys Ile Ala Arg Pro Val Asp Glu Leu Arg
    210                 215                 220

Gly Arg Leu Phe Phe
225
```

<210> SEQ ID NO 119
<211> LENGTH: 2178
<212> TYPE: DNA
<213> ORGANISM: Artificial Sequence
<220> FEATURE:
<223> OTHER INFORMATION: HcKan_T-YPT31 plasmid

<400> SEQUENCE: 119

```
aagaaaggcc cacccgtgaa ggtgagccag tgagttgatt gcagtccagt tacgctggag      60
tccgtctcgt agcgagatat tttgcagcag ttgcgcactt gcatgtgaat gactcttctc     120
ccctttaatt ctgtgctata tttttacaat tttctgctga catatagttt atatacatat     180
agaacgcata taggaaattg aagtaaacag aatacacaag tagaggccgg tatgtacgac     240
attttgctta ctactcttta aaatcatcgt cttcttcgtc ttcatcgtct tcttcttttt     300
```

```
caccatatcc tacatcatct ttagagcctg tgctaggttc cttcttgtct aattcttctg       360
cagtcttttt atagtcaatt actttgccgc gtgttcttct tccggatgtg atgatattag       420
aggtatcaat ttctgccaaa tcgtcctctt cttcttctcc ctcatttccc atcaatgcgt       480
ctaacttggc atcgtccata tcagacctcc gagacgactg accatttaaa tcatacctga       540
cctccatagc agaaagtcaa aagcctccga ccggaggctt ttgacttgat cggcacgtaa       600
gaggttccaa ctttcaccat aatgaaataa gatcactacc gggcgtattt tttgagttat       660
cgagattttc aggagctaag gaagctaaaa tgagccatat tcaacgggaa acgtcttgct       720
cgaggccgcg attaaattcc aacatggatg ctgatttata tgggtataaa tgggctcgcg       780
ataatgtcgg gcaatcaggt gcgacaatct atcgattgta tgggaagccc gatgcgccag       840
agttgtttct gaaacatggc aaaggtagcg ttgccaatga tgttacagat gagatggtca       900
ggctaaactg gctgacggaa tttatgcctc ttccgaccat caagcatttt atccgtactc       960
ctgatgatgc atggttactc accactgcga tcccagggaa aacagcattc caggtattag      1020
aagaatatcc tgattcaggt gaaaatattg ttgatgcgct ggcagtgttc ctgcgccggt      1080
tgcattcgat tcctgtttgt aattgtcctt ttaacggcga tcgcgtattt cgtctcgctc      1140
aggcgcaatc acgaatgaat aacggtttgg ttggtgcgag tgattttgat gacgagcgta      1200
atggctggcc tgttgaacaa gtctggaaag aaatgcataa gcttttgcca ttctcaccgg      1260
attcagtcgt cactcatggt gatttctcac ttgataacct tattttttgac gaggggaaat      1320 taataggttg tattgatgtt ggacgagtcg aatcgcaga ccgataccag gatcttgcca      1380
tcctatggaa ctgcctcggt gagttttctc cttcattaca gaaacggctt tttcaaaaat      1440
atggtattga taatcctgat atgaataaat tgcagtttca cttgatgctc gatgagtttt      1500
tctaatgagg gcccaaatgt aatcacctgg ctcaccttcg ggtgggcctt tctgcgttgc      1560
tggcgttttt ccataggctc cgcccccctg acgagcatca caaaaatcga tgctcaagtc      1620
agaggtggcg aaacccgaca ggactataaa gataccaggc gtttccccct ggaagctccc      1680
tcgtgcgctc tcctgttccg accctgccgc ttaccggata cctgtccgcc tttctccctt      1740
cgggaagcgt ggcgctttct catagctcac gctgtaggta tctcagttcg gtgtaggtcg      1800
ttcgctccaa gctgggctgt gtgcacgaac ccccgttca gcccgaccgc tgcgccttat      1860
ccggtaacta tcgtcttgag tccaacccgg taagacacga cttatcgcca ctggcagcag      1920
ccactggtaa caggattagc agagcgaggt atgtaggcgg tgctacagag ttcttgaagt      1980
ggtggcctaa ctacggctac actagaagaa cagtatttgg tatctgcgct ctgctgaagc      2040
cagttacctc ggaaaaagag ttggtagctc ttgatccggc aaacaaacca ccgctggtag      2100
cggtggtttt tttgtttgca agcagcagat tacgcgcaga aaaaaggat ctcaagaaga      2160 tcctttgatt ttctaccg                                                    2178
```

<210> SEQ ID NO 120
<211> LENGTH: 5404
<212> TYPE: DNA
<213> ORGANISM: Artificial Sequence
<220> FEATURE:
<223> OTHER INFORMATION: pGAH-YPRCd15 plasmid

<400> SEQUENCE: 120

```
gcaaaaggcc aggaaccgta aaaaggccgc gttgctggcg ttttttccata ggctccgccc        60 ccctgacgag catcacaaaa atcgacgctc aagtcagagg tggcgaaacc cgacaggact       120
```

-continued

```
ataaagatac caggcgtttc cccctggaag ctccctcgtg cgctctcctg ttccgaccct    180
gccgcttacc ggatacctgt ccgcctttct cccttcggga agcgtggcgc tttctcatag    240
ctcacgctgt aggtatctca gttcggtgta ggtcgttcgc tccaagctgg gctgtgtgca    300 cgaaccccc gttcagcccg accgctgcgc cttatccggt aactatcgtc ttgagtccaa    360
cccggtaaga cacgacttat cgccactggc agcagccact ggtaacagga ttagcagagc    420
gaggtatgta ggcggtgcta cagagttctt gaagtggtgg cctaactacg gctacactag    480
aaggacagta tttggtatct gcgctctgct gaagccagtt accttcggaa aaagagttgg    540
tagctcttga tccggcaaac aaaccaccgc tggtagcggt ggtttttttg tttgcaagca    600
gcagattacg cgcagaaaaa aaggatctca agaagatcct ttgatctttt ctacggggtc    660
tgacgctcag tggaacgaaa actcacgtta agggattttg gtcatgagat tatcaaaaag    720
gatcttcacc tagatccttt taaattaaaa atgaagtttt aaatcaatct aaagtatata    780
tgagtaaact ggtctgaca gttaccaatg cttaatcagt gaggcaccta tctcagcgat    840
ctgtctattt cgttcatcca tagttgcctg actccccgtc gtgtagataa ctacgatacg    900
ggagggctta ccatctggcc ccagtgctgc aatgataccg cggctcccac gctcaccggc    960
tccagattta tcagcaataa accagccagc cggaagggcc gagcgcagaa gtggtcctgc    1020
aactttatcc gcctccatcc agtctattaa ttgttgccgg gaagctagag taagtagttc    1080
gccagttaat agtttgcgca acgttgttgc cattgctaca ggcatcgtgg tgtcacgctc    1140
gtcgtttggt atggcttcat tcagctccgg ttcccaacga tcaaggcgag ttacatgatc    1200
ccccatgttg tgcaaaaaag cggttagctc cttcggtcct ccgatcgttg tcagaagtaa    1260
gttggccgca gtgttatcac tcatggttat ggcagcactg cataattctc ttactgtcat    1320
gccatccgta agatgctttt ctgtgactgg tgagtactca accaagtcat tctgagaata    1380
gtgtatgcgg cgaccgagtt gctcttgccc ggcgtcaata cgggataata ccgcgccaca    1440
tagcagaact ttaaaagtgc tcatcattgg aaaacgttct tcggggcgaa aactctcaag    1500
gatcttaccg ctgttgagat ccagttcgat gtaacccact cgtgcaccca actgatcttc    1560
agcatctttt actttcacca gcgtttctgg gtgagcaaaa acaggaaggc aaaatgccgc    1620
aaaaaaggga ataagggcga cacggaaatg ttgaatactc atactcttcc ttttttcaata    1680 ttattgaagc atttatcagg gttattgtct catgagcgga tacatatttg aatgtattta    1740
gaaaaataaa caaatagggg ttccgcgcac atttccccga aaagtgccac ggtctctgtc    1800
agataacgcc aggcgccttt atatcatata attaagacac aaaaggataa aacaaaggtg    1860
ttaactattc tgcatactca ctatcgtaaa ctgtcctgca aatcgtgtaa atatgtattt    1920
catttttttt gcagtgaaaa aaggcatgta aaataccgca tcaagtaact ctactccgcc    1980
tgtggtttca agactaacgg cttgagacaa aatgggaaga aatgattgca gaaaagccat    2040
atgtgtaata gcaaaaagct ggatactgct taccagatgt ttaccttaat ttcttggtga    2100
attagagaag tacagaagtt ttactattaa tcccaccata gaaatttgta taggaaagta    2160
gtttattgga gttattggat atactgtgta aactatttct tgaaattgta atcttaagat    2220
gctcttctta ttctattaaa aatagaaaat gattttcata tttatttatt tatttatatt    2280
ttggcattac tcttcatcat ttttttccct ctaagaagct tccttctttt ttataaggat    2340
aacaaaacca aaaggaatat tgggtcagat gaatggacgc gaatgcaaga cagaagtcca    2400
aatcacgtca agacaaagaa agaaagaaag aaaaactaac acattaatgt agttttaaaa    2460
tttcaaatcc gaacaacaga gcatagggtt tcgcaaatct ctacctggct cgaagcagcg    2520
```

-continued

```
gtatttcaca ccgcatagat ccgtcgagtt caagagaaaa aaaaagaaaa agcaaaaaga    2580
aaaaaggaaa gcgcgcctcg ttcagaatga cacgtataga atgatgcatt accttgtcat    2640
cttcagtatc atactgttcg tatacatact tactgacatt cataggtata catatataca    2700
catgtatata tatcgtatgc tgcagcttta aataatcggt gtcactacat aagaacacct    2760
ttggtggagg gaacatcgtt ggtaccattg ggcgaggtgg cttctcttat ggcaaccgca    2820
agagccttga acgcactctc actacggtga tgatcattct tgcctcgcag acaatcaacg    2880
tggagggtaa ttctgctagc ctctgcaaag cttttcaagaa aatgcgggat catctcgcaa    2940
gagagatctc ctactttctc cctttgcaaa ccaagttcga caactgcgta cggcctgttc    3000
gaaagatcta ccaccgctct ggaaagtgcc tcatccaaag gcgcaaatcc tgatccaaac    3060 cttttttactc cacgcacggc ccctaggggc tctttaaaag cttgaccgag agcaatcccg    3120
cagtcttcag tggtgtgatg gtcgtctatg tgtaagtcac caatgcactc aacgattagc    3180
gaccagccgg aatgcttggc cagagcatgt atcatatggt ccagaaaccc tatacctgtg    3240
tggacgttaa tcacttgcga ttgtgtggcc tgttctgcta ctgcttctgc ctcttttct    3300 gggaagatcg agtgctctat cgctagggga ccacccttta aagagatcgc aatctgaatc    3360
ttggtttcat ttgtaatacg ctttactagg gctttctgct ctgtcatctt tgccttcgtt    3420
tatcttgcct gctcattttt tagtatattc ttcgaagaaa tcacattact ttatataatg    3480
tataattcat tatgtgataa tgccaatcgc taagaaaaaa aaagagtcat ccgctaggtg    3540
gaaaaaaaaa aatgaaaatc attaccgagg cataaaaaaa tatagagtgt actagaggag    3600
gccaagagta atagaaaaag aaaattgcgg gaaaggactg tgttatgact tccctgtgca    3660
ccacctcagg cagagaacct agagacggca atacgcaaac cgcctctccc cgcgcgttgg    3720
ccgattcatt aatgcagctg gcacgacagg tttcccgact ggaaagcggg cagtgagcgc    3780
aacgcaatta atgtgagtta gctcactcat taggcacccc aggctttaca ctttatgctt    3840
ccggctcgta tgttgtgtgg aattgtgagc ggataacaat ttcacacata ctagagaaag    3900
aggagaaata ctagatggct tcctccgaag acgttatcaa agagttcatg cgtttcaaag    3960
ttcgtatgga aggttccgtt aacggtcacg agttcgaaat cgaaggtgaa ggtgaaggtc    4020
gtccgtacga aggtacccag accgctaaac tgaaagttac caaaggtggt ccgctgccgt    4080
tcgcttggga catcctgtcc ccgcagttcc agtacggttc caaagcttac gttaaacacc    4140
cggctgacat cccggactac ctgaaactgt ccttcccgga aggtttcaaa tgggaacgtg    4200
ttatgaactt cgaagacggt ggtgttgtta ccgttaccca ggactcctcc ctgcaagacg    4260
gtgagttcat ctacaaagtt aaactgcgtg gtaccaactt cccgtccgac ggtccggtta    4320
tgcagaaaaa aaccatgggt tgggaagctt ccaccgaacg tatgtacccg gaagacggtg    4380
ctctgaaagg tgaaatcaaa atgcgtctga actgaaaga cggtggtcac tacgacgctg    4440
aagttaaaac cacctacatg gctaaaaaac cggttcagct gccgggtgct tacaaaaccg    4500
acatcaaact ggacatcacc tcccacaacg aagactacac catcgttgaa cagtacgaac    4560
gtgctgaagg tcgtcactcc accggtgctt aataacgctg atagtgctag tgtagatcgc    4620
tactagagcc aggcatcaaa taaaacgaaa ggctcagtcg aaagactggg cctttcgttt    4680
tatctgttgt ttgtcggtga acgctctcta ctagagtcac actggctccg tctcatgagc    4740
gcttggaagg tcgggatgag catatacaag cactaagaag aacaatacag aactctacac    4800
ggtattattg tgctacaagc tcgagtaaaa ccgagtgttt tgacgatact aacgttgtta    4860
```

-continued

```
agaaagtaac ttgttatcaa actcattacc aacttgtgat taattggtga ataatatgat       4920
aattgtcgaa attccattgt tggtaaagcc tataatatta tgtatacaga ttatactaga       4980
aattctctcg agaatataag aatccccaaa attgaatcgg tatttctaca tactaatatt       5040
accattactt ctcctttcgt tttatatgtt tcattcctat tacattatcg atctttgcat       5100
ttcagcttcc attatatttg atgtctgttt tatgtcccca cgttacaccg catgtgacag       5160
tatactagta acatgagtgc taccgaatag atgacatttt agactttcat tccaacaact       5220
tggttgacag aatgttacgt accctatatc taatctatat gaggcctgaa tctaactgaa       5280
aggtggaatt tcagtaattt atcaagcttt aataagtttg ggtagtttaa ctgtgcaaaa       5340
aggtatttac cttacatact gaatcttgtc tgtttggtag cggctgcttt atgtcggaga       5400
gacc                                                                    5404

<210> SEQ ID NO 121
<211> LENGTH: 6264
<212> TYPE: DNA
<213> ORGANISM: Artificial Sequence
<220> FEATURE:
<223> OTHER INFORMATION: pGAH-YPRCd15-GFP-SpyCatcher plasmid

<400> SEQUENCE: 121
gcaaaaggcc aggaaccgta aaaaggccgc gttgctggcg ttttttccata ggctccgccc         60 ccctgacgag catcacaaaa atcgacgctc aagtcagagg tggcgaaacc cgacaggact        120
ataaagatac caggcgtttc cccctggaag ctccctcgtg cgctctcctg ttccgaccct        180
gccgcttacc ggatacctgt ccgcctttct cccttcggga agcgtggcgc tttctcatag        240
ctcacgctgt aggtatctca gttcggtgta ggtcgttcgc tccaagctgg gctgtgtgca        300
cgaacccccc gttcagcccg accgctgcgc cttatccggt aactatcgtc ttgagtccaa        360
cccggtaaga cacgacttat cgccactggc agcagccact ggtaacagga ttagcagagc        420
gaggtatgta ggcggtgcta cagagttctt gaagtggtgg cctaactacg gctacactag        480
aaggacagta tttggtatct gcgctctgct gaagccagtt accttcggaa aaagagttgg        540
tagctcttga tccggcaaac aaaccaccgc tggtagcggt ggtttttttg tttgcaagca        600
gcagattacg cgcagaaaaa aaggatctca agaagatcct ttgatctttt ctacggggtc        660
tgacgctcag tggaacgaaa actcacgtta agggattttg gtcatgagat tatcaaaaag        720
gatcttcacc tagatccttt taaattaaaa atgaagtttt aaatcaatct aaagtatata        780
tgagtaaact tggtctgaca gttaccaatg cttaatcagt gaggcaccta tctcagcgat        840
ctgtctattt cgttcatcca tagttgcctg actccccgtc gtgtagataa ctacgatacg        900
ggagggctta ccatctggcc ccagtgctgc aatgataccg cggctccac gctcaccggc        960 tccagattta tcagcaataa accagccagc cggaagggcc gagcgcagaa gtggtcctgc       1020
aactttatcc gcctccatcc agtctattaa ttgttgccgg gaagctagag taagtagttc       1080
gccagttaat agtttgcgca acgttgttgc cattgctaca ggcatcgtgg tgtcacgctc       1140
gtcgtttggt atggcttcat tcagctccgg ttcccaacga tcaaggcgag ttacatgatc       1200
ccccatgttg tgcaaaaaag cggttagctc cttcggtcct ccgatcgttg tcagaagtaa       1260
gttggccgca gtgttatcac tcatggttat ggcagcactg cataattctc ttactgtcat       1320
gccatccgta agatgctttt ctgtgactgg tgagtactca accaagtcat tctgagaata       1380
gtgtatgcgg cgaccgagtt gctcttgccc ggcgtcaata cgggataata ccgcgccaca       1440
tagcagaact ttaaaagtgc tcatcattgg aaaacgttct tcggggcgaa aactctcaag       1500
```

```
gatcttaccg ctgttgagat ccagttcgat gtaacccact cgtgcaccca actgatcttc   1560
agcatctttt actttcacca gcgtttctgg gtgagcaaaa acaggaaggc aaaatgccgc   1620
aaaaaaggga ataagggcga cacggaaatg ttgaatactc atactcttcc tttttcaata   1680
ttattgaagc atttatcagg gttattgtct catgagcgga tacatatttg aatgtattta   1740
gaaaaataaa caaataggg ttccgcgcac atttccccga aaagtgccac ggtctctgtc   1800
agataacgcc aggcgccttt atatcatata attaagacac aaaaggataa aacaaaggtg   1860
ttaactattc tgcatactca ctatcgtaaa ctgtcctgca aatcgtgtaa atatgtattt   1920
catttttttt gcagtgaaaa aaggcatgta aaataccgca tcaagtaact ctactccgcc   1980
tgtggtttca agactaacgg cttgagacaa aatgggaaga aatgattgca gaaaagccat   2040
atgtgtaata gcaaaaagct ggatactgct taccagatgt ttaccttaat ttcttggtga   2100
attagagaag tacagaagtt ttactattaa tcccaccata gaaatttgta taggaaagta   2160
gtttattgga gttattggat atactgtgta aactatttct tgaaattgta atcttaagat   2220
gctcttctta ttctattaaa aatagaaaat gattttcata tttatttatt tatttatatt   2280
ttggcattac tcttcatcat tttttttccct ctaagaagct tcctttcttt ttataaggat   2340
aacaaaacca aaaggaatat tgggtcagat gaatggacgc gaatgcaaga cagaagtcca   2400
aatcacgtca agacaaagaa agaaagaaag aaaaactaac acattaatgt agttttaaaa   2460
tttcaaatcc gaacaacaga gcatagggtt tcgcaaatct ctacctggct cgaagcagcg   2520
gtatttcaca ccgcatagat ccgtcgagtt caagagaaaa aaaagaaaa agcaaaaaga   2580 aaaaaggaaa gcgcgcctcg ttcagaatga cacgtataga atgatgcatt accttgtcat   2640
cttcagtatc atactgttcg tatacatact tactgacatt cataggtata catatataca   2700
catgtatata tatcgtatgc tgcagcttta aataatcggt gtcactacat aagaacacct   2760
ttggtggagg gaacatcgtt ggtaccattg ggcgaggtgg cttctcttat ggcaaccgca   2820
agagccttga acgcactctc actacggtga tgatcattct tgcctcgcag acaatcaacg   2880
tggagggtaa ttctgctagc ctctgcaaag ctttcaagaa aatgcgggat catctcgcaa   2940
gagagatctc ctactttctc cctttgcaaa ccaagttcga caactgcgta cggcctgttc   3000
gaaagatcta ccaccgctct ggaaagtgcc tcatccaaag cgcaaatcc tgatccaaac   3060 ctttttactc cacgcacggc ccctagggcc tctttaaaag cttgaccgag agcaatcccg   3120
cagtcttcag tggtgtgatg gtcgtctatg tgtaagtcac caatgcactc aacgattagc   3180
gaccagccgg aatgcttggc cagagcatgt atcatatggt ccagaaaccc tatacctgtg   3240
tggacgttaa tcacttgcga ttgtgtggcc tgttctgcta ctgcttctgc ctcttttct   3300 gggaagatcg agtgctctat cgctagggga ccacccttta aagagatcgc aatctgaatc   3360
ttggtttcat ttgtaatacg ctttactagg gctttctgct ctgtcatctt tgccttcgtt   3420
tatcttgcct gctcattttt tagtatattc ttcgaagaaa tcacattact ttatataatg   3480
tataattcat tatgtgataa tgccaatcgc taagaaaaaa aaagagtcat ccgctaggtg   3540
gaaaaaaaaa aatgaaaatc attaccgagg cataaaaaaa tatagagtgt actagaggag   3600
gccaagagta atagaaaaag aaaattgcgg gaaaggactg tgttatgact tccctgtgca   3660
ccacctcagg cagagaacct ggctgtgatg tctaagtaac ctttatggta tatttcttaa   3720 tgtgaaaga tactagcgcg cgcacccaca cacaagcttc gtcttttctt gaagaaaaga   3780
ggaagctcgc taaatgggat tccactttcc gttccctgcc agctgatgga aaaaggttag   3840
```

-continued

```
tggaacgatg aagaataaaa agagagatcc actgaggtga aatttcagct gacagcgagt      3900
ttcatgatcg tgatgaacaa tggtaacgag ttgtggctgt tgccagggag ggtggttctc      3960 aactttttaat gtatggccaa atcgctactt gggtttgtta tataacaaag aagaaataat     4020
gaactgattc tcttcctcct tcttgtcctt tcttaattct gttgtaatta ccttcctttg      4080
taattttttt tgtaattatt cttcttaata atccaaacaa acacacatat tacaatagat      4140
gggttcttct catcatcacc atcaccattc ttctgggatg tctaaaggtg aagaattatt      4200
cactggtgtt gtcccaattt tggttgaatt agatggtgat gttaatggtc acaaattttc      4260
tgtctccggt gaaggtgaag gtgatgctac ttacggtaaa ttgaccttaa aatttatttg      4320
tactactggt aaaattgccag ttccatggcc aaccttagtc actactttaa cttatggtgt      4380
tcaatgtttt tctagatacc cagatcatat gaaacaacat gacttttttca agtctgccat      4440 gccagaaggt tatgttcaag aaagaactat tttttttcaaa gatgacggta actacaagac      4500
cagagctgaa gtcaagtttg aaggtgatac cttagttaat agaatcgaat aaaaaggtat      4560
tgattttaaa gaagatggta acattttagg tcacaaattg gaatacaact ataactctca      4620
caatgtttac atcatggctg acaaacaaaa gaatggtatc aaagttaact tcaaaattag      4680
acacaacatt gaagatggtt ctgttcaatt agctgaccat tatcaacaaa atactccaat      4740
tggtgatggt ccagtcttgt taccagacaa ccattactta tccactcaat ctaaattatc      4800
caaagatcca aacgaaaaga gagatcacat ggtcttgtta gaatttgtta ctgctgctgg      4860
tattacccat ggtatggatg aattgtacaa aggttctggt ggttctgatt ctgctactca      4920
tattaagttc tccaagaggg acgaagatgg taaagaattg gctggtgcaa ctatggaatt      4980
gagagattct tctggtaaga ccatttccac ctggatttct gatggtcaag ttaaggattt      5040
ctacttgtac ccaggtaagt acactttcgt tgaaactgct gctccagatg gttatgaagt      5100
tgctactgct attactttca ccgtcaatga acaaggtcaa gtcactgtta atggttagcg      5160
agatattttg cagcagttgc gcacttgcat gtgaatgact cttctcccct ttaattctgt      5220
gctatatttt tacaatttttc tgctgacata tagtttatat acatatagaa cgcatatagg      5280
aaattgaagt aaacagaata cacaagtaga ggccggtatg tacgacattt tgcttactac      5340
tctttaaaat catcgtcttc ttcgtcttca tcgtcttctt ctttttcacc atatcctaca      5400
tcatctttag agcctgtgct aggttccttc ttgtctaatt cttctgcagt cttttttatag      5460 tcaattactt tgccgcgtgt tcttcttccg gatgtgatga tattagaggt atcaatttct      5520
gccaaatcgt cctcttcttc ttctccctca tttcccatca atgcgtctaa cttggcatcg      5580
tccatatcag acctctgagc gcttggaagg tcgggatgag catatacaag cactaagaag      5640
aacaatacag aactctacac ggtattattg tgctacaagc tcgagtaaaa ccgagtgttt      5700
tgacgatact aacgttgtta agaaagtaac ttgttatcaa actcattacc aacttgtgat      5760
taattggtga ataatatgat aattgtcgaa attccattgt tggtaaagcc tataatatta      5820
tgtatacaga ttatactaga aattctctcg agaatataag aatccccaaa attgaatcgg      5880
tatttctaca tactaatatt accattactt ctcctttcgt tttatatgtt tcattcctat      5940
tacattatcg atctttgcat ttcagcttcc attatatttg atgtctgttt tatgtcccca      6000
cgttacaccg catgtgacag tatactagta acatgagtgc taccgaatag atgacatttt      6060
agactttcat tccaacaact tggttgacag aatgttacgt accctatatc taatctatat      6120
gaggcctgaa tctaactgaa aggtggaatt tcagtaattt atcaagcttt aataagtttg      6180
```

```
ggtagtttaa ctgtgcaaaa aggtatttac cttacatact gaatcttgtc tgtttggtag   6240
cggctgcttt atgtcggaga gacc                                          6264
```

BACTERIAL MICROCOMPARTMENT VIRUS-LIKE PARTICLES

FIELD OF THE INVENTION

The present invention relates to a bacterial microcompartment virus-like particle (VLP) carrying a cargo molecule, a method for producing the bacterial microcompartment VLP, an isolated plasmid or vector nucleic acid used to produce the VLP, a composition comprising at least one said VLP, a use of the said VLP, and a method of treatment using the said VLP.

BACKGROUND

Bacterial microcompartments (BMCs) are protein shells found in some species of bacteria and are thought to have evolved as a strategy to compartmentalize certain challenging biochemical reactions [Kerfeld, C. A., et al., *Nature Reviews Microbiology* 16: 277-290 (2018)]. These protein complexes are comprised of hundreds to thousands of polypeptide subunits that self-assemble into polygonal structures, with diameters ranging from 40 nm to 400 nm. The carboxysome, found in cyanobacteria and some chemotrophic bacteria species, is the earliest known example of a BMC. This protein shell encapsulates ribulose-1,5-bisphosphate carboxylase (RuBisCO) and improves its catalytic efficiency by concentrating its substrates, $CO_2$ and ribulose-1,5-bisphosphate, in close proximity to RuBisCO. Carboxysomes are classified into two main groups depending on the class of RuBisCO that is encapsulated. Alpha-carboxysomes contain Form 1A RuBisCO that is found in α-cyanobacteria (generally saltwater cyanobacteria) and chemoautotrophs, while beta-carboxysomes house Form 1B RuBisCO that are observed in β-cyanobacteria (typically freshwater cyanobacteria) [Turmo, A., et al., *FEMS Microbiol Lett* 364: (2017)].

Numerous atomic-scale structures of the subunits that comprise BMC shells, along with that of three intact shells—a reduced component beta-carboxysome from *Halothece* sp. PCC 7418, a synthetic glycyl-radical associated BMC group 2 (GRM2) from *Klebsiella pneumoniae* and a BMC of undetermined function from *Haliangium ochraceum* (HO-BMC)—have been reported in recent years [Kalnins, G., et al., *Nature Communications* 11: 388 (2020); Sutter, M., et al., *Science* 356(6344): 1293-1297 (2017); Sutter, M., et al., *Plant Physiology* (2019)]. Despite the diversity in the appearances and functions of BMCs, the tertiary structures of the main building blocks are conserved. The BMC-H domain protein (pfam00936) is the stoichiometrically major module and forms a homo-hexamer with $C_6$ geometry. The BMC-T protein is formed by a tandem repeat of two BMC-H domains and assembles as a trimer, or as a double stack of appressed trimers, with pseudo-hexagonal symmetry. The BMC-P domain unit (pfam03319) is a minor but important module in a BMC shell complex. The BMC-P protomers assemble into homo-pentamers with pyramidal geometry that occupy the vertices of the shell, capping the flat facets formed by the BMC-T and -H proteins. This gives rise to the polygonal appearance of BMCs. A detailed molecular understanding of the architecture of the components has contributed to the field of BMC shell engineering. Such endeavors include targeting heterologous protein cargo into the shell lumen by the use of encapsulation peptides (EP), which are short peptide sequences derived from cognate luminal proteins, or by protein engineering of the shell components [Lawrence, A. D., et al., *ACS Synthetic Biology* 3: 454-465 (2014)]. These modifications are aimed at repurposing BMCs into intracellular nanoreactors or as scaffolds for delivery of biomolecules The alpha-carboxysome from *Halothiobacillus neapolitanus* has been previously produced in *Escherichia coli* by transplantation of the entire alpha-carboxysome operon (cso) (FIG. 1) into the recombinant host [Bonacci, W., et al. *PNAS* 109: 478-483 (2012)]. Genes found in the operon include three BMC-H paralogs (cso1ABC), one BMC-T protein (csoS1D) and two BMC-P paralogs (csoS4AB), along with the genes that encode the RuBisCO large and small units (cbbLS), carbonic anhydrase (csoS3/SCA) and an intrinsically disordered protein (IDP), csoS2. This IDP is known to be critical for alpha-carboxysome assembly by facilitating interactions between the shell and luminal proteins [Cai, F. et al. *Life (Basel, Switzerland)* 5: 1141-1171 (2015)]. BMCs bereft of their native cargo are more suited for engineered utility, since heterologous cargo can be packaged more efficiently into the lumen. However, the *H. neapolitanus* alpha-carboxysome has never been recombinantly expressed in a structurally enclosed form with fewer than the aforementioned ten genes, despite decades of study into its structure and biochemical processes [Bonacci, W., et al. *PNAS* 109: 478-483 (2012)].

There is a need to provide bacterial microcompartment virus-like particles with improved efficiency of production in recombinant bacterial and yeast hosts, and alternative ways to encapsulate and/or present on the surface cargo molecules.

SUMMARY OF THE INVENTION

It has surprisingly been found that BMC VLPs can be formed using only two or three types of BMC protomers from *Halothiobacillus neapolitanus* and *Haliangium ochraceum*, respectively. The *H. neapolitanus* BMC VLPs are termed Cso-BMC and the *H. ochraceum* BMC VLPs are termed HO-BMC. In addition, cargo molecules may be encapsulated within the Cso-BMC using a novel short peptide derived from CsoS2 and termed S2CP or a variant thereof termed S2CP(30). Cso-BMCs which encapsulated a cargo molecule had a distinct shell conformation not observed in Cso-BMCs that did not encapsulate a cargo molecule. Of note, the peptide termini of the protomers of both shells face outwards, allowing genetic fusion of proteins of interest. Therefore, a cargo molecule may be displayed on the outer surface of the BMC VLPs of the invention by expressing it fused to the terminal end of a protomer or via the cargo molecule having a complementary binding partner to a biochemical tag attached to a protomer terminal end.

According to a first aspect, the present invention provides a method for producing a bacterial microcompartment virus-like particle (VLP) carrying a cargo molecule, said method comprising A) introducing into a host cell or organism one or more heterologous polynucleotides comprising (i) a first sequence encoding bacterial microcompartment shell protomers; and (ii) a second sequence encoding a cargo molecule fused to an encapsulation peptide, wherein the encapsulation peptide comprises the amino acid sequence set forth in SEQ ID NO: 1 (SKITGSSGNDTQGSLITYSGGARG) or SEQ ID NO: 94 (KPEKPGSKITGSSGNDTQGSLITYSGGARG), or a functional variant thereof;

a) expressing the first and second sequences; and b) forming a microcompartment that encapsulates the cargo molecule; or B) introducing into a host cell or organism one or more polynucleotides comprising (i) a first sequence encoding bacterial microcompartment shell protomers; and (ii) a second sequence encoding at least one of said protomers fused with a cargo molecule or a biochemical tag;

a) expressing the first and second sequences; and b) forming a microcompartment that expresses the cargo molecule on an exterior surface, or forming a microcompartment that expresses the biochemical tag on an exterior surface to which a cargo molecule comprising a complementary tag can bind.

In some embodiments, a functional variant of the encapsulation peptide set forth in SEQ ID NO: 1 comprises, at its amino terminus, 1, 2, 3, 4, or 5 of the additional amino acids at the amino terminus of SEQ ID NO: 94. For example, a variant of the encapsulation peptide of SEQ ID NO: 1 could comprise, at its amino terminus, 'G', 'PG', 'KPG' etc., and retain function. Such variants are intermediates between the sequences SEQ ID NO: 1 and SEQ ID NO: 94.

In some embodiments, said encapsulation peptide is encoded by a polynucleotide sequence having at least 80% identity, at least 85% identity, at least 90% identity, at least 95% identity, or 100% identity with the nucleic acid sequence set forth in SEQ ID NO: 7 or SEQ ID NO: 95 (S2CP(30)), respectively, due to redundancy of the genetic code.

In some embodiments, the bacterial microcompartment protomers are derived from *Halothiobacillus neapolitanus* or *Haliangium ochraceum*.

In some embodiments, the bacterial microcompartment protomers are CsoS1A (SEQ ID NO: 2) and CsoS4A (SEQ ID NO: 3) from *Halothiobacillus neapolitanus*; or HO-H (SEQ ID NO: 4), HO-P (SEQ ID NO: 5) and HO-T1 (SEQ ID NO: 6) from *Haliangium ochraceum*, and variants thereof.

In some embodiments, the cargo molecule is at least one peptide, such as an enzyme and/or fluorescent protein and/or immunogenic peptide.

In some embodiments, the biochemical tag may be selected from the group comprising Strep-Tag II (SII), SpyCatcher/SpyTag (SC/ST) pair and CC-Di-A/B (CCA/CCB) pair.

In some embodiments, the expression of CsoS1A is controlled by promoter PT7; CsoS4A is controlled by promoter $P_{CONS}$; HO-H is controlled by yeast promoter $P_{TDH3}$; HO-P is controlled by yeast promoter $P_{PYK1}$ and HO-T1 is controlled by yeast promoter $P_{YEF3}$.

In some embodiments, the host organism is *E. coli* or *S. cerevisiae*.

According to a second aspect, the present invention provides an engineered bacterial microcompartment VLP carrying a cargo molecule, comprising: i) bacterial microcompartment shell protomers, and a cargo molecule fused to an encapsulation peptide, wherein the encapsulation peptide comprises the amino acid sequence set forth in SEQ ID NO: 1 (SKITGSSGNDTQGSLITYSGGARG) or SEQ ID NO: 94 (KPEKPGSKITGSSGNDTQGSLITYSGGARG), or a functional variant thereof; or ii) bacterial microcompartment shell protomers and a cargo molecule, wherein the cargo molecule is fused to an end of at least one of said protomers, or wherein at least one of said protomers is fused to a tag and a cargo molecule comprising a complementary tag is bound to it on the exterior surface of the VLP.

In some embodiments, the bacterial microcompartment protomers are derived from *Halothiobacillus neapolitanus* or *Haliangium ochraceum.*

In some embodiments, the bacterial microcompartment protomers are CsoS1A, comprising the amino acid sequence set forth in SEQ ID NO: 2, and CsoS4A, comprising the amino acid sequence set forth in SEQ ID NO: 3, from *Halothiobacillus neapolitanus*; or HO-H comprising the amino acid sequence set forth in SEQ ID NO: 4, HO-P comprising the amino acid sequence set forth in SEQ ID NO: 5 and HO-T1 comprising the amino acid sequence set forth in SEQ ID NO: 6 from *Haliangium ochraceum*, and variants thereof.

In some embodiments, the cargo molecule is at least one peptide, such as an enzyme and/or fluorescent protein and/or immunogenic peptide.

In some embodiments, the biochemical tag may be selected from the group comprising Strep-Tag II (SII), SpyCatcher/SpyTag (SC/ST) pair and CC-Di-A/B (CCA/CCB) pair.

According to a third aspect, the present invention provides an isolated plasmid or vector nucleic acid comprising:

a) a first DNA sequence that encodes bacterial microcompartment shell protomers, each of which is operably linked to a promoter, and b) a second DNA sequence that encodes a cargo molecule fused to an encapsulation peptide, operably linked to a promoter, wherein the encapsulation peptide comprises the amino acid sequence set forth in SEQ ID NO: 1 (SKITGSSGNDTQGSLITYSGGARG) or SEQ ID NO: 94 (KPEKPGSKITGSSGNDTQGSLITYSGGARG), or a functional variant thereof; or c) a first DNA sequence that encodes bacterial microcompartment shell protomers, each of which is operably linked to a promoter, and d) a second DNA sequence encoding at least one of said protomers fused with a cargo molecule or a biochemical tag.

In some embodiments, the isolated plasmid or vector nucleic acid comprises bacterial microcompartment shell protomers, promoters, cargo molecules and tags as defined previously.

In some embodiments, the isolated plasmid or vector nucleic acid DNA sequences encoding said bacterial microcompartment shell protomers, cargo molecules and tags set forth in SEQ ID Nos: 1-6 and 94 have at least 70%, at least 80%, at least 90%, or 100% identity with the nucleic acid sequences set forth in SEQ ID Nos 7-12 and 95-S2CP(30), respectively, due to redundancy of the genetic code.

According to a fourth aspect, the present invention provides a composition or combination comprising at least one engineered VLP of any aspect of the invention for use in: a) the prophylaxis or treatment of disease in a subject; or b) a biochemical process.

In some embodiments, the at least one engineered VLP comprises an enzyme for conversion of a prodrug.

In some embodiments, the composition may comprise one or more additional therapeutic agents. The composition may be used as a vaccine.

According to a fifth aspect, the present invention provides a use of at least one engineered VLP of any aspect of the invention in the manufacture of a medicament for the prophylaxis or treatment of a disease in a subject.

According to a sixth aspect, the present invention provides a method of prophylaxis or treatment, comprising administering to a subject in need of such treatment an efficacious amount of an engineered VLP of any aspect of the invention.

It will be appreciated that the present invention is not limited to the specific embodiments described in detail below.

BRIEF DESCRIPTION OF THE FIGURES

FIG. 1 shows a schematic of the alpha-carboxysome operon (cso) from *Halothiobacillus neapolitanus*. The dotted line indicates ten genes between csos1B and csoS1 D that are unlikely to be associated with the carboxysome. Gene lengths and intervening distances are not drawn to scale.

FIG. 2A-D shows schematics of developed plasmids. (A) TU acceptor plasmid, pESX contains a streptomycin selection marker (Strep$^R$) along with the pUC origin of replication. The RFP cassette is displaced by an incoming TU through digestion with the restriction enzyme (RE) BsmBI. (B) The pathway acceptor plasmid, pCKH, accepts TUs released from pESX plasmids by digestion with the RE BsaI. pCKH contains the kanamycin selection marker (Kan$^R$). (C and D) Modified HcKan_O plasmids that can attach either the SII or His$_6$ tag or one of four FPs (mT2, meGFP, mKOκ, mCh) at either N- or C-terminus of an ORF. After insertion of the ORF by BsaI, the ORF-tag fusion product (separated by a Gly-Ser-Ser linker), is released by BsmBI.

FIG. 4A-B shows identification of a cargo targeting peptide sequence for the alpha-carboxysome system. (A) Multiple sequence alignment of CsoS2 orthologs (top 9 from different genera are shown) with that from *H. neapolitanus* reveals that the C-terminal region is highly conserved, as depicted by the sequence logo. (B) Pull-down assay of His6-meGFP-S2CP with the shell proteins CsoS1A-SII, SII-CsoS1D and CsoS4A-SII demonstrate that S2CP mediates interaction with CsoS1A-SII only.

FIG. 5A-B shows the expression and purification of alpha-carboxysome shell components. (A) Schematics of the synthetic operons used to express the alpha-carboxysome components. The shell modules are also represented by their geometric icons; Cso4A: pentagon; CsoS1D: trimeric hexagon; CsoS1A: hexameric hexagon. (B) Fluorescence micrographs of cells expressing the pathway Cso-P$_{mCh}$THC. Colocalization of meGFP-S2CP and CsoS4A-mCherry can be seen. DIC: differential interference contrast channel. Scale bars (white, bottom right) represent 2 μm. (C-F) TEM visualization of purified protein shells at the 0.4 M NaCl elution fraction following AIEX purification for (C) Cso-P$_{mCh}$THC, (D) Cso-P$_{SII}$THC, (E) Cso-P$_{SII}$TH and (F) Cso-P$_{SII}$H. Scale bars (black, bottom right) represent 50 nm.

FIG. 8A-B shows fluorescence micrographs of the shell probes (A) CsoS4A-mCherry and (B) meGFP-S2CP used for investigating interactions between shell components in-vivo. Probes were generally homogenously distributed within the cytosol when expressed individually. Scale bars (bottom right) represent 2 μm.

FIG. 10A-B shows purification of Cso-P$_{SII}$TH. (A) AIEX chromatogram and (B) TEM micrograph for the elution fraction corresponding to 0.3 M NaCl. Scale bar (bottom right) represents 50 nm.

FIG. 11A-E shows purification of Cso-P$_{SII}$H. (A) AIEX chromatogram for affinity purified proteins from Cso-P$_{SII}$H. (B) TEM micrograph for the elution fraction from Cso-P$_{SII}$H corresponding to 0.3 M NaCl. TEM micrographs for (C) CsoS1A-SII, (D) CsoS1A-SII co-expressed with CsoS1D and (E) CsoS4A-SII co-expressed with CsoS1D demonstrating that these combinations do not form protein shells. Scale bars (bottom right) represent 50 nm.

FIG. 12A-D shows sodium dodecyl sulfate—polyacrylamide gel electrophoresis (SDS-PAGE) analyses of fractions collected from AIEX purification of (A) Cso-P$_{mCh}$THC, (B) P$_{SII}$THC, (C) P$_{SII}$H and (D) P$_{SII}$H. Arrows indicate fractions used for TEM analysis, with the left and right arrows corresponding to [NaCl]=0.3 M and 0.4 M respectively. Protein ladder lane is marked as L with the masses (kDa) indicated.

FIG. 13 shows particle size distribution of protein shells as measured by 15 dynamic light scattering. (A) Cso-P$_{mCh}$THC, (B) Cso-P$_{SII}$THC, (C) Cso-P$_{SII}$TH and (D) Cso-P$_{SII}$H.

FIG. 14 shows a table summarizing the differences between the purified Cso-BMC and HO-BMC.

FIG. 17A-D shows assessment of the stability of Cso-BMC shells against common denaturing factors. (A-D) DLS spectra of empty Cso-BMC tested against the conditions indicated. The baseline is vertically displaced by 0.2 for each subsequent spectrum so that all spectra can be seen in one graph.

FIG. 18A-E shows loading of the APEX2 and LacZ enzymes into Cso-BMC shells. (A-B) SDS-PAGE and Western blot analyses (using anti-His$_6$ antibody) of Cso-BMC co-expressed with the enzymes. (C-D) TEM micrographs of Cso-BMC loaded with enzymes. Scale bars (black, bottom right) represent 50 nm. (E) DLS spectra of Cso-BMC co-expressed with enzymes, with empty Cso-BMC shells as a reference.

FIG. 19 shows Michaelis-Menten kinetics of free and Cso-BMC encapsulated APEX2 and LacZ enzymes.

FIG. 20A-D shows assessment of stabilizing effects of Cso-BMCs conferred on APEX2 and LacZ against denaturing conditions. Residual enzymes activities of free and encapsulated (+shell) enzymes were obtained by normalizing the activity to that of the pristine sample, shown as (A) 23° C., (B) 0% v/v methanol, (C) no freeze-thawing, and (D) pH 8. Error bars represent one standard deviation of the mean.

FIG. 21A-E shows the purification of the HO-BMC shells: HO-HTP and HO-HT$_{ST}$P+GFP-SpyCatcher. (A-B) SDS-PAGE analysis of purified shells, (C) Western blot analysis (using anti-GFP antibody) indicating the presence of GFP-SpyCatcher in the HO-HT$_{ST}$P+GFP-SpyCatcher sample, (D-E) TEM micrographs of both HO-BMC constructs. Scale bars (black, bottom right) represent 50 nm.

DETAILED DESCRIPTION OF THE INVENTION

Figure 3:
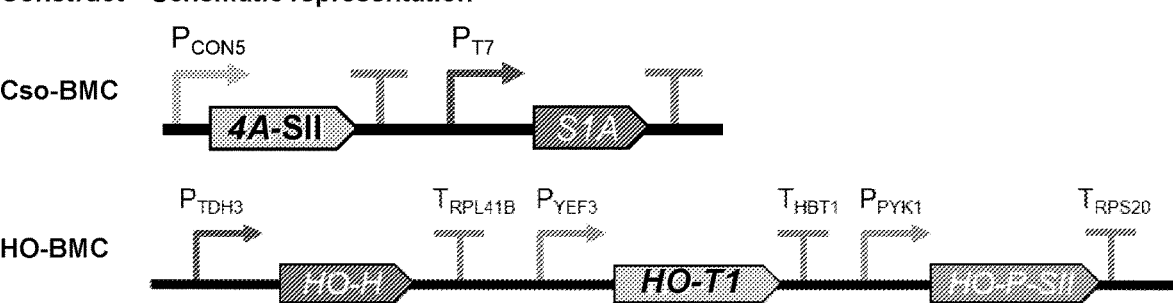
FIG. 3 shows a schematic diagram of VLP pathways created. For Cso-BMC, all terminators used were T$_{T7}$. The greyscale intensities on the promoter arrows symbolize their relative strengths, with darker being stronger.

Bibliographic references mentioned in the present specification are for convenience listed in the form of a list of references and added at the end of the examples. The whole content of such bibliographic references is herein incorporated by reference.

Definitions

Certain terms employed in the specification, examples and appended claims are collected here for convenience.

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

As used herein, the term Cso-P$_{SH}$H is used interchangeably with the term Cso-BMC.

The term "variant" as used herein, refers to an amino acid sequence that is altered by one or more amino acids, but retains the ability to function as an encapsulation peptide in the present invention. The variant may have "conservative" changes, wherein a substituted amino acid has similar structural or chemical properties (e.g., replacement of leucine with isoleucine). More rarely, a variant may have "non-conservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR® software (DNASTAR, Inc. Madison, Wisconsin, USA). A type of variant is, for example, a peptide having the amino acid sequence set forth in SEQ ID NO: 94, which is longer than the sequence set forth in SEQ ID NO: 1, is also derived from CsoS2, and retains the encapsulation functionality of SEQ ID NO: 1. Other variants having amino acid sequences intermediate between SEQ ID NO: 1 and SEQ ID NO: 94, would be expected to retain functionality.

A composition or combination of the present invention will generally be administered as a pharmaceutical formulation in admixture with a pharmaceutically acceptable adjuvant, diluent or carrier, which may be selected with due regard to the intended route of administration and standard pharmaceutical practice. Such pharmaceutically acceptable carriers may be chemically inert to the active compounds and may have no detrimental side effects or toxicity under the conditions of use. Suitable pharmaceutical formulations may be found in, for example, Remington The Science and Practice of Pharmacy, 19th ed., Mack Printing Company, Easton, Pennsylvania (1995). For parenteral administration, a parenterally acceptable aqueous solution may be employed, which is pyrogen free and has requisite pH, isotonicity, and stability. Suitable solutions will be well known to the skilled person, with numerous methods being described in the literature. A brief review of methods of drug delivery may also be found in e.g. Langer, (Science 249: 1527 (1990)).

Otherwise, the preparation of suitable formulations may be achieved routinely by the skilled person using routine techniques and/or in accordance with standard and/or accepted pharmaceutical practice.

The amount of a composition or combination in any pharmaceutical formulation used in accordance with the present invention will depend on various factors, such as the severity of the condition to be treated, the particular patient to be treated, as well as the compound(s) which is/are employed. In some embodiments the BMC-VLP displays an antigenic molecule on its surface and functions as a vaccine. In any event, the amount of a composition or combination in the formulation may be determined routinely by the skilled person.

For example, a solid oral composition such as a tablet or capsule may contain from 1 to 99% (w/w) active ingredient; from 0 to 99% (w/w) diluent or filler; from 0 to 20% (w/w) of a disintegrant; from 0 to 5% (w/w) of a lubricant; from 0 to 5% (w/w) of a flow aid; from 0 to 50% (w/w) of a granulating agent or binder; from 0 to 5% (w/w) of an antioxidant; and from 0 to 5% (w/w) of a pigment. A controlled release tablet may in addition contain from 0 to 90% (w/w) of a release-controlling polymer.

A parenteral formulation (such as a solution or suspension for injection or a solution for infusion) may contain from 1 to 50% (w/w) active ingredient; and from 50% (w/w) to 99% (w/w) of a liquid or semisolid carrier or vehicle (e.g. a solvent such as water); and 0-20% (w/w) of one or more other excipients such as buffering agents, antioxidants, suspension stabilisers, tonicity adjusting agents and preservatives.

Depending on the disorder, and the patient, to be treated, as well as the route of administration, compositions or combinations comprising BMC-VLPs of the invention may be administered at varying therapeutically effective doses to a patient in need thereof.

However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated.

Having now generally described the invention, the same will be more readily understood through reference to the following examples which are provided by way of illustration, and are not intended to be limiting of the present invention.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

Example 1

Materials and Methods

Bacterial Strains and Culture

*E. coli* Acella (DE3) (EdgeBio) cells were used for both molecular cloning and protein expression of Cso-BMC VLPs. Cells were grown in either lysogeny broth (LB) or Terrific broth (TB) supplemented with the appropriate antibiotics (kanamycin or streptomycin) at 50 µg/mL.

*Saccharomyces cerevisiae* (henceforth simply referred to as yeast) cells were used for both molecular cloning and protein expression of HO-BMC VLPs. Plasmid-based expression in yeast is based on nutritional selection, which requires a formulated growth medium. The medium lacks a key nutrient required by engineered yeast strains, which can be produced by a protein encoded by a gene on the plasmid. On pCKU, the gene product, Ura3p, produces uracil. As this chemically defined medium is expensive (about SGD 30/L), we sought to chromosomally integrate the pathways into the yeast genome so that the yeast strain can still express the pathway proteins on a non-defined culture medium (yeast-peptone-dextrose) that is less expensive (about SGD 5/L). We thus developed pGAU-YMRWδ15 that installs homology sites flanking the pathway to be integrated into yeast. Using the endogenous homologous recombination machinery in yeast, the desired pathway is inserted into the YMRWδ15 chromosomal site in yeast and the proteins on the pathway can be expressed without the need for selection.

Golden Gate Assembly of Plasmids

The Golden Gate one-pot plasmid assembly largely follows previously published protocols, with slight modifications [Guo, Y. et al., *Nucleic Acids Res* 43: e88 (2015)]. For the insertion of one to three fragments, in a reaction pot was prepared 1 µL of T4 ligase buffer (NEB), 0.5 µL of 10× purified bovine serum albumin (BSA, NEB), 5 U of BsaI (NEB) or Esp3I (Thermo), 0.2 U of T4 ligase (Thermo), 15 ng of destination plasmid, 1 to 3 µL of insert(s) and topped up to 10 µL with water. The reaction pot was subject to a 37° C. to 18° C. thermocycling process with 5 min incubation at each step for 15 cycles, followed by a 55° C. step for 15 min to digest unassembled plasmids while inhibiting ligation so as to reduce the number of colonies harboring the original destination vector. For the assembly of more than three inserts, the amount of restriction enzyme and ligase was doubled, the amount of destination plasmid was increased to 75 ng, the number of thermocycles was increased to 70 and the inserts and destination plasmids were added in a 2:1 molar ratio rather than as fixed volumes. These were done with the aim of increasing the number of correctly assembled plasmids.

Codon-optimized BMC genes were synthesized (BioBasic) and cloned into HcKan_O. The promoters and terminator parts were amplified from various templates as PCR products and cloned into HcKan_P and HcKan_T respectively.

meGFP, which is the monomeric form of eGFP obtained through a A206K mutation, was created by site-directed mutagenesis (SDM) using NEBuilder® HiFi assembly. The plasmids pES1-7, pCKH and modified HcKan_O plasmids used for adding fluorescent protein, S2CP or purification tags to ORFs, were likewise created using HiFi assembly.

Primers for Sequencing

The specific oligonucleotide primers used to sequence various plasmid constructs are shown in Table 1.

TABLE 1

Primers for sequencing

| Primer name | Plasmid(s) used for | Sequence | SEQ ID NO |
|---|---|---|---|
| HcK-an_chc_F' | HcKan | GATCCTTTGATTTTCTACCG | 85 |
| HcK-an_chc_R' | HcKan | CTCGATAACTCAAAAAATACG | 86 |
| pES_Chc_F' | pESX | CGGAGCCTATGGAAAAACGC | 87 |
| pES_Chc_R' | pESX | CCGCAGTGTCTTGGGTCTCT | 88 |
| His_chc_F' | pCKH | TAGAGTGTACTAGAGGAGGCCAA | 89 |
| CEN_chc_R' | pCKH/pCKU | GGTGATGACGGTGAAAACCT | 90 |
| Ura_chc_F' | pCKU | TCTGTTCGGAGATTACCGAAT CAA | 91 |
| pGau_chc_F' | pGAU-YMRWδ15/ pGAH-YPRCδ15 | CCACCTCAGGCAGAGAACCT | 92 |
| pGau_chc_R' | pGAU-YMRWδ15/ pGAH-YPRCδ15 | GGAAAAACGCCAGCAACGC | 93 |

Sequence Alignment

The CsoS2 sequences were aligned with Clustal Omega and output alignment file was prepared with JalView 2 [Waterhouse, A. M. et al., *Bioinformatics* 25: 1189-1191 (2009); Sievers, F. and Higgins, D. G. *Methods in Molecular Biology* (Clifton, N.J.) 1079: 105-116 (2014)]. Accession numbers for the sequences used in sequence alignment are detailed in Table 2.

TABLE 2

GenBank accession numbers of the sequences shown and used in multiple sequence alignments.

| Gene | Organism | GenBank accession number |
|---|---|---|
| csos2 | *Halothiobacillus neapolitanus* | ACX95763.1 |
| | *Acidithiobacillus ferrivorans* | OYV82041.1 |
| | *Burkholderiales bacterium* | TNF63637.1 |

TABLE 2-continued

GenBank accession numbers of the sequences shown
and used in multiple sequence alignments.

| Gene | Organism | GenBank accession number |
|---|---|---|
| | Gallionellaceae bacterium | TAJ81120.1 |
| | Hydrogenophilales bacterium | OZA28367.1 |
| | Thiobacillus thioparus | WP_018507371.1 |
| | Comamonadaceae bacterium | KJS73712.1 |
| | Acidithiobacillus ferridurans | BBF66259.1 |
| | Betaproteobacteria bacterium | TSA22668.1 |
| | Ferrovum sp. Z-31 | WP_062187313.1 |
| csos1A | Halothiobacillus neapolitanus | WP_012823794.1 |
| Hoch_5815 (BMC-H) | Haliangium orchraceum | WP_012830883.1 |
| ccmK2 | Halothece sp. 7418 | WP_015227514.1 |
| eutM | Salmonella enterica | VFS02811.1 |
| pduA | Citrobacter freundii | WP_098065011.1 |
| cmcC | Klebsiella pneumoniae | WP_004146125.1 |
| csos4A | Halothiobacillus neapolitanus | WP_012823797.1 |
| Hoch_5814 (BMC-P) | Haliangium orchraceum | WP_012830882.1 |
| ccmL | Halothece sp. 7418 | WP_015227516.1 |
| eutN | Salmonella enterica | EBA6053551.1 |
| pduN | Citrobacter freundii | WP_038641685.1 |
| cmcD | Klebsiella pneumoniae | WP_009486245.1 |

Purification and Cargo-Loading Analysis of VLPs

For Cso-BMC: Acella(DE3) cells were cultured in 500 mL terrific broth (TB, BioBasic) supplemented with kanamycin at 50 mg/L and shaken at 37° C. until the optical density (at $\lambda$=600 nm) value of the culture reached approximately 0.6 to 1.0. The cultures were then cooled to 25° C. and isopropyl $\beta$-D-1-thiogalactopyranoside (IPTG, Gold-Bio) was added to 50 μM for protein induction. The cells were cultured at 25° C. for approximately 30 h before harvesting by centrifugation. Cells were lysed using a M-110P microfluidizer (Microfluidics) at 15,000 psi for three passes. To the cell lysate was added 0.1 mM of phenylmethylsulfonyl fluoride (PMSF) protease inhibitor. The lysate was spun twice at 20,000×g for 20 min each time. The clarified lysate was loaded onto a StrepTrap™ HP 5 mL column (GE Life Sciences) at 1 mL/min linear flow rate. Purification was performed using an ÄKTA FPLC with 12 column volumes (CV) of washing with binding buffer (Tris·HCl 100 mM, NaCl 150 mM, pH 8.0) and 6 CVs of elution with the elution buffer (binding buffer supplemented with 2.5 mM desthiobiotin) at 3 mL/min linear flow rate.

In order to get high quality protein shells for structural studies, anion exchange (AIEX) chromatography was performed following StrepTrap™ affinity purification. AIEX Buffer A (Tris·HCl 50 mM, pH 8.0) was added to dilute the pooled StrepTrap™ elution fractions two-fold. The sample was loaded onto a 10 mL bed resin volume Q Sepharose (GE Life Sciences) column at 1 mL/min. A two-step gradient protocol consisting of 0 to 60% AIEX Buffer B (Tris·HCl 50 mM, NaCl 1.0 M, pH 8.0) over 6 CV and 60 to 100% IEX Buffer B over 2 CV, both at 2 mL/min linear flow rate, was used for elution.

Proteins were analyzed using 13% stacking sodium dodecyl sulfate polyacrylamide gel electrophoresis (SDS-PAGE) gels and stained using InstantBlue (Expedeon). Densitometric analysis was performed using the Bio-Rad image lab software in accordance with previous reports on BMC cargo quantification [Hagen, et al., Nature Communications 9: 2881, doi:10.1038/s41467-018-05162-z (2018)]. Background subtraction was performed and peak areas corresponding to bands of interest were used for quantification. Absolute protein concentrations were measured using a DeNovix spectrophotometer using calculated molar attenuation coefficients at 280 nm ($\varepsilon_{280}$). The calculated $\varepsilon_{280}$ of T=3 shells, taken as the summation of the $\varepsilon_{280}$ of its individual components, was 1 588 200 $M^{-1} \cdot cm^{-1}$. The $\varepsilon_{280}$ of the T=4 shell was calculated to be 1 677 600 $M^{-1} \cdot cm^{-1}$. The small difference in calculated $\varepsilon_{280}$ values between both shell types is due to the low $\varepsilon_{280}$ of CsoS1A (1490 $M^{-1} \cdot cm^{-1}$). Most of the $\varepsilon_{280}$ contribution comes from CsoS4A (23 490 $M^{-1} \cdot cm^{-1}$), which has the same number of copies in both shell types. Determination of average number of GFP per shell using fluorescence was performed in accordance with a protocol described by Hagen et. al. [Hagen, et al., Nature Communications 9: 2881, doi: 10.1038/s41467-018-05162-z (2018)].

For HO-BMC: After growing in 8 L of YPD (yeast extract 1%, peptone 2%, glucose 2%, BioBasic) for 48 h at 25° C., yeast cells were pelleted and lysed using the M-110P microfluidizer at 20,000 psi for eight passes. The lysate was spun twice at 20,000×g for 20 min each time and the clarified lysate was adjusted to pH 8 using 1 M Tris·HCl pH 12. The lysate was also incubated with 300 μL of biotin blocking buffer (IBA Lifesciences) with gentle stirring for 15 min. StrepTrap™ affinity purification was performed in the same way as described above.

Pull-Down Assay and Immunoblotting

Purified $His_6$-meGFP-S2CP and $His_6$-meGFP were separately incubated with clarified E. coli lysate containing CsoS1A-SII, SII-CsoS1D or CsoS4A-SII with 1 h of gentle stirring at 25° C. The lysate mixtures were purified using the abovementioned StrepTrap™ protocol. Immunoblotting detection of the eGFP epitope was done using GFP-HRP conjugated antibody (GF28R, Invitrogen) and for detection of the $His_6$ epitope, THE His Tag antibody conjugated with HRP (Genscript) was used. Detection was performed in accordance with the manufacturers' recommended protocols.

Fluorescence Microscopy

E. coli cells were grown in accordance to the conditions described and 0.1 mL of culture was collected and pelleted. The pellet was resuspended in PBS with 1% formaldehyde and allowed to stand at room temperature for 10 min. The cells were washed twice with PBS and resuspended in 0.5 mL PBS. A small amount (~3 μL) of cell suspension was mixed with an equivolume of ProLong™ Diamond Antifade Mountant (Thermo Scientific) before mounting onto poly-L-lysine microscope slides (Thermo Scientific). Samples were allowed to cure in the dark for at least 24 h before imaging. Slides were imaged using an Olympus FV1200 confocal microscope at 100× objective lens magnification. Co-localization analysis was performed using ImageJ software.

Transmission Electron Microscopy

Formvar/carbon coated copper grids were subject to glow discharge before 5 μL of purified protein samples (diluted to $A_{280}$~0.05 or lower) were mounted for 60 s before the droplets were removed with filter paper. The grids were then negatively-stained by adding a 5 μL droplet of 2.5% gadolinium(II) acetate, incubating for 90 s, and similarly blotted off. Grids were imaged using a JEOL JEM-1220 TEM.

Shell Particle Size and Stability Measurements

Particle size distribution was determined by dynamic light scattering (DLS) using the Uncle™ instrument (Unchained labs). Samples were diluted to 1 mg/mL in TBS-50/350 pH 8.0, (Tris·HCl 50 mM, NaCl 350 mM, pH 8.0), unless otherwise specified, and spun at 20,000 g for 5 min to remove aggregates prior to measurement. Care was taken to use the top-most supernatant for analysis. To the mini cuvette was added 9 µL of sample. All DLS measurements were done in triplicates and performed at 20° C. unless stated otherwise. Analysis of particle size distribution was done using the Uncle™ analysis software.

For shell stability measurements at various temperatures, shell samples were aliquoted into thin-walled PCR tubes and subject to temperatures ranging from 20-80° C. in 10° C. increments for 15 min in the Uncle™ instrument. At the end of the 15 min incubation, DLS spectra were taken.

For shell stability measurements in various buffer conditions, TBS-50/350 pH 8.0 buffers containing 10% and 20% (v/v) methanol were freshly prepared from stock solutions of Tris·HCl 1.0 M pH 8.0, NaCl 5.0 M and 99.8% methanol (ACS reagent grade, Sigma) and used within the day of preparation. Due to the heat of mixing generated when methanol is mixed with water, methanol-containing buffers were allowed to equilibrate back to room temperature for at least 1 h after preparation. For making of buffers at various pH, the following components were used at 50 mM for the pH range indicated: glycine·HCl for pH 2-4; 4-morpholineethansulfonic acid (MES) sodium salt for pH 5-7; Tris·HCl for pH 8-9; N-cyclohexyl-3-aminopropanesulfonic acid (CAPS) sodium salt for pH 10-11; arginine·HCl for pH 12-13. All buffers contained 350 mM NaCl. Shells were incubated in the abovementioned buffers for 15 min to allow time for possible shell dissociation/protein denaturation before particle size measurement.

For freeze-thaw stability, shell samples in TBS-50/350 pH 8.0 were aliquoted into thin-walled PCR tubes and flash-frozen in liquid $N_2$. Samples were thawed at room temperature until no ice crystals were seen by standing for 15 min before re-freezing.

Enzyme Steady-State Kinetics Assays.

For APEX2, all reagents were made to the appropriate working concentrations using TBS-50/350 pH 8.0. Working solutions of guaiacol and $H_2O_2$, both at 10 mM, were prepared on the day of assay. The guaiacol solution was shaken vigorously at 30° C. to ensure complete dissolution before equilibration back to room temperature. The assay concentration for APEX2 was 10 nM, $H_2O_2$ 1 mM and that for guaiacol ranged from 0.20 to 2.0 mM. Total reaction volume was 200 µL. Reactions were monitored by the absorbance of tetraguaiacol formed at 470 nm using a BioTek Synergy™ HT microplate reader. Rate of tetraguaicol formation was found to be constant until 90 s. This time point was taken for initial rate, $V_0$, measurement. Kinetic constants were obtained using non-linear least square Michaelis-Menten fitting in GraphPad Prism software.

For steady-state kinetics of LacZ, all reagents were made to the appropriate working concentrations using TBS-50/350 pH 8.0 supplemented with 1 mM $MgCl_2$. Working solutions of ONPG at 10 mM were prepared from a 50 mM stock solution in DMSO on the day of assay. The assay concentration for LacZ was 10 nM and that for ONPG (ortho-nitrophenyl-β-galactoside) ranged from 0.050 to 1.5 mM. Total reaction volume was 100 µL. Hydrolysis of ONPG was tracked by absorbance measurements at 405 nm. Rate of production formation was found to be constant until 60 s, and this time point was taken for Vo measurement.

Enzyme/Enzyme-Shell Activity and Stability Assays.

All enzyme activity measurements were performed at ambient temperature (23° C.) and working concentrations of enzymes were 10 nM. Measurements were performed in triplicates. Enzyme activity measurements were determined as initial rates of product formation using saturating substrate concentrations (i.e. near $V_{max}$). For APEX2, this was 1.4 mM guaiacol and 1 mM $H_2O_2$. For LacZ, this was 1.5 mM ONPG.

For heat shock assays, enzyme/enzyme-shell samples were aliquoted into thin-walled PCR tubes and subject to the elevated temperatures indicated (FIG. 6B) in a thermocycler for 15 min. Following incubation, samples were cooled to 20° C. and equilibrated back to ambient temperature for 15 min before assay.

For stability measurement in buffers containing methanol and under various pH conditions, enzyme/enzyme-shell samples were dialyzed to the various buffers as described in the particle size measurement section. Solutions were allowed to stand for at least 15 min before assay to allow time for possible protein denaturation.

For freeze-thaw stability, enzyme/enzyme—shell samples were aliquoted in thin-walled PCR tubes and flash-frozen in liquid $N_2$. Samples were thawed at room temperature until no ice crystals were seen by standing for 15 min before re-freezing or assay.

Cryo-Electron Microscopy and Structural Analysis

Protein solutions were diluted to a concentration of 0.5 mg/ml using ice-cold TBS-50/400 buffer (Tris·HCl 50 mM, NaCl 400 mM, pH 8.0). To glow discharged R 1.2/1.3 and R2/2 Molybdenum 200 grids with a holey carbon support film (Quantifoil) was applied 2.5 µL of the protein samples. Grids were transferred to a Leica EM GP plunge freezer, blotted over 2 s at 90% humidity and flash frozen in liquid ethane that was kept cool by liquid $N_2$. Grids were stored under liquid $N_2$ temperatures to prevent formation of crystalline ice.

The best cryoEM grid preparation conditions were screened for on a Talos™ Arctica Cryo-TEM (ThermoFisher Scientific) at the Institute for Protein Research, Osaka University, equipped with FEG operated at 200 kV at minimal dose system. Images were captured at an exposure time of 33.67 seconds giving a dose of approximately 20 e⁻/Å² with 92,000× magnification and defocus values of 1.6 to 2.5 µm. Images were recorded using a BM-Falcon3 camera in counting mode with exposure settings of 1.1 Å pixel size and fractions of 70 frames/individual images. For data collection, grids were prepared and imaged on a Titan™ Krios™ (FEI) (ThermoFisher Scientific), at the Research Center for Ultra-High Voltage Electron Microscopy (UHVEM), Osaka University, equipped with FEG operated at 300 kV and a minimal dose system. Imaging was done using the EPU software (FEI) attached to the Titan™ Krios™. Images were recorded at nominal magnification of 96,000, without using objective aperture, actual defocus range between 1.5 to 2.2 µm with a dose rate of 64.3 to 68.1 e⁻/Å² and exposure time of 1 second with 8 image acquisitions per hole. Images were recorded using a Falcon II detector (FEI) at a pixel size of 0.86 Å/pixel and a frame rate of 17 frames/individual images.

About 2100 to 2500 raw movies were collected from different microscope sessions and processed in RELION 3.0 software [Zivanov, J. et al., *eLife* 7: e42166 (2018)]. Drifts were motion corrected with MotionCor2 software and the CTF for each micrograph was estimated with CTFFind-4.1 software and Gctf software [Zhang, K. *J Struct Biol* 193: 1-12 (2016)]. Micrographs with good observed CTF estimations were selected for further processing. Shells were manually picked and extracted at a box size of 300×300 pixels in RELION 3.0. Particles from 2D classes displaying clear secondary structure elements were selected. Initial 3D reference models were prepared using RELION toolbox kit cylinder. 3D refinement was performed with a low pass filter of 20 Å with solvent flattening. CTF refinement was performed without particle polishing (no effect with particle polishing) and final 3D refinements performed. With post processing using solvent flattening and a soft mask, final resolutions were attained for the protein shells.

Model Building and Structure Analysis

Biological assembly models for the pentamer (PDB ID: 2RCF) [Tanaka, S., et al., *Science* 319: 1083-1086 (2008)] and hexamer (PDB ID: 2EWH) [Tsai, Y. et al., *PLOS Biology* 5: e144 (2007)] were manually fit into the electron density maps using UCSF Chimera [Pettersen, E. F., et al., *J Comput Chem* 25: 1605-1612 (2004)]. Asymmetric units of the icosahedral reconstructions were extracted and rebuilt in COOT [Emsley, P., et al., *Acta Crystallogr. D Biol. Crystallogr.* 66: 486-501 (2010)]. Whole-shell models were obtained by symmetry expansion and real space refinement in PHENIX [Liebschner, D., et al., *Acta Crys D* 75: 861-877 (2019)] and CCP4 [Winn, M. D., *Acta Crystallogr. D Biol. Crystallogr.* 67: 235-242 (2011)].

Example 2

Genetic Toolkit for Modular Construction of Microcompartment Parts

Our Golden-Gate cloning based genetic part assembly toolkit expands on the published YeastFab suite of plasmids, used for metabolic engineering in yeast [Guo, Y., et al., *Nucleic Acids Res* 43: e88 (2015)]. Briefly, it is a hierarchical approach towards DNA assembly in which genetic part, i.e. promoters (Pro), open reading frames (ORF) and terminators (Ter) are modularized. These parts are termed as Level 0 plasmids. Level 1 plasmids link up Pro-ORF-Ter together to form a gene expression cassette and are termed as POTX plasmids, (X=1 to 11). Level 2 plasmids chain up two or more expression cassettes to form a pathway combination. Level 3 plasmids are used for chromosomal integration of the pathways into the genome. For our yeast expression, we used the YeastFab Level 0 and 1 plasmid in the published YeastFab toolkit, but developed our own Level 2 and 3 plasmids to better suit our requirements. For *E. coli* expression we retained the use of the YeastFab Level 0 plasmids, but developed our own Level 1 and 2 plasmids. We did not develop Level 3 (genomic integration) plasmids for *E. coli*.

The Level 0 plasmids, termed HcKan_P, _O, and _T, are used for maintenance of Pro, ORF and Ter parts, respectively, for both *E. coli* and yeast as described in Table 3.

TABLE 3

List of genetic parts and corresponding maintenance plasmids (for storage and release of genetic parts) used for expression of our VLPs in *E. coli* and yeast

| Genetic part/level | SEQ ID NO (for genetic part) | Name | SEQ ID NO (for maintenance plasmids) | Function |
|---|---|---|---|---|
| Pro/0 | 84 | P$_{Con2}$ | 83 | Strong bacterial constitutive promoter from Anderson collection (Anderson, 2006), ID: BBa_J23100 |
| | 77 | P$_{Con3}$ | 40 | Strong bacterial constitutive promoter from Anderson collection, ID: BBa_J23108 |
| | 78 | P$_{Con4}$ | 41 | Moderate strength bacterial constitutive promoter from Anderson collection, ID: BBa_J23105 |
| | 24 | P$_{Con5}$ | 42 | Weak bacterial constitutive promoter from Anderson collection, ID: BBa_J23114 |
| | 23 | P$_{T7}$ | 43 | T7 bacteriophage promoter, regulated by the lac operon. Used for very high levels of protein production in *E. coli* strains with the λDE3 lysogen (Baneyx, 1999). |
| | 25 | P$_{TDH3}$ | 65 | Strong yeast constitutive promoter |
| | 27 | P$_{YEF3}$ | 66 | Moderate strength yeast constitutive promoter |
| | 26 | P$_{PYK1}$ | 67 | Moderate strength yeast constitutive promoter |
| | 104 | P$_{GPM1}$ | 115 | Moderate strength yeast constitutive promoter |
| ORF/0 | 2, 8 | CsoS1A | 53 | Hexameric BMC protomer |
| | 3, 9 | CsoS4A | 54 | Pentameric BMC protomer |
| | 4 and 10 | HO-H | 68 | Hexameric BMC protomer |
| | 5 and 11 | HO-P | 69 | Pentameric BMC protomer |
| | 6 and 12 | HO-T1 | 70 | Trimeric BMC protomer |
| | 97 | HO-T1-SpyTag | 116 | Trimeric BMC protomer with internal SpyTag |
| | 45, 46 | meGFP | 44 | Monomeric enhanced green fluorescent protein. |
| | 30 and 29 | mCherry | 28 | Monomeric red fluorescent protein. |

TABLE 3-continued

List of genetic parts and corresponding maintenance plasmids (for storage and release
of genetic parts) used for expression of our VLPs in *E. coli* and yeast

| Genetic part/level | SEQ ID NO (for genetic part) | Name | SEQ ID NO (for maintenance plasmids) | Function |
|---|---|---|---|---|
| | 48, 49 | UmuD$^{1-40}$-meGFP-S2CP | 47 | UmuD$^{1-40}$ degradation tag fused to meGFP-S2CP |
| | 51, 52 | UmuD$^{1-40}$-meGFP | 50 | UmuD$^{1-40}$ degradation tag fused to meGFP |
| | 99 | GFP-SpyCatcher | 121 | GFP fused to SpyCatcher |
| | 110 | APEX2-S2CP(30) | 109 | Engineered pea ascorbate peroxidase (Lam et al., 2015) fused to S2CP(30) |
| | 103 | LacZ-S2CP(30) | 106 | *E. coli* beta-galactosidase fused to S2CP(30) |
| Ter/0 | 79 | T$_{T7}$ | 55 | HcKan_T-TT7 construct containing T7 transcriptional terminator (Banexyx, 1999). |
| | 80 | T$_{RPL41B}$ | 71 | Yeast transcriptional terminator |
| | 81 | T$_{HBT1}$ | 72 | Yeast transcriptional terminator |
| | 82 | T$_{RPS20}$ | 73 | Yeast transcriptional terminator |
| | 105 | T$_{YPT31}$ | 119 | Yeast transcriptional terminator |
| Gene expression/1 | N.A. | pESN (N = 1-7) | 56 to 62 | Receives Pro-ORF-Ter to form a gene expression cassette |
| | N.A. | POTX (X = 1-11) | N.A. | Receives Pro-ORF-Ter to form a gene expression cassette |
| Pathway/2 | N.A. | pCKH | 63 | Accepts pESN plasmids starting from N = 2, continuing with even numbered pES and ending with an odd numbered pES |
| | N.A. | pCKU | 74 | Accepts POTX plasmids starting from N = 1 or 2, continuing with even numbered POT and ending with an odd numbered POT |
| Integration/3 | N.A. | pGAU-YMRWδ15 | 75 | Integrates pathways into YMRWδ15 in the yeast genome |
| | N.A. | pGAU-YPRCδ15 | 76 | Integrates pathways into YPRCδ15 in the yeast genome |

The Level 1 plasmids were modified to tailor to protein expression in *E. coli* by removing genetic elements from the POTX plasmids that can add unnecessary burden to the host cell. We term the *E. coli* Level 1 plasmids as pESN (N=1 to 7), which contain the minimum genetic elements required for TU maintenance (FIG. 2A). For assembly of multiple Pro-ORF-Ter from POTX or pESN plasmids, we developed the Level 2 plasmids pCKU (SEQ ID NO: 74) and pCKH (SEQ ID NO: 63) (FIG. 2B), designated for yeast and *E. coli* respectively. Plasmid-based expression in yeast is based on nutritional selection, which requires a formulated growth medium. The medium lacks a key nutrient required by engineered yeast strains, which can be produced by a protein encoded by a gene on the plasmid. On pCKU, the gene product, Ura3p, produces uracil. As this chemically defined medium is expensive ($SGD 30/L), we sought to chromosomally integrate the pathways into the yeast genome so that the yeast strain can still express the pathway proteins on a non-defined culture medium (yeast-peptone-dextrose) that is less expensive ($SGD 5/L). We thus developed pGAU-YMRWδ15 (SEQ ID NO: 75) that installs homology sites flanking the pathway to be integrated into yeast. Using the endogenous homologous recombination machinery in yeast, the desired pathway is inserted into the YMRWδ15 chromosomal site in yeast and the proteins on the pathway can be expressed without the need for selection. For pathway expression in *E. coli*, we do not find pathway expression necessary at this point in time as plasmid selection in the bacterium is typically performed using the appropriate antibiotic (kanamycin in this case) in a non-defined culture medium (lysogeny broth or terrific broth).

We also modified the HcKan_O plasmids to install a fluorescent protein (FP), a biochemical/affinity tag, or an encapsulation peptide at either the amino or carboxy end of the ORF (FIGS. 2C and D).

Four FPs were chosen—mTurquoise2 (mT2), monomeric-enhanced GFP (meGFP), monomeric Kusabira orange-kappa (mKOκ) and mCherry (mCh)—are known to exhibit monomeric behavior, which should reduce artefactual aggregation of the fusion product. An example of a modified HcKan_O plasmid is HcKan_O-CmCherry (SEQ ID NO: 28) which tags mCherry to the C-terminus of an ORF. Two affinity tags introduced were the hexahistidine (His$_6$) and Strep-tag II (SII) tags, permitting protein purification by immobilized metal affinity chromatography (IMAC) or by Strep-Tactin respectively. Examples of modified HcKan_O plasmids are HcKan_O-CHis6 (SEQ ID NO: 32) which tags His$_6$ to the C-terminus of an ORF, and HcKan_O-CSII (SEQ ID NO: 31) which tags Strep-Tag I to the C-terminus of an ORF.

Other tags include the SpyCatcher/SpyTag (ST/SC) pair (SEQ ID NOs: 13 and 16) and CC-Di-A/B (CCA/CCB) pair (SEQ ID Nos: 17-20). Examples of modified HcKan_O plasmids are HcKan_O-CSpyCatcher (SEQ ID NO: 37) which tags SpyCatcher to the C-terminus of an ORF; HcKan_O-CSpyTag (SEQ ID NO: 38) which tags SpyTag to the C-terminus of an ORF; HcKan_O-CCCDiA (SEQ ID NO: 35) which tags coiled-coil dimeric-A to the C-terminus of an ORF; and HcKan_O-CCCDiB (SEQ ID NO: 36) which tags coiled-coil dimeric-B to the C-terminus of an ORF. The SII tag (SEQ ID NOs: 21 and 22) has been widely used for purification of proteins and protein complexes while the ST/SC and CCA/CCB pairs have found use in the functionalization of VLPs and other protein nanostructures [Fletcher, J. M. et al., *Science* 340: 595-599 (2013); Keeble, A. H., & Howarth, M. *Methods in Enzymology*, 617, 443-461(2019)]. A protein tagged with SpyCatcher (SEQ ID NOs: 13 and 14) forms a covalent isoamide bond with another protein tagged with SpyTag, (SEQ ID Nos: 15 and 16) while a protein tagged with CC-Di-A (SEQ ID Nos: 17 and 18) forms strong intermolecular interactions (dissociation constant, $K_d$~1 nM) with another tagged with CC-Di-B (SEQ ID NOs: 19 and 20) [Thomas, F., et al., *Journal of the American Chemical Society* 135: 5161-5166, (2013)]. Installing one member of the SC/ST or CCA/CCB pairs on the surface of the VLPs allows guest proteins tagged with the other corresponding member in the pair to conjugate to the shell surface.

Controlling the intracellular stoichiometry of shell protomers is known to be important for successful assembly of BMC shells [Kerfeld, C. A., et al., *Nature Reviews Microbiology* 16: 277 (2018)]. To tune the expression of each of the components, we incorporated five constitutively active promoters from the Anderson collection into HcKan_P (Table 4) [Anderson, J. C. *Anderson Promoter Library Registry of Standard Biological Parts* (2006)].

TABLE 4

List of constitutively active Anderson collection promoters ($P_{CON2-5}$) used in this study, along with the original identities and characterized relative strengths

| Promoter | Anderson collection identity | Relative strength | SEQ ID NO. |
|---|---|---|---|
| $P_{CON2}$ | BBa_J23100 | 1.00 | 84 |
| $P_{CON3}$ | BBa_J23108 | 0.50 | 77 |
| $P_{CON4}$ | BBa_J23105 | 0.24 | 78 |
| $P_{CON5}$ | BBa_J23114 | 0.10 | 24 |

We renamed these promoters $P_{CON1}$ to $P_{CON5}$ for brevity, with $P_{CON2}$ being the strongest and $P_{CON5}$ being the weakest. $P_{CON2}$ to $P_{CON5}$ sequences (SEQ ID Nos: 84, 77, 78 and 24, respectively) are shown in lowercase within SEQ ID Nos: 83 and 40 to 42, respectively. We also included the T7 promoter ($P_{T7}$; SEQ ID NO: 23), along with the lac repressor and lac operator sequence (Lacl+$P_{T7}$), for inducible expression of genes by addition of the inducer, isopropyl β-D-1-thiogalactopyranoside (IPTG). For transcription termination, we made use of the T7 terminator ($T_{T7}$) throughout all TUs. Using this multi-monocistronic system of DNA assembly, the expression levels of BMC components can be tailored in pESN plasmids (Table 5).

TABLE 5

Compilation of TUs (assembled in pES plasmids). The transcriptional units (TUs) are annotated with letters A-D. Abbreviations used are $P_Y$: $P_{CONY}$ (Table 4); $P_{T7}$: $P_{T7}$ with lacI and lac operator; meG: meGFP; mCh: mCherry. All TUs are terminated by $T_{T7}$.

| pES | A | B | C | D |
|---|---|---|---|---|
| 2 | $P_4$-meG-S2CP | $P_5$-CsoS4A-SII | $P_4$-UmuD$^{1-40}$-meG-S2CP | $P_4$-UmuD$^{1-40}$-meG |
| 3 | $P_{T7}$-CsoS1A | | | |

TABLE 5-continued

Compilation of TUs (assembled in pES plasmids). The transcriptional units (TUs) are annotated with letters A-D. Abbreviations used are $P_Y$: $P_{CONY}$ (Table 4); $P_{T7}$: $P_{T7}$ with lacI and lac operator; meG: meGFP; mCh: mCherry. All TUs are terminated by $T_{T7}$.

| pES | A | B | C | D |
|---|---|---|---|---|
| 4 | $P_4$-CsoS1D | | | |
| 5 | $P_{T7}$-CsoS1A | | | |
| 6 | $P_5$-CsoS4A-mCh | $P_5$-CsoS4A-SII | | |
| 7 | $P_{T7}$-CsoS1A | | | |

For encapsulation of cargo in Cso-BMC, we have identified an encapsulation peptide (EP) sequence (SKITGSSGNDTQGSLITYSGGARG; SEQ ID NO: 1), which we term S2CP, which mediates sequestration of protein cargo into the simplified carboxysomes. An example of a modified HcKan_O plasmid which tags S2CP to the C-terminus of an ORF is HcKan_O-S2CP (SEQ ID NO: 39). Details on identifying S2CP as an EP are discussed later. For encapsulation of cargo in HO-BMC, although the reported EP for HO-BMC has been reported to function when *E. coli* was the recombinant host, we found that it did not work in yeast [Lassila, J. K., et al., *Journal of molecular biology* 426: 2217-2228 (2014)]. Schematics of the synthetic operons for the pathway used to make Cso-BMC in *E. coli* and the HO-ACB pathway used to express HO-BMC in yeast are shown in FIG. 3.

The Golden Gate one-pot plasmid assembly largely follows previously published protocols, with slight modifications [Guo, Y., et al., *Nucleic Acids Research,* 43(13), e88 (2015)]. For the insertion of one to three fragments, in a reaction pot was prepared 1 μL of T4 ligase buffer, 0.5 μL of 10× purified bovine serum albumin (BSA), 5 U of BsaI (for Level 0 and 2 assembly) or Esp3I (for Level 1 assembly), 10 U of T4 ligase, 20 ng of destination plasmid, 1 to 3 μL of insert(s) and topped up to 10 μL with water. All enzymes and BSA used were from New England Biolabs (NEB). The reaction pot was subject to a 37° C. to 18° C. thermocycling process with 5 min incubation at each step for 70 cycles, followed by a 55° C. step for 15 min. Plasmids were transformed into *E. coli* Acella (DE3) strain (EdgeBio) and verified by Sanger sequencing.

Transformation of plasmids and chromosomal integration of genes into yeast was performed in accordance with the high-efficiency lithium acetate/single-stranded DNA/PEG-3350 protocol as described by Schiestl and co-workers [Gietz, R. D. and Schiestl, R. H. *Nature Protocols* 2: 31 (2007)].

Example 3

Identifying a Targeting Peptide for the Cso System

A key strategy for repurposing bacterial BMCs into intracellular nanoreactors is to encapsulate heterologous enzymes within the shells by installing EPs to the cargo. While EP sequences have been identified and characterized for some BMC systems, such a sequence has not been reported for the alpha-carboxysome [Kerfeld, C. A., et al., *Nature Reviews: Microbiology,* 16, 277 (2018)]. An EP sequence has been suggested to reside on CsoS2 [Oltrogge, L. M., et al., *Nature Structural & Molecular Biology* 27: 281-287 (2020)]. Studies performed on CsoS2 suggest that it initiates assembly of the carboxysome by recruiting luminal cargo through its N-terminus while its C-terminal region anchors to shell proteins [Oltrogge, L. M., et al., *Nature Structural & Molecular Biology* 27: 281-287 (2020)]. Multiple sequence alignment of 100 CsoS2 orthologs revealed that the C-terminal region is highly conserved, especially at the terminal residues (FIG. 4A). This suggests functional importance. We thus decided to interrogate the function of the terminal 24 residues of *H. neapolitanus* CsoS2 (SKITGSSGNDTQGSLITYSGGARG; SEQ ID NO: 1) and termed it "S2CP" as an abbreviation for CsoS2 C-terminal Peptide. The nucleic acid sequence that encodes the S2CP peptide is set forth in SEQ ID NO: 7. We also considered the possibility that a slightly longer variant of S2CP might improve encapsulation efficacy without adding too much additional bulk on heterologous protein cargo. To this end, we chose the terminal 30 residues of *H. neapolitanus* CsoS2 (KPEKPG SKITGSSGNDTQGSLITYSGGARG SEQ ID NO: 94) as an encapsulation peptide variant and termed it "S2CP(30)". The nucleic acid sequence that encodes the S2CP(30) peptide is set forth in SEQ ID NO: 95.

We used a pull-down assay to investigate if non-native protein cargo tagged with S2CP can interact with CsoS1A, CsoS1D or CsoS4A—representing the BMC-H, BMC-T and BMC-P shell protein types, respectively. We created pES2-$P_{con4}$-His$_6$-meGFP-S2CP-T$_{T7}$, purified His$_6$-meGFP-S2CP and incubated the protein with *E. coli* lysates in which either CsoS1A-SII, SII-CsoS1D or CsoS4A-SII were expressed using $P_T7$. As negative controls, purified His$_6$-meGFP was similarly incubated with the same shell protein containing lysates. The mixtures were subject to purification via Strep-Tactin and purified fractions from the six mixtures were analyzed by Western blotting for the presence of GFP. It was found that His$_6$-meGFP-S2CP co-eluted with CsoS1A-SII, but not with SII-CsoS1D or CsoS4A-SII (FIG. 4B). His$_6$-meGFP was also not seen to co-elute with CsoS1A-SII, SII-CsoS1D or CsoS4A-SII. This demonstrates that S2CP was required for His$_6$-meGFP to interact with CsoS1A. While a previous report demonstrated that full-length CsoS2 interacts with CsoS1A (Cai et al., 2015), we have shown that just the terminal 24 residues of CsoS2 are sufficient for interaction. The association of S2CP with CsoS1A, a major shell module in the alpha-carboxysome, should allow this peptide sequence to target protein cargo to the shell complex. However, based on this result alone, it cannot yet be ascertained whether S2CP is able to mediate cargo encapsulation within the shell or merely targets it to the shell periphery.

Example 4

Recombinant Formation of Simplified Alpha-Carboxysome Shells

Figure 8:
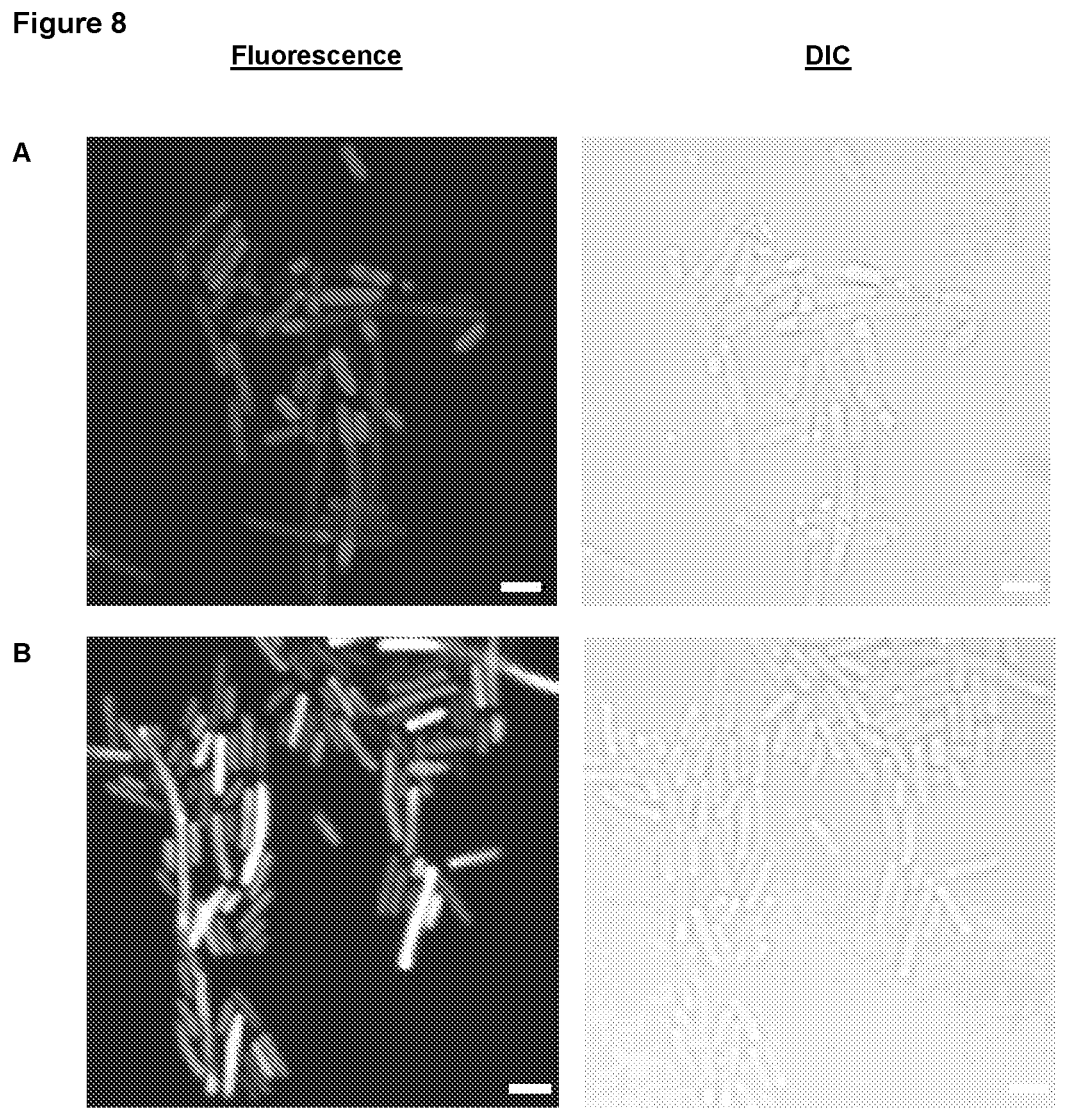

We sought to investigate the interactions between Cso components with the aim of constructing a simplified microcompartment shell based on knowledge of the component structures. Our approach involved translational fusion of FPs to shell components and to S2CP to serve as probes of protein-protein interactions. Using the HcKan_O-FP plasmids, we fused the four FPs (mTurquoise2, meGFP, mKOκ and mCherry) to both the amino and carboxy termini of CsoS4A and expressed the hybrid proteins in *E. coli* using the $P_{CON5}$ promoter from the pES6 plasmid. Only CsoS4A-mCherry was shown to be generally homogenously distributed within the cytosol (FIG. 8A). The rest of the fusion products demonstrated various degrees of aggregation (data not shown), making them less ideal for utilization as probes.

Hence, CsoS4A-mCherry was chosen as the shell component probe. We also expressed meGFP-S2CP using $P_{CON4}$ in pES2 plasmid and found that the protein was generally diffuse within the cytosol (FIG. 8B).

With the shell (CsoS4A-mCherry) and targeting peptide (meGFP-S2CP) probes established, we next expressed CsoS1D and CsoS1A alongside these probes using the pathway plasmid pCKH-Cso-$P_{mCh}$THC (FIG. 5A, Table 6).

TABLE 6

List of pathways plasmids and the corresponding pES TU (Table 5) used in their assembly.

|  | Assembled TUs |
| --- | --- |
| Cso-$P_{mCh}$THC | 2A-4A-6A-7A |
| Cso-$P_{SII}$THC | 2A-4A-6B-7A |
| Cso-$P_{SII}$TH | 2B-4A-5A |
| Cso-$P_{SII}$H | 2B-3A |
| Cso-$P_{SII}$THC$_{U, S2CP}$ | 2C-4A-6B-7A |
| Cso-$P_{SII}$THC$_U$ | 2D-4A-6B-7A |

In our pathway nomenclature, $P_{mCh}$ represents the pentameric shell protein (CsoS4A) fused to mCherry, T represents trimeric (CsoS1D), H for hexameric (CsoS1A) and C for the cargo (meGFP-S2CP). In cells expressing these four components, it was seen that CsoS4A-mCherry and meGFP-S2CP co-localized upon addition of IPTG to 50 µM (FIG. 5B). We quantified the degree of co-localization using the Mander's co-localization coefficients (MCC), [tM$_1$, tM$_2$], where tM$_1$ is the fraction of green signal found in areas where there is red signal, while tM$_2$ the fraction of red signal found in areas with green [Dunn, K. W., et al., *American Journal of Physiology—Cell Physiology* 300: C723-C742 (2011)]. From the cells surveyed, the MCC values were found to be [0.688, 0.758], suggesting there was a significant proportion of co-localized probes.

Figure 9:
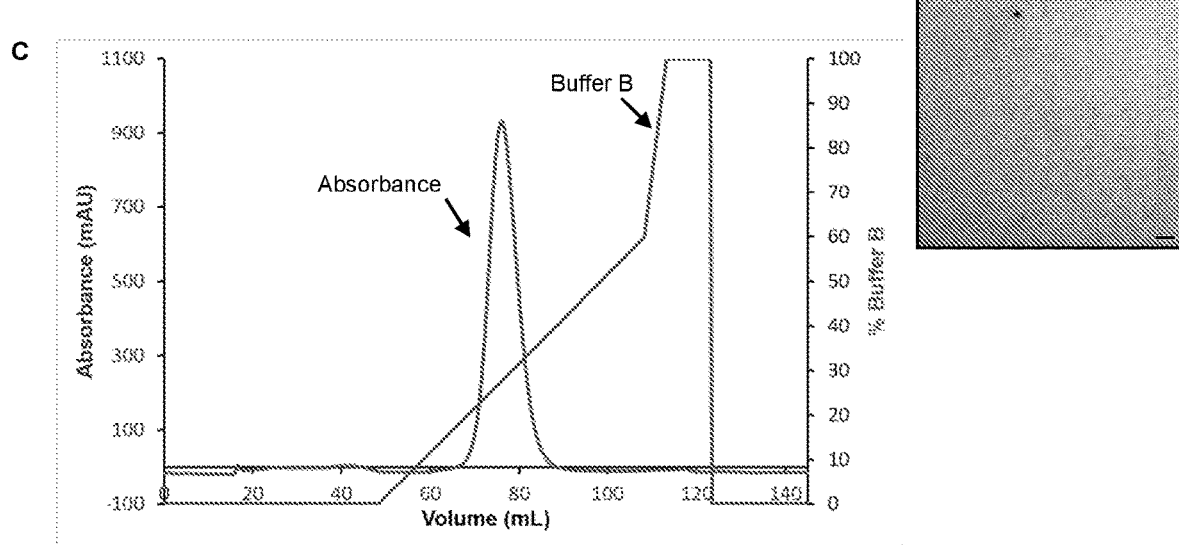
FIG. 9A-C shows anion-exchange (AIEX) chromatograms for the affinity-purified proteins from (A) Cso-P$_{mCh}$-THC pathway construct, (B) Cso-P$_{SII}$THC and (C) CsoS4A-SII. Blue trace (left Y-axis) indicates absorbance (mAU) at 280 nm while green trace (right Y-axis) indicates percentage of AIEX buffer B (Tris 50 mM, NaCl 1.0 M, pH 7.9) used for the indicated elution volume. TEM micrographs on the right are viewings of elution fractions obtained at 0.3 M NaCl. It can be seen that CsoS4A-SII, expressed by itself, does not form protein shells. Scale bar (bottom right) represents 50 nm.
Figure 15:
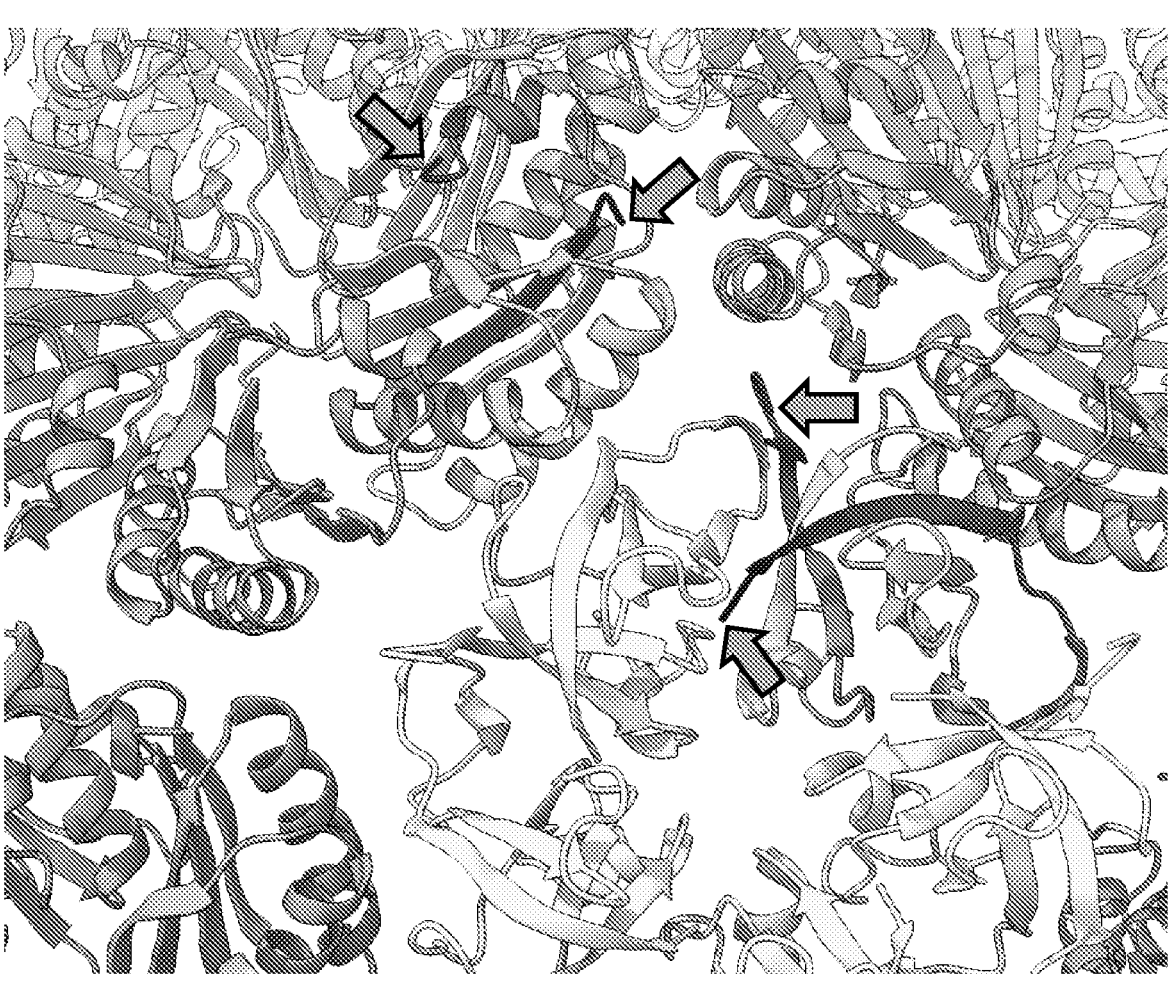
FIG. 15 shows a close-up view of the Cso-BMC exterior demonstrating that the N- and C-termini of the hexameric subunits (grey) and pentameric subunits (light grey) point away from the shell lumen. The N-termini and C-termini of a selected hexameric chain and a pentameric chain are indicated by arrows. The topologies of the Cso-BMC hexameric and pentameric subunits shown are representative of the HO-BMC.

We proceeded to determine if the fluorescent foci observed might be indicative of protein assemblies that can be purified. Two purification strategies were attempted. The first was to incubate *E. coli* lysate expressing Cso-$P_{mCh}$THC with pure CsoS4A-SII before purification by Strep-Tactin. The second was to replace CsoS4A-mCherry with CsoS4A-SII in the Cso-$P_{mCh}$THC pathway, thus creating a new pathway, Cso-$P_{SII}$THC. Proteins purified via Strep-Tactin were further purified by anion exchange ion chromatography (AIEX) using Q Sepharose. For both purification strategies, two elution peaks were seen at 0.3 M and 0.4 M NaCl in the AIEX chromatograms (FIG. 9A-B). Fractions from both peaks were viewed using transmission electron microscopy (TEM) and numerous capsid-like structures approximately 20 nm in diameter were seen in the 0.4 M NaCl elution fractions (FIG. 5C-D), with significantly fewer of such structures seen in the 0.3 M NaCl fractions (FIG. 9A-B). We reasoned that while the capsid-like structures eluted primarily at 0.4 M NaCl, some were observed at the 0.3 M NaCl fraction due to overlap of these two peaks. We also noted that CsoS4A-SII alone, when subject to the same AIEX procedure, eluted in a single peak at 0.3 M NaCl (FIG. 9C). Hence, the 0.3 M NaCl peak observed for Cso-$P_{mCh}$THC and Cso-$P_{SII}$THC likely corresponded to CsoS4A-SII not incorporated within the shells.

It has been proposed that CsoS2 is critical for the assembly of the alpha-carboxysome by recruiting shell proteins through its C-terminal [Oltrogge, L. M., et al., *Nature Structural & Molecular Biology* 27: 281-287 (2020)]. In the Cso-$P_{mCh}$THC and Cso-$P_{SII}$THC constructs, the terminal 24 residues of CsoS2 (S2CP; SEQ ID NO: 1) could have assisted in shell assembly. We wished to investigate whether S2CP was essential for the formation of the shells derived from alpha-carboxysome components. We therefore constructed the pathway Cso-P$_{SH}$TH, in which S2CP was absent. In addition to similar AIEX chromatograms (FIG. 10A), capsid-like structures indistinguishable from those produced by Cso-P$_{mCh}$THC and Cso-P$_{SH}$THC were seen in the Cso-P$_{SH}$TH combination. These structures were again more abundant in the 0.4 M NaCl fraction than the 0.3 M NaCl one (FIG. 5E for 0.4 M NaCl, FIG. 10B for 0.3 M NaCl). These results demonstrate S2CP was unnecessary for the formation of the protein shells observed.

Next, we sought to determine the minimal components required for shell assembly. Given that CsoS1A and CsoS1D are constructed from the same protein domain, we considered the possibility that protein shells could be constructed from just CsoS1A and CsoS4A, each from a different protein domain. A new pathway combination, Cso-P$_{SH}$H, which expresses CsoS1A and CsoS4A-SII, was constructed (pCKH-Cso-BMC; SEQ ID NO: 64) and proteins were purified as before (FIG. 11A). Capsid-like structures that looked similar to those purified from previous pathway combinations were again seen (FIG. 11B for 0.3 M NaCl fraction, FIG. 5D for 0.4 M NaCl). No capsid-like structures were seen to assemble from CsoS1A-SII alone (FIG. 11C). In addition, constructs in which either CsoS1A and CsoS1D were co-expressed or CsoS1D and CsoS4A were co-expressed failed to produce protein shells (FIG. 11D-E). Taken together, these results indicate that CsoS1A and CsoS4A are necessary and sufficient for the assembly of the capsid-like shells.

Example 5

S2CP Targets Cargo Into the Lumen of the Simplified Carboxysome Shells

Figure 6:
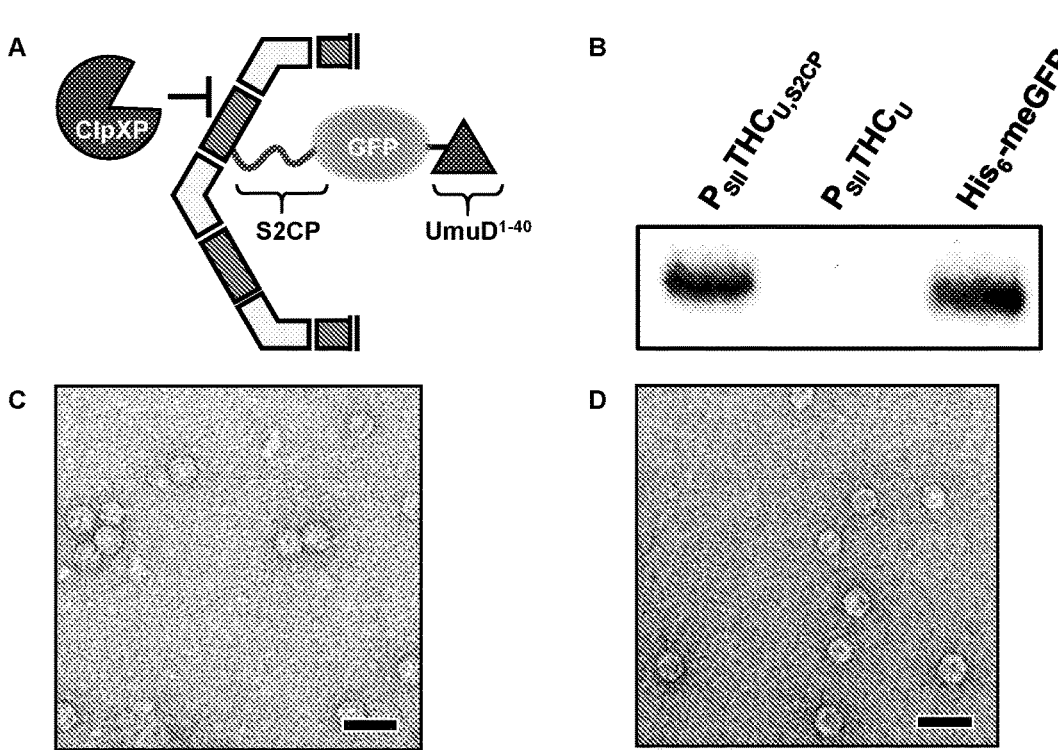
FIG. 6A-D shows how S2CP acts as an encapsulation peptide. (A) Schematic depicting how encapsulation of the UmuD$^{1-40}$ protease signal tagged GFP by S2CP may protect it from the endogenous ClpXP protease. (B) S2CP was able to target UmuD$^{1-40}$-meGFP into the lumen of the simplified carboxysome. Purified shells were subject to Western blot analysis by use of an anti-GFP antibody. UmuD$^{1-40}$meGFP was detected only from Cso-P$_{SII}$THC$_{U,S2CP}$ and not Cso-P$_{SII}$THC$_U$. Electron micrographs show that shells produced by (C) Cso-P$_{SII}$THC$_{U,S2CP}$ and (D) Cso-P$_{SII}$THC$_U$ were similar. Scale bars (black, bottom right) represent 50 nm.

To ascertain whether S2CP is able to target cargo into lumen of the simplified carboxysome shells, we fused the *E. coli* UmuD N-terminal degradation tag (residues 1-40) to the amino-end of meGFP-S2CP [Neher, S. B. et al., *Proceedings of the National Academy of Sciences* 100: 13219-13224 (2003)]. We co-expressed UmuD$^{1-40}$-meGFP-S2CP with CsoS1A, CsoS1D and CsoS4A by constructing the plasmid pCKH-Cso-P$_{SH}$THC$_{U,S2CP}$. We hypothesized that if S2CP is able to target UmuD$^{1-40}$-meGFP into the carboxysome, UmuD$^{1-40}$-meGFP-S2CP (SEQ ID NO: 49) would be protected from proteolysis by the endogenous ClpXP protease that recognizes and degrades proteins tagged with the N-terminal region of UmuD (FIG. 6A). On the other hand, if S2CP only targets cargo to the shell exterior, UmuD$^{1-40}$-meGFP-S2CP would be exposed to ClpXP and be degraded. A similar construct, pCKH-Cso-P$_{SH}$THC$_U$, where the only difference was the absence of S2CP from UmuD$^{1-40}$- meGFP, served to account for stochastic encapsulation of UmuD$^{1-40}$-meGFP by the shells. Western blotting was used for detection of GFP (FIG. 6B). In the lane corresponding to purified proteins from Cso-P$_{SH}$THC$_{U,S2CP}$, UmuD$^{1-40}$-meGFP-S2CP was detected. In the lane corresponding to the same quantity of purified proteins (determined by absorbance at 280 nm) from Cso-P$_{SH}$THC$_U$, UmuD$^{1-40}$-meGFP (SEQ ID NO: 52) could not be detected. As a further confirmatory analysis, similar protein shells could be seen in the elution fractions for both pathway combinations (FIG. 6C-D). This demonstrates that the protection of UmuD$^{1-40}$-meGFP from proteolysis was likely due to its encapsulation into the shells as mediated by S2CP.

Example 6

Atomic Models of the Simplified Alpha-Carboxysome Shells

To better understand the molecular architecture of the simplified alpha-carboxysomes, cryo-electron microscopy (cryo-EM) was used to obtain near atomic-scale models of Cso-P$_{SH}$THC, Cso-P$_{SH}$TH and Cso-P$_{SH}$H. Two distinct shell sizes were seen for Cso-P$_{SH}$THC, corresponding to icosahedral capsid triangulation numbers T=3 and T=4. Shell models were obtained at resolutions of 3.24 and 2.90 Å respectively. For Cso-P$_{SH}$TH and Cso-P$_{SH}$H, only T=3 shells were seen, and structures were obtained at resolutions of 3.35 and 3.14 Å respectively. The proportion of T=3 shells observed in Cso-P$_{SH}$THC was 14.6% while that for the T=4 shell was 85.4%. The reported X-ray crystal structures of *H. neapolitanus* CsoS1A (PDB: 2EWH) and CsoS4A (PDB: 2RCF) were used for model fitting [Tanaka, S. et al., Science 319: 1083-1086 (2008); Tsai, Y. et al., *PLOS Biology* 5: e144 (2007)]. *H. neapolitanus* CsoS1D is expected to assemble as double stacking layers of trimers, as deduced from the structure of CsoS1D from Prochlorococcus *marinus* MED4, with which it shares 60% identical residues [Klein, M. G., et al., *Journal of Molecular Biology* 392: 319-333 (2009)]. However, we were unable to discern double stacking layers in the electron density maps for Cso-P$_{SH}$THC and Cso-P$_{SH}$TH, suggesting CsoS1D was not incorporated within these shells. Electron density was also not detected for the meGFP-S2CP cargo in the luminal space of shells purified from Cso-P$_{SH}$THC. Nonetheless, in light of computational studies that suggest interactions between shell protomers and cargo affect shell size and shape, it is conceivable that formation of the T=4 shell, which is seen only in Cso-P$_{SH}$THC, may be affected by cargo encapsulation while shells without cargo assemble as the smaller T=3 form.

As there was no appreciable difference among the three pathway combinations used to obtain the T=3 shell models, we focused on the shells produced by Cso-P$_{SH}$THC for model building and refinement (Table 7).

TABLE 7

| Cryo-EM data collection, map and model refinement, and model validation | | | | |
| --- | --- | --- | --- | --- |
| | Cso-P$_{SH}$THC | | Cso-P$_{SH}$TH | Cso-P$_{SH}$H |
| | T = 3 | T = 4 | T = 3 | T = 3 |
| Accession codes | | | | |
| Map (EMDB) | EMD-30384 | EMD-30385 | Not deposited, structure almost the | Not deposited, structure almost the |
| Coordinates (PDB) | 7CKB | 7CKC | | |

TABLE 7-continued

| Cryo-EM data collection, map and model refinement, and model validation | | | | |
|---|---|---|---|---|
| | Cso-P$_{SII}$THC | | Cso-P$_{SII}$TH | Cso-P$_{SII}$H |
| | T = 3 | T = 4 | T = 3 | T = 3 |
| | | | same as Cso-P$_{SII}$THC T = 3 | same as Cso-P$_{SII}$THC T = 3 |
| Data collection | | | | |
| Microscope | Titan Krios (Research Center for Ultra-High Voltage Electron Microscopy, Osaka University, Osaka Prefecture, Japan | | | |
| Voltage (kV) | 300 kV | | | |
| Detector | Falcon II | | | |
| Magnification | 96 k | | | |
| Pixel size (Å) | 0.86 | | | |
| Defocus range (μm) | 1.5~1.9 | 1.5~1.9 | 1.5~2.2 | 1.5~2.2 |
| Electron exposure (e⁻/Å²) | 64.3 | 64.3 | 68.1 | 68.1 |
| Reconstruction | | | | |
| Software | | | | |
| Initial particle images (no.) | 94129 | 94129 | 14401 | 15680 |
| Final particle images (no.) | 11468 | 67192 | 9349 | 7678 |
| Box size (pixels) | | | | |
| Symmetry imposed | | | | |
| Accuracy rotations (°) | | | | |
| Accuracy translations (pixels) | | | | |
| Map resolution (Å) | 3.24 | 2.9 | 3.35 | 3.14 |
| FSC threshold | 0.143 | 0.143 | 0.143 | 0.143 |
| Map resolution range (Å) | ∞~3.24 | ∞~2.90 | ∞~3.35 | ∞~3.14 |
| Map sharpening B factor (Å²) | | | | |
| Model building & refinement | | | | |
| Software | Chimera(Pettersen et al., 2004), Coot(Emsley & Cowtan, 2004), Phenix(Adams et al., 2010) | | | |
| Initial model used (PDB code) | 2RCF, 2EWH | | | |
| Model resolution (Å) | 2.15, 1.40 | | | |
| FSC threshold | | | | |
| Model resolution range (Å) | | | | |
| Model composition | | | | |
| Non-hydrogen atoms | 114840 | 150300 | | |
| Protein residues | 15840 | 20820 | | |
| Ligands & water | 0 | 0 | | |
| B factors overall (Å²) | 10.67 | 13.91 | | |
| R.m.s. deviations | | | | |
| Bond lengths (Å) | 0.0076 | 0.0076 | | |
| Bond angles (°) | 0.87 | 1.23 | | |
| Validation | | | | |
| MolProbity score | 1.67 | 1.33 | | |
| Clashscore | 6.97 | 5.49 | | |
| Poor rotamers (%) | 1.05 | 0 | | |
| Cβ deviations (%) | 0 | 0 | | |
| Ramachandran plot | | | | |
| Favored (%) | 96.01 | 97.84 | | |
| Allowed (%) | 3.99 | 2.16 | | |
| Disallowed (%) | 0 | 0 | | |

Figure 7:
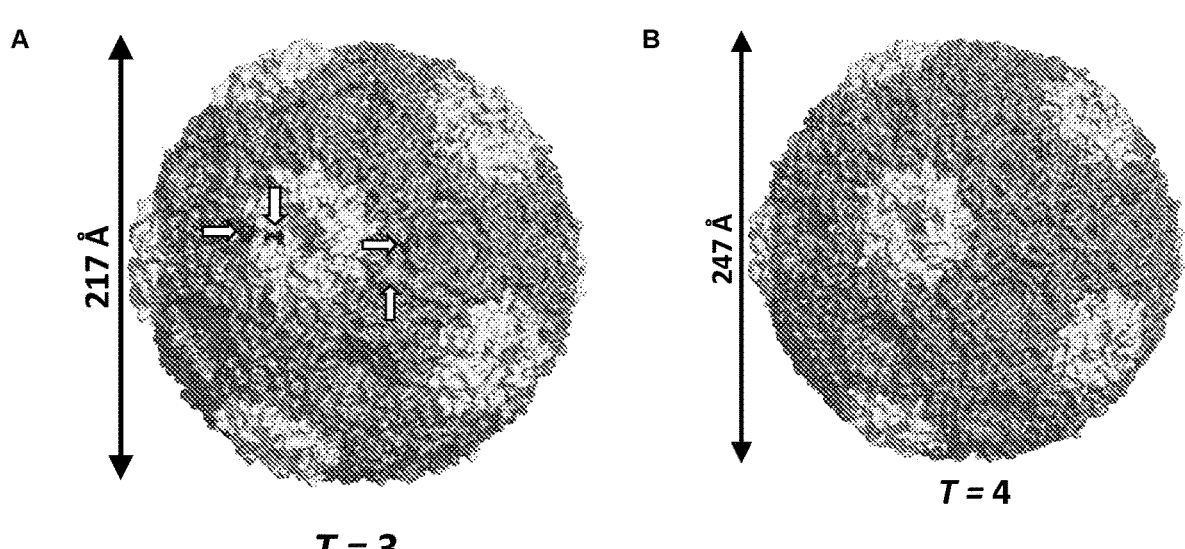
FIG. 7A-B shows atomic models of the simplified alpha carboxysome shells. (A, B) Surface representation of the shells, with the CsoS1A colored grey and CsoS4A in light grey. The right and down arrows over light grey indicate N- and C-termini of a CsoS4A monomer, respectively, and the upward and right arrows over grey those of a CsoS1A monomer, respectively.

The T=3 shell contains 12 homo-pentamers of CsoS4A and 20 homo-hexamers of CsoS1A, with an external diameter of 217 Å, and a calculated molecular mass of 1.7 MDa (FIG. 7A). The T=4 shell contains 12 homo-pentamers and 30 homo-hexamers, with an external diameter of 247 Å, and a mass of 2.3 MDa (FIG. 71B). Both shell types are largely similar in other aspects. The concave sides of CsoS1A and CsoS4A, wherein the N and C termini reside, face the outside of the shell (FIG. 7A).

Example 7

Determining Encapsulation Efficacies of S2CP and S2CP(30) for the Cso-BMC

Figure 16:
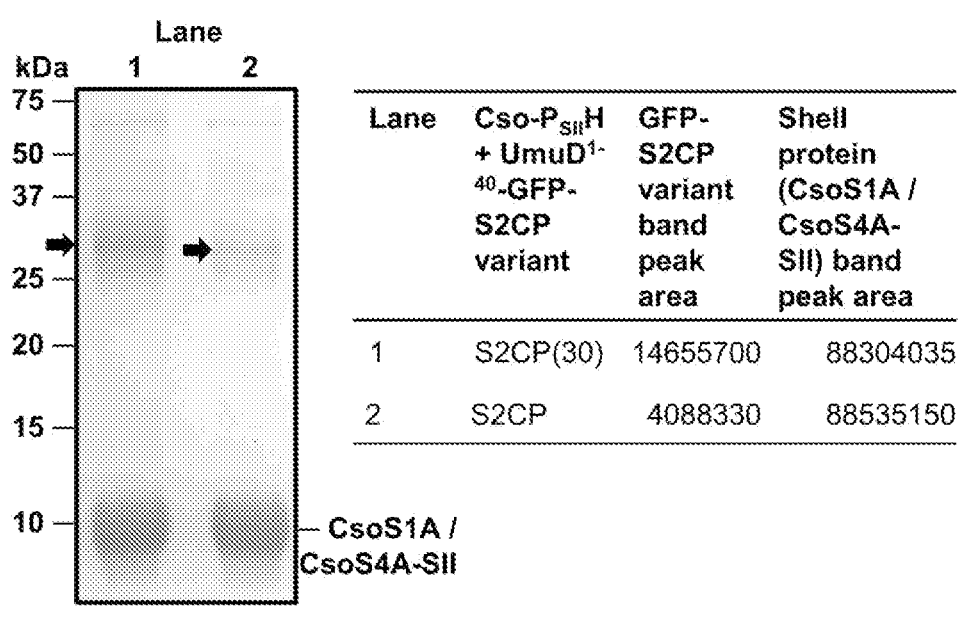
FIG. 16 shows densitometric analysis of Cso-P$_{SII}$H shells co-expressed with either UmuD$^{1-40}$-GFP-S2CP or UmuD$^{1-40}$-GFP-S2CP(30). Approximately the same amount of shells (as judged by band peak area) were loaded per shell sample so that the relative amounts of UmuD$^{1-40}$-GFP-S2CP and UmuD$^{1-40}$-GFP-S2CP(30) could be directly compared. Arrows indicate UmuD$^{1-40}$-GFP-S2CP and UmuD$^{1-40}$-GFP-S2CP(30).

Using the Cso-BMC shell structure, the average copy numbers of UmuD$^{1-40}$-GFP-S2CP and UmuD$^{1-40}$-GFP-S2CP(30) could be quantified via GFP fluorescence. Based on cryogenic electron microscopy observations, for all calculations involving shell molecular masses we presumed all shells co-expressed with cargo to be a mixture of T=3 and 4 forms. As the proportions of shell forms may vary among samples, two values, calculated by presuming all shells in a sample were either T=3 or 4, are provided. It was determined that an average of 7.7-8.0 copies of UmuD$^{1-40}$-GFP-S2CP (30) were encapsulated per shell, compared to 1.6-1.7 copies of UmuD$^{1-40}$-GFP-S2CP. Densitometric analysis of Cso-P$_{SH}$H shells encapsulating either UmuD$^{1-40}$-GFP-S2CP or UmuD$^{1-40}$-GFP-S2CP(30) also indicated that there were approximately 4 times UmuD$^{1-40}$-GFP-S2CP(30) found within the shells compared to UmuD$^{1-40}$-GFP-S2CP (FIG. 16). Hence, S2CP(30) is a more efficacious encapsulation peptide than S2CP.

TABLE 8

Quantifying the average number of encapsulated UmuD$^{1-40}$-GFP cargo mediated by S2CP or S2CP(30). As the proportions of the shell forms are unknown, values calculated by presuming all shells are either T = 3 or 4 are given.

| Encapsulation peptide | Number of residues | Average number of UmuD$^{1-40}$-GFP cargo per shell | |
|---|---|---|---|
| | | T = 3 | T = 4 |
| S2CP | 24 | 1.6 | 1.7 |
| S2CP(30) | 30 | 7.7 | 8.0 |

Example 8

Stabilization of Enzymatic Activities Using Cso-BMCs

Figure 17:
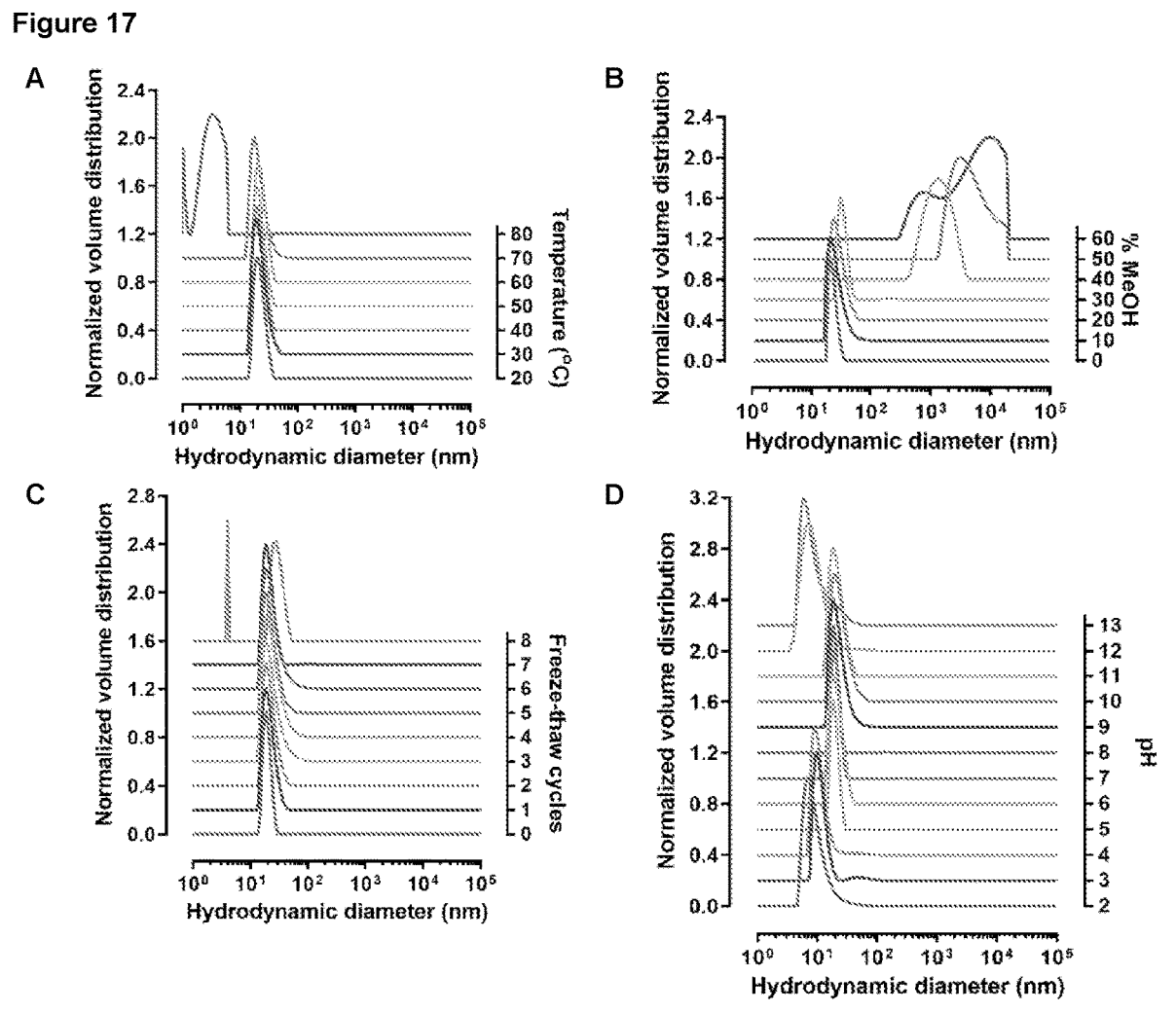

Protein shells have been garnering attention as platforms for conferring stability on enzymes against physical insults, such as heating or freezing, or chemical insults, such as the presence of organic co-solvents or non-physiological pH [Demchuk & Patel, *Biotechnology Advances,* 41: 107547 (2020); Silva, C., et al., *Critical Reviews in Biotechnology,* 38(3): 335-350 (2018)]. Enzyme confinement often reduces their conformational flexibility, which sometimes confers stability against structural changes that lead to denaturation [Das, Zhao, (2020) *Biochemistry,* 59(31): 2870-2881; Küchler, et al., *Nature Nanotechnology,* 11(5): 409-420 (2016)]. Currently, homomeric protein shells are more established for hosting enzymes, attributable to their relative ease of assembly and particle size homogeneity, which improves predictability and tractability during engineering [Patterson, D. P., Prevelige, P. E., & Douglas, T. (2012). *ACS Nano,* 6(6): 5000-5009; Patterson, D. P., Schwarz, B., El-Boubbou, K., van der Oost, J., Prevelige, P. E., & Douglas, T. (2012). *Soft Matter,* 8(39): 10158-10166; Sánchez-Sánchez et al., *Journal of Nanotechnology* 13(1): 66 (2015); Tan, Xue, & Yew, *Molecules* 26(5): 1389 (2021)]. Due to their heteromeric composition, minimal BMC-derived shells represent emerging scaffolds for hosting enzymes, as these shells can provide more avenues for purposeful modifications, while their generally homogenous particle size still confers predictability to facilitate engineering [Turmo, A., Gonzalez-Esquer, C. R., & Kerfeld, C. A. *FEMS Microbiology Letters,* 364(18): fnx176 (2017)]. However, minimal BMC-derived shells have yet to be explored for hosting heterologous enzymes [Cai, F., Bernstein, S. L., Wilson, S. C. & Kerfeld, C. A. *Plant Physiol* 170: 1868-1877 (2016); Hagen, A., et al., *Nature Communications* 9: 2881, (2018)]. This encouraged us to investigate if the Cso-BMC could host and stabilize enzymes. Empty Cso-BMCs (Cso-P$_{SH}$H) were first tested for their stability against heat shock, freezing, presence of methanol co-solvent and environments with pH from 2 to 13. The DLS spectra of shells subject to these conditions were compared to that of shells in Tris·HCl-50/350 (Tris·HCl 50 mM pH 8.0, NaCl 350 mM). Significant changes in particle size distributions and/or appearance of multiple peaks indicate protein shell disassembly [Yu, Z., Reid, J. C., & Yang, Y.-P. *Journal of Pharmaceutical Sciences* 102(12): 4284-4290 (2013)]. Based on the conditions tested, Cso-BMCs were considered to be stable up to 70° C. for 15 min, 20% v/v methanol, seven consecutive freeze-thawing and between pH 5-11 (FIG. 17).

To probe the capacity of the Cso-BMC for encasing enzymes of considerably different molecular sizes, an evolved pea cytosolic ascorbate peroxidase (APEX2), a 27.0 kDa monomer [Lam et al., *Nature Methods* 12(1): 51-54 (2015)], and *E. coli* beta-galactosidase (LacZ), a 466.0 kDa homotetramer, were chosen for encapsulation [Golan, et al., *Biochimica et Biophysica Acta (BBA)—Bioenergetics,* 1293 (2): 238-242; Lam et al., *Nature Methods* 12(1): 51-54 (2015)]. S2CP(30) was fused to the C-termini of the enzymes to mediate encapsulation as it was found to be more efficacious than S2CP for mediating encapsulation of recombinant proteins. Enzymes were also N-terminally tagged with the hexahistidine (His6) tag to facilitate downstream removal of unencapsulated enzymes that might co-purify with shells (Nichols, Kennedy, & Tullman-Ercek, 2019). Cso-P$_{SH}$H shells co-expressed with enzymes were constructed and purified. SDS-PAGE analysis and Western blotting confirmed the presence of the target enzymes in shell samples (FIG. 18A-B) and the average copy numbers of enzymes per shell were estimated by Coomassie blue densitometry (Table 8) [Hagen, A., et al., *Nature Communications* 9: 2881 (2018); Nichols et al., *Methods in Enzymology,* 617, 155-186 (2019)]. Encapsulation of these enzymes did not appear to significantly affect Cso-BMC size and morphology (FIG. 18C-E).

Encapsulation of an enzyme into a protein shell is known to alter the enzyme's catalytic properties in some cases. To probe how encapsulation by the Cso-BMC might affect the catalytic efficiencies of APEX2 and LacZ, we performed steady-state kinetics of both free and encapsulated enzymes and fitted the data to the Michaelis-Menten model to obtain the turnover number ($k_{cat}$), Michaelis-Menten constant ($K_M$), and catalytic efficiency ($k_{cat}/K_M$) (Table 8, FIG. 19). For encapsulated APEX2, $k_{cat}/K_M$ decreased to approximately 30% of the free enzyme. For encapsulated LacZ, $k_{cat}/K_M$ was not significantly different from the free enzyme. The kinetic constants, $k_{cat}$ and $K_M$, obtained for both free enzymes were in reasonable agreement with previous work, suggesting the presence of S2CP(30) did not affect the activities of the free enzymes [Juers, Hakda, Matthews, & Huber, *Biochemistry,* 42(46), 13505-13511 (2003); Lam et al., *Nature Methods* 12(1): 51-54 (2015)].

To determine possible stabilizing effects of the Cso-BMC on enzymes, free enzyme and shell-encapsulated enzyme samples were challenged with the abovementioned conditions under which empty shells were found to be stable. Enzyme activities were normalized to that of the pristine sample to determine the residual activity (FIG. 20). The Cso-BMC conferred a moderate level of thermostability on both enzymes. Encapsulated enzymes retained approximately 90% of their activities following incubation at 40° C. for 15 min, in contrast to 40% for free enzymes. At 50° C., encapsulated APEX2 retained about half its activity while the free enzyme was essentially inactive. However, the activity of encapsulated LacZ was only marginally higher than free enzyme at 50° C. At 60° C. and above, all enzyme samples were inactive. The Cso-BMC had a protective effect on APEX2 up to 20% v/v methanol. On the other hand, for both free and encapsulated LacZ in methanol, increases in activities were seen. It has been reported that the presence of up to 40% v/v methanol does not denature LacZ but rather enhances its activity [Shifrin & Hunn, *Archives of Biochemistry and Biophysics*, 130, 530-535 (1969)]. Hence, Cso-BMC was unlikely to have stabilized LacZ against methanol. For freeze-thaw stability, the Cso-BMC stabilized both enzyme species up to seven consecutive cycles.

Encapsulated enzymes displayed higher activities within the Cso-BMC at pH 10-11, but lower activities at pH 5-6. We reasoned that the acidic microenvironment within the Cso-BMC likely shifted the pH-activity profile of encapsulated enzymes to more alkaline conditions compared to free enzyme. The influence of anionic scaffolds on the pH-dependent activities of enzymes has been observed for synthetic maleic acid polymer scaffolds on trypsin and chymotrypsin, and more recently for the DNA polyphosphate backbone on the glucose oxidase-horseradish peroxidase (GOx-HRP) cascade [Goldstein, *Biochemistry* 11(22): 4072-4084 (1972); Goldstein, Levin, & Katchalski, *Biochemistry*, 3(12): 1913-1919 (1964); Zhang, Tsitkov, & Hess, *Nature Communications*, 7(1): 13982 (2016)].

Figure 18:
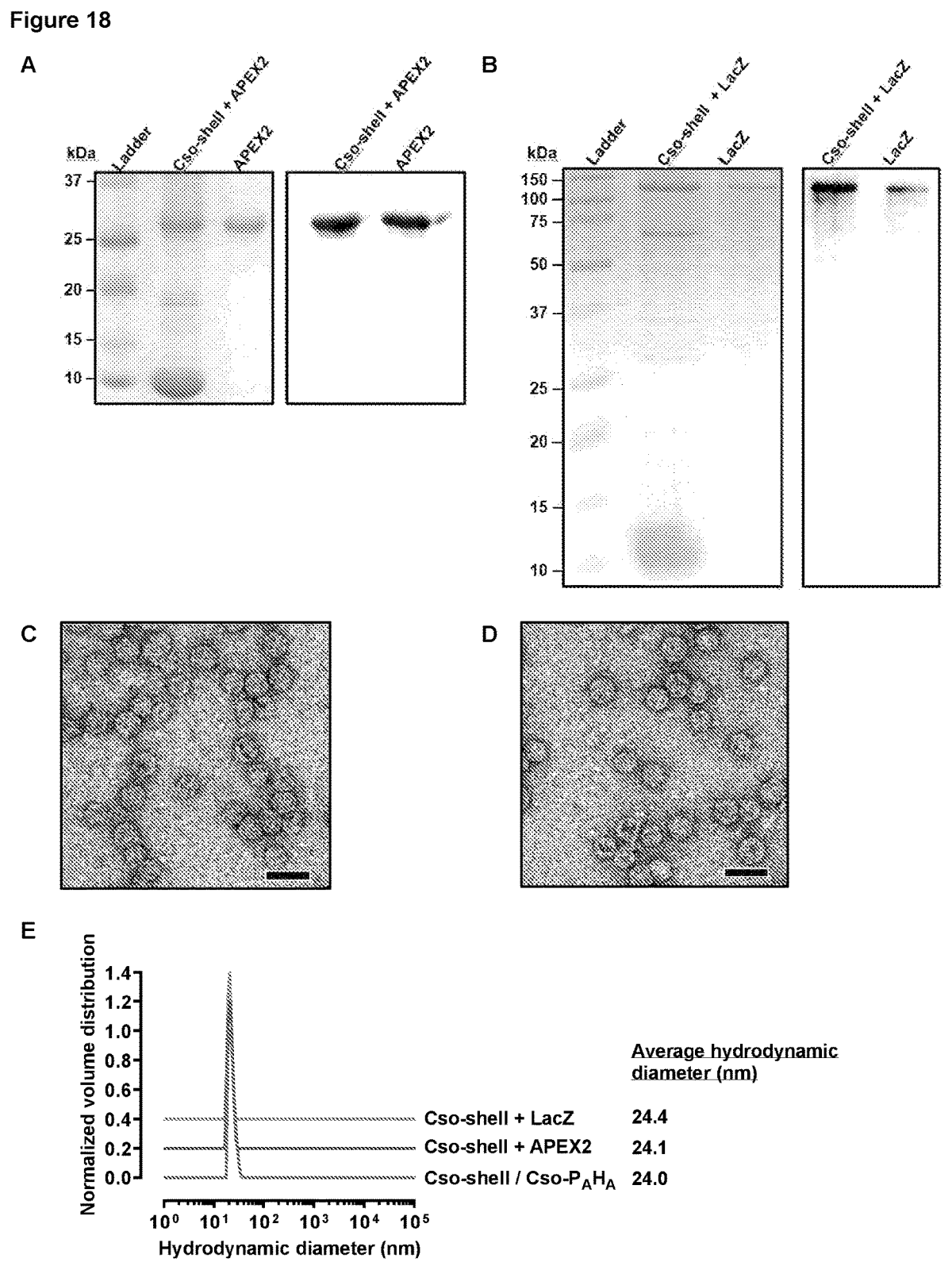

To date, the Cso-BMC likely demonstrates the highest heterologous cargo loading via encapsulation peptides among minimal BMC-derived shells. The use of encapsulation peptides for such shells has been largely inefficacious and cargo often could not be detected via Coomassie blue staining, requiring more sensitive techniques such as immunoblotting or fluorescence [Cai, F., et al., *Plant Physiol* 170: 1868-1877 (2016); Hagen, A., et al., *Nature Communications* 9: 2881 (2018); Lassila, Bernstein, Kinney, Axen, & Kerfeld, (2014)]. In contrast, for the Cso-BMC and S2CP (30) system, all three heterologous protein cargo tested (GFP, APEX2, LacZ) could be clearly identified in Coomassie-blue stained gels (FIGS. 16 and 18).

TABLE 8

Quantification of the average copy number of enzymes encapsulated
per shell and kinetic constants of encapsulated and free enzymes.
For average enzyme copy number per shell, values calculated
by presuming all shells are either T = 3 or 4 are provided.
Kinetic measurements were performed in triplicates and the
mean values are shown with the standard error.

| Enzyme sample | Average enzyme copy number per shell (T = 3/4) | $k_{cat}$ ($s^{-1}$) | $K_M$ (mM) | $k_{cat}/K_M \times 10^5$ ($s^{-1} \cdot M^{-1}$) |
|---|---|---|---|---|
| Free APEX2 | N.A. | 460 ± 20 | 0.58 ± 0.07 | 7.93 ± 1.02 |
| APEX2 + shell | 11.0/14.6 | 208 ± 14 | 0.79 ± 0.12 | 2.63 ± 0.44 |
| LacZ | N.A. | 258 ± 17 | 0 17 ± 0.02 | 15.2 ± 2.05 |
| LacZ + shell | 3.29/4.37 | 200 ± 14 | 0.14 ± 0.02 | 14.3 ± 2.27 |

Example 9

Production of HO-BMC VLPs in *S. cerevisiae*

Golden-Gate Cloning System

Constructs to express HO-BMC VLPs comprised components described in Table 3, FIG. 2 and FIG. 3 and were assembled according to methods described in Example 2. Briefly, the yeast promoter $P_{TDH3}$ was cloned into HcKan_P and designated HcKan_P-TDH3 (SEQ ID NO: 65). The yeast promoter $P_{YEF3}$ was cloned into HcKan_P and designated HcKan_P-YEF3 (SEQ ID NO: 66). The yeast promoter PPYK1 was cloned into HcKan_P and designated HcKan_P-PYK1 (SEQ ID NO: 67). The yeast promoter $P_{GPM1}$ was cloned into HcKan_P and designated HcKan_P-GPM1 (SEQ ID NO: 115)

The HO-H ORF was cloned into HcKan_O and designated HcKan_O-HO-H (SEQ ID NO: 68). The HO-P ORF was cloned into HcKan_O and designated HcKan_O-HO-P (SEQ ID NO: 69). The HO-T1 ORF was cloned into HcKan_O and designated HcKan_O-HO-T1 (SEQ ID NO: 70). The HO-T1-SpyTag ORF was cloned into HcKan_O and designated HcKan_O-HO-T1-SpyTag (SEQ ID NO: 116)

The yeast terminator $T_{RPL41B}$ (SEQ ID NO: 80) was cloned into HcKan_T and designated HcKan_T-RPL41B (SEQ ID NO: 71). The yeast terminator $T_{HBT1}$ (SEQ ID NO: 81) was cloned into HcKan_T and designated HcKan_T-HBT1 (SEQ ID NO: 72). The yeast terminator $T_{RPS20}$ (SEQ ID NO: 82) was cloned into HcKan_T and designated HcKan_T-RPS20 (SEQ ID NO: 73). The yeast terminator $T_{YPT31}$ (SEQ ID NO: 105) was cloned into HcKan_T and designated HcKan_T-YPT31 (SEQ ID NO: 119).

The promoter, ORF and terminator parts described above were assembled into the pathway assembly plasmid, pCKU (SEQ ID NO: 74). The assembled HO-BMC pathway was then sub-cloned into pGAU-YMRWδ15 (SEQ ID NO: 75), for chromosomal integration of pathways into the yeast YMRWδ15 site. The construct comprising HO-BMC for integration of the HO-BMC pathway into the yeast YMRWδ15 site was named pGAU-YMRW515-HO-BMC (SEQ ID NO: 76). The construct comprising $P_{GPM1}$-GFP-SpyCatcher-$T_{RPS}20$ for integration of GFP-SpyCatcher into the yeast YPRC615 sites was named pGAH-YPRC515-GFP-SpyCatcher (SEQ ID NO: 121)

Transformation of plasmids and chromosomal integration of genes into yeast was performed in accordance with the high-efficiency lithium acetate/single-stranded DNA/PEG-3350 protocol as described by Schiestl and co-workers [Gietz, R. D. and Schiestl, R. H. *Nature Protocols* 2: 31 (2007)].

For encapsulation of cargo within HO-BMC, although the EP for HO-BMC has been reported to function when *E. coli* was the recombinant host, we found that it did not work in yeast [Lassila, J. K. et al., *Journal of Molecular Biology* 426: 2217-2228 (2014)]. Hence, an alternative methodology for cargo encapsulation, using the SpyCatcher/SpyTag protein conjugation system, into the HO-shell was adopted [Hagen, A., et al., *Nature Communications* 9: 2881 (2018)]. This method involved grafting the SpyTag sequence into a shell-facing peptide loop in HO-T1. This modified HO-T1 subunit is termed HO-T1-SpyTag. Cargo proteins with a fusion SpyCatcher domain can therefore form a covalent isopeptide bond with HO-T1-SpyTag and be encapsulated within the HO-shell. The transcriptional units that constitute the HO-shell in yeast are compiled in Table 9 and the yeast strains expressing the HO-shell pathways are compiled in Table 10.

A schematic of the synthetic operons of the pathway used to make Cso-BMC in *E. coli* and the HO-ACB pathway used to express HO-BMC in yeast are shown in FIG. 3.

TABLE 9

Compilation of transcriptional units (TUs) (assembled in POT plasmids). The (TUs) are annotated with letters A-D.

| POT | A | B |
|---|---|---|
| 2 | $P_{TDH3}$-HO-H-$T_{RPL41B}$ | |
| 4 | $P_{YEF3}$-HO-T1-$T_{RPL41B}$ | $P_{YEF3}$-HO-T1-SpyTag-$T_{RPL41B}$ |
| 5 | $P_{PYK1}$-HO-P-SII-$T_{RPS20}$ | |

TABLE 10

List of yeast strains expressing HO-shell pathways in relation to Table 9.

| | Assembled TUs |
|---|---|
| HO-PTH | 2A-4A-5A (integrated at YMRWδ15) |
| HO-PT$_{S7}$H + GFP-SpyCatcher | 2A-4B-5A (integrated at YMRWδ15) + GFP-SpyCatcher (integrated at YPRCδ15) |

Purification of VLPs

After growing in 8 L of YPD (yeast extract 1%, peptone 2%, glucose 2%, BioBasic) for 48 h at 25° C., yeast cells were pelleted and lysed using the M-110P microfluidizer at 20,000 psi for eight passes. The lysate was spun twice at 20,000×g for 20 min each time and the clarified lysate was adjusted to pH 8 using 1 M Tris·HCl pH 12. The lysate was also incubated with 300 μL of biotin blocking buffer (IBA Lifesciences) with gentle stirring for 15 min. StrepTrap affinity purification was performed in the same way as described above.

Results

Purification of Cso-BMC and HO-BMC

Using the synthetic operons constructed (FIG. 3), we purified Cso-BMC from *E. coli* and HO-BMC from yeast. To the inventor's knowledge, this is the first known instance of recombinant protein shell formation using only two components from the H. *neapolitanus* cso operon. While Silver and co-workers have reported the formation of *H. neapolitanus* carboxysomes in *E. coli*, it was done by transplanting the entire cso operon, which encodes ten genes, into *E. coli* [Bonacci, W. et al., *Proceedings of the National Academy of Sciences* 109: 478-483 (2012)]. Our system has simplified the formation of protein shells to only two genes, csoS1A, and csoS4A. CsoS1A assembles into hexamers that form flat hexagonal tiles while CsoS4A assembles into pentamers that occupy the vertices of the shell, capping the flat tiles formed by CsoS1A and giving the shell its icosahedral geometry. While the resultant Cso-BMC shells are smaller (22 nm in diameter) than the native *H. neapolitanus* carboxysomes (90 to 110 nm in diameter), the synthetic shells are highly uniform in size, as evidenced by DLS measurements (FIG. 17).

Kerfeld and co-workers have reported recombinant expression of HO-BMC in *E. coli* obtained its atomic-scale structure using three shell protomers, HO-H, HO-P and HO-T1 [Sutter, M. et al., *Science* 356: 1293-1297 (2017)]. The structures and geometric functions of HO-H are similar to that of CsoS1A, while HO-P is analogous to CsoS4A. HO-T1, which resembles a tandem repeat of two HO-H, assembles into trimers that likewise form flat hexagonal tiles. We have managed to reconstruct the HO-BMC in yeast. Based on our current understanding of the literature, this is the first instance of recombinant expression of a BMC-derived protein shell in yeast. While recombinant protein titers in yeast are typically lower compared to *E. coli* (FIG. 14), expression of the HO-BMC VLP in yeast opens up avenues for tailoring by the eukaryotic post-translational modification machinery [Sudbery, P. E. *Curr Opin Biotechnol* 7 (1996)]. It is also noteworthy that many yeast-derived biomolecules, and the organism itself, are afforded the Generally Regarded as Safe (GRAS) status, placing HO-BMC in a good position for vaccine development [Sewalt, V. et al., *Industrial Biotechnology* 12: 295-302 (2016)].

Viewed under the TEM, Cso-BMC appears as capsid-like structures, approximately 20 nm in diameter, with some having angled facets. This shape is reminiscent of the native *H. neapolitanus* carboxysomes, though as previously mentioned, the diameter of the synthetic Cso-BMC is about 20% of the native carboxysome. A plausible reason that accounts for the smaller size of the Cso-BMC is that its luminal space is empty. In the native carboxysome it is known that there are hundreds to thousands of proteins that are tightly packed within the shell [Bonacci, W. et al. *Proceedings of the National Academy of Sciences* 109: 478-483 (2012)]. For bioengineering purposes, it should be more desirable for VLPs to be bereft of their native luminal proteins so that recombinant protein cargo can be more efficiently encapsulated within these shells [Schwarz, B. et al., *Advances in Virus Research* 97: 1-60 (2017)].

Our yeast expressed HO-BMC shells closely resemble those expressed from *E. coli* as reported by Kerfeld and co-workers in terms of size and shape [Sutter et al., *Science* 356: 1293-1297 (2017)]. Sodium dodecyl sulfate polyacrylamide gel (SDS-PAGE) analysis of the protein eluates from affinity purification of Cso-BMC and HO-BMC indicates the presence of the expected shell protomer proteins. As the hexameric (CsoS1A, HO-H) and pentameric (CsoS4A, HO-P) have similar molecular masses (10±1 kDa), they cannot be resolved well by SDS-PAGE. Nonetheless, given the presence of the protein shells, it can be deduced that both species are present in the ~10 kDa protein bands seen. Atomic-level structural details of both the Cso-BMC and HO-shell indicate that these particles are largely uniform in size [Sutter, M. et al., *Science* 356: 1293-1297 (2017); Tan, Ali, et al., *Biomacromolecules* doi:10.1021/acs.biomac.1c00533 (2021)]. This uniformity in size is a useful feature in VLP engineering, as it translates to predictability when functionalizing VLPs as biomaterials [Schwarz, B. et al., *Advances in Virus Research* 97: 1-60 (2017)].

SUMMARY

BMCs are promising platforms for spatial programming of metabolic reactions in microbial cell factories, and can be repurposed into specialized biochemical delivery vehicles [Kerfeld C. A. et al. *Nature Reviews Microbiology* 16: 277 (2018)]. However, a major hurdle in utilizing these protein shells for such purposes is their often-intricate nature of assembly, which is not easily translatable into recombinant systems. The assembly of protein shells using two types of shell proteins is a significant reduction from the ten identified components from the *H. neapolitanus* cso operon that produced native-like alpha-carboxysomes [Bonacci, W. et al. *Proceedings of the National Academy of Sciences* 109: 478-483 (2012)]. Furthermore, we have identified a sequence, S2CP, which is able to target a heterologous protein cargo into the simplified carboxysome shell. An encapsulation peptide variant that contains 6 more residues, S2CP(30), is shown to be approximately 4 times more efficacious than S2CP at mediating encapsulation of a GFP cargo protein into the Cso-BMC. Hence, both S2CP and S2CP(30) are useful for controlling the quantity of heterologous protein cargo to be packaged within the Cso-BMC. The Cso-BMC is also able to stabilize two enzymes, APEX2 and LacZ, against common enzyme denaturing factors, such as thermal shock, the presence of methanol co-solvent, consecutive freeze-thaw cycles and highly alkaline environments. To the best of our knowledge, this is the first demonstration of utilizing a minimal component BMC-derived shell for hosting and stabilizing enzymes against such denaturing factors. The Cso-BMC expands the current scope of VLPs that can be used to encapsulate and stabilize enzymes [Demchuk & Patel, *Biotechnology Advances,* 41: 107547 (2020)].

We have also recombinantly expressed the HO-BMC in yeast and provide evidence that the shell is able to encapsulate recombinant protein cargo. To the best of our knowledge, this is the first demonstration of recombinant expression of BMC shells in yeast.

REFERENCES

Any listing or discussion of an apparently prior-published document in this specification should not necessarily be taken as an acknowledgement that such document is part of the state of the art or is common general knowledge.

Adams, P. D., Afonine, P. V., Bunkóczi, G., Chen, V. B., Davis, I. W., Echols, N., Zwart, P. H. (2010). PHENIX: a comprehensive Python-based system for macromolecular structure solution. *Acta Crystallographica. Section D: Biological Crystallography,* 66(Pt 2), 213-221. doi: 10.1107/s0907444909052925.

Anderson, J. C. (2006). Anderson Promoter Library Registry of Standard Biological Parts. Retrieved from parts.igem.org/Promoters/Catalog/Anderson.

Baneyx, F. (1999). Recombinant protein expression in *Escherichia coli. Current Opinion in Biotechnology,* 10(5), 411-421. doi:10.1016/S0958-1669(99)00003-8.

Bonacci, W., Teng, P. K., Afonso, B., Niederholtmeyer, H., Grob, P., Silver, P. A., & Savage, D. F. (2012). Modularity of a carbon-fixing protein organelle. *Proceedings of the National Academy of Sciences,* 109(2), 478-483. doi: 10.1073/pnas.1108557109.

Cai, F., Bernstein, S. L., Wilson, S. C., & Kerfeld, C. A. (2016). Production and Characterization of Synthetic Carboxysome Shells with Incorporated Luminal Proteins. *Plant Physiology,* 170(3), 1868-1877. doi:10.1104/pp. 15.01822.

Cai, F., Dou, Z., Bernstein, S. L., Leverenz, R., Williams, E. B., Heinhorst, S., Kerfeld, C. A. (2015). Advances in Understanding Carboxysome Assembly in Prochlorococcus and Synechococcus Implicate CsoS2 as a Critical Component. *Life (Basel),* 5(2), 1141-1171. doi:10.3390/ life5021141.

Das, S., Zhao, L., Elofson, K., & Finn, M. G. (2020). Enzyme Stabilization by Virus-Like Particles. *Biochemistry,* 59(31), 2870-2881. doi:10.1021/ acs.biochem.0c00435.

Demchuk, A. M., & Patel, T. R. (2020). The biomedical and bioengineering potential of protein nanocompartments. *Biotechnology Advances,* 41, 107547. doi:10.1016/j.biotechadv.2020.107547.

Dunn, K. W., Kamocka, M. M., & McDonald, J. H. (2011). A practical guide to evaluating colocalization in biological microscopy. *American Journal of Physiology—Cell Physiology,* 300(4), C723-C742. doi:10.1 152/ajp-cell.00462.2010.

Emsley, P., & Cowtan, K. (2004). Coot: model-building tools for molecular graphics. *Acta Crystallographica. Section D: Biological Crystallography,* 60(Pt 12 Pt 1), 2126-2132. doi:10.1107/s0907444904019158.

Fletcher, J. M., Harniman, R. L., Barnes, F. R. H., Boyle, A. L., Collins, A., Mantell, J., Woolfson, D. N. (2013). Self-Assembling Cages from Coiled-Coil Peptide Modules. *Science,* 340(6132), 595-599. doi:10.1126/science.1233936.

Gietz, R. D., & Schiestl, R. H. (2007). High-efficiency yeast transformation using the LiAc/SS carrier DNA/PEG method. *Nature Protocols,* 2, 31. doi:10.1038/ nprot.2007.13.

Golan, R., Zehavi, U., Naim, M., Patchornik, A., & Smirnoff, P. (1996). Inhibition of *Escherichia coli* beta-galactosidase by 2-nitro-1-(4,5-dimethoxy-2-nitrophenyl) ethyl, a photoreversible thiol label. *Biochimica et Biophysica Acta (BBA)—Bioenergetics,* 1293(2), 238-242. doi:10.1016/0167-4838(95)00254-5.

Goldstein, L. (1972). Microenvironmental effects on enzyme catalysis. Kinetic study of polyanionic and polycationic derivatives of chymotrypsin. *Biochemistry,* 11(22), 4072-4084. doi:10.1021/bi00772a009.

Goldstein, L., Levin, Y., & Katchalski, E. (1964). A Water-insoluble Polyanionic Derivative of Trypsin. II. Effect of the Polyelectrolyte Carrier on the Kinetic Behavior of the Bound Trypsin*. *Biochemistry,* 3(12), 1913-1919. doi: 10.1021/bi00900a022.

Guo, Y., Dong, J., Zhou, T., Auxillos, J., Li, T., Zhang, W., Dai, J. (2015). YeastFab: the design and construction of standard biological parts for metabolic engineering in *Saccharomyces cerevisiae. Nucleic Acids Research,* 43(13), e88. doi:10.1093/nar/gkv464.

Hagen, A., Sutter, M., Sloan, N., & Kerfeld, C. A. (2018). Programmed loading and rapid purification of engineered bacterial microcompartment shells. *Nature Communications,* 9(1), 2881. doi:10.1038/s41467-018-05162-z.

Juers, D. H., Hakda, S., Matthews, B. W., & Huber, R. E. (2003). Structural Basis for the Altered Activity of Gly794 Variants of *Escherichia coli* β-Galactosidase. *Biochemistry,* 42(46), 13505-13511. doi:10.1021/ bi035506j.

Kalnins, G., Cesle, E.-E., Jansons, J., Liepins, J., Filimonenko, A., & Tars, K. (2020). Encapsulation mechanisms and structural studies of GRM2 bacterial microcompartment particles. *Nature Communications,* 11(1), 388. doi: 10.1038/s41467-019-14205-y.

Keeble, A. H., & Howarth, M. (2019). Insider information on successful covalent protein coupling with help from SpyBank. *Methods in Enzymology,* 617, 443-461. doi: 10.1016/bs.mie.2018.12.010.

Kerfeld, C. A., Aussignargues, C., Zarzycki, J., Cai, F., & Sutter, M. (2018). Bacterial microcompartments. *Nature Reviews: Microbiology,* 16, 277. doi:10.1038/nrmicro.2018.10.

Klein, M. G., Zwart, P., Bagby, S. C., Cai, F., Chisholm, S. W., Heinhorst, S., Kerfeld, C. A. (2009). Identification and structural analysis of a novel carboxysome shell protein with implications for metabolite transport. *Journal of Molecular Biology,* 392(2), 319-333. doi:10.1016/ j.jmb.2009.03.056.

Kúchler, A., Yoshimoto, M., Luginbuhl, S., Mavelli, F., & Walde, P. (2016). Enzymatic reactions in confined environments. *Nature Nanotechnology,* 11(5), 409-420. doi: 10.1038/nnano.2016.54.

Lam, S. S., Martell, J. D., Kamer, K. J., Deerinck, T. J., Ellisman, M. H., Mootha, V. K., & Ting, A. Y. (2015). Directed evolution of APEX2 for electron microscopy and proximity labeling. *Nature Methods,* 12(1), 51-54. doi: 10.1038/nmeth.3179.

Lassila, J. K., Bernstein, S. L., Kinney, J. N., Axen, S. D., & Kerfeld, C. A. (2014). Assembly of robust bacterial microcompartment shells using building blocks from an organelle of unknown function. *Journal of Molecular Biology,* 426(11), 2217-2228. doi:10.1016/j.jmb.2014.02.025.

Lawrence, A. D., Frank, S., Newnham, S., Lee, M. J., Brown, I. R., Xue, W.-F., Warren, M. J. (2014). Solution Structure of a Bacterial Microcompartment Targeting Peptide and Its Application in the Construction of an Ethanol Bioreactor. *ACS Synthetic Biology,* 3(7), 454-465. doi:10.1021/sb4001118.

Liebschner, D., Afonine, P. V., Baker, M. L., Bunkoczi, G., Chen, V. B., Croll, T. I., Adams, P. D. (2019). Macromolecular structure determination using X-rays, neutrons and electrons: recent developments in Phenix. *Acta Crystallographica Section D: Structural Biology,* 75(10), 861-877. doi:10.1107/S2059798319011471.

Neher, S. B., Sauer, R. T., & Baker, T. A. (2003). Distinct peptide signals in the UmuD and UmuD' subunits of UmuD/D' mediate tethering and substrate processing by the ClpXP protease. *Proceedings of the National Academy of Sciences,* 100(23), 13219-13224. doi:10.1073/pnas.2235804100.

Nichols, T. M., Kennedy, N. W., & Tullman-Ercek, D. (2019). Cargo encapsulation in bacterial microcompartments: Methods and analysis. *Methods in Enzymology,* 617, 155-186. doi:10.1016/bs.mie.2018.12.009.

Oltrogge, L. M., Chaijarasphong, T., Chen, A. W., Bolin, E. R., Marqusee, S., & Savage, D. F. (2020). Multivalent interactions between CsoS2 and Rubisco mediate α-carboxysome formation. *Nature Structural & Molecular Biology,* 27(3), 281-287. doi:10.1038/s41594-020-0387-7.

Patterson, D. P., Prevelige, P. E., & Douglas, T. (2012). Nanoreactors by Programmed Enzyme Encapsulation Inside the Capsid of the Bacteriophage P22. *ACS Nano,* 6(6), 5000-5009. doi:10.1021/nn300545z.

Patterson, D. P., Schwarz, B., El-Boubbou, K., van der Oost, J., Prevelige, P. E., & Douglas, T. (2012). Virus-like particle nanoreactors: programmed encapsulation of the thermostable CelB glycosidase inside the P22 capsid. *Soft Matter,* 8(39), 10158-10166. doi:10.1039/C2SM26485D.

Pettersen, E. F., Goddard, T. D., Huang, C. C., Couch, G. S., Greenblatt, D. M., Meng, E. C., & Ferrin, T. E. (2004). UCSF Chimera—a visualization system for exploratory research and analysis. *Journal of Computational Chemistry,* 25(13), 1605-1612. doi:10.1002/jcc.20084.

Sánchez-Sánchez, L., Tapia-Moreno, A., Juarez-Moreno, K., Patterson, D. P., Cadena-Nava, R. D., Douglas, T., & Vazquez-Duhalt, R. (2015). Design of a VLP-nanovehicle for CYP450 enzymatic activity delivery. *Journal of Nanobiotechnology,* 13(1), 66. doi:10.1186/s12951-015-0127-z.

Schwarz, B., Uchida, M., & Douglas, T. (2017). Chapter One—Biomedical and Catalytic Opportunities of Virus-Like Particles in Nanotechnology. In M. Kielian, T. C. Mettenleiter, & M. J. Roossinck (Eds.), *Advances in Virus Research* (Vol. 97, pp. 1-60): Academic Press.

Sewalt, V., Shanahan, D., Gregg, L., La Marta, J., & Carrillo, R. (2016). The Generally Recognized as Safe (GRAS) Process for Industrial Microbial Enzymes. *Industrial Biotechnology,* 12(5), 295-302. doi:10.1089/ind.2016.0011.

Shifrin, S., & Hunn, G. (1969). Effect of alcohols on the enzymatic activity and subunit association of β-galactosidase. *Archives of Biochemistry and Biophysics,* 130, 530-535. doi:10.1016/0003-9861(69)90066-6.

Sievers, F., & Higgins, D. G. (2014). Clustal Omega, accurate alignment of very large numbers of sequences. *Methods in Molecular Biology,* 1079, 105-116. doi:10.1007/978-1-62703-646-7_6.

Silva, C., Martins, M., Jing, S., Fu, J., & Cavaco-Paulo, A. (2018). Practical insights on enzyme stabilization. *Critical Reviews in Biotechnology,* 38(3), 335-350. doi: 10.1080/07388551.2017.1355294.

Sudbery, P. E. (1996). The expression of recombinant proteins in yeasts. *Current Opinion in Biotechnology,* 7. doi:10.1016/s0958-1669(96)80055-3.

Sutter, M., Greber, B., Aussignargues, C., & Kerfeld, C. A. (2017). Assembly principles and structure of a 6.5-MDa bacterial microcompartment shell. *Science,* 356(6344), 1293-1297. doi:10.1126/science.aan3289.

Sutter, M., Laughlin, T. G., Sloan, N. B., Serwas, D., Davies, K. M., & Kerfeld, C. A. (2019). Structure of a synthetic beta-carboxysome shell. *Plant Physiology,* 181(3), 1050-1058. doi:10.1104/pp. 19.00885.

Tan, Y. Q., Ali, S., Xue, B., Teo, W. Z., Ling, L. H., Go, M. K., . . . Yew, W. S. (2021). Structure of a Minimal α-Carboxysome-Derived Shell and Its Utility in Enzyme Stabilization. *Biomacromolecules.* doi:10.1021/acs.biomac.1c00533.

Tan, Y. Q., Xue, B., & Yew, W. S. (2021). Genetically Encodable Scaffolds for Optimizing Enzyme Function. *Molecules,* 26(5), 1389. Retrieved from wwwdotmdpidotcom/1420-3049/26/5/1389.

Tanaka, S., Kerfeld, C. A., Sawaya, M. R., Cai, F., Heinhorst, S., Cannon, G. C., & Yeates, T. O. (2008). Atomic-Level Models of the Bacterial Carboxysome Shell. *Science,* 319(5866), 1083-1086. doi:10.1126/science.1151458.

Thomas, F., Boyle, A. L., Burton, A. J., & Woolfson, D. N. (2013). A Set of de Novo Designed Parallel Heterodimeric Coiled Coils with Quantified Dissociation Constants in the Micromolar to Sub-nanomolar Regime. *Journal of the American Chemical Society,* 135(13), 5161-5166. doi:10.1021/ja312310g.

Tsai, Y., Sawaya, M. R., Cannon, G. C., Cai, F., Williams, E. B., Heinhorst, S., . . . Yeates, T. O. (2007). Structural Analysis of CsoS1A and the Protein Shell of the *Halothiobacillus neapolitanus* Carboxysome. *PLoS Biology,* 5(6), e144. doi:10.1371/journal.pbio.0050144.

Turmo, A., Gonzalez-Esquer, C. R., & Kerfeld, C. A. (2017). Carboxysomes: metabolic modules for $CO_2$ fixation. *FEMS Microbiology Letters,* 364(18), fnx176. doi: 10.1093/femsle/fnx176.

Waterhouse, A. M., Procter, J. B., Martin, D. M. A., Clamp, M., & Barton, G. J. (2009). Jalview Version 2—a multiple sequence alignment editor and analysis workbench. *Bioinformatics,* 25(9), 1189-1191. doi:10.1093/bioinformatics/btp033.

Winn, M. D., Ballard, C. C., Cowtan, K. D., Dodson, E. J., Emsley, P., Evans, P. R., . . . Wilson, K. S. (2011). Overview of the CCP4 suite and current developments.

*Acta Crystallographica. Section D: Biological Crystallography,* 67(Pt 4), 235-242. doi:10.1107/s0907444910045749.

Yu, Z., Reid, J. C., & Yang, Y.-P. (2013). Utilizing Dynamic Light Scattering as a Process Analytical Technology for Protein Folding and Aggregation Monitoring in Vaccine Manufacturing. *Journal of Pharmaceutical Sciences,* 102 (12), 4284-4290. doi:10.1002/jps.23746.

Zhang, K. (2016). Gctf: Real-time CTF determination and correction. *Journal of Structural Biology,* 193(1), 1-12. doi:10.1016/j.jsb.2015.11.003

Zhang, Y., Tsitkov, S., & Hess, H. (2016). Proximity does not contribute to activity enhancement in the glucose oxidase-horseradish peroxidase cascade. *Nature Communications,* 7(1), 13982. doi:10.1038/ncomms13982

Zivanov, J., Nakane, T., Forsberg, B. O., Kimanius, D., Hagen, W. J. H., Lindahl, E., & Scheres, S. H. W. (2018). New tools for automated high-resolution cryo-EM structure determination in RELION-3. *eLife,* 7, e42166. doi:10.7554/eLife.42166.

What is claimed is:

1. A method for producing a bacterial microcompartment virus-like particle (VLP) carrying a cargo molecule, said method comprising A) introducing into a host cell or organism one or more heterologous polynucleotides comprising
   (i) a first sequence encoding bacterial microcompartment shell protomers; and
   (ii) a second sequence encoding a cargo molecule fused to an encapsulation peptide, wherein the encapsulation peptide comprises the amino acid sequence set forth in SEQ ID NO: 1 (SKITGSSGNDTQGSLITYSGGARG) or SEQ ID NO: 94 (KPEKPGSKITGSSGNDTQGSLITYSGGARG), or a functional variant thereof;
   a) expressing the first and second sequences; and
   b) forming a microcompartment that encapsulates the cargo molecule; or B) introducing into a host cell or organism one or more polynucleotides comprising
   (i) a first sequence encoding bacterial microcompartment shell protomers, wherein the bacterial microcompartment protomers consist of HO-H comprising the amino acid sequence set forth in SEQ ID NO: 4, HO-P comprising the amino acid sequence set forth in SEQ ID NO: 5 and HO-T1 comprising the amino acid sequence set forth in SEQ ID NO: 6 from Haliangium ochraceum, and variants thereof; and
   (ii) a second sequence encoding at least one of said protomers fused with a cargo molecule or a biochemical tag;
   a) expressing the first and second sequences; and
   b) forming a microcompartment that expresses the cargo molecule on an exterior surface, or
   c) forming a microcompartment that expresses the biochemical tag on an exterior surface to which a cargo molecule comprising a complementary tag can bind.

2. The method of claim 1, wherein the functional variant of the encapsulation peptide set forth in SEQ ID NO: 1 comprises, at its amino terminus, 1, 2, 3, 4, or 5 of the additional amino acids at the amino terminus of SEQ ID NO: 94.

3. The method of claim 1, wherein:
   the bacterial microcompartment protomers in A)(i) are CsoS1A (SEQ ID NO: 2) and CsoS4A (SEQ ID NO: 3) from Halothiobacillus neapolitanus; and variants thereof.

4. The method of claim 1, wherein:
   i) the cargo molecule is at least one peptide, and/or
   ii) the biochemical tag is selected from the group comprising Streptavidin-binding Strep-tag II peptide (Strep-Tag II), Streptococcus pyogenes-derived SpyCatcher protein/SpyTag peptide covalent binding pair (SpyCatcher/SpyTag pair) and Coiled-Coil Dimer A peptide/Coiled-Coil Dimer B peptide (CC-Di-A/B pair).

5. The method of claim 3, wherein the expression of CsoS1A is controlled by promoter $P_{T7}$; CsoS4A is controlled by promoter $P_{CONS}$; HO-H is controlled by yeast promoter $P_{TDH3}$; HO-P is controlled by yeast promoter $P_{PYK1}$ and HO-T1 is controlled by yeast promoter $P_{YEF3}$.

6. The method of claim 1, wherein the host organism is E. coli or S. cerevisiae.

7. An engineered bacterial microcompartment VLP carrying a cargo molecule, comprising:
   i) bacterial microcompartment shell protomers, and a cargo molecule fused to an encapsulation peptide, wherein the encapsulation peptide comprises the amino acid sequence set forth in SEQ ID NO: 1 or SEQ ID NO: 94, or a functional variant thereof; or
   ii) bacterial microcompartment shell protomers and a cargo molecule, wherein the cargo molecule is fused to an end of at least one of said protomers, or wherein at least one of said protomers is fused to a tag and a cargo molecule comprising a complementary tag is bound to it on the exterior surface of the VLP, wherein the bacterial microcompartment protomers consist of HO-H comprising the amino acid sequence set forth in SEQ ID NO: 4, HO-P comprising the amino acid sequence set forth in SEQ ID NO: 5 and HO-T1 comprising the amino acid sequence set forth in SEQ ID NO: 6 from Haliangium ochraceum, and variants thereof.

8. The engineered VLP of claim 7, wherein the functional variant of the encapsulation peptide set forth in SEQ ID NO: 1 comprises, at its amino terminus, 1, 2, 3, 4, or 5 of the additional amino acids at the amino terminus of SEQ ID NO: 94.

9. The engineered VLP of claim 7, wherein
   the bacterial microcompartment protomers of i) are CsoS1A comprising the amino acid sequence set forth in SEQ ID NO: 2 and CsoS4A comprising the amino acid sequence set forth in SEQ ID NO: 3 from Halothiobacillus neapolitanus; and variants thereof.

10. The engineered VLP of claim 7, wherein the cargo molecule is at least one peptide.

11. The engineered VLP of claim 7, wherein the biochemical tag is selected from the group comprising Strep-Tag II peptide (Strep-Tag II), Streptococcus pyogenes-derived SpyCatcher protein/SpyTag peptide covalent binding pair (SpyCatcher/SpyTag pair) and Coiled-Coil Dimer A peptide/Coiled-Coil Dimer B peptide (CC-Di-A/B pair).

12. An isolated plasmid or vector comprising:
   a) a first DNA sequence that encodes bacterial microcompartment shell protomers, each of which is operably linked to a promoter, and
   b) a second DNA sequence that encodes a cargo molecule fused to an encapsulation peptide, operably linked to a promoter, wherein the encapsulation peptide comprises the amino acid sequence set forth in SEQ ID NO: 1 or SEQ ID NO: 94, or a functional variant thereof; or c) a first DNA sequence that encodes bacterial microcompartment shell protomers, each of which is operably linked to a promoter, wherein the bacterial microcompartment protomers consist of HO-H comprising the amino acid sequence set forth in SEQ ID NO: 4, HO-P comprising the amino acid sequence set forth in SEQ ID NO: 5 and HO-T1 comprising the amino acid sequence set forth in SEQ ID NO: 6 from *Haliangium ochraceum*, and variants thereof, and d) a second DNA sequence encoding at least one of said protomers fused with a cargo molecule or a biochemical tag.

13. The isolated plasmid or vector of claim 12, wherein the functional variant of the encapsulation peptide set forth in SEQ ID NO: 1 comprises, at its amino terminus, 1, 2, 3, 4, or 5 of the additional amino acids at the amino terminus of SEQ ID NO: 94.

14. The isolated plasmid or vector of claim 12, wherein the DNA sequences encoding said bacterial microcompartment shell protomers, cargo molecules and tags have at least 70%, at least 80%, at least 90%, or 100% identity with SEQ ID Nos 7-12 and 95 due to redundancy of the genetic code.

15. A composition comprising at least one engineered VLP of claim 7.

16. The composition of claim 15, wherein the at least one engineered VLP comprises;

i) an enzyme for conversion of a prodrug; and/or ii) one or more additional therapeutic agents.

17. The isolated plasmid or vector nucleic acid of claim 12, wherein the bacterial microcompartment protomers of a) are CsoS1A comprising the amino acid sequence set forth in SEQ ID NO: 2 and CsoS4A comprising the amino acid sequence set forth in SEQ ID NO: 3 from *Halothiobacillus neapolitanus* and variants thereof.

\*   \*   \*   \*   \*